US010703747B2

(12) United States Patent
Thatcher et al.

(10) Patent No.: US 10,703,747 B2
(45) Date of Patent: Jul. 7, 2020

(54) BENZOTHIOPHENE-BASED SELECTIVE MIXED ESTROGEN RECEPTOR DOWNREGULATORS

(71) Applicant: The Board of Trustees of the University of Illnois, Urbana, IL (US)

(72) Inventors: Gregory R. Thatcher, Urbana, IL (US); Rui Xiong, Urbana, IL (US); Yunlong Lu, Urbana, IL (US); Jiong Zhao, Urbana, IL (US); Debra A. Tonetti, Urbana, IL (US)

(73) Assignee: The Board of Directors of the University of Illinois, Urbana, IL (US)

( * ) Notice: Subject to any disclaimer, the term of this patent is extended or adjusted under 35 U.S.C. 154(b) by 0 days.

(21) Appl. No.: 16/393,258

(22) Filed: Apr. 24, 2019

(65) Prior Publication Data

US 2019/0248780 A1    Aug. 15, 2019

Related U.S. Application Data

(63) Continuation of application No. PCT/US2017/058145, filed on Oct. 24, 2017.

(60) Provisional application No. 62/411,988, filed on Oct. 24, 2016.

(51) Int. Cl.
| | |
|---|---|
| *C07D 333/52* | (2006.01) |
| *C07D 417/10* | (2006.01) |
| *C07D 413/10* | (2006.01) |
| *C07D 333/56* | (2006.01) |
| *A61P 1/00* | (2006.01) |
| *C07D 333/00* | (2006.01) |
| *A61P 5/24* | (2006.01) |
| *C07D 333/60* | (2006.01) |

(52) U.S. Cl.
CPC ............. *C07D 417/10* (2013.01); *A61P 1/00* (2018.01); *A61P 5/24* (2018.01); *C07D 333/00* (2013.01); *C07D 333/56* (2013.01); *C07D 333/60* (2013.01); *C07D 413/10* (2013.01)

(58) Field of Classification Search
CPC .. C07D 417/10; C07D 413/10; C07D 333/00; C07D 333/60; C07D 333/56; C07D 333/52; A61P 1/00; A61P 5/24
USPC ........................................................ 549/58
See application file for complete search history.

(56) References Cited

U.S. PATENT DOCUMENTS

| | | | |
|---|---|---|---|
| 4,133,814 A | 1/1979 | Jones et al. | |
| 4,418,068 A | 11/1983 | Jones | |
| 4,659,516 A | 4/1987 | Bowler et al. | |
| 5,393,763 A | 2/1995 | Black et al. | |

(Continued)

FOREIGN PATENT DOCUMENTS

| | | |
|---|---|---|
| EP | 0752421 A1 | 1/1997 |
| EP | 0802184 B1 | 6/2002 |

(Continued)

OTHER PUBLICATIONS

Abdelhamid et al. "Benzothiophene Selective Estrogen Receptor Modulators Provide Neuroprotection by a Novel GPR30-Dependent Mechanism" ACS Chem. Neuro., Mar. 15, 2011; 2: 256-268.

(Continued)

*Primary Examiner* — Taylor V Oh
(74) *Attorney, Agent, or Firm* — Knowles Intellectual Property Strategies, LLC

(57) ABSTRACT

This invention is benzothiophene-based selective mixed estrogen receptor downregulators and their compositions and uses to treat estrogen-related disorders.

30 Claims, 2 Drawing Sheets

(56) References Cited

U.S. PATENT DOCUMENTS

| | | | |
|---|---|---|---|
| 5,457,117 | A | 10/1995 | Black et al. |
| 5,478,847 | A | 12/1995 | Draper |
| 5,491,123 | A | 2/1996 | Hagen et al. |
| 5,780,497 | A | 7/1998 | Miller et al. |
| 5,998,402 | A | 12/1999 | Miller et al. |
| 6,005,102 | A | 12/1999 | Raveendranath et al. |
| 6,326,392 | B1 | 12/2001 | Gast et al. |
| 6,403,614 | B1 | 6/2002 | Dodge et al. |
| 6,479,535 | B1 | 11/2002 | Pickar et al. |
| 6,512,002 | B2 | 1/2003 | Lee et al. |
| 6,583,170 | B1 | 6/2003 | Pickar et al. |
| 6,632,834 | B2 | 10/2003 | Thompson et al. |
| 6,756,401 | B2 | 6/2004 | Day et al. |
| 6,777,424 | B2 | 8/2004 | Littman et al. |
| 6,797,719 | B2 | 9/2004 | Arbuthnot et al. |
| 6,821,989 | B2 | 11/2004 | Rosati |
| 7,371,774 | B2 | 5/2008 | Moinet |
| 8,030,330 | B2 | 10/2011 | Arbuthnot et al. |
| 8,455,534 | B2 | 6/2013 | Smith et al. |
| 8,642,632 | B2 | 2/2014 | Miller |
| 8,703,810 | B2 | 4/2014 | Kahraman et al. |
| 8,853,423 | B2 | 10/2014 | Govek et al. |
| 9,078,871 | B2 | 7/2015 | Kahraman et al. |
| 9,193,714 | B2 | 11/2015 | Smith et al. |
| 9,475,798 | B2 | 10/2016 | Govek et al. |
| 2015/0284357 | A1 | 10/2015 | Thatcher et al. |
| 2016/0184265 | A1 | 6/2016 | Burks et al. |

FOREIGN PATENT DOCUMENTS

| | | | |
|---|---|---|---|
| EP | | 1947085 A1 | 7/2008 |
| GB | | 2483736 A | 3/2012 |
| WO | WO 1999/024027 A2 | | 5/1999 |
| WO | WO 2002/003975 A2 | | 1/2002 |
| WO | WO 2002/003976 A2 | | 1/2002 |
| WO | WO 2002/003977 A2 | | 1/2002 |
| WO | WO 2002/003986 A2 | | 1/2002 |
| WO | WO 2002/003988 A2 | | 1/2002 |
| WO | WO 2002/003989 A2 | | 1/2002 |
| WO | WO 2002/003990 A2 | | 1/2002 |
| WO | WO 2002/003991 A2 | | 1/2002 |
| WO | WO 2002/003992 A2 | | 1/2002 |
| WO | WO 2002/004418 A2 | | 1/2002 |
| WO | WO 2002/013802 A2 | | 2/2002 |
| WO | WO 2005/016929 A1 | | 2/2005 |
| WO | WO 2006/078834 A1 | | 7/2006 |
| WO | WO 2006/084338 A1 | | 8/2006 |
| WO | WO 2007/087684 A1 | | 8/2007 |
| WO | WO 2008/002490 A2 | | 1/2008 |
| WO | WO 2009/013195 A1 | | 1/2009 |
| WO | WO 2010/093578 A1 | | 8/2010 |
| WO | WO 2010/127452 A1 | | 11/2010 |
| WO | WO 2011/139769 A2 | | 12/2011 |
| WO | WO 2011/156518 A2 | | 12/2011 |
| WO | WO 2012/037410 A2 | | 3/2012 |
| WO | WO 2012/037411 A2 | | 3/2012 |
| WO | WO 2012/084711 A1 | | 6/2012 |
| WO | WO 2013/083568 A1 | | 6/2013 |
| WO | WO 2013/090829 A1 | | 6/2013 |
| WO | WO 2013/090836 A1 | | 6/2013 |
| WO | WO 2013/090921 A1 | | 6/2013 |
| WO | WO 2013/142266 A1 | | 9/2013 |
| WO | WO 2014/066692 A1 | | 5/2014 |
| WO | WO 2014/066695 A1 | | 5/2014 |
| WO | WO 2014/130310 A1 | | 8/2014 |
| WO | WO 2014/151899 A1 | | 9/2014 |
| WO | WO 2014/191726 A1 | | 12/2014 |
| WO | WO 2014/203129 A1 | | 12/2014 |
| WO | WO 2014/203132 A1 | | 12/2014 |
| WO | WO 2014/205136 A1 | | 12/2014 |
| WO | WO 2014/205138 A1 | | 12/2014 |
| WO | WO 2015/028409 A1 | | 3/2015 |
| WO | WO 2015/092634 A1 | | 6/2015 |
| WO | WO 2015/136016 A2 | | 9/2015 |
| WO | WO 2015/136017 A1 | | 9/2015 |
| WO | WO 2015/149045 A1 | | 10/2015 |
| WO | WO 2016/097071 A1 | | 6/2016 |
| WO | WO 2016/097072 A1 | | 6/2016 |
| WO | WO 2016/097073 A1 | | 6/2016 |
| WO | WO 2016/189011 A1 | | 12/2016 |
| WO | WO 2016/202161 A1 | | 12/2016 |
| WO | WO 2017/056115 A1 | | 4/2017 |
| WO | WO 2017/059139 A1 | | 4/2017 |
| WO | WO 2017/060326 A1 | | 4/2017 |
| WO | WO 2017/072792 A1 | | 5/2017 |
| WO | WO 2017/080338 A1 | | 5/2017 |

OTHER PUBLICATIONS

Bolton et al. "Potential Mechanisms of Estrogen Quinone Carcinogenesis" Chem. Res. Toxicol., Dec. 2007 ; 21: 93-101.

Bolton et al. "Quinoids Formed from Estrogens and Antiestrogens" Methods in Enzymology 2004; 378: 110-122.

Bolton et al. "Genotoxic Estrogen Pathway: Endogeneous and Equine Estrogen Hormone Replacement Therapy" The Chemical Biology of DNA Damage 2010; 185-199.

Chandrasena, et al. "Problematic Detoxification of Estrogen Quinones by NAD(P)H-Dependent Quinone Oxidoreductase and Gluthathione-S-transferase" Chem. Res. Toxicol 2008; 21: 1324-1329.

Dowers, et al. Bioactivation of Selective Estrogen Receptor Modulators (SERMs) Chem. Res. Toxicol. 2006; 19: 1125-1137.

Gherezghiher et al. "The Naphthol Selective Estrogen Receptor Modulator (SERM), LY2066948, is Oxidized to an o-quinone Analogous to the Naphthol Equine Estrogen, Equilenin" Chemico-Biological Interactions 196 (2012); 1-10.

Hamilton et al. "A Phase 1 Study of AZD9496, a Novel Oral, Selective Estrogen Receptor Degrader (SERD) in Women with Estrogen Receptor Positive, HER-2 Negative Advanced Breast Cancer (ABC)" Poster Presented at San Antonio Breas Cancer Symposium, Dec. 6-10, 2016.

Hemachandra et al. Hops (*Humulus lupulus*) Inhibits Oxidative Estrogen Metabolism and Estrogen-Induced Malignant Transformation in Human Mammary Epithelial Cells (MCF-10A) Published OnlineFirst Oct. 13, 2011; DOI: 10.1158/1940-6207.CAPR-11-0348.

Hemachandra et al."SERMs Attenuate Estrogen-Induced Malignant Transformation of Human Mammary Epithelial Cells by Upregulating Detoxification of Oxidative Metabolites" Published OnlineFirst Mar. 5, 2014; DOI: 10.1158/1940-6207. CAPR-13-0296.

Kastrati et al. "A Novel Aspirin Prodrug Inhibits NFkB Activity and Breast Cancer Stem Cell Properties" BMC Cancer (2015) 15:845.

Kastrati et al. "Estrogen-Induced Apoptosis of Breast Epithelial Cells is Blocked by NO/cGMP and Mediated by Extranuclear Estrogen Receptors" Department of Medicinal Chemistry and Pharmacognosy, College of Pharmacy, University of Illinois at Chicago, Chicago, Illinois 60612.

Kastrati et al. "Raloxifene and Desmethylarzoxifene Block Estrogen-Induced Malignant Transformation of Human Breast Epithelial Cells" Department of Medicinal Chemistry and Pharmacognosy, College of Pharmacy, University of Illinois of Chicago, Illinois, United States.

Kim et al. "Click Synthesis of Estradiol-Cyclodextrin Conjugates as Cell Compartment Selective Estrogens" Bioorganic & Medicinal Chemistry 18 (2010) 809-821.

Liu et al. "Bioactivation of the Selective Estrogen Receptor Modulator Desmethylated Arzoxifene to Quinoids: 4'-Fluoro Substitution Prevents Quinoid Formation" Chem. Res. Toxicol. 2005, 18: 162-173.

Liu et al. "Bioactivation of the Selective Estrogen Receptor Modulator Desmethylated Arzoxifene to Quinoids: 4'-Fluoro Substitution Prevents Quinoid Formation" Chem. Res. Toxicol. 2005, 18: 174-182.

Liu et al. "Analysis of Protein Covalent Modification by Xenobiotics Using a Covert Oxidatively Activated Tag: Raloxifene Proof-of-Principle Study" Chem. Res. Toxicol. 2005, 18: 1485-1496.

Liu et al. "Chemical Modification Modulates Estrogenic Activity, Oxidative Reactivity, and Metabolic Stability in 4'F-DMA, a New Benzothiophene Selective Estrogen Receptor Modulator" Chem. Res. Toxicol. 2006, 19: 779-787.

(56) References Cited

OTHER PUBLICATIONS

Liu et al. "Uterine Peroxidase-Catalyzed Formation of Diquinone Methides from the Selective Estrogen Receptor Modulators Raloxifene and Desmethylated Arzoxifene" Chem. Res. Toxicol. 207, 20: 1676-1684.
Michalsen et al. "Selective Estrogen Receptor Modulator (SERM) Lasofoxifene Forms Reactive Quinones Similar to Estradiol" Chem. Res. Toxicol. 2012, 25: 1472-1483.
Molloy et al. "Novel Selective Estrogen Mimics for the Treatment of Tamoxifen-Resistant Breast Cancer" Published OnlineFirst Sep. 9, 2014: DOI: 10.1158/1535-7163.MCT-14-0319.
Overk et al. "Structure-Activity Relationships for a Family of Benzothiophene Selective Estrogen Receptor Modulators Including Raloxifene and Arzoxifene" ChemMedChem 2007, 2: 1520-1526.
Patel et al. "A Chimeric SERM-Histone Deacetylase Inhibitor Approach to Breast Cancer Therapy" ChemMedChem 2014, 9: 602-613.
Peng et al. "Selective Estrogen Receptor Modulator Delivery of Quinone Warheads to DNA Triggering Apoptosis in Breast Cancer Cells" ACS Chemical Biology, 2009 vol. 4 No. 12, 1039-1049.
Peng et al. "Unexpected Hormonal Activity of a Catechol Equine Estrogen Metabolite Reveals Reversible Glutathione Conjugation" Chem. Res. Toxicol. 2010, 23: 1374-1383.
Pubchem: Substance Record for SID 236885489. Feb. 13, 2015. Retrieved from the Internet. <URL:https://pubchem.ncbi.nlm.nih.gov/substance/236885489>.
Qin et al. "Structural Modulation of Oxidative Metabolism in Design of Improved Benzothiophene Selective Estrogen Receptor Modulators" Drug Metabolism and Disposition; vol. 37, No. 1.
Qin et al. "Benzothiophene Selective Estrogen Receptor Modulators with Modulated Oxidative Activity and Receptor Affinity" J. Med. Chem. 2007, 50: 2682-2692.
Romagnoli et al. "Synthesis and Biological Evaluation of 2- and 3-Aminobenzo[b]thiophene Derivatives as Antimitotic Agents and Inhibitors of Tubulin Polymerization", J. Med. Chem. 2007, vol. 50, pp. 2273-2277.
Romagnoli et al. "Synthesis and biological evaluation of 2-(3', 4', 5''-trimethoxybenzoyl)-3-aryl/arylaminobenzo[b]thiophene derivatives as novel class of antiproliferative agents", Eur J Med Chem. 2010. vol. 45(12), pp. 5781-5791.
Thatcher et al. "Endocrine-independent ER+ breast cancer therapy: Benzothiophene SERMs, SERDs, SMERDs, SEMs, and ShERPAs" PowerPoint presented at 252nd ACS National Meeting, Aug. 21, 2016.
Toader et al. "Nitrosation, Nitration, and Autoxidation of the Selective Estrogen Receptor Modulator Raloxifene by Nitric Oxide, Peroxynitrite, and Reactive Nitrogen/Oxygen Species" Chem. Res. Toxicol. 2003, 16: 1264-1276.
Vandevrede et al. "A NO Donor Approach to Neuroprotective and Procognitive Estrogen Therapy Overcomes Loss of NO Synthase Function and Potentially Thrombotic Risk" PLOS ONE, Aug. 2013, vol. 8, Issue 8.
Wang et al. "Development of a Liquid Chromatography Electrospray Ionization Tandem Mass Spectrometry Method for Analysis of Stable 4-Hydroxyequilenin-DNA Adducts in Human Breast Cancer Cells" Chem. Res. Toxicol. 2009, 22: 1129-1136.
Wang et al. "Redox Cycling of Catechol Estrogens Generating Apurinic/Apyrimidinic Sites and 8-oxo-Deoxyguanosine via Reactive Oxygen Species Differentiates Equine and Human Estrogens" Chem. Res. Toxicol. 2010, 23: 1365-1373.
Wang et al. "Estrogen Receptor a Enhances the Rate of Oxidative DNA Damage by Targeting an Equine Estrogen Catechol Metabolite to the Nucleus" The Journal of Biological Chemistry vol. 284, No. 13, 8633-8642, Mar. 27, 2009.
Weir et al. "AZD9496: An Oral Estrogen Receptor Inhibitor That Blocks the Growth of ER-Positive and ESR1-Mutant Breast Tumors in Preclinical Models" Published OnlineFirst Mar. 28, 2016: DOI: 10.1158/0008-5472.Can-15-2357.
Xiong et al. "Selective Human Estrogen Receptor Partial Agonists (ShERPAs) for Tamoxifen-Resistant Breast Cancer" J. Med. Chem. 2016, 59: 219-237.
Xiong et al. "Novel Selective Estrogen Receptor Downregulators (SERDs) Developed against Treatment-Resistant Breast Cancer" J. Med. Chem. 2017, 60: 1325-1342.
Yu et al. "Comparative Methods for Analysis of Protein Covalent Modification by Electrophilic Quinoids Formed from Xenobiotics" Bioconjugate Chem. 2009, 20: 728-741.
Yu et al. "Structural Modulation of Reactivity/Activity in Design of Improved Benzothiophene Selective Estrogen Receptor Modulators: Induction of Chemopreventive Mechanisms" Mol. Cancer, Ther. 2007, 6(9), Sep. 2007.
International Search Report and Written Opinion for PCT/US2017/058145 dated Mary 3, 2018.

BENZOTHIOPHENE-BASED SELECTIVE MIXED ESTROGEN RECEPTOR DOWNREGULATORS

CROSS REFERENCE TO RELATED APPLICATIONS

This application is a continuation of International Patent Application No. PCT/US2017/058145 filed Oct. 24, 2017, which claims the benefit of U.S. Provisional Application No. 62/411,988, filed Oct. 24, 2016. These applications are hereby incorporated by reference for all purposes.

STATEMENT OF GOVERNMENTAL INTEREST

This invention was made with government support under contract no. 1R01CA188017 awarded by the National Institutes of Health. The government has certain rights in this invention.

TECHNICAL FIELD

This invention provides compounds and compositions that include benzothiophene-based estrogen receptor ligands and use of these compounds to treat estrogen-related medical disorders.

BACKGROUND OF THE INVENTION

Estrogens are the primary female hormones responsible for the development and regulation of the female reproductive system and secondary female sex characteristics. Estrogens also have pleotropic roles in protein synthesis, coagulation, lipid balance, fluid balance, melanin, gastrointestinal track function, lung function, cognition, immune response, and heart disease, among others.

The estrogen receptor ("ER") is a ligand-activated transcriptional regulatory protein that mediates induction of the variety of biological effects through its interaction with endogenous estrogens, including 17β-estradiol and estrones. ER has been found to have two isoforms, ER-α and ER-β, and both receptors are involved in the regulation and development of the female reproductive tract.

ERs and estrogens regulate biological processes through several distinct pathways. The classical pathway involves the binding of a ligand-activated ER to a specific DNA sequence motif called an estrogen response element (ERE). ERs can also participate in non-classical pathways such as ERE-independent gene transcription via protein-protein interactions with other transcription factors, non-genomic pathways with rapid effects, and ligand-independent pathways that involve activation through other signaling pathways. This ER signaling is not only crucial for the development and maintenance of female reproductive organs, but also for bone metabolism and mass, lipid metabolism, cardiovascular protection, and central nervous system signaling.

Research in this area has confirmed the enormous complexity of estrogen and ER activities. A goal of drug development has been to create new compounds that modulate estrogen activity, either by acting as an antagonist or an agonist, or a partial antagonist or partial agonist.

One goal has been to identify complete anti-estrogens (complete antagonists) that have the effect of shutting down all estrogenic activity in the body. Fulvestrant is an example of a complete estrogen receptor antagonist with no agonist activity. It is a selective estrogen receptor downregulator (SERD). Fulvestrant was disclosed by Imperial Chemical Industries (ICI) in U.S. Pat. No. 4,659,516 and is sold by AstraZeneca under the name Faslodex. It is indicated for the treatment of hormone receptor positive metastatic breast cancer in post-menopausal women with disease progression following anti-estrogen therapy. Fulvestrant has limited water solubility and requires monthly intramuscular (IM) injections. Fulvestrant's aqueous insolubility creates a challenge to achieve and maintain efficacious serum concentrations.

Another class of anti-estrogens are selective estrogen receptor modulators (SERMs) which act as antagonists or agonists in a gene-specific and tissue-specific fashion. A goal of SERM therapy is to identify drugs with mixed profiles that afford beneficial target anti-estrogenic activity and either avoid adverse off-target effects or exhibit incidental beneficial estrogenic side effects. An example of a SERM is tamoxifen, initially sold by AstraZeneca under the name Nolvadex. Tamoxifen was also disclosed by ICI in U.S. Pat. No. 4,659,516, (see also U.S. Pat. Nos. 6,774,122 and 7,456,160). Tamoxifen is a prodrug that is metabolized to 4-hydroxytamoxifen and N-desmethyl-4-hydroxytamoxifen which have high binding affinity to the estrogen receptor. Tamoxifen is indicated to prevent further breast cancer after breast cancer treatment and to treat node-positive breast cancer in women following mastectomy and radiation. Tamoxifen can affect bone health. In pre-menopausal women, tamoxifen can cause bone thinning, while it can be beneficial for bone health in post-menopausal woman. Serious side effects have been noted, including increased risk of uterine cancer in post-menopausal women and "tumor flares" in women with breast cancer that has spread to the bone. In addition to these side effects, some women who initially respond to tamoxifen experience acquired resistance over time, and in some cases ER positive breast cancer not only becomes resistant to tamoxifen, but tamoxifen becomes an agonist which induces tumor proliferation.

A third line of treatment for breast cancer includes steroidal and non-steroidal aromatase inhibitors that block the production of estrogen and therefore block ER-dependent growth. These drugs, which include letrozole, anastrozole, and exemestane, have the risk of removing all estrogens from women after menopause, increasing the risk of bone thinning, osteoporosis, and fractures.

A number of SERDs, SERMs, and aromatase inhibitors have been disclosed. The SERM raloxifene was disclosed by Eli Lilly in 1981 (U.S. Pat. Nos. 4,418,068; 5,478,847; 5,393,763; and 5,457,117) for prevention of breast cancer and treatment of osteoporosis. In June 2011, Aragon Pharmaceuticals disclosed benzopyran derivatives and acolbifene analogs for treatment of tamoxifen-resistant breast cancer (see WO2011/156518, U.S. Pat. Nos. 8,455,534 and 8,299,112). Aragon became Seragon in 2013, and was purchased by Genentech in 2014. See also U.S. Pat. Nos. 9,078,871; 8,853,423; 8,703,810; US 2015/0005286; and WO 2014/205138. Genentech is now developing Brilanstrant (GDC-0810, formerly ARN-810) for the treatment of locally advanced or metastatic estrogenic receptor positive breast cancer.

Genentech disclosed a series of tetrahydro-pyrido[3,4-b] indol-1-yl compounds with estrogen receptor modulation activity in US2016/0175289 and a combination therapy of three compounds, one of which was GDN-0810, for estrogen receptor modulation in US2015/0258080.

AstraZeneca is currently developing AZD9496, a novel, oral selective estrogen receptor downregulator in patients with estrogen receptor positive breast cancer (WO 2014/191726).

Additional anti-estrogenic compounds are disclosed in WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497 and 5,880,137.

J-Pharma is currently developing benzothiophene compounds for the treatment of disorders related to urate transportation. See for example WO 2012/048058.

Bionomics LTD is developing benzofurans, benzothiophenes, benzoselenophenes, and indoles for treatment of tubulin polymerization related disorders. See for example WO 2007/087684.

US2017/166550, US2017/166551, WO2017/100712, and WO2017/100715, all assigned to the Board of Trustees of the University of Illinois and licensed to G1 Therapeutics, describe benzothiophene compounds that are used as SERDs.

Additional benzothiophene compounds are disclosed in WO 2010/127452, WO 2010/093578, WO 2009/013195, EP1947085, JP 2005-129430, US 2007/0112009, WO 2005/016929, EP0752421, EP0622673, EP0551849, EP0545478, U.S. Pat. No. 5,491,123, and WO 2006/084338.

Given the often-devastating effects of estrogen-modulated disorders, including cancer, tumors, and in particular breast cancer, there remains a strong need to create new drugs that have significant anti-estrogenic efficacy without unacceptable side effects.

SUMMARY OF THE INVENTION

Benzothiophene compounds and their pharmaceutically acceptable salts are provided that have advantageous selective estrogen receptor modulating activity, and in particular, anti-estrogenic activity. The compounds can be used for the treatment of a patient, typically a human, with an estrogen-related medical disorder, including but not limited to a cancer or a tumor by administering an effective amount to a patient in need thereof, optionally in a pharmaceutically acceptable carrier. In certain embodiments, the cancer is selected from breast, ovarian, endometrial, kidney, and uterine cancer. In another embodiment, the cancer is metastatic endocrine therapy resistant breast cancer. Alternatively, a compound or its pharmaceutically acceptable salt can be used to prevent an estrogen-mediated disorder, including but not limited to a cancer or a tumor, including breast, ovarian, endometrial, kidney, and uterine cancer. In some embodiments, the compound is used following traditional chemotherapy or radiation treatment to avoid recurrence, or instead of traditional chemotherapy or radiation as a primary treatment.

In one embodiment, the compound of the present invention is a selective mixed estrogen receptor downregulator (SMERD). In one embodiment, the compound antagonizes $E_2$ in breast cancer epithelial cells and causes significant degradation of ERα.

In one aspect, a compound of the present invention or its pharmaceutically acceptable salt or prodrug, can be used to treat a hormone-related cancer or tumor that has metastasized to the brain, bone, or other organ. In one embodiment of this aspect, the hormone-related cancer is estrogen mediated. In another embodiment, the estrogen mediated cancer is selected from breast, uterine, ovarian, and endometrial cancer. In other embodiments, a compound of the present invention or its pharmaceutically acceptable salt or prodrug, can be used to prevent a hormone-related cancer or tumor from metastasizing to the brain, bone, or other organ, including a hormone-related cancer that is estrogen mediated, for example, breast, uterine, ovarian, or endometrial cancer.

In one aspect, this invention is a compound of Formula (I), Formula (II), Formula (III), Formula (IV), Formula (V), Formula (VI), Formula (VII), or Formula (VIII), or a pharmaceutically acceptable salt or prodrug thereof. In another aspect, this invention includes a pharmaceutical composition that includes an effective amount of a compound of Formula (I), Formula (II), Formula (III), Formula (IV), Formula (V), Formula (VI), Formula (VII) or Formula (VIII), and a pharmaceutically acceptable carrier or excipient. In another aspect, this invention is a method to treat or prevent a tumor or cancer that includes administering to a subject, typically a human, in need of such treatment, a therapeutically effective amount of a compound of Formula (I), Formula (II), Formula (III), Formula (IV), Formula (V), Formula (VI), Formula (VII), or Formula (VIII), or a pharmaceutically acceptable salt thereof.

In an alternative aspect, this invention is a compound of Formula (IX), Formula (X), Formula (XI), Formula (XII), Formula (XIII), or Formula (XIV), or a pharmaceutically acceptable salt or prodrug thereof. In another alternative aspect, this invention includes a pharmaceutical composition that includes an effective amount of a compound of Formula (IX), Formula (X), Formula (XI), Formula (XII), Formula (XIII), or Formula (XIV), and a pharmaceutically acceptable carrier or excipient. In a further alternative aspect, this invention is a method to treat or prevent a tumor or cancer that includes administering to a subject, typically a human, in need of such treatment, a therapeutically effective amount of a compound of Formula (IX), Formula (X), Formula (XI), Formula (XII), Formula (XIII), or Formula (XIV), or a pharmaceutically acceptable salt thereof.

In one aspect, this invention is a compound of Formula (I), or a pharmaceutically acceptable salt or prodrug thereof:

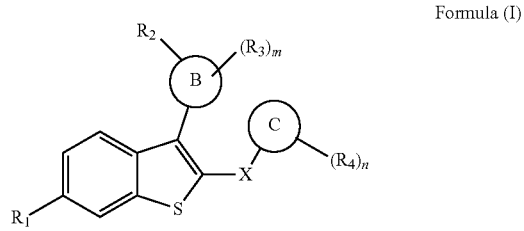

Formula (I)

wherein:
m is 0, 1, 2, 3, or 4;
n is 0, 1, 2, 3, or 4;
X is selected from —C(O)—, —O—, —CF$_2$—, C$_3$cycloalkyl, —CH$_2$—, —S—, —NH—, and —N(Me)-;
Ring B is phenyl, naphthyl, quinolinyl, 5- or 6-membered monocyclic heteroaryl, or 8-, 9-, or 10-membered bicyclic heterocyclyl;

Ring C is phenyl, thienyl, $C_3$-$C_6$cycloalkyl, 5- or 6-membered monocyclic heteroaryl or 8-, 9-, or 10-membered bicyclic heterocyclyl;

$R_1$ is selected from hydroxyl, hydrogen, halogen, —O($C_1$-$C_6$alkyl), —OC(O)($C_1$-$C_6$alkyl), —OC(O)$C_6H_5$, —OC(O)O($C_1$-$C_6$alkyl), —OC(O)O$C_6H_5$, and —OSO$_2$($C_2$-$C_6$alkyl);

$R_2$ is selected from —CH=CHCOOH, —OCH=CHCOOH, —NHC(O)COOH, —COOH, —$C_2$-$C_6$alkylene-COOH, and —$C_2$-$C_6$alkynylene-COOH; and $R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (I) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (I) or a pharmaceutically acceptable salt thereof.

In another aspect, this invention is a compound of Formula (II), or a pharmaceutically acceptable salt or prodrug thereof:

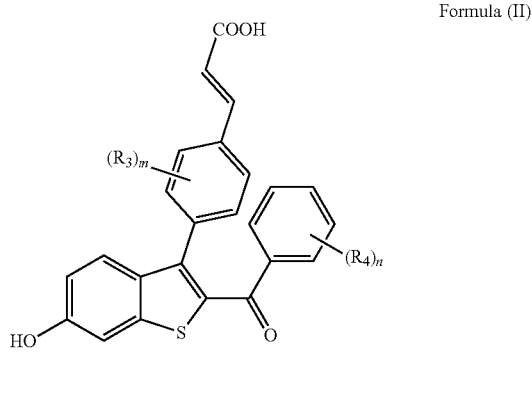

Formula (II)

wherein:
m is 0, 1, 2, 3, or 4;
n is 0, 1, 2, 3, or 4; and $R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (II) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (II) or a pharmaceutically acceptable salt thereof.

In another aspect, this invention is a compound of Formula (III), or a pharmaceutically acceptable salt or prodrug thereof:

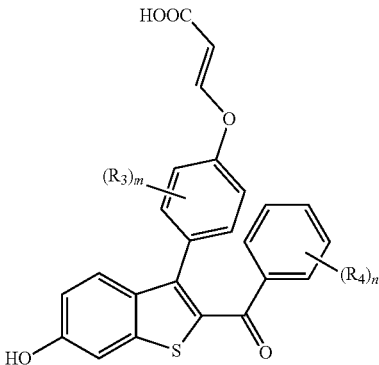

Formula (III)

wherein:
m is 0, 1, 2, 3, or 4;
n is 0, 1, 2, 3, or 4; and $R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (III) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (III) or a pharmaceutically acceptable salt thereof.

In another aspect, this invention is a compound of Formula (IV), or a pharmaceutically acceptable salt or prodrug thereof:

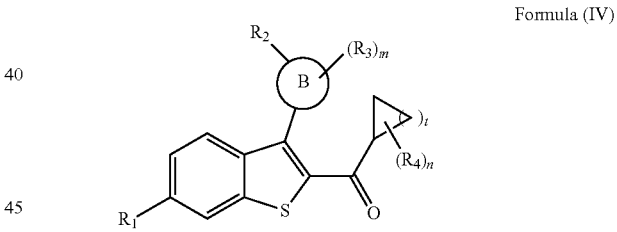

Formula (IV)

wherein:
m is 0, 1, 2, 3, or 4;
n is 0, 1, 2, 3, or 4;
t is 1, 2, 3, or 4;
Ring B is phenyl, naphthyl, quinolinyl, 5- or 6-membered monocyclic heteroaryl, or 8-, 9-, or 10-membered bicyclic heterocyclyl;

$R_1$ is selected from hydroxyl, hydrogen, halogen, —O($C_1$-$C_6$alkyl), —OC(O)($C_1$-$C_6$alkyl), —OC(O)$C_6H_5$, —OC(O)O($C_1$-$C_6$alkyl), —OC(O)O$C_6H_5$, and —OSO$_2$($C_2$-$C_6$alkyl);

$R_2$ is selected from —CH=CHCOOH, —OCH=CHCOOH, —NHC(O)COOH, —COOH, —$C_2$-$C_6$alkylene-COOH, and —$C_2$-$C_6$alkynylene-COOH; and $R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (IV) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (IV) or a pharmaceutically acceptable salt thereof.

In another aspect, this invention is a compound of Formula (V), or a pharmaceutically acceptable salt or prodrug thereof:

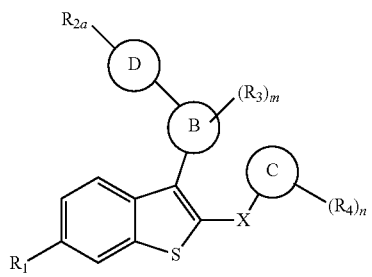

Formula (V)

wherein:

m is 0, 1, 2, 3, or 4;

n is 0, 1, 2, 3, or 4;

X is selected from —C(O)—, —O—, —CF$_2$—, C$_3$cycloalkyl, —CH$_2$—, —S—, —NH—, and —N(Me)-;

Ring B is phenyl, naphthyl, quinolinyl, 5- or 6-membered monocyclic heteroaryl, or 8-, 9-, or 10-membered bicyclic heterocyclyl;

Ring C is phenyl, thienyl, C$_3$-C$_6$cycloalkyl, 5- or 6-membered monocyclic heteroaryl, or 8-, 9-, or 10-membered bicyclic heterocyclyl;

Ring D is C$_3$-C$_6$cycloalkyl, phenyl, naphthyl, quinolinyl, 5- or 6-membered monocyclic heteroaryl, or 8-, 9-, or 10-membered bicyclic heterocyclyl;

R$_1$ is selected from hydroxyl, hydrogen, halogen, —O(C$_1$-C$_6$alkyl), —OC(O)(C$_1$-C$_6$alkyl), —OC(O)C$_6$H$_5$, —OC(O)O(C$_1$-C$_6$alkyl), —OC(O)OC$_6$H$_5$, and —OSO$_2$(C$_2$-C$_6$alkyl);

R$_{2a}$ is selected from —OH, —NH(CO)NHOH, —CH=CHCOOH, —NH(CO)COOH, —COOH, —NH$_2$, —C$_2$-C$_6$alkylene-COOH, and —C$_2$-C$_6$alkynylene-COOH; and R$_3$ and R$_4$ are independently selected at each occurrence from hydrogen, halogen, hydroxyl, —NO$_2$, C$_1$-C$_6$alkyl, C$_1$-C$_6$fluoroalkyl, —CN, —O(C$_1$-C$_6$alkyl), and —O(C$_1$-C$_6$fluoroalkyl).

In another aspect, this invention includes a pharmaceutical composition that includes a compound of Formula (V) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (V) or a pharmaceutically acceptable salt thereof.

In another aspect, this invention is a compound of Formula (VI), or a pharmaceutically acceptable salt or prodrug thereof:

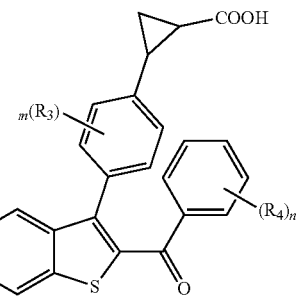

Formula (VI)

wherein:

m is 0, 1, 2, 3, or 4;

n is 0, 1, 2, 3, or 4; and

R$_3$ and R$_4$ are independently selected at each occurrence from hydrogen, halogen, hydroxyl, —NO$_2$, C$_1$-C$_6$alkyl, C$_1$-C$_6$fluoroalkyl, —CN, —O(C$_1$-C$_6$alkyl), and —O(C$_1$-C$_6$fluoroalkyl).

In another aspect, this invention includes a pharmaceutical composition that includes a compound of Formula (VI) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (VI) or a pharmaceutically acceptable salt thereof.

In another aspect, this invention is a compound of Formula (VII), or a pharmaceutically acceptable salt or prodrug thereof:

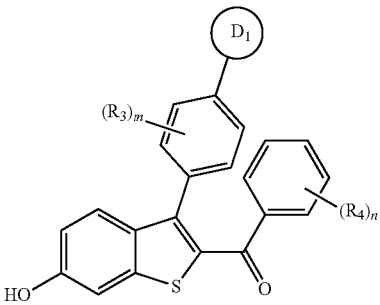

Formula (VII)

wherein:

m is 0, 1, 2, 3, or 4;

n is 0, 1, 2, 3, or 4;

Ring D$_1$ is selected from

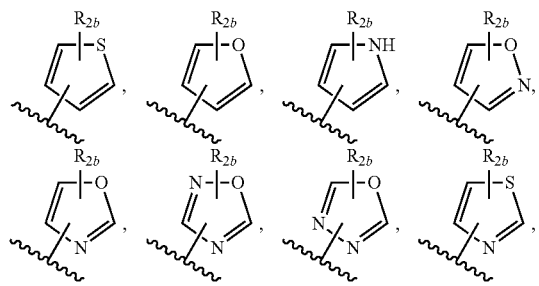

-continued

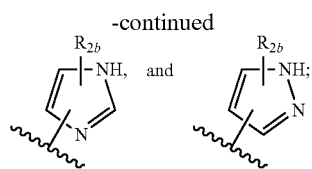

R$_{2b}$ is selected from —OH, —NH$_2$, and —COOH; and

R$_3$ and R$_4$ are independently selected at each occurrence from hydrogen, halogen, hydroxyl, —NO$_2$, C$_1$-C$_6$alkyl, C$_1$-C$_6$fluoroalkyl, —CN, —O(C$_1$-C$_6$alkyl), and —O(C$_1$-C$_6$fluoroalkyl).

In another aspect, this invention includes a pharmaceutical composition that includes a compound of Formula (VII) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (VII) or a pharmaceutically acceptable salt thereof.

In another aspect, this invention is a compound of Formula (VIII), or a pharmaceutically acceptable salt or prodrug thereof:

Formula (VIII)

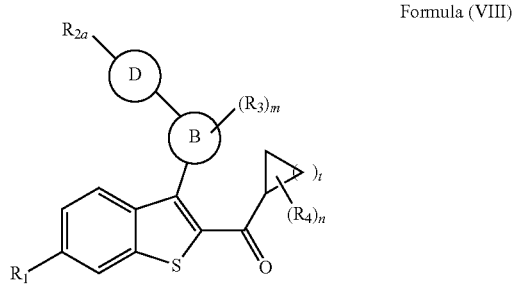

wherein:
m is 0, 1, 2, 3, or 4;
n is 0, 1, 2, 3, or 4;
t is 1, 2, 3, or 4;
Ring B is phenyl, naphthyl, quinolinyl, 5- or 6-membered monocyclic heteroaryl, or 8-, 9-, or 10-membered bicyclic heterocyclyl;
Ring D is C$_3$-C$_6$cycloalkyl, phenyl, naphthyl, quinolinyl, 5- or 6-membered monocyclic heteroaryl, or 8-, 9-, or 10-membered bicyclic heterocyclyl;
R$_1$ is selected from hydroxyl, hydrogen, halogen, —O(C$_1$-C$_6$alkyl), —OC(O)(C$_1$-C$_6$alkyl), —OC(O)C$_6$H$_5$, —OC(O)O(C$_1$-C$_6$alkyl), —OC(O)OC$_6$H$_5$, and —OSO$_2$(C$_2$-C$_6$alkyl);
R$_{2a}$ is selected from —OH, —NH(CO)NHOH, —CH=CHCOOH, —NH(CO)COOH, —COOH, —NH$_2$, —C$_2$-C$_6$alkylene-COOH, and —C$_2$-C$_6$alkynylene-COOH; and
R$_3$ and R$_4$ are independently selected at each occurrence from hydrogen, halogen, hydroxyl, —NO$_2$, C$_1$-C$_6$alkyl, C$_1$-C$_6$fluoroalkyl, —CN, —O(C$_1$-C$_6$alkyl), and —O(C$_1$-C$_6$fluoroalkyl).

In another aspect, this invention includes a pharmaceutical composition that includes a compound of Formula (VIII) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (VIII) or a pharmaceutically acceptable salt thereof.

In one aspect, this invention is a compound of Formula (IX), or a pharmaceutically acceptable salt or prodrug thereof:

Formula (IX)

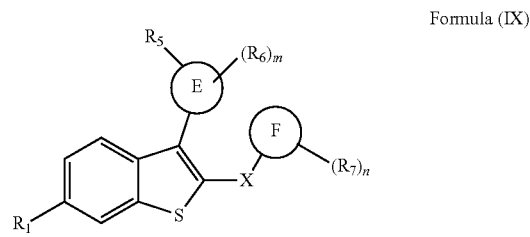

wherein:
m is 0, 1, 2, 3, or 4;
n is 0, 1, 2, 3, or 4;
X is selected from —C(O)—, —O—, —CF$_2$—, C$_3$cycloalkyl, —CH$_2$—, —S—, —NH—, and —N(Me)-;
Ring E is phenyl, naphthyl, quinolinyl, 5- or 6-membered monocyclic heteroaryl, or 8-, 9-, or 10-membered bicyclic heterocyclyl;
Ring F is phenyl, thienyl, 5- or 6-membered monocyclic heteroaryl or 8-, 9-, or 10-membered bicyclic heterocyclyl;
R$_1$ is selected from hydroxyl, hydrogen, halogen, —O(C$_1$-C$_6$alkyl), —OC(O)(C$_1$-C$_6$alkyl), —OC(O)C$_6$H$_5$, —OC(O)O(C$_1$-C$_6$alkyl), —OC(O)OC$_6$H$_5$, and —OSO$_2$(C$_2$-C$_6$alkyl);
R$_5$ is selected from —CH=CHCOOH, —OCH=CHCOOH, —NHC(O)COOH, —COOH, —C$_2$-C$_6$alkylene-COOH, and —C$_2$-C$_6$alkynylene-COOH;
R$_6$ is selected from halogen, —CN, —NO$_2$, C$_1$-C$_6$alkyl, and C$_1$-C$_6$fluoroalkyl; and
R$_7$ is selected from hydrogen, halogen, hydroxyl, C$_1$-C$_6$alkyl, C$_1$-C$_6$fluoroalkyl, —CN, —O(C$_1$-C$_6$alkyl), and —O(C$_1$-C$_6$fluoroalkyl).

In another aspect, this invention includes a pharmaceutical composition that includes a compound of Formula (IX) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (IX) or a pharmaceutically acceptable salt thereof.

In another aspect, this invention is a compound of Formula (X), or a pharmaceutically acceptable salt or prodrug thereof:

Formula (X)

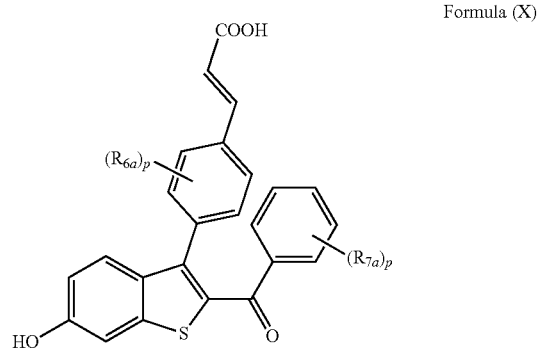

wherein:

p is 0, 1, 2, 3, or 4;

$R_{6a}$ is selected from hydrogen, halogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl); and $R_{7a}$ is selected from hydrogen, halogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (X) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (X) or a pharmaceutically acceptable salt thereof.

In another aspect, this invention is a compound of Formula (XI), or a pharmaceutically acceptable salt or prodrug thereof:

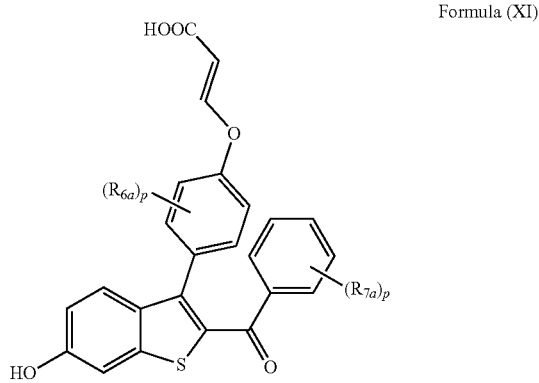

Formula (XI)

wherein:

p is 0, 1, 2, 3, or 4;

$R_{6a}$ is selected from hydrogen, halogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl); and $R_{7a}$ is selected from hydrogen, halogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (XI) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (XI) or a pharmaceutically acceptable salt thereof.

In another aspect, this invention is a compound of Formula (XII), or a pharmaceutically acceptable salt or prodrug thereof:

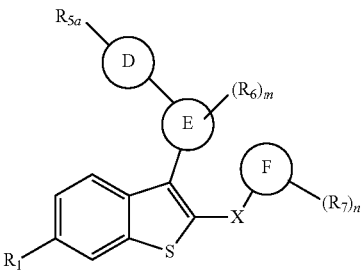

Formula (XII)

wherein:

m is 0, 1, 2, 3, or 4;

n is 0, 1, 2, 3, or 4;

X is selected from —C(O)—, —O—, —$CF_2$—, $C_3$cycloalkyl, —$CH_2$—, —S—, —NH—, and —N(Me)-;

Ring E is phenyl, naphthyl, quinolinyl, 5- or 6-membered monocyclic heteroaryl, or 8-, 9-, or 10-membered bicyclic heterocyclyl;

Ring F is phenyl, thienyl, 5- or 6-membered monocyclic heteroaryl, or 8-, 9-, or 10-membered bicyclic heterocyclyl;

Ring D is $C_3$-$C_6$cycloalkyl, phenyl, naphthyl, quinolinyl, 5- or 6-membered monocyclic heteroaryl, or 8-, 9-, or 10-membered bicyclic heterocyclyl;

$R_1$ is selected from hydroxyl, hydrogen, halogen, —O($C_1$-$C_6$alkyl), —OC(O)($C_1$-$C_6$alkyl), —OC(O)$C_6H_5$, —OC(O)O($C_1$-$C_6$alkyl), —OC(O)O$C_6H_5$, and —OSO$_2$($C_2$-$C_6$alkyl);

$R_{5a}$ is selected from —OH, —NH(CO)NHOH, —CH=CHCOOH, —NH(CO)COOH, —COOH, —$C_2$-$C_6$alkylene-COOH, and —$C_2$-$C_6$alkynylene-COOH;

$R_6$ is selected from halogen, —CN, —$NO_2$, $C_1$-$C_6$alkyl, and $C_1$-$C_6$fluoroalkyl; and $R_7$ is selected from hydrogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (XII) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (XII) or a pharmaceutically acceptable salt thereof.

In another aspect, this invention is a compound of Formula (XIII), or a pharmaceutically acceptable salt or prodrug thereof:

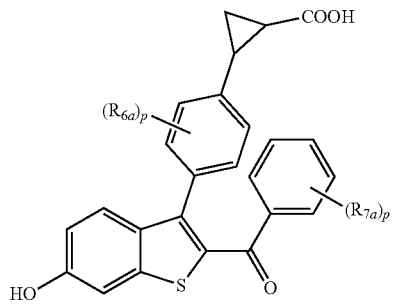

Formula (XIII)

wherein:

p is 0, 1, 2, 3, or 4;

$R_{6a}$ is selected from hydrogen, halogen, hydroxyl, $C_1$-$C_6$alkyl, $C_1$-$C_6$fluoroalkyl, —CN, —O($C_1$-$C_6$alkyl), and O($C_1$-$C_6$fluoroalkyl); and $R_{7a}$ is selected from hydrogen, halogen, hydroxyl, $C_1$-$C_6$alkyl, $C_1$-$C_6$fluoroalkyl, —CN, —O($C_1$-$C_6$alkyl), and O($C_1$-$C_6$fluoroalkyl).

In another aspect, this invention includes a pharmaceutical composition that includes a compound of Formula (XIII) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (XIII) or a pharmaceutically acceptable salt thereof.

In another aspect, this invention is a compound of Formula (XIV), or a pharmaceutically acceptable salt or prodrug thereof:

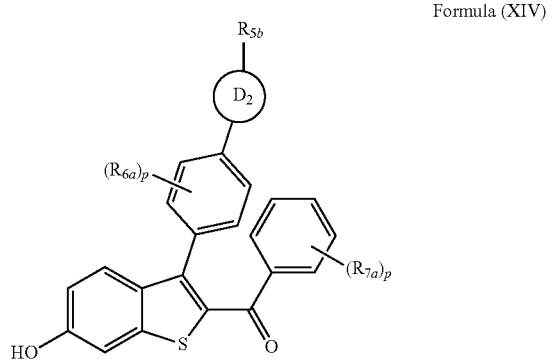

Formula (XIV)

wherein:

p is 0, 1, 2, 3, or 4;

Ring $D_2$ is selected from

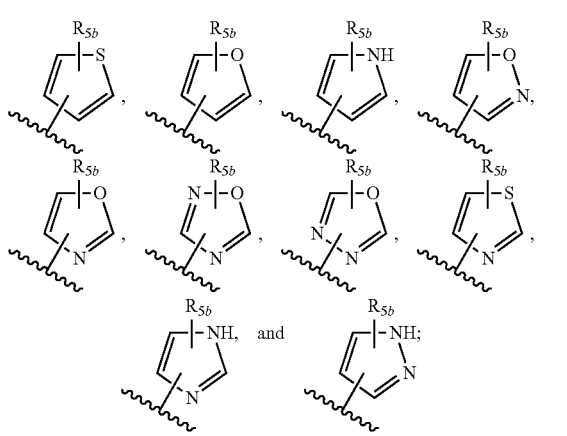

$R_{5b}$ is selected from —OH, —NH$_2$, and —COOH;

$R_{6a}$ is selected from hydrogen, halogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl); and $R_{7a}$ is selected from hydrogen, halogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl).

In another aspect, this invention includes a pharmaceutical composition that includes a compound of Formula (XIV) and a pharmaceutically acceptable carrier or excipient.

In another aspect, this invention is a method to treat or prevent a tumor or cancer that includes administering to a subject, typically a human, in need of such treatment, a therapeutically effective amount of a compound of Formula (XIV) or a pharmaceutically acceptable salt thereof.

In certain embodiments, the compound has the structure selected from the following, or is a pharmaceutically acceptable salt or prodrug thereof:

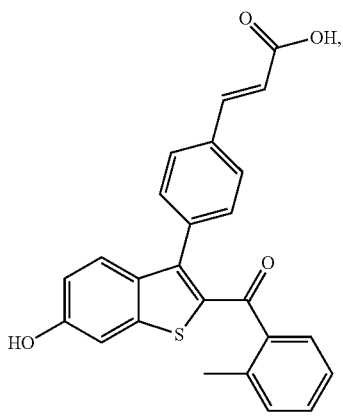

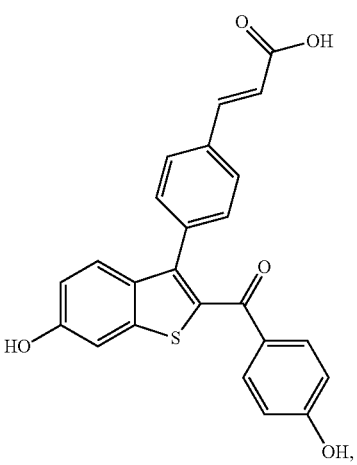

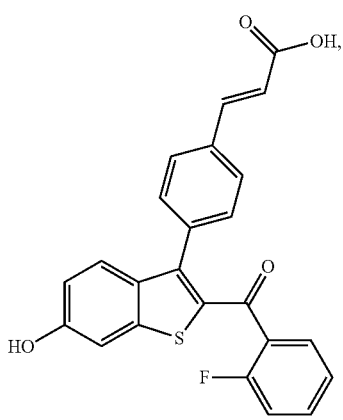

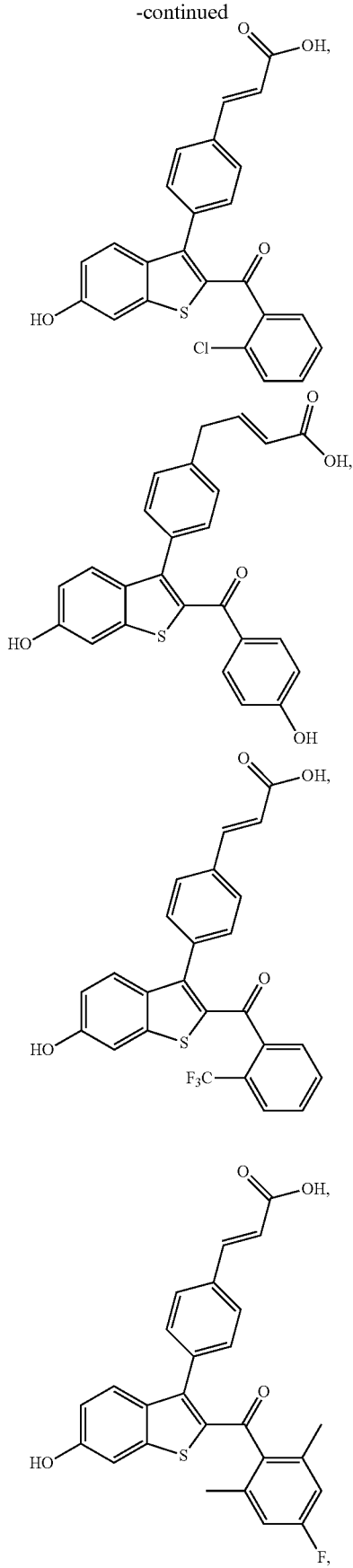
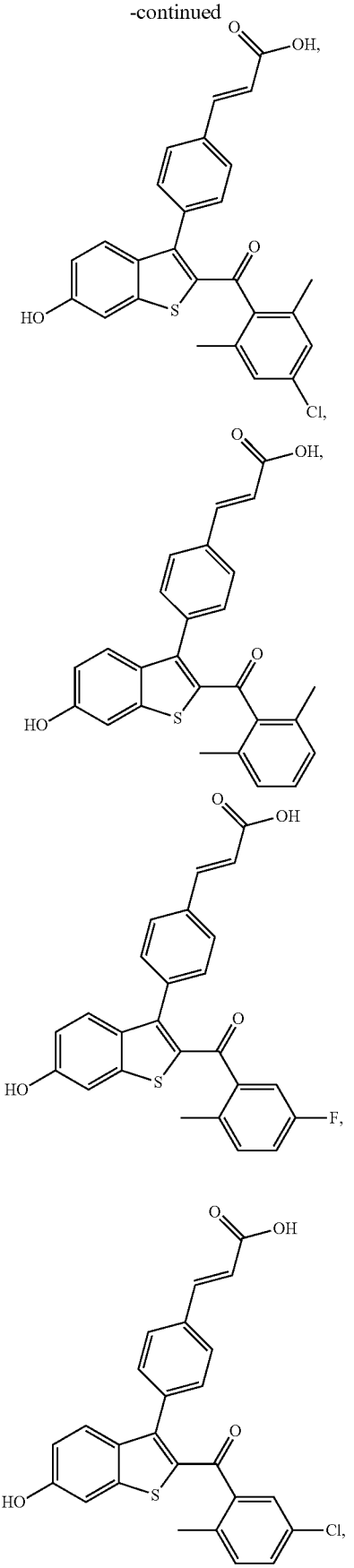

-continued

-continued
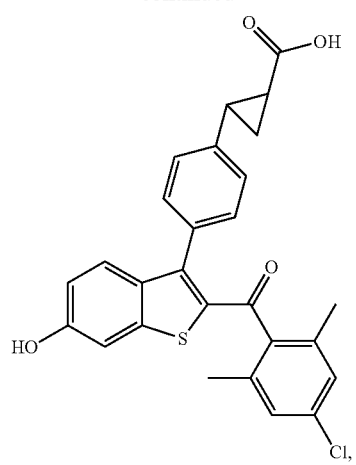
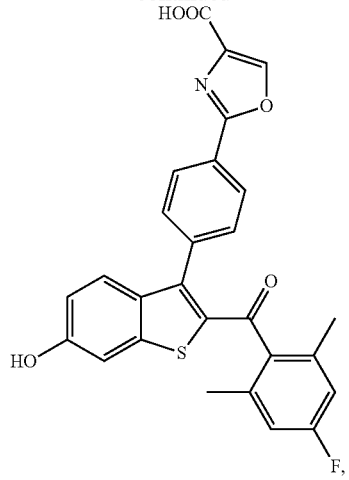
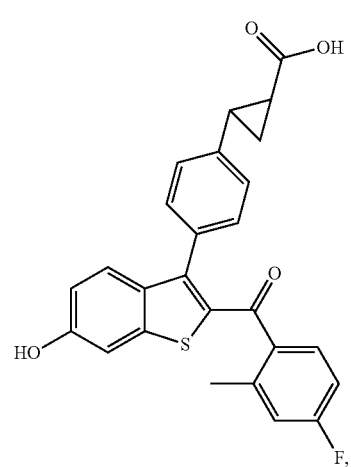
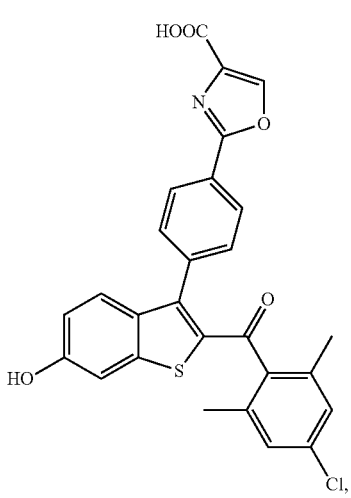
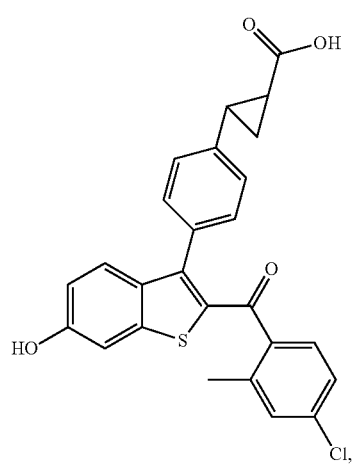
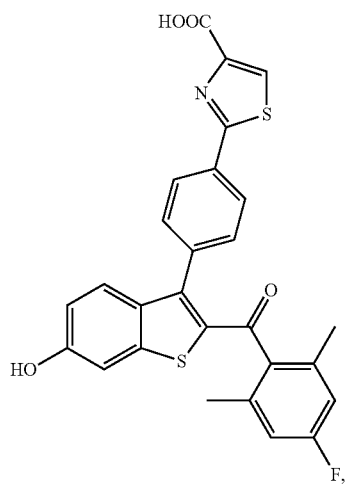

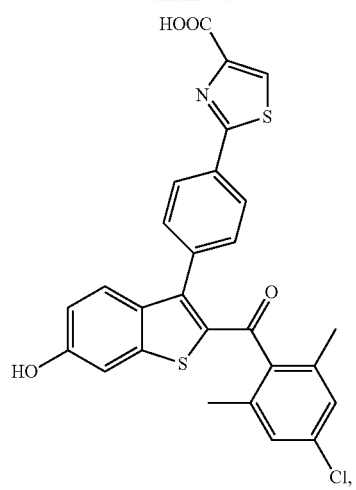
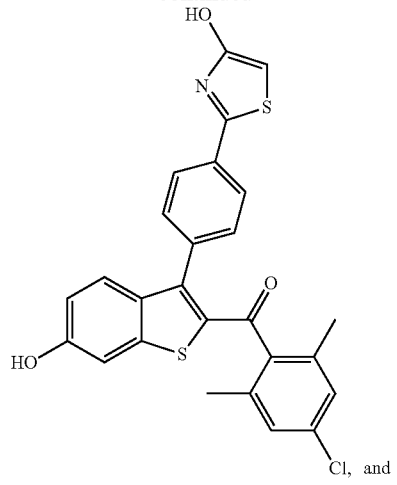
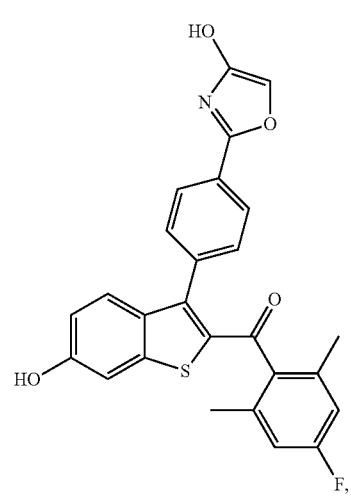
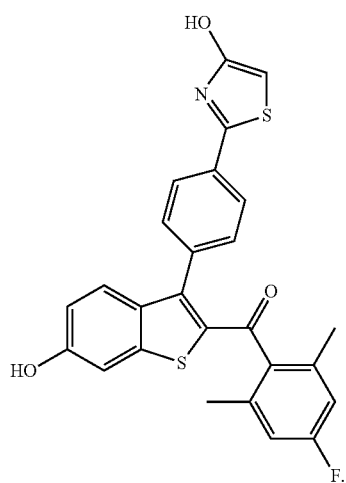
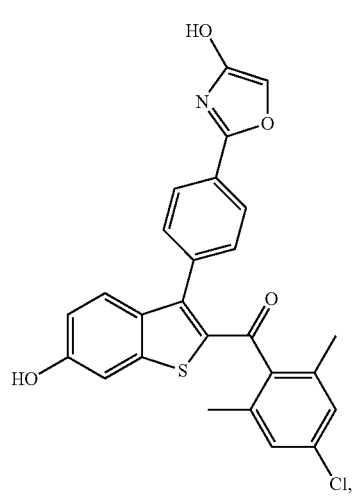
In alternative embodiments, the compound has the structure of the following, or is a pharmaceutically acceptable salt or prodrug thereof:
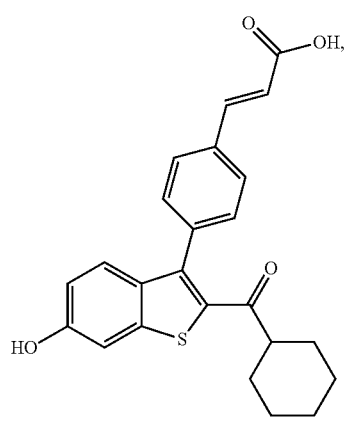

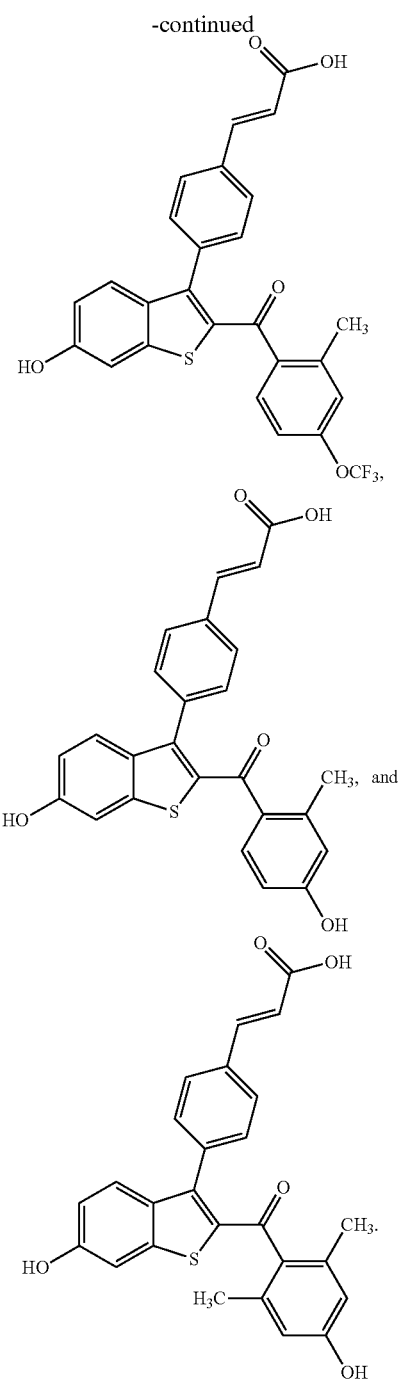

In certain embodiments of the above structures that have a —CO₂H, the compound can be presented, for example, as an ester, amide, or ether prodrug. The ester may be, for example, —CO₂R, wherein R is alkyl (including cycloalkyl), heteroalkyl, alkenyl, alkynyl, aryl, heteroaryl, heterocyclic, or any other moiety that is metabolized in vivo to provide the parent drug.

The present invention includes at least the following features:

(a) a compound as described herein or a pharmaceutically acceptable salt or prodrug thereof;

(b) a compound as described herein, or a pharmaceutically acceptable salt or prodrug thereof, that is useful in the treatment or prevention of an estrogen-related disorder, including without limitation a tumor or cancer;

(c) use of a compound as described herein, or a pharmaceutically acceptable salt or prodrug thereof, in the manufacture of a medicament for the treatment or prevention of an estrogen-related disorder, including but not limited to a tumor or cancer;

(d) a method for manufacturing a medicament for the therapeutic use to treat or prevent a disorder of abnormal cellular proliferation, including but not limited to a tumor or cancer, characterized in that a compound of the present invention or its salt or prodrug as described herein is used in the manufacture;

(e) a compound as described herein or its pharmaceutically acceptable salt or prodrug for use in the treatment or prevention of breast, kidney, uterine, ovarian, or endometrial cancer;

(f) use of a compound as described herein or a pharmaceutically acceptable salt or prodrug thereof in the manufacture of a medicament for the treatment or prevention of breast, kidney, uterine, ovarian, or endometrial cancer;

(g) a method for manufacturing a medicament for therapeutic use in treating or preventing breast, kidney, uterine, ovarian, or endometrial cancer, characterized in that a compound as described herein or its pharmaceutically acceptable salt or prodrug is used in the manufacture;

(h) a compound as described herein or a pharmaceutically acceptable salt or prodrug thereof for use in the treatment or prevention of hormone receptor positive metastatic breast cancer;

(i) use of a compound as described herein or a pharmaceutically acceptable salt or prodrug thereof in the manufacture of a medicament for the treatment or prevention of a hormone receptor positive metastatic breast cancer tumor;

(j) a method of manufacturing a medicament for treatment or prevention of a hormone receptor positive metastatic breast cancer, characterized in that a compound as described herein or its pharmaceutically acceptable salt or prodrug is used in the manufacture;

(k) a compound as described herein or a pharmaceutically acceptable salt or prodrug thereof for use to treat or prevent bone loss, including osteoporosis;

(l) use of a compound as described herein or a pharmaceutically acceptable salt or prodrug thereof in the manufacture of a medicament for the treatment or prevention of bone loss, including osteoporosis;

(m) a method for manufacturing a medicament for use to treat or prevent bone loss, including osteoporosis, characterized in that a compound as described herein is used in the manufacture;

(n) a pharmaceutical formulation comprising an effective treatment or prevention amount of a compound as described herein or a pharmaceutically acceptable salt or prodrug thereof together with a pharmaceutically acceptable carrier or diluent;

(o) a compound as described herein, or its pharmaceutically acceptable salt or prodrug as a mixture of enantiomers or diastereomers (as relevant), including as a racemate, or includes at least one atom that is isotopically enriched;

(p) a compound of the present invention as described herein in enantiomerically or diastereomerically (as relevant) enriched form, including as an isolated enantiomer or diastereomer (i.e., greater than 85, 90, 95, 97, or 99% pure); and, (q) a process for the preparation of a therapeutic product that contains an effective amount of a compound as described herein, or its pharmaceutically acceptable salt or prodrug.

DETAILED DESCRIPTION OF THE INVENTION

Definitions

Figure 1:
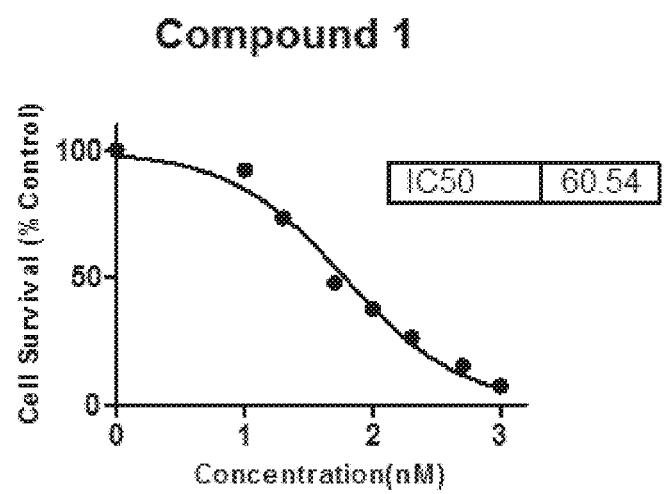
FIG. 1 is a graph of the efficacy of Compound 1 against tamoxifen-resistant MCF-7:5 cells normalized to 1 uM fulvestrant. The y-axis is cell survival as a percent of the control and the x-axis is the concentration of the compound measured in nanomolar units.

The following terms and expressions used herein have the indicated meanings.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$ alkyl indicate the same functionality; similarly, arylalkyl and -alkylaryl indicate the same functionality.

"Alkenyl" means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

"Alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

"Aryl" means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. In certain embodiments of the disclosure, the aryl group is phenyl or naphthyl. In certain other embodiments, the aryl group is phenyl.

"Cyano" and "nitrile" mean a —CN group.

"Halo" or "halogen" means —Cl, —Br, —I or —F. In certain embodiments, "halo" or "halogen" refers to —Cl or —F.

"Haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl. In certain embodiments, each "haloalkyl" is a fluoroalkyl, for example, a polyfluoroalkyl such as a substantially perfluorinated alkyl.

"Heteroaryl" means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. In certain embodiments of the disclosure, the heteroaryl group is furyl, imidazolyl, pyridinyl, pyrimidinyl, pyrazinyl, pyrazolyl, pyrrolyl, thiazolyl, thienyl, triazolyl, benzimidazolyl, benzofuranyl, indazolyl, indolyl, or quinolinyl.

"Heterocyclyl" means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl,1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. In certain embodiments of the disclosure, the heterocyclyl is pyrrolidinyl, piperidinyl, piperazinyl, or morpholinyl.

"Saturated" means the referenced chemical structure does not contain any multiple carbon-carbon bonds. For example, a saturated cycloalkyl group as defined herein includes cyclohexyl, cyclopropyl, and the like.

"Unsaturated" means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Pharmaceutically acceptable salt" refers to both acid and base addition salts.

"Modulating" or "modulate" refers to the treating, prevention, suppression, enhancement or induction of a function, condition or disorder.

"Treating" or "treatment" refer to the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, or slowing progression of one or more symptoms of the disease or disorder.

"Subject" refers to a warm-blooded animal such as a mammal, preferably a human, or a human child, which is afflicted with, or has the potential to be afflicted with one or more diseases and disorders described herein.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Nonlimiting examples of prodrugs include those with covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

In some embodiments, the compounds of the present invention may have at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^{2}H$, $^{3}H$, $^{11}C$, $^{13}C$, $^{14}C$, $^{15}N$, $^{18}F$ $^{31}P$, $^{32}I$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any of Formula (I), Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV). In one non-limiting embodiment, the substitution of a hydrogen atom for a deuterium atom occurs within a group selected from any of X, Ring B, Ring C, Ring D, Ring $D_1$, Ring $D_2$, Ring E, Ring F, $R_1$, $R_2$, $R_{2a}$, $R_{2b}$, $R_3$, $R_4$, $R_5$, $R_{5a}$, $R_{5b}$, $R_6$, $R_{6a}$, $R_7$, and $R_{7a}$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The materials, compounds, compositions, articles, and methods described herein may be understood more readily by reference to the following non-limiting detailed description of specific aspects of the disclosed subject matter and the Examples and Figures. It is to be understood that the aspects described below are not limited to specific embodiments which may, of course, vary, as known to those skilled in the art. It is also to be understood that the terminology used herein is for the purpose of describing particular aspects only and is not intended to be limiting.

Compounds

Benzothiophene based estrogen receptor ligands of the invention include compounds of Formula (I), Formula (II), Formula (III), Formula (IV), Formula (V), Formula (VI), Formula (VII), or Formula (VIII):

Formula (I)

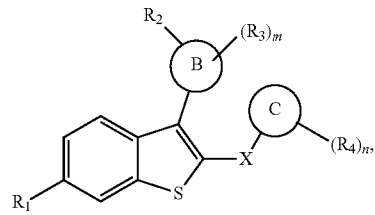

Formula (II)

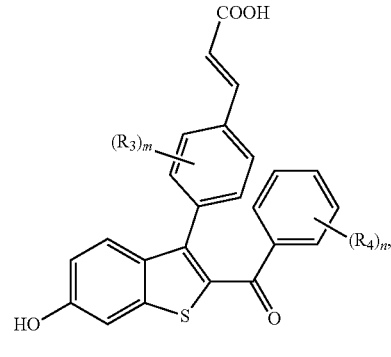

Formula (III)

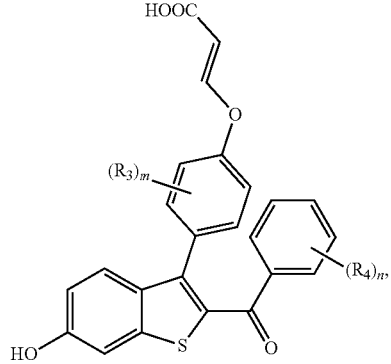

Formula (IV)

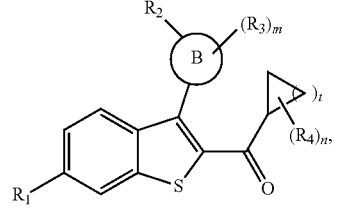

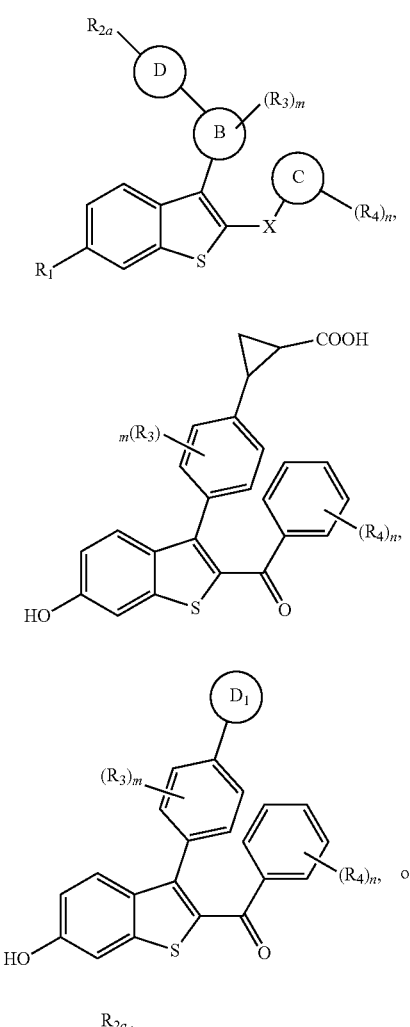

Formula (V)

Formula (VI)

Formula (VII)

Formula (VIII)

or a pharmaceutically acceptable salt or prodrug thereof; wherein:
m is 0, 1, 2, 3, or 4;
n is 0, 1, 2, 3, or 4;
t is 1, 2, 3, or 4;
X is selected from —C(O)—, —O—, —CF$_2$—, C$_3$cycloalkyl, —CH$_2$—, —S—, —NH—, and —N(Me)-;
Ring B is phenyl, naphthyl, quinolinyl, 5- or 6-membered monocyclic heteroaryl, or 8-, 9-, or 10-membered bicyclic heterocyclyl;
Ring C is phenyl, thienyl, C$_3$-C$_6$cycloalkyl, 5- or 6-membered monocyclic heteroaryl or 8-, 9-, or 10-membered bicyclic heterocyclyl;
Ring D is C$_3$-C$_6$cycloalkyl, phenyl, naphthyl, quinolinyl, 5- or 6-membered monocyclic heteroaryl, or 8-, 9-, or 10-membered bicyclic heterocyclyl;

Ring D$_1$ is selected from

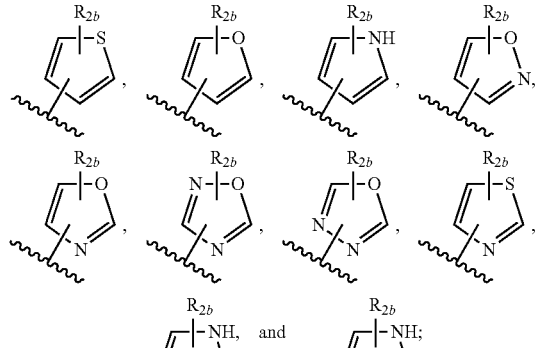

R$_1$ is selected from hydroxyl, hydrogen, halogen, —O(C$_1$-C$_6$alkyl), —OC(O)(C$_1$-C$_6$alkyl), —OC(O)C$_6$H$_5$, —OC(O)O(C$_1$-C$_6$alkyl), —OC(O)OC$_6$H$_5$, and —OSO$_2$(C$_2$-C$_6$alkyl);

R$_2$ is selected from —CH=CHCOOH, —OCH=CHCOOH, —NHC(O)COOH, —COOH, —C$_2$-C$_6$alkylene-COOH, and —C$_2$-C$_6$alkynylene-COOH;

R$_{2a}$ is selected from —OH, —NH(CO)NHOH, —CH=CHCOOH, —NH(CO)COOH, —COOH, —NH$_2$, —C$_2$-C$_6$alkylene-COOH, and —C$_2$-C$_6$alkynylene-COOH;

R$_{2b}$ is selected from —OH, —NH$_2$, and —COOH; and

R$_3$ and R$_4$ are independently selected at each occurrence from hydrogen, halogen, hydroxyl, —NO$_2$, C$_1$-C$_6$alkyl, C$_1$-C$_6$fluoroalkyl, —CN, —O(C$_1$-C$_6$alkyl), and —O(C$_1$-C$_6$fluoroalkyl).

In an alternative aspect, benzothiophene-based estrogen receptor ligands of the present invention include compounds of Formula (IX), Formula (X), Formula (XI), Formula (XII), Formula (XIII), or Formula (XIV):

Formula (IX)

Formula (X)

33

-continued

Formula (XI)

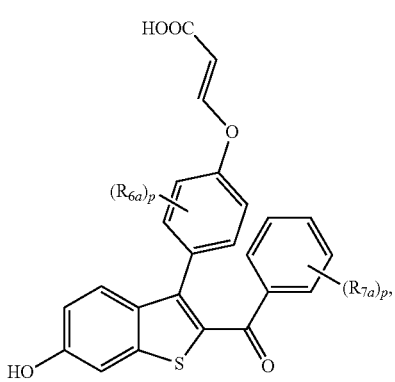

Formula (XII)

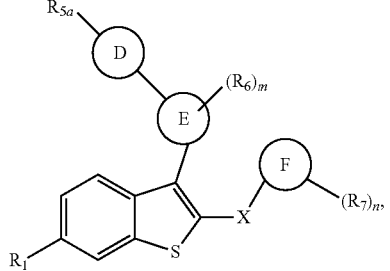

Formula (XIII)

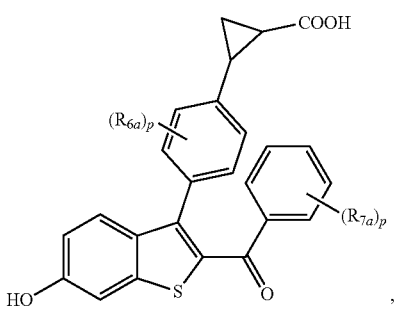

Formula (XIV)

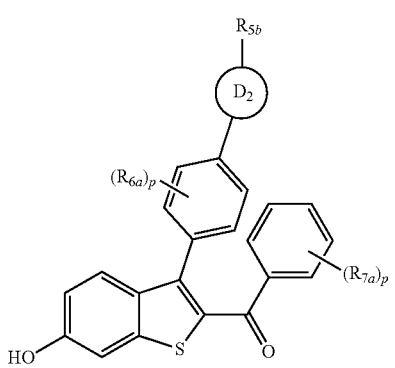

or a pharmaceutically acceptable salt or prodrug thereof; wherein:
X, $R_1$, D, m, and n are defined as above;
p is 0, 1, 2, 3, or 4;

Ring $D_2$ is selected from

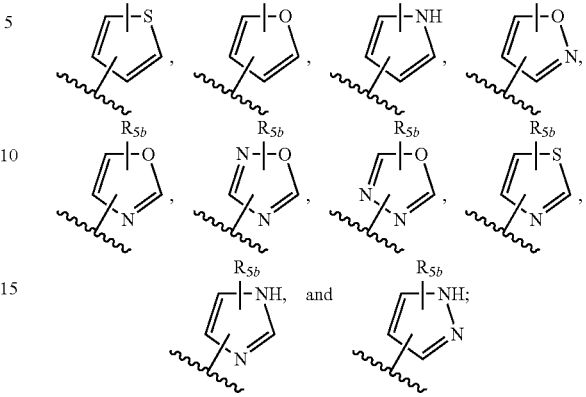

Ring E is phenyl, naphthyl, quinolinyl, 5- or 6-membered monocyclic heteroaryl, or 8-, 9-, or 10-membered bicyclic heterocyclyl;

Ring F is phenyl, thienyl, 5- or 6-membered monocyclic heteroaryl or 8-, 9-, or 10-membered bicyclic heterocyclyl;

$R_5$ is selected from —CH=CHCOOH, —OCH=CHCOOH, —NHC(O)COOH, —COOH, —$C_2$-$C_6$alkylene-COOH, and —$C_2$-$C_6$alkynylene-COOH;

$R_{2a}$ is selected from —OH, —NH(CO)NHOH, —CH=CHCOOH, —NH(CO)COOH, —COOH, —$C_2$-$C_6$alkylene-COOH, and —$C_2$-$C_6$alkynylene-COOH;

$R_{5b}$ is selected from —OH, —$NH_2$, and —COOH;

$R_6$ is selected from halogen, —CN, —$NO_2$, $C_1$-$C_6$alkyl, and $C_1$-$C_6$fluoroalkyl;

$R_{6a}$ is selected from hydrogen, halogen, hydroxyl, $C_1$-$C_6$alkyl, $C_1$-$C_6$fluoroalkyl, —CN, —O($C_1$-$C_6$alkyl), and O($C_1$-$C_6$fluoroalkyl);

$R_7$ is selected from hydrogen, hydroxyl, $C_1$-$C_6$alkyl, $C_1$-$C_6$fluoroalkyl, —CN, —O($C_1$-$C_6$alkyl), and —O($C_1$-$C_6$fluoroalkyl); and $R_{7a}$ is selected from hydrogen, halogen, hydroxyl, $C_1$-$C_6$alkyl, $C_1$-$C_6$fluoroalkyl, —CN, —O($C_1$-$C_6$alkyl), and O($C_1$-$C_6$fluoroalkyl).

In one embodiment, $R_1$ is hydroxyl. In one embodiment, $R_1$ is hydrogen. In one embodiment, $R_1$ is halogen. In an alternative embodiment, $R_1$ is fluoro. In an alternative embodiment, $R_1$ is chloro. In an alternative embodiment, $R_1$ is bromo. In one embodiment, $R_1$ is —O($C_1$-$C_6$alkyl). In an alternative embodiment, $R_1$ is methoxy. In one embodiment, $R_1$ is —OC(O)($C_1$-$C_6$alkyl). In an alternative embodiment, $R_1$ is $OC(O)CH_3$. In one embodiment, $R_1$ is —OC(O)$C_6H_5$. In one embodiment, $R_1$ is —OC(O)O($C_1$-$C_6$alkyl). In one embodiment, $R_1$ is —OC(O)O$C_6H_5$. In one embodiment, $R_1$ is —$OSO_2$($C_2$-$C_6$alkyl).

In one embodiment, $R_2$ is —CH=CHCOOH. In another embodiment, $R_2$ is —OCH=CHCOOH. In one embodiment, $R_2$ is —NHC(O)COOH. In one embodiment, $R_2$ is —COOH. In one embodiment, $R_2$ is —$C_2$-$C_6$alkylene-COOH. In one embodiment, $R_2$ is —$C_2$-$C_6$alkynylene-COOH.

In one embodiment, $R_{2a}$ is —OH. In one embodiment, $R_{2a}$ is —NHC(O)NHOH. In one embodiment, $R_{2a}$ is —CH=CHCOOH. In one embodiment, $R_{2a}$ is —NH(CO)COOH. In one embodiment, $R_{2a}$ is —COOH. In one embodiment, $R_{2a}$ is —$NH_2$. In one embodiment, $R_{2a}$ is —$C_2$-$C_6$alkylene-COOH. In one embodiment, $R_{2a}$ is —$C_2$-$C_6$alkynylene-COOH.

In one embodiment, $R_{2b}$ is —OH. In one embodiment, $R_{2b}$ is —NH$_2$. In another embodiment, $R_{2b}$ is —COOH.

In one embodiment, $R_3$ is hydrogen. In one embodiment, $R_3$ is halogen. In one embodiment, $R_3$ is fluoro. In one embodiment, $R_3$ is chloro. In one embodiment, $R_3$ is bromo. In one embodiment, $R_3$ is hydroxyl. In one embodiment, $R_3$ is —CN. In one embodiment, $R_3$ is —NO$_2$. In one embodiment, $R_3$ is —C$_1$-C$_6$alkyl. In one embodiment, $R_3$ is methyl. In one embodiment, $R_3$ is C$_1$-C$_6$fluoroalkyl. In one embodiment, $R_3$ is trifluoromethyl. In one embodiment, $R_3$ is —O(C$_1$-C$_6$alkyl). In one embodiment, $R_3$ is methoxy. In one embodiment, $R_3$ is —O(C$_1$-C$_6$fluoroalkyl). In one embodiment, $R_3$ is trifluoromethoxy.

In one embodiment, $R_4$ is hydrogen. In another embodiment, $R_4$ is halogen. In one embodiment, $R_4$ is fluoro. In one embodiment, $R_4$ is chloro. In one embodiment, $R_4$ is bromo. In a further embodiment, $R_4$ is hydroxyl. In one embodiment, $R_4$ is —NO$_2$. In one embodiment, $R_4$ is C$_1$-C$_6$alkyl. In one embodiment, $R_4$ is methyl. In another embodiment, $R_4$ is C$_1$-C$_6$fluoroalkyl. In one embodiment, $R_4$ is trifluoromethyl. In one embodiment, $R_4$ is —CN. In one embodiment, $R_4$ is —O(C$_1$-C$_6$alkyl). In one embodiment, $R_4$ is methoxy. In one embodiment, $R_4$ is —O(C$_1$-C$_6$fluoroalkyl). In one embodiment, $R_4$ is trifluoromethoxy.

In one embodiment, $R_5$ is —CH=CHCOOH. In one embodiment, $R_5$ is —OCH=CHCOOH. In one embodiment, $R_5$ is —NHC(O)COOH. In one embodiment, $R_5$ is —COOH. In one embodiment, $R_5$ is —C$_2$-C$_6$alkylene-COOH. In one embodiment, $R_5$ is C$_2$-C$_6$alkynylene-COOH.

In one embodiment, $R_{5a}$ is —OH. In one embodiment, $R_{5a}$ is —NH(CO)NHOH. In one embodiment, $R_{5a}$ is —CH=CHCOOH. In one embodiment, $R_{5a}$ is —NH(CO)COOH. In one embodiment, $R_{5a}$ is —COOH. In one embodiment, $R_{5a}$ is —C$_2$-C$_6$alkylene-COOH. In one embodiment, $R_{5a}$ is —C$_2$-C$_6$alkynylene-COOH.

In one embodiment, $R_{5b}$ is —OH. In one embodiment, $R_{5b}$ is —NH$_2$. In one embodiment, $R_{5b}$ is —COOH.

In one embodiment, $R_6$ is halogen. In an alternative embodiment, $R_6$ is fluoro. In an alternative embodiment, $R_6$ is chloro. In an alternative embodiment, $R_6$ is bromo. In one embodiment, $R_6$ is —CN. In one embodiment, $R_6$ is —NO$_2$. In one embodiment, $R_6$ is C$_1$-C$_6$alkyl. In an alternative embodiment, $R_6$ is methyl. In one embodiment, $R_6$ is C$_1$-C$_6$fluoroalkyl. In an alternative embodiment, $R_6$ is trifluoromethyl.

In one embodiment, $R_{6a}$ is hydrogen. In one embodiment, $R_{6a}$ is halogen. In an alternative embodiment, $R_{6a}$ is fluoro. In an alternative embodiment, $R_{6a}$ is chloro. In an alternative embodiment, $R_{6a}$ is bromo. In one embodiment, $R_{6a}$ is hydroxyl. In one embodiment, $R_{6a}$ is C$_1$-C$_6$alkyl. In an alternative embodiment, $R_{6a}$ is methyl. In one embodiment, $R_{6a}$ is C$_1$-C$_6$fluoroalkyl. In an alternative embodiment, $R_{6a}$ is trifluoromethyl. In one embodiment, $R_{6a}$ is —CN. In one embodiment, $R_{6a}$ is —O(C$_1$-C$_6$alkyl). In an alternative embodiment, $R_{6a}$ is methoxy. In one embodiment, $R_{6a}$ is —O(C$_1$-C$_6$fluoroalkyl). In an alternative embodiment, $R_{6a}$ is trifluoromethoxy.

In one embodiment, $R_7$ is hydrogen. In one embodiment, $R_7$ is halogen. In an alternative embodiment, $R_7$ is fluoro. In an alternative embodiment, $R_7$ is chloro. In an alternative embodiment, $R_7$ is bromo. In one embodiment, $R_7$ is hydroxyl. In one embodiment, $R_7$ is C$_1$-C$_6$alkyl. In an alternative embodiment, $R_7$ is methyl. In one embodiment, $R_7$ is C$_1$-C$_6$fluoroalkyl. In an alternative embodiment, $R_7$ is trifluoromethyl. In one embodiment, $R_7$ is —CN. In one embodiment, $R_7$ is —O(C$_1$-C$_6$alkyl). In an alternative embodiment, $R_7$ is methoxy. In one embodiment, $R_7$ is —O(C$_1$-C$_6$fluoroalkyl). In an alternative embodiment, $R_7$ is trifluoromethoxy.

In one embodiment, $R_{7a}$ is hydrogen. In one embodiment, $R_{7a}$ is halogen. In an alternative embodiment, $R_{7a}$ is fluoro. In an alternative embodiment, $R_{7a}$ is chloro. In an alternative embodiment, $R_{7a}$ is bromo. In one embodiment, $R_{7a}$ is hydroxyl. In one embodiment, $R_{7a}$ is C$_1$-C$_6$alkyl. In an alternative embodiment, $R_{7a}$ is methyl. In one embodiment, $R_{7a}$ is C$_1$-C$_6$fluoroalkyl. In an alternative embodiment, $R_{7a}$ is trifluoromethyl. In one embodiment, $R_{7a}$ is —CN. In one embodiment, $R_{7a}$ is —O(C$_1$-C$_6$alkyl). In an alternative embodiment, $R_{7a}$ is methoxy. In one embodiment, $R_{7a}$ is —O(C$_1$-C$_6$fluoroalkyl). In an alternative embodiment, $R_{7a}$ is trifluoromethoxy.

In one embodiment of the invention, X is —C(O)—. In one embodiment, X is —O—. In one embodiment, X is —CF$_2$—. In one embodiment, X is C$_3$cycloalkyl. In one embodiment, X is —CH$_2$—. In one embodiment, X is —NH—. In one embodiment, X is —N(Me)-.

In one embodiment, Ring B is phenyl. In one embodiment, Ring B is naphthyl. In one embodiment, Ring B is quinolinyl.

In one embodiment, Ring C is phenyl. In one embodiment, Ring C is thienyl. In one embodiment, Ring C is C$_3$-C$_6$cycloalkyl. In one embodiment, Ring C is cyclohexyl.

In one embodiment, Ring D is C$_3$-C$_6$cycloalkyl. In one embodiment, Ring D is phenyl. In one embodiment, Ring D is naphthyl. In one embodiment, Ring D is quinolinyl.

In one embodiment, Ring $D_1$ is

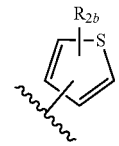

In one embodiment, Ring $D_1$ is

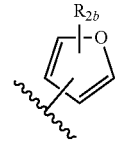

In one embodiment, Ring $D_1$ is

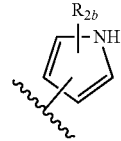

In one embodiment, Ring $D_1$ is

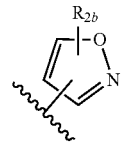

In one embodiment, Ring D₁ is

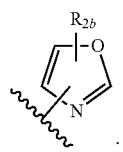

In one embodiment, Ring D₁ is

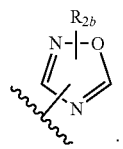

In one embodiment, Ring D₁ is

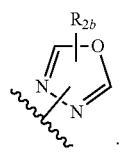

In another embodiment, Ring D₁ is

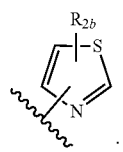

In one embodiment, Ring D₁ is

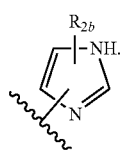

In one embodiment, Ring D₁ is

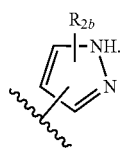

In one embodiment, Ring D₂ is

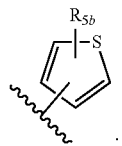

In one embodiment, Ring D₂ is

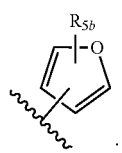

In one embodiment, Ring D₂ is

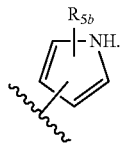

In one embodiment, Ring D₂ is

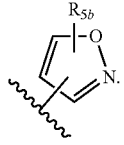

In one embodiment, Ring D₂ is

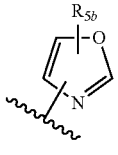

In one embodiment, Ring D₂ is

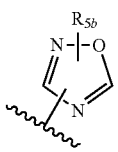

In one embodiment, Ring D₂ is

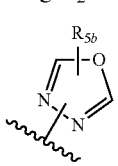

In one embodiment, Ring $D_2$ is

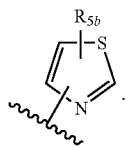

In one embodiment, Ring $D_2$ is

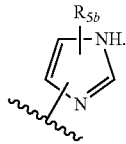

In one embodiment, Ring $D_2$ is

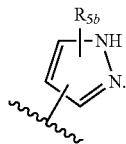

In one embodiment, Ring E is phenyl. In one embodiment, Ring E is naphthyl. In one embodiment, Ring E is quinolinyl.

In one embodiment, Ring F is phenyl. In one embodiment, Ring F is thienyl.

In one embodiment, m is 0. In one embodiment, m is 1. In one embodiment, m is 2. In one embodiment, m is 3. In one embodiment, m is 4.

In one embodiment, n is 0. In one embodiment, n is 1. In one embodiment, n is 2. In one embodiment, n is 3. In one embodiment, n is 4.

In one embodiment, m is 0 and n is 0.
In one embodiment, m is 0 and n is 1.
In one embodiment, m is 0 and n is 2.
In one embodiment, m is 0 and n is 3.
In one embodiment, m is 0 and n is 4.
In one embodiment, m is 1 and n is 0.
In one embodiment, m is 1 and n is 1.
In one embodiment, m is 1 and n is 2.
In one embodiment, m is 1 and n is 3.
In one embodiment, m is 1 and n is 4.
In one embodiment, m is 2 and n is 0.
In one embodiment, m is 2 and n is 1.
In one embodiment, m is 2 and n is 2.
In one embodiment, m is 2 and n is 3.
In one embodiment, m is 2 and n is 4.
In one embodiment, m is 3 and n is 0.
In one embodiment, m is 3 and n is 1.
In one embodiment, m is 3 and n is 2.
In one embodiment, m is 3 and n is 3.
In one embodiment, m is 3 and n is 4.
In one embodiment, m is 4 and n is 0.
In one embodiment, m is 4 and n is 1.
In one embodiment, m is 4 and n is 2.
In one embodiment, m is 4 and n is 3.
In one embodiment, m is 4 and n is 4.

In one embodiment, p is 0. In one embodiment, p is 1. In one embodiment, p is 2. In one embodiment, p is 3. In one embodiment, p is 4.

In one embodiment, t is 1. In one embodiment, t is 2. In one embodiment, t is 3. In one embodiment, t is 4.

In one embodiment,

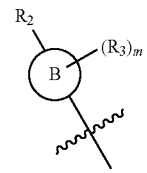

is selected from:

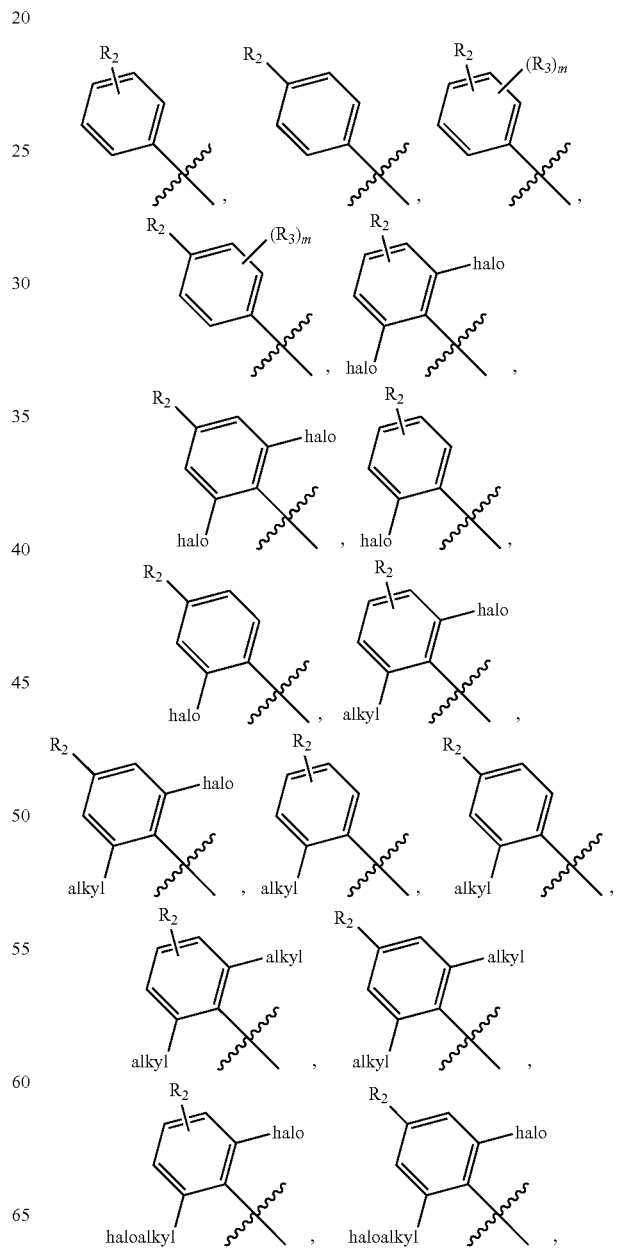

-continued

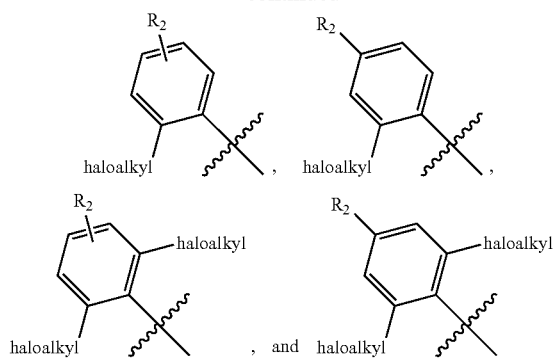

In one embodiment of the above B-ring embodiments, alkyl is methyl. In another embodiment of the above B-ring embodiments, alkyl is independently, methyl, ethyl, propyl, or cyclopropyl. In one embodiment of the above B-ring embodiments, halo is fluoro. In another embodiment of the above B-rings, halo is independently fluoro or chloro, including wherein one halo is fluoro and the other is chloro. In one embodiment of the above B-ring embodiments, haloalkyl is independently mono-, di- or trifluoromethyl.

In another embodiment,

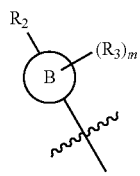

is selected from:

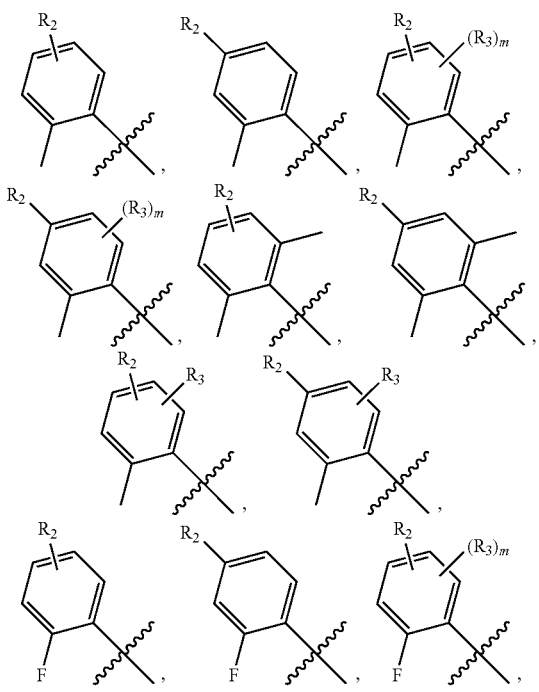

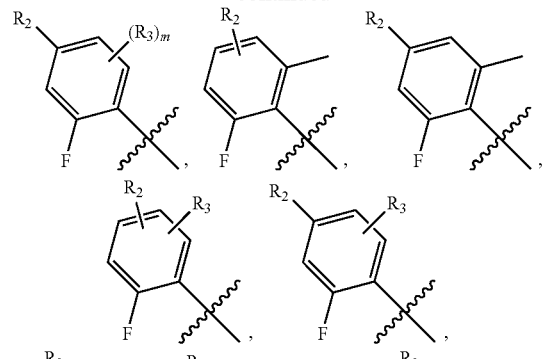

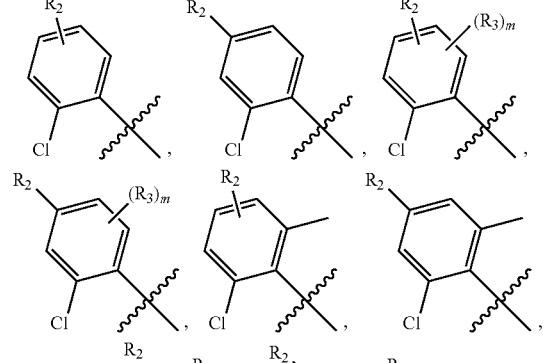

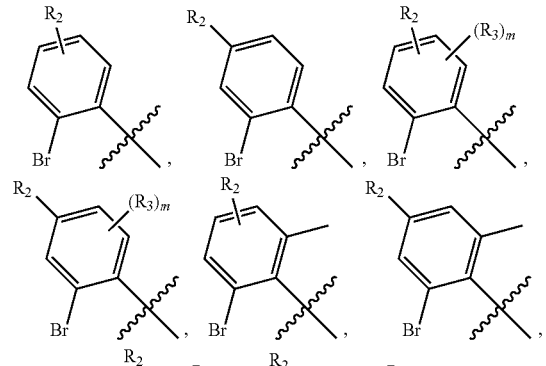

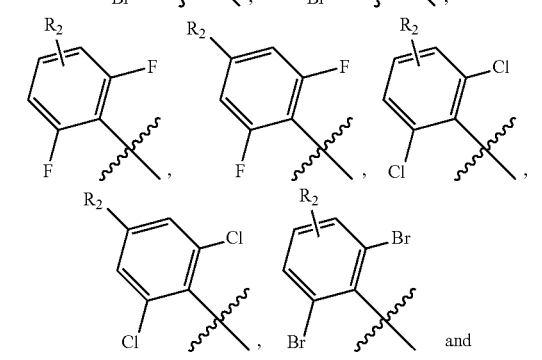

-continued

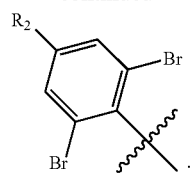

In one embodiment,

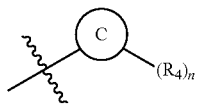

is selected from:

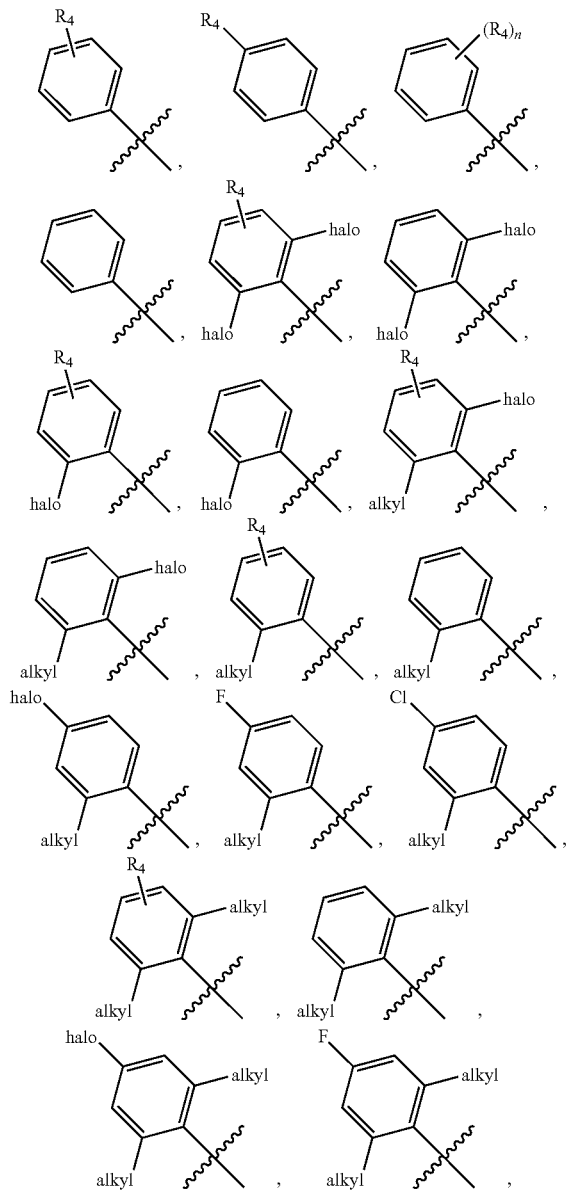

-continued

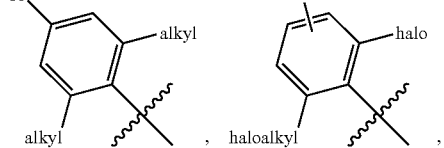

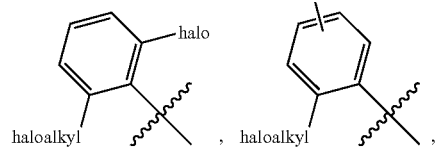

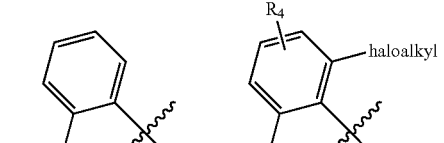

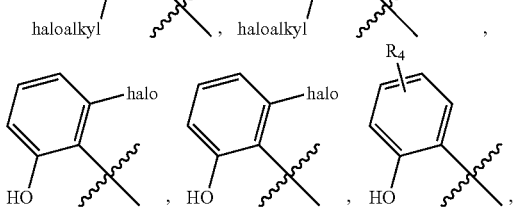

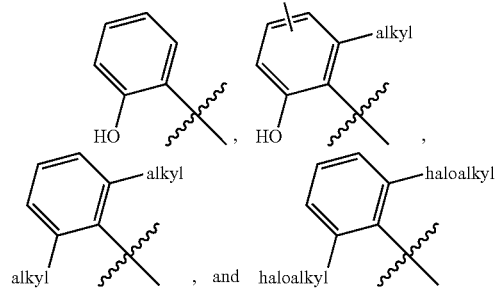

In one embodiment of the above C-ring embodiments, alkyl is methyl. In another embodiment of the above C-ring embodiments, alkyl is independently, methyl, ethyl, propyl, or cyclopropyl. In one embodiment of the above C-ring embodiments, halo is fluoro. In another embodiment of the above C-rings, halo is independently fluoro or chloro, including wherein one halo is fluoro and the other is chloro. In one embodiment of the above B-ring embodiments, haloalkyl is independently mono-, di- or trifluoromethyl.

In another embodiment,

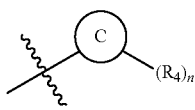

is selected from:

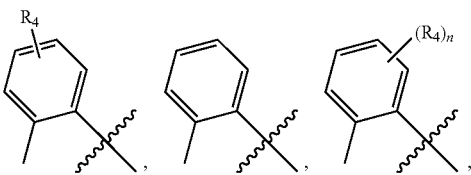

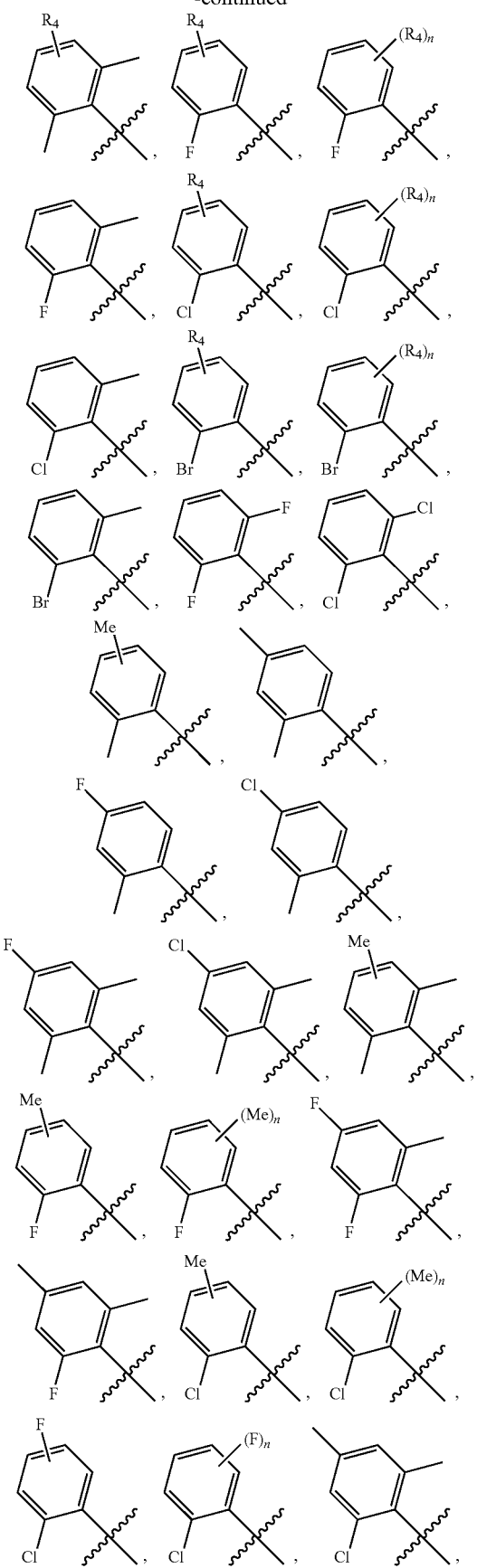

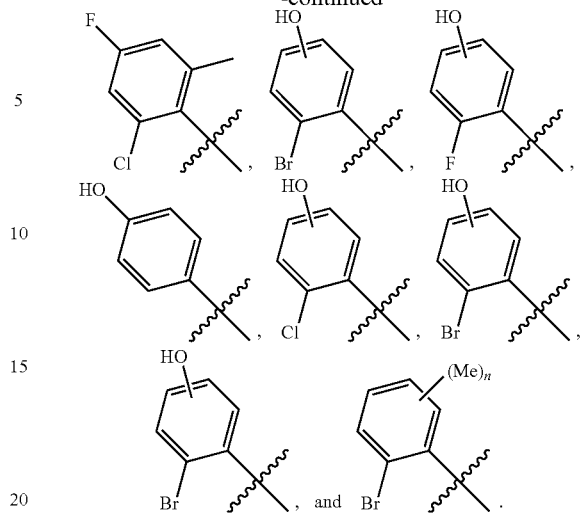

In one embodiment of the above C-ring embodiments, $R_4$ is hydrogen. In another embodiment, $R_4$ is —$C_1$-$C_6$alkyl, such as methyl, ethyl, or propyl. In yet another embodiment, $R_4$ is —$C_1$-$C_6$fluoroalkyl, including trifluoromethyl, difluoromethyl, fluoromethyl, fluoroethyl, and difluoroethyl. In other embodiments, $R_4$ is selected from —CN, —O($C_1$-$C_6$alkyl), and —O($C_1$-$C_6$fluoroalkyl).

In one embodiment,

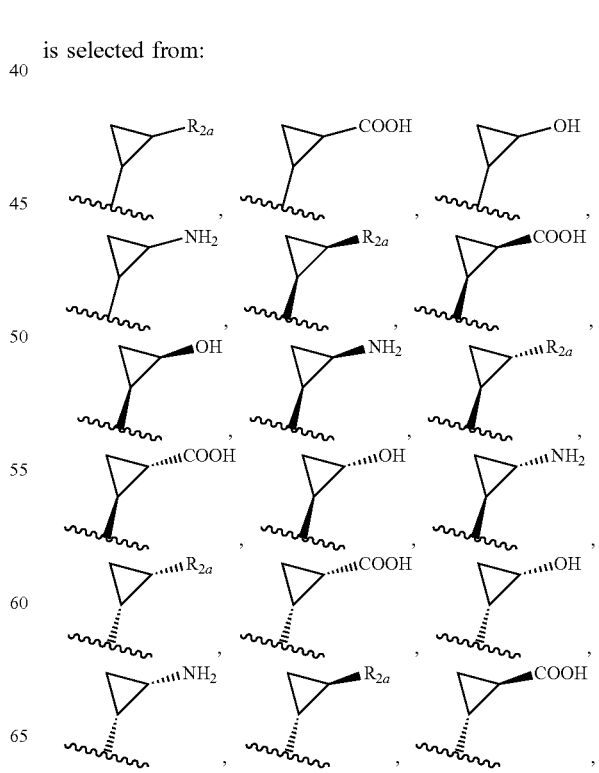

is selected from:

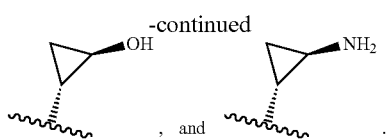
In another embodiment,
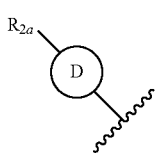
is selected from:
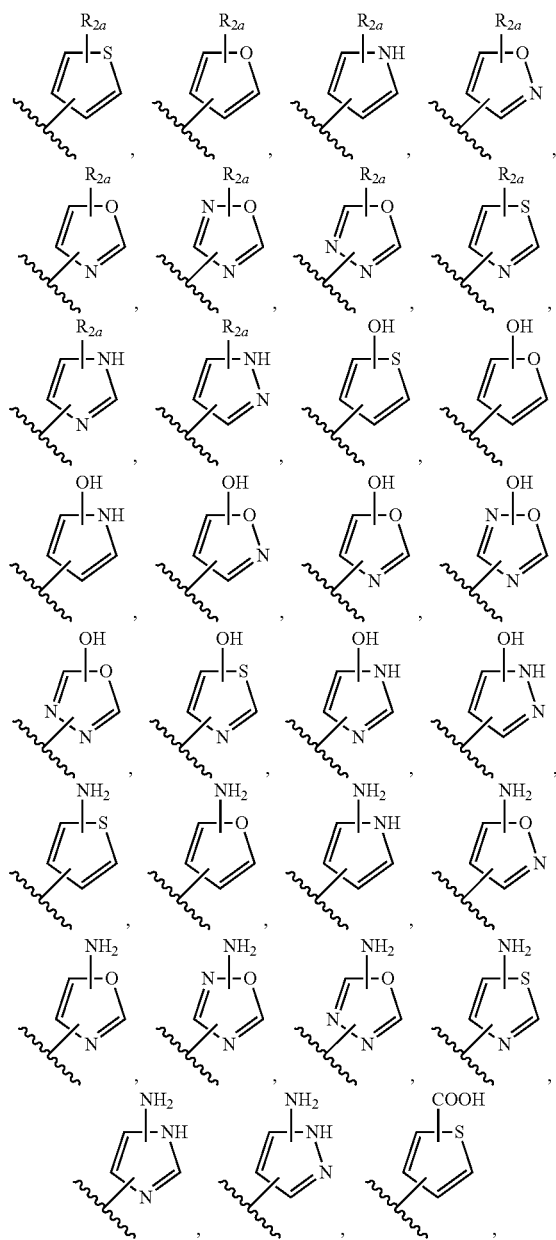
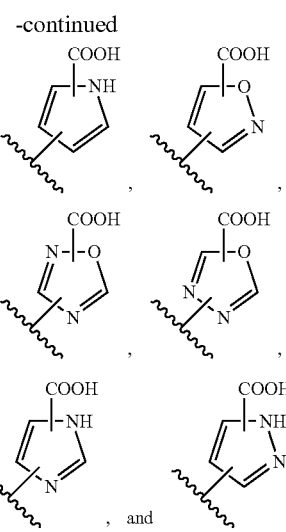
In one embodiment,
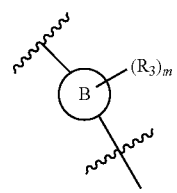
is selected from:
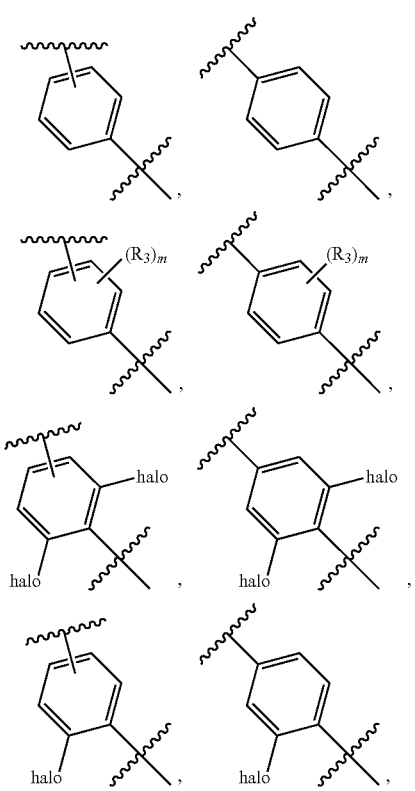

-continued

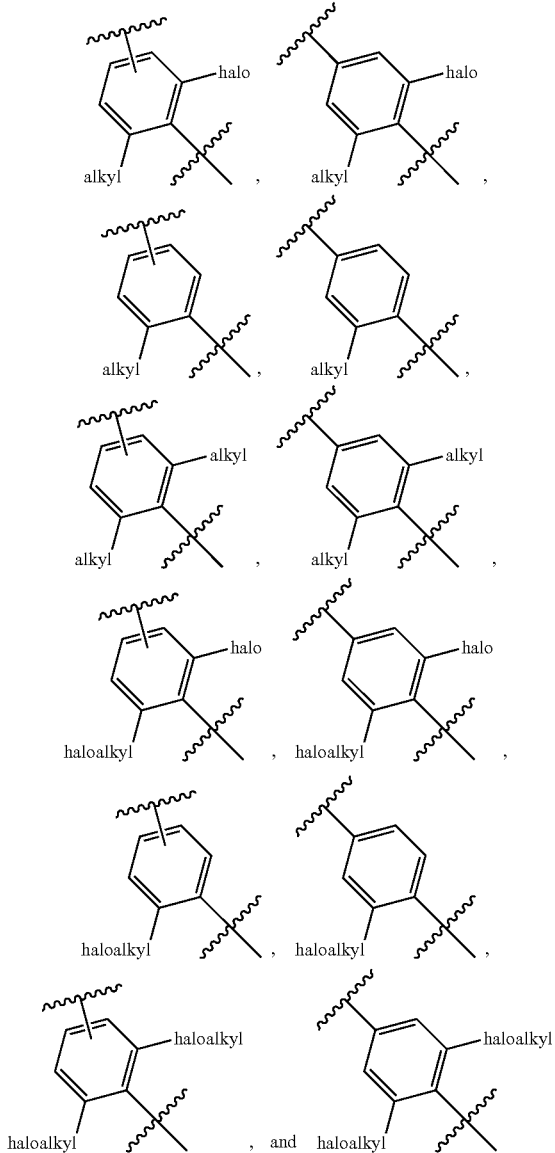

In one embodiment of the above B-ring embodiments, alkyl is methyl. In another embodiment of the above B-ring embodiments, alkyl is independently, methyl, ethyl, propyl, or cyclopropyl. In one embodiment of the above B-ring embodiments, halo is fluoro. In another embodiment of the above B-rings, halo is independently fluoro or chloro, including wherein one halo is fluoro and the other is chloro. In one embodiment of the above B-ring embodiments, haloalkyl is independently mono-, di- or trifluoromethyl.

In another embodiment,

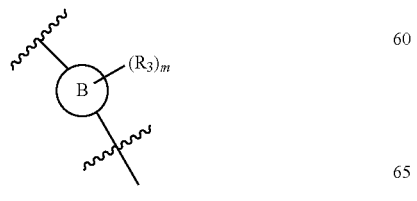

is selected from:

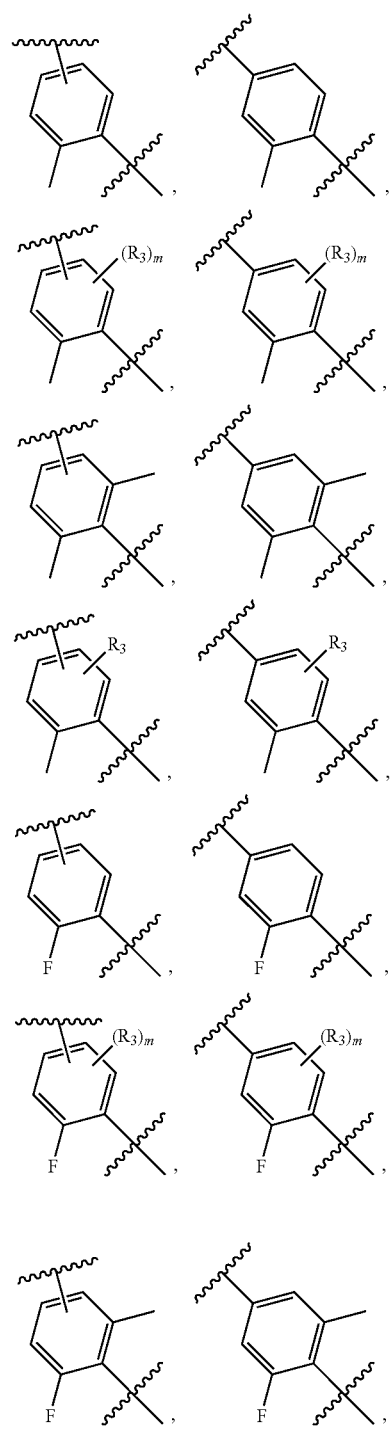

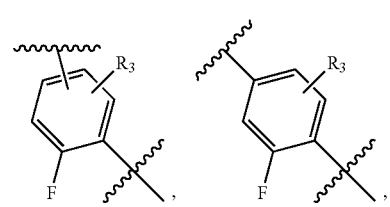

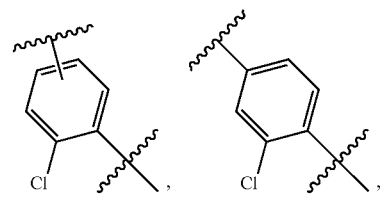
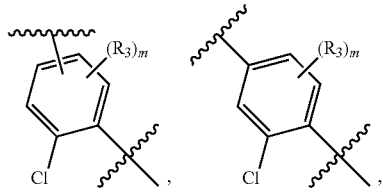
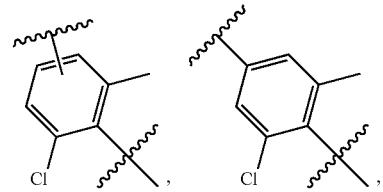
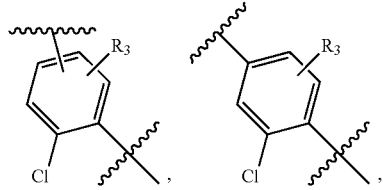
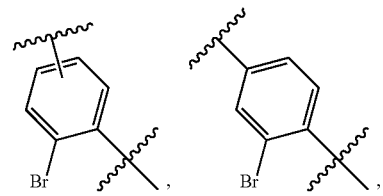
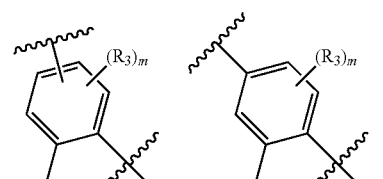
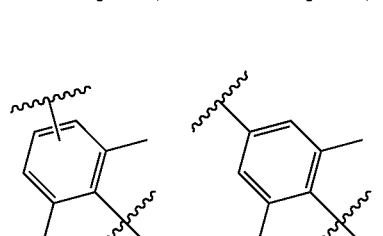
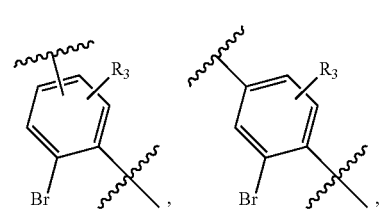
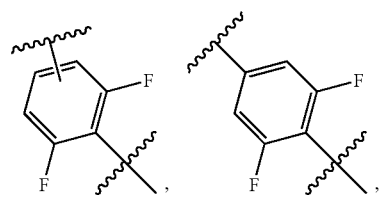
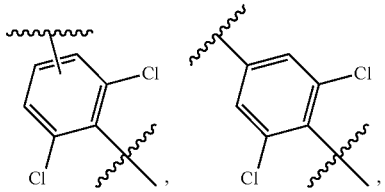
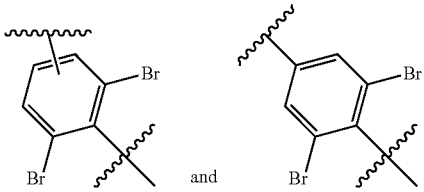
Additional non-limiting examples of compounds of the present invention of include:
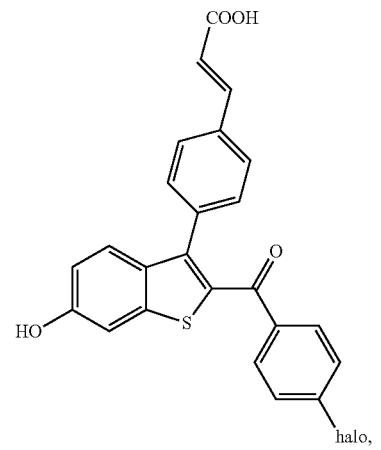
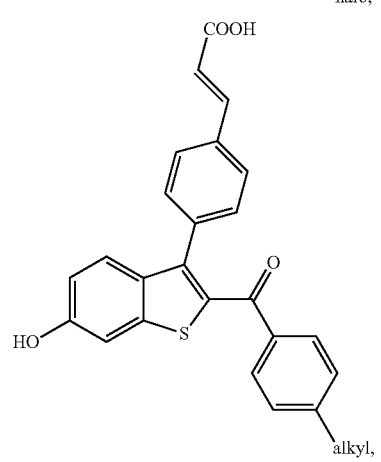

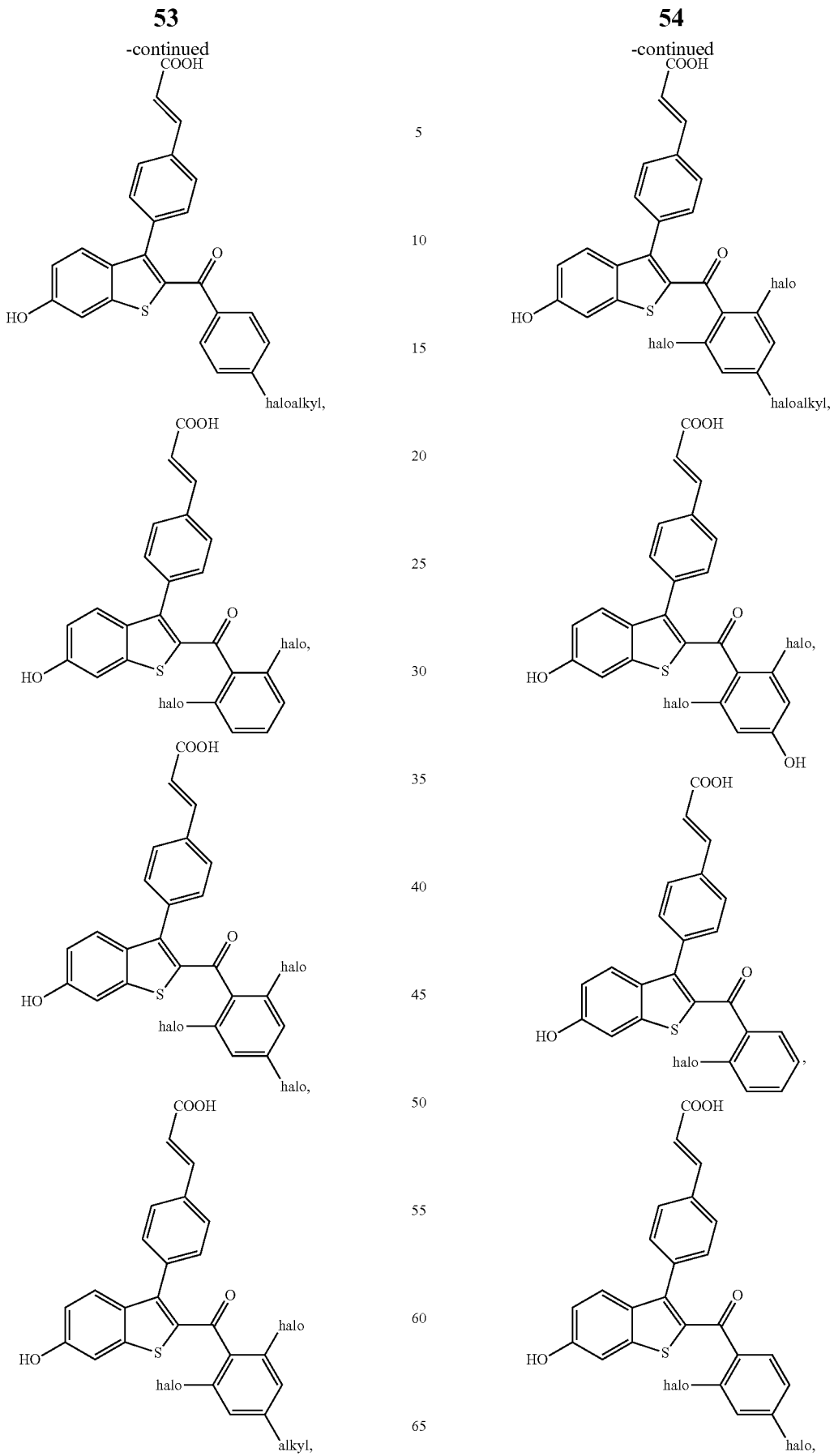

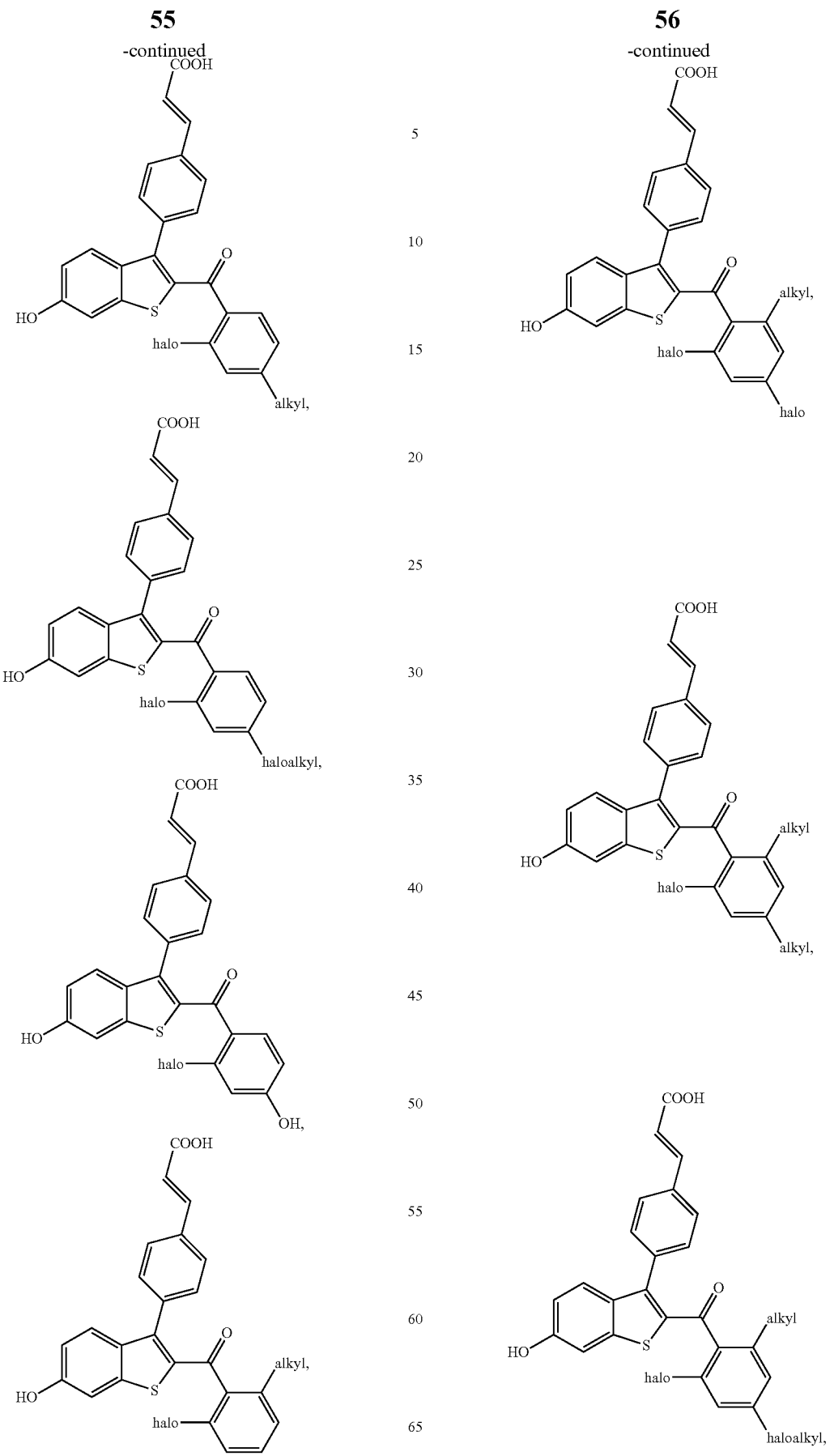

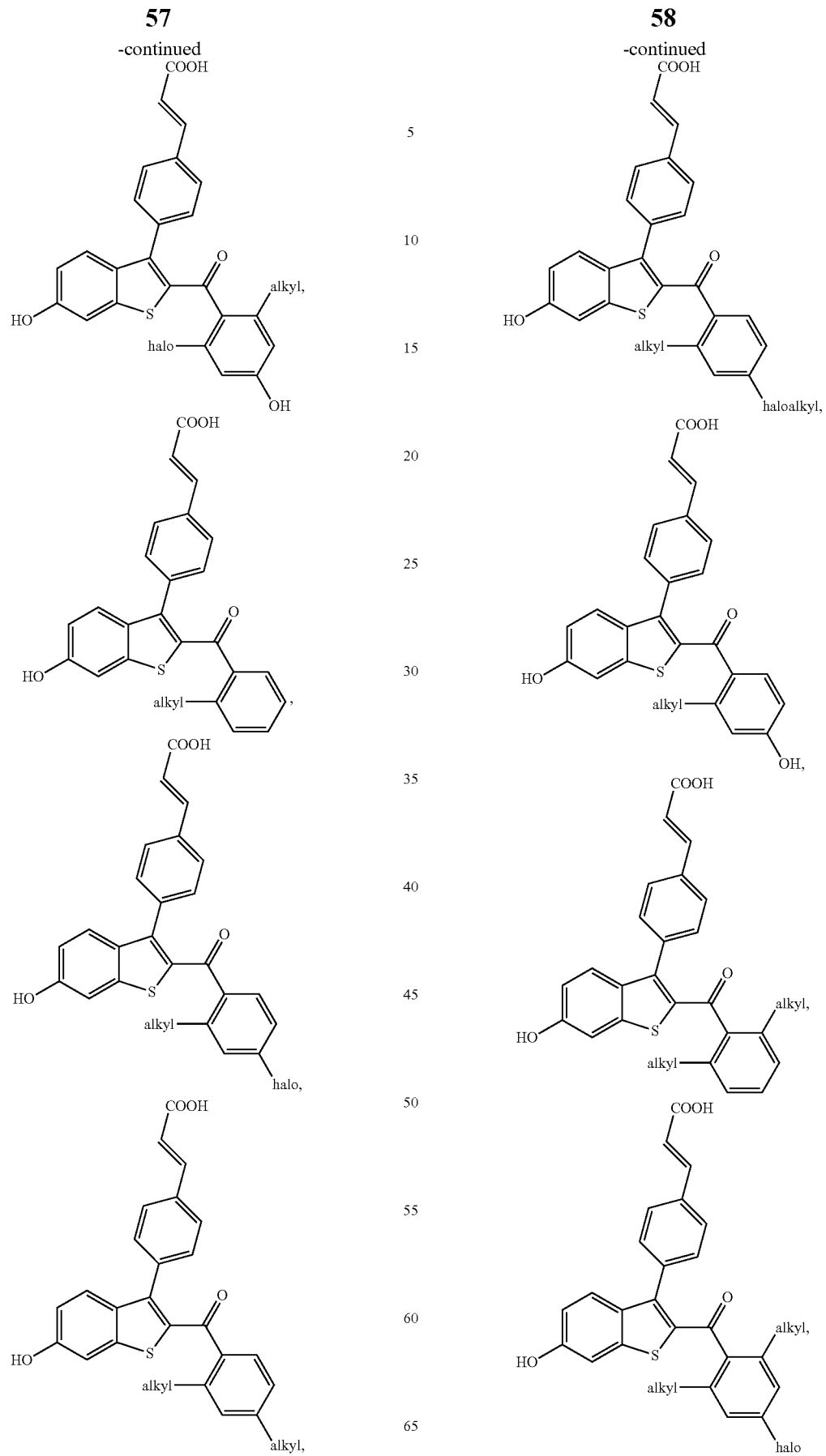

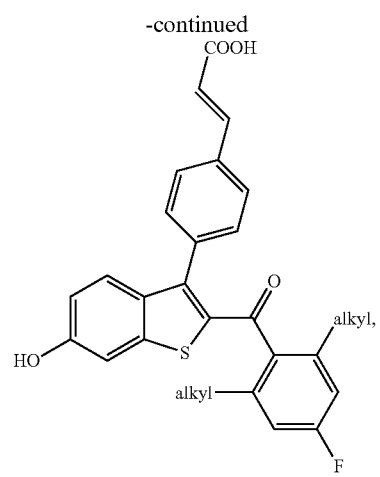
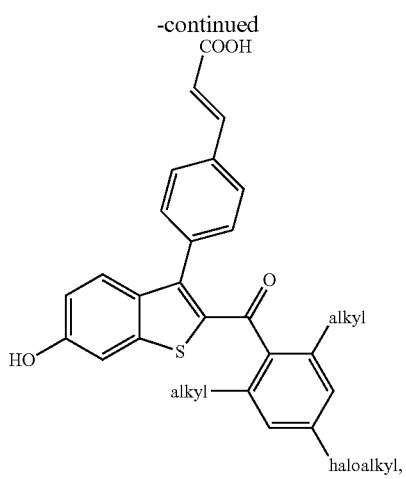
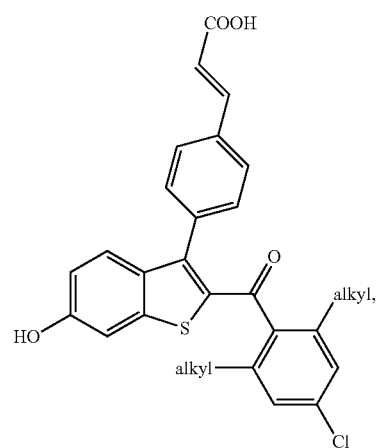
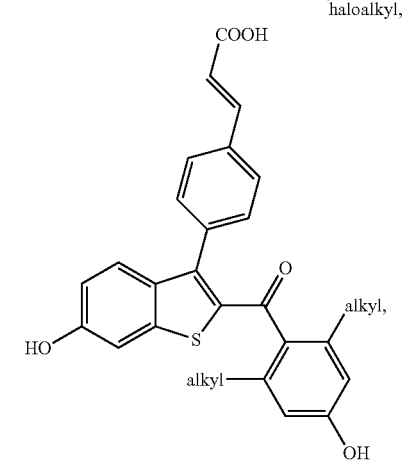
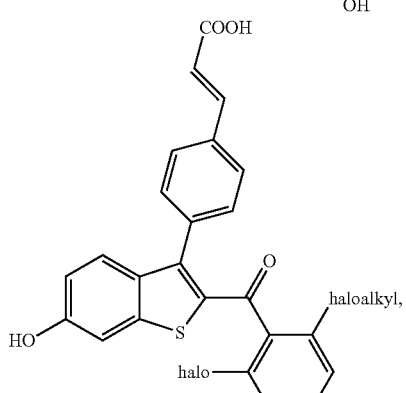
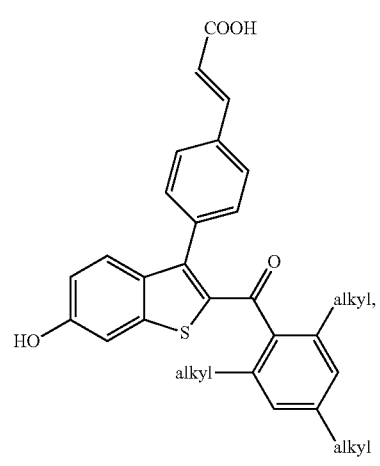
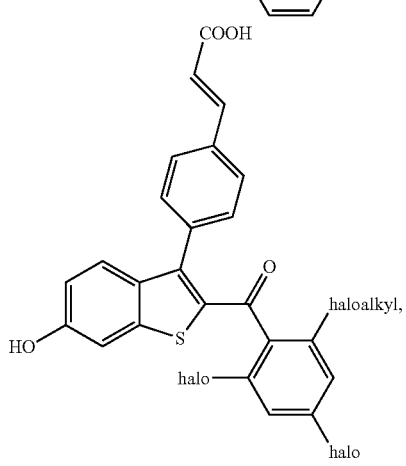

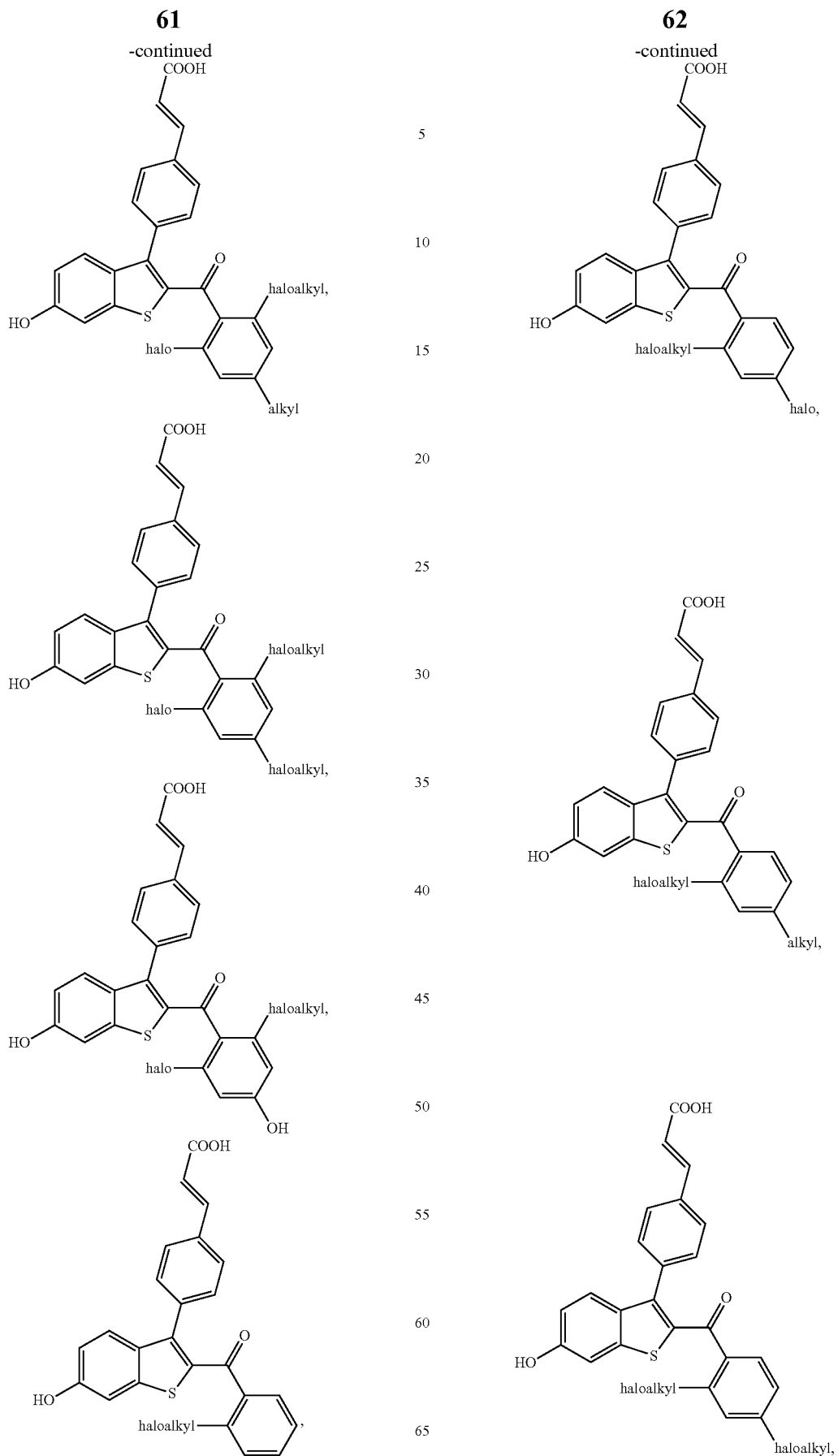

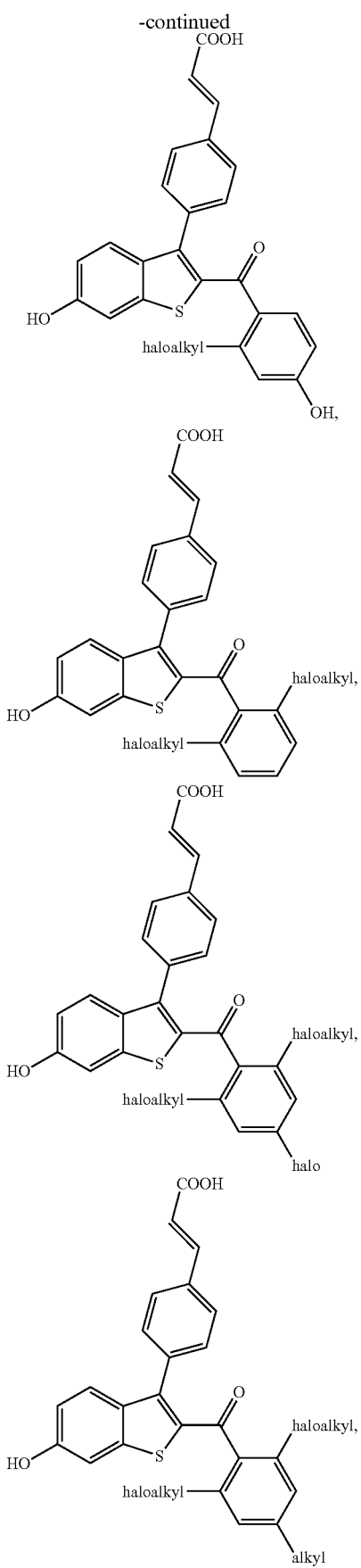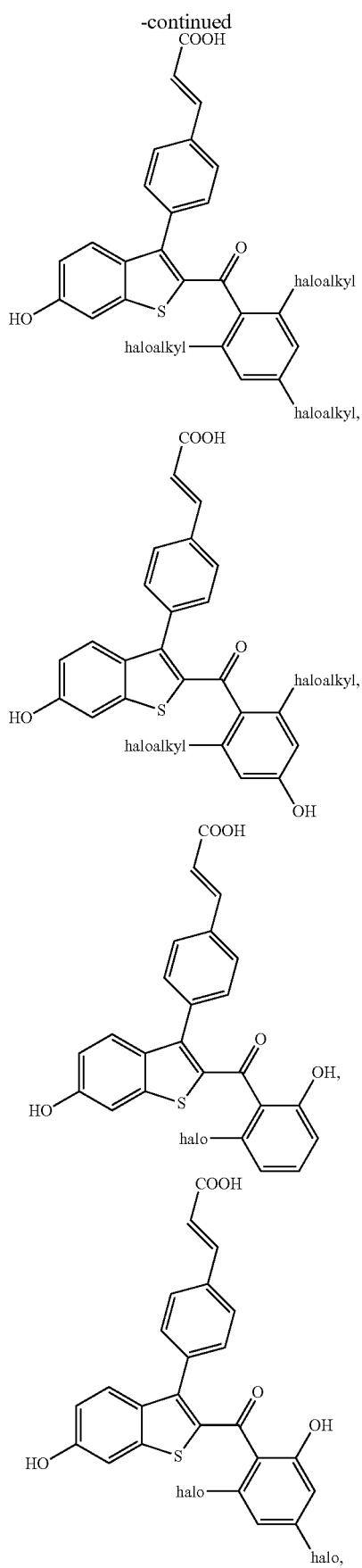

-continued
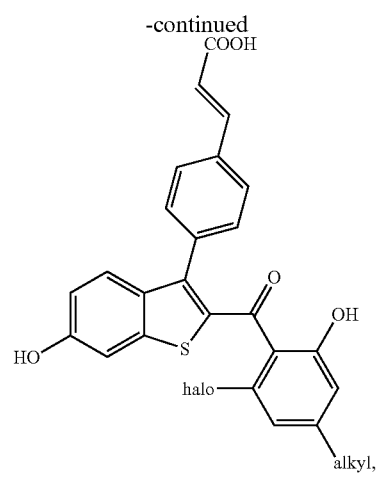
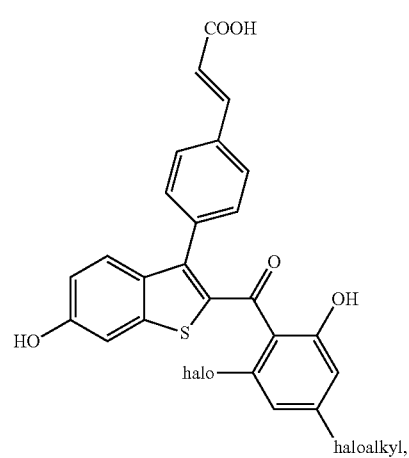
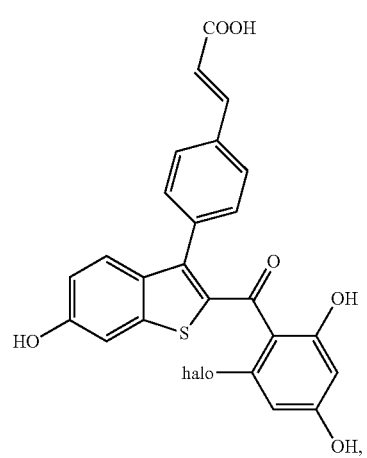
-continued
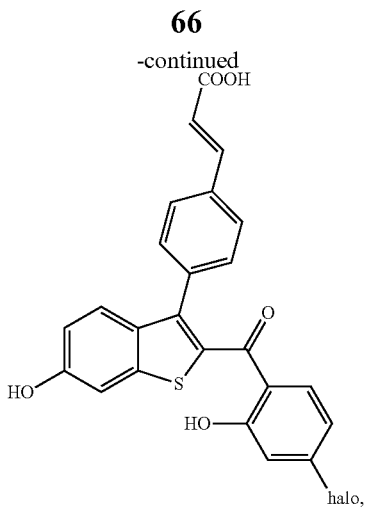
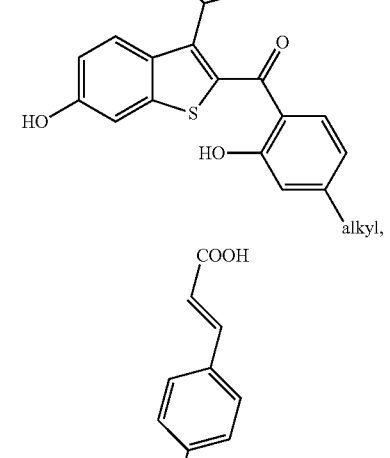
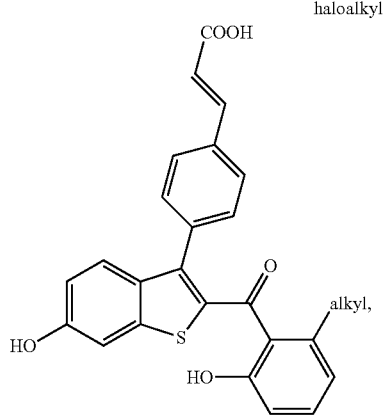

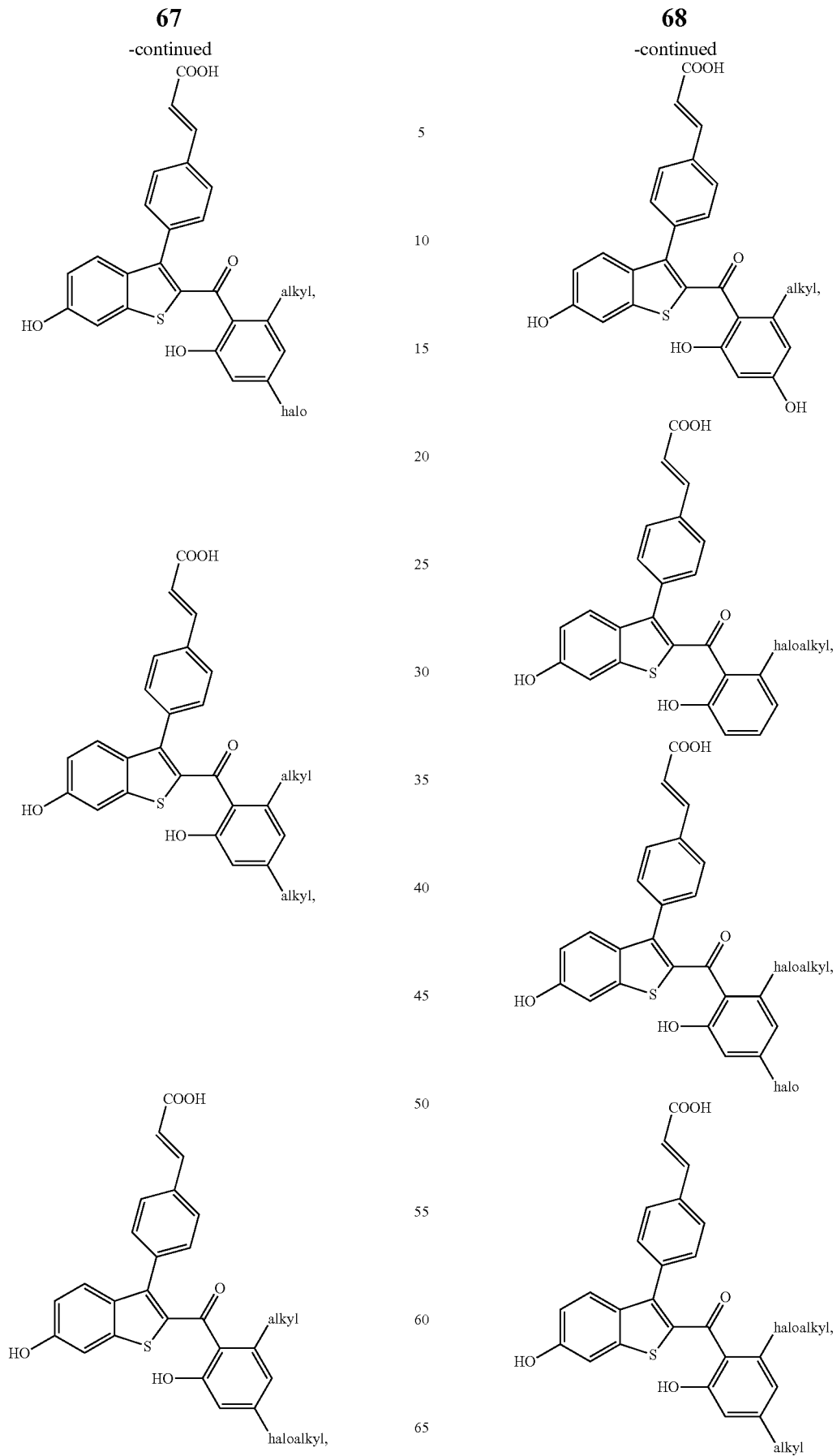

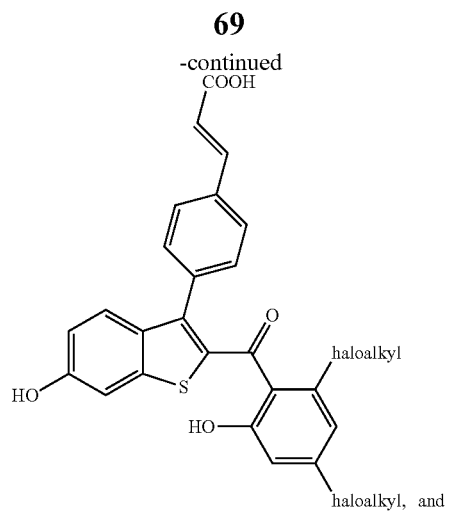

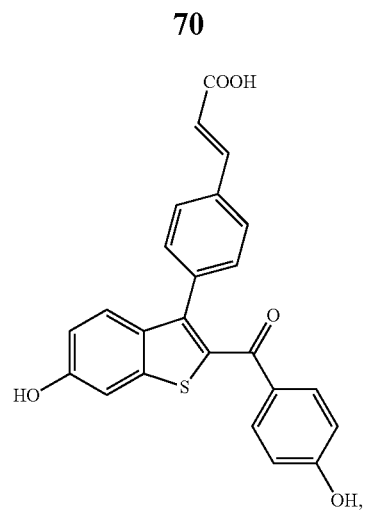

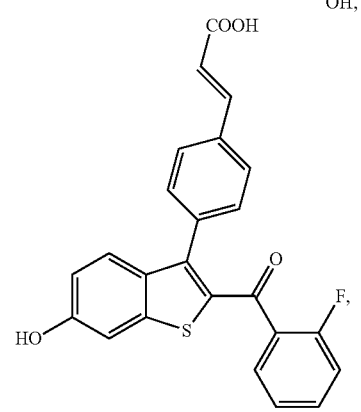

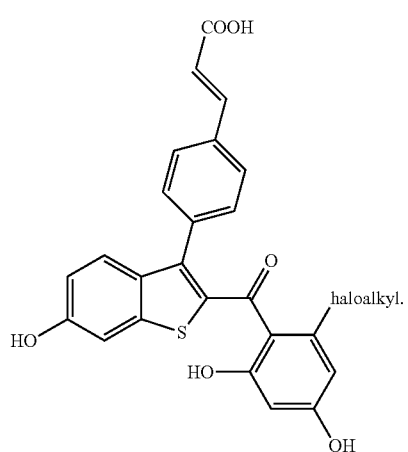

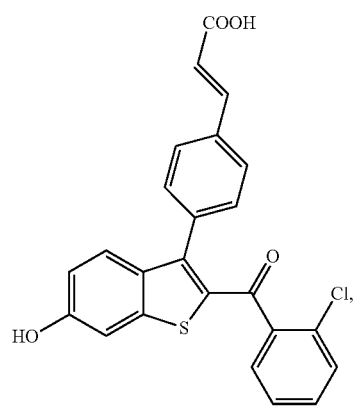

In certain embodiments of the above structures, alkyl is methyl. In other embodiments of the above structures embodiments, alkyl is independently methyl, ethyl, propyl, or cyclopropyl. In some embodiments of the above embodiments, halo is fluoro. In some of the above embodiments, halo is chloro. In some embodiments, haloalkyl is independently mono-, di- or trifluoromethyl. In certain embodiments where the benzene ring has two halos, the halos can be one fluoro and one chloro; two fluoros; or two chloros. In certain embodiments where the benzene ring has three halos, the halos can be one fluoro and two chloros; two fluoros and one chloro; three fluoros; or three chloros.

Additional representative compounds of the present invention include, but are not limited to, compounds of formula:

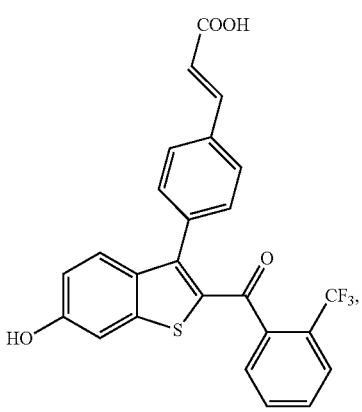

-continued
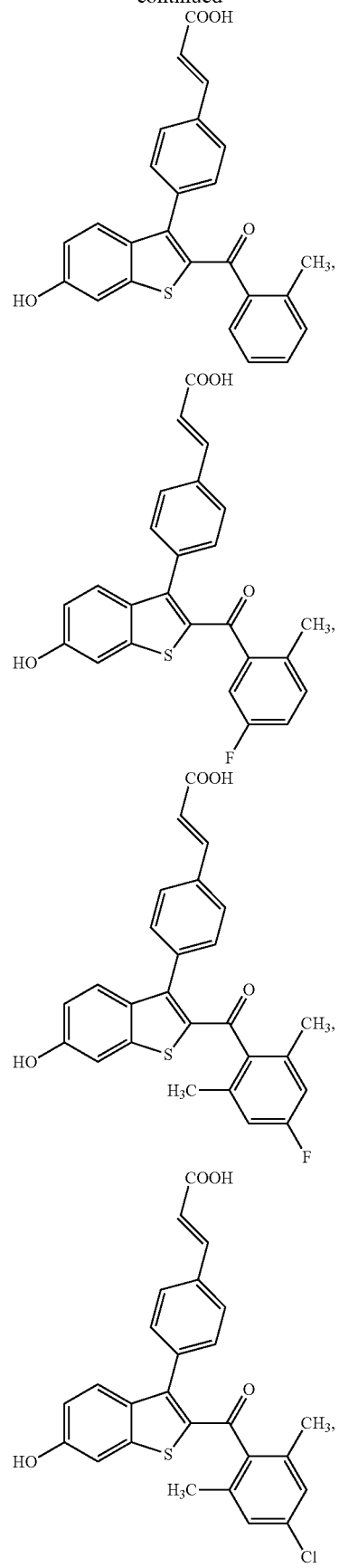
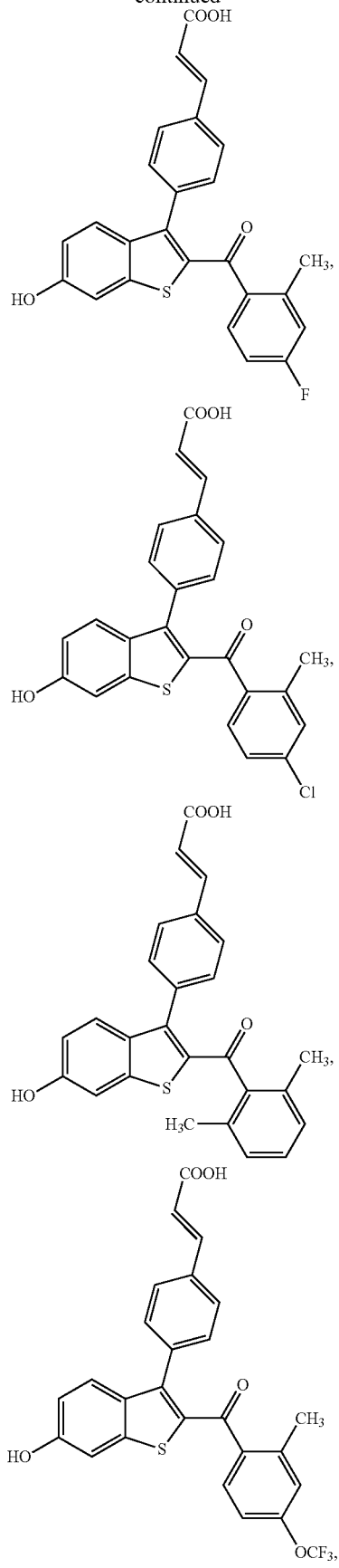

-continued
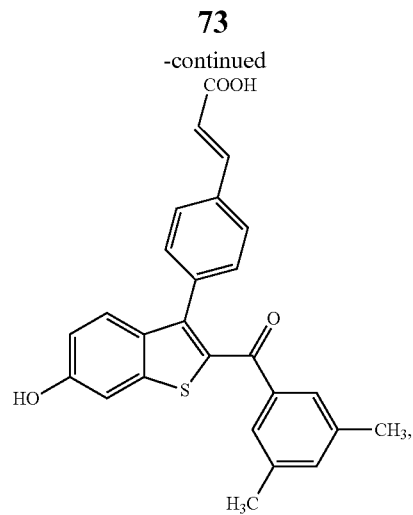
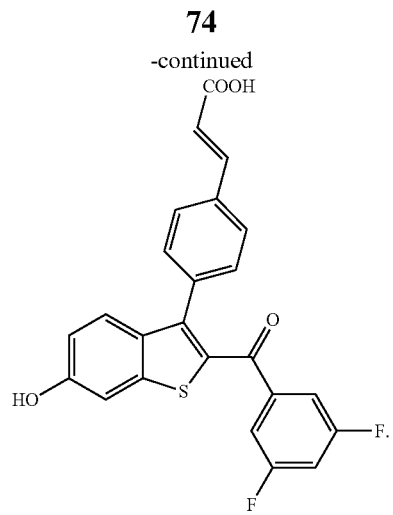
Additional non-limiting examples of compounds of the present invention of include:
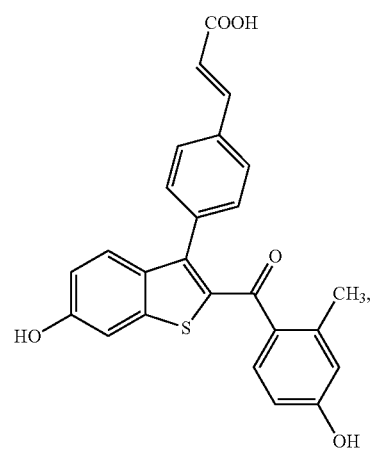
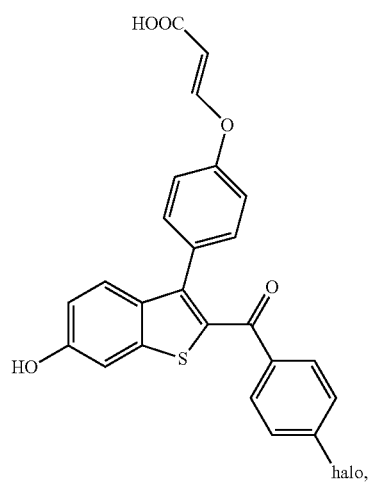
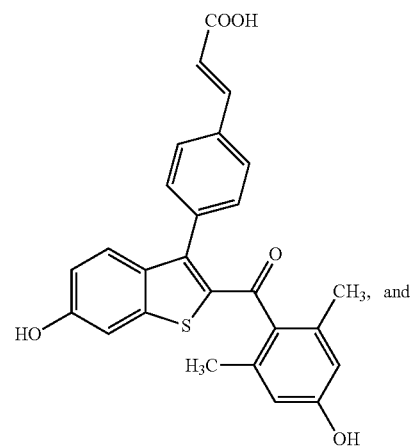
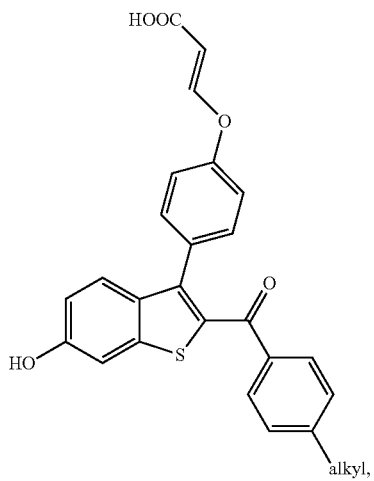

-continued
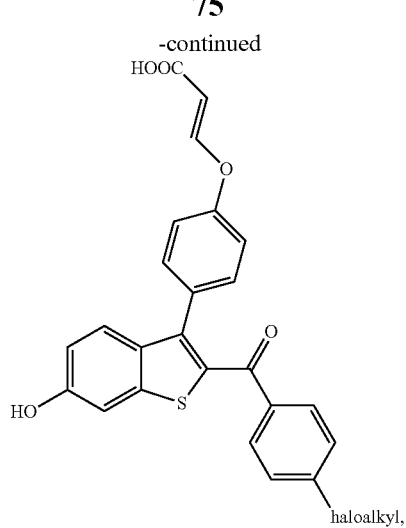
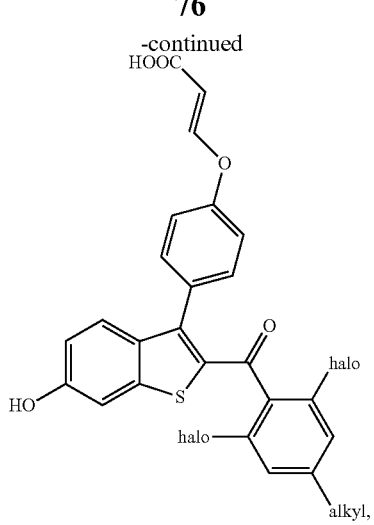
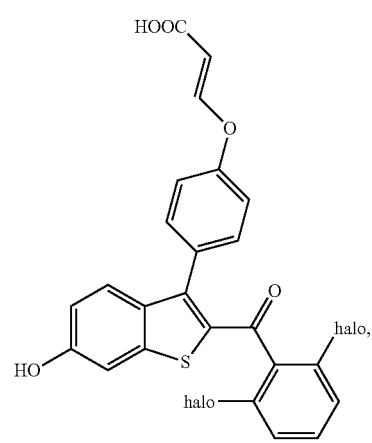
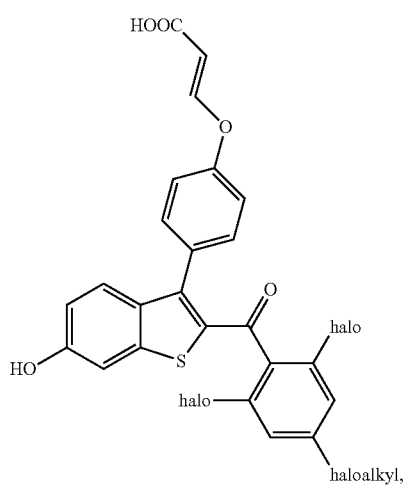
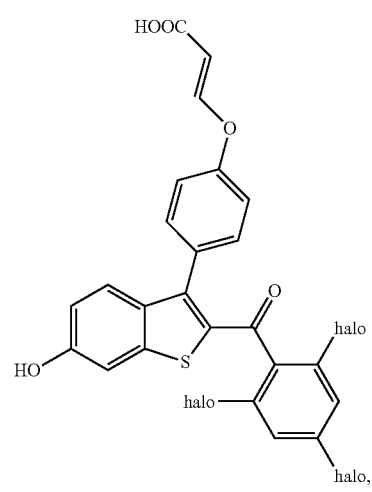
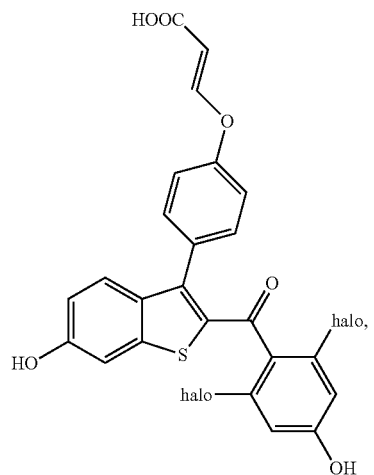

77
-continued
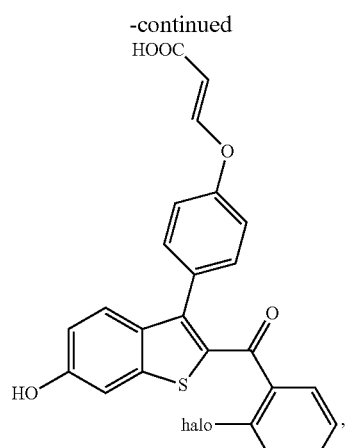
78
-continued
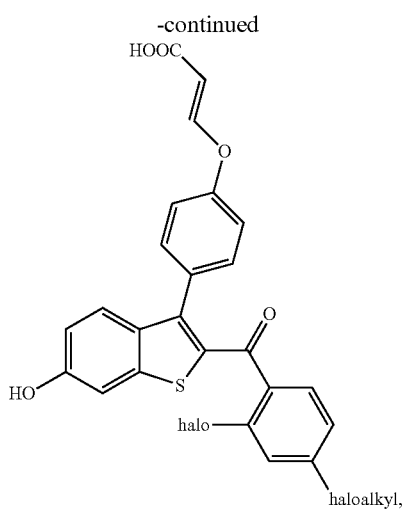
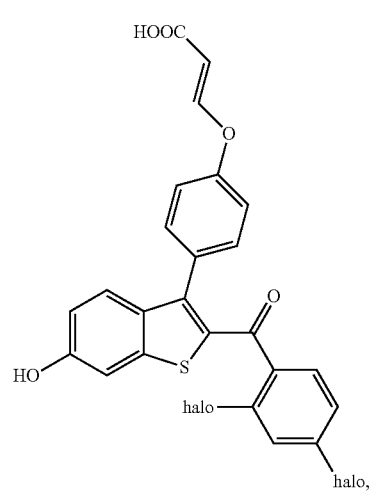
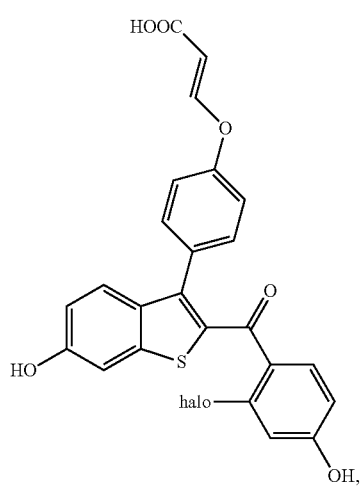
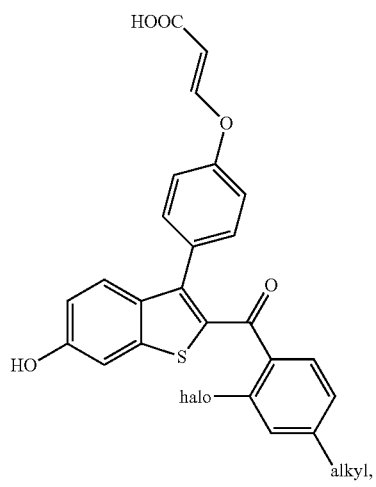
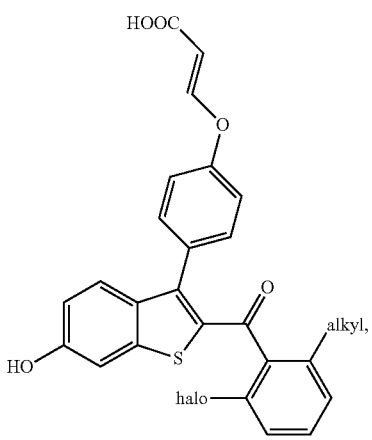

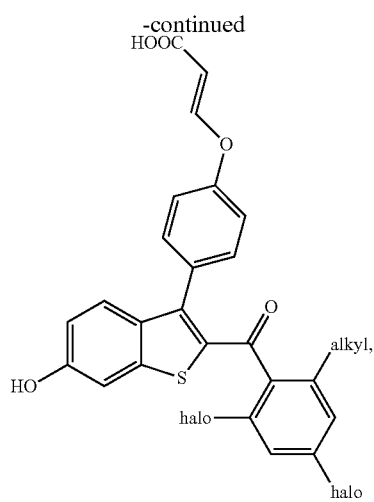
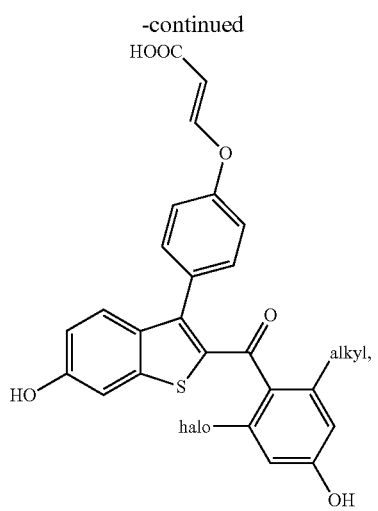
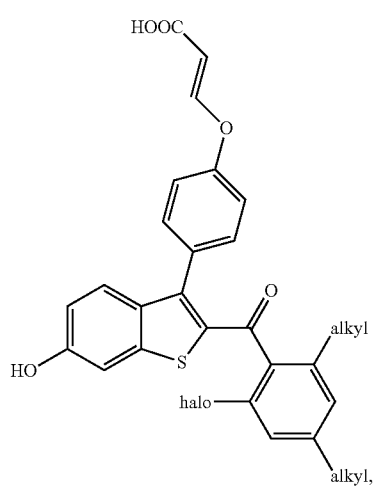
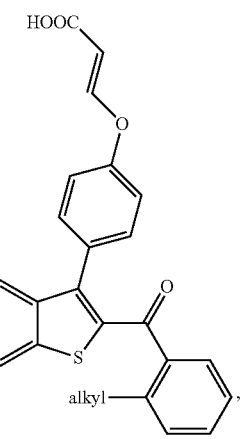
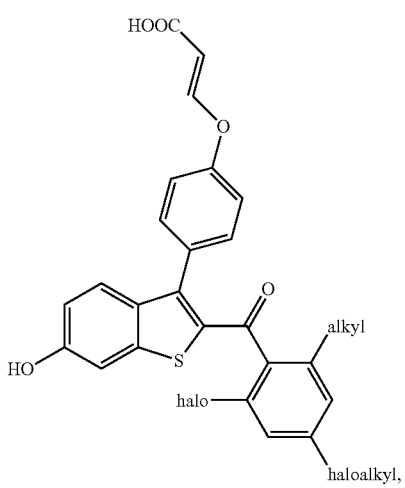
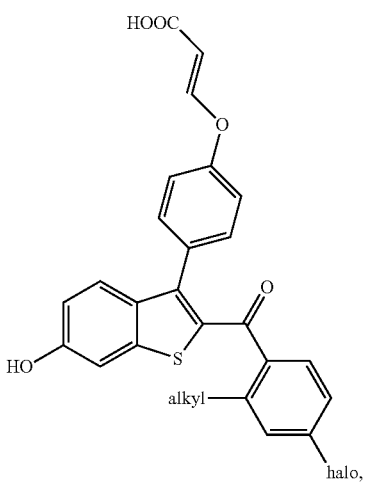

-continued
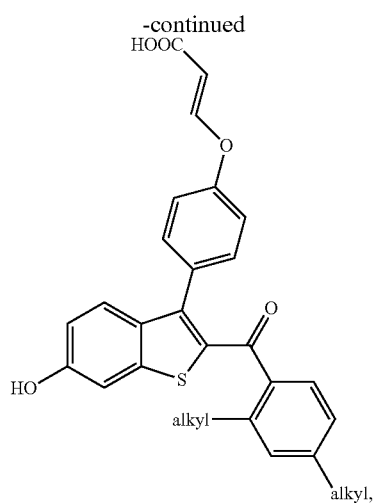
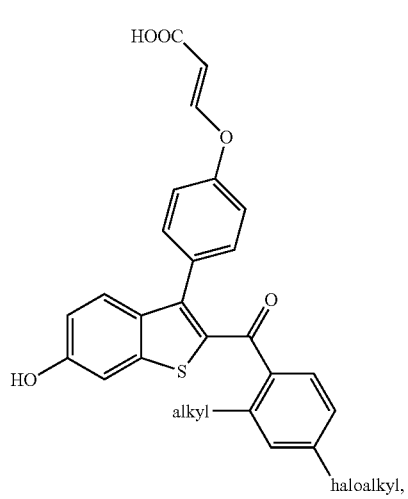
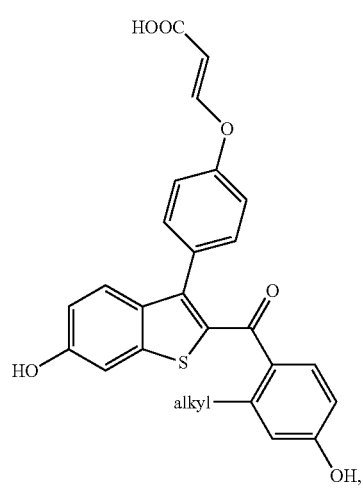
-continued
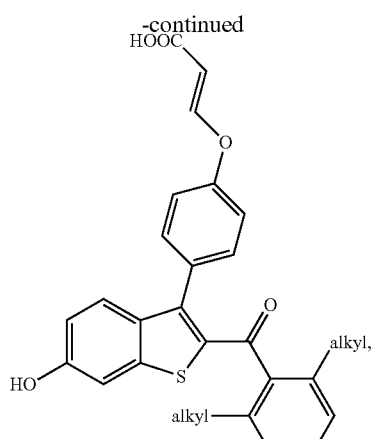
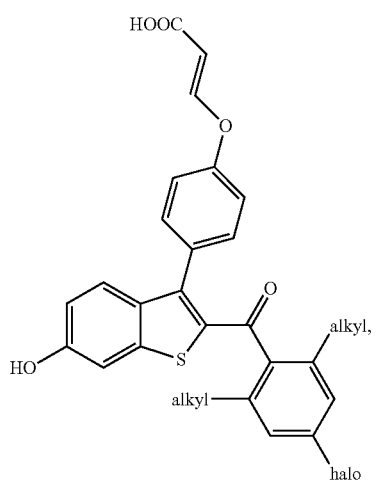
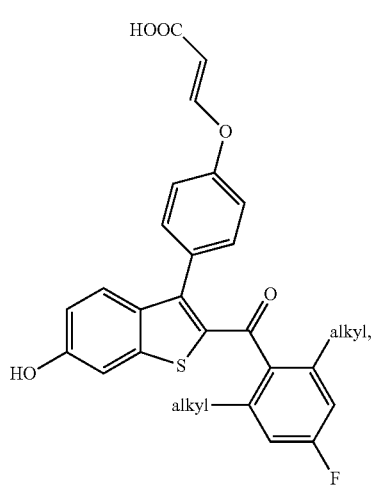

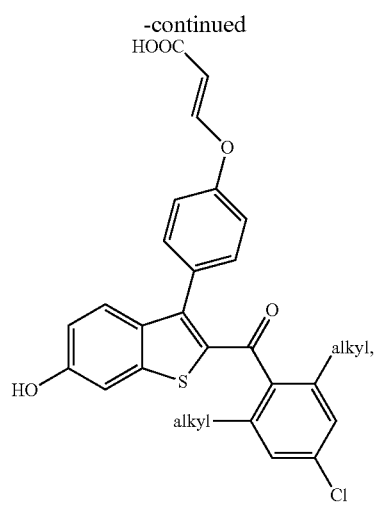
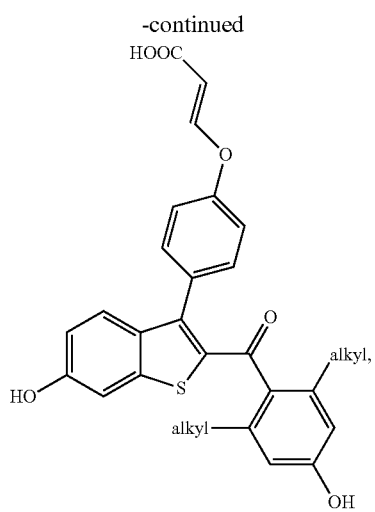
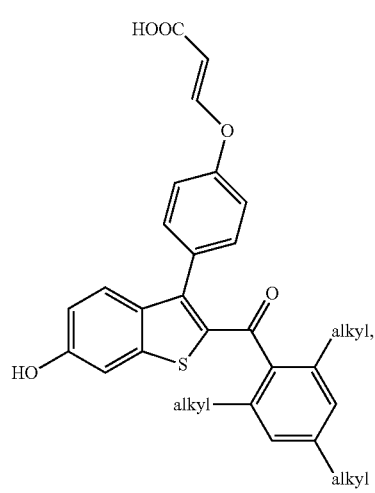
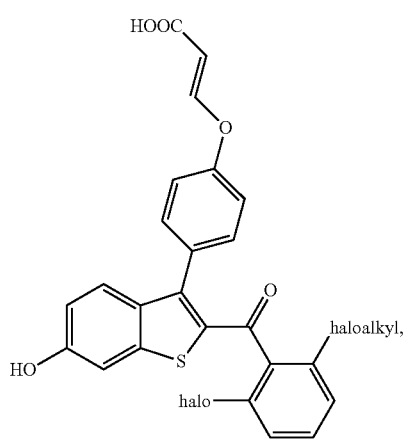
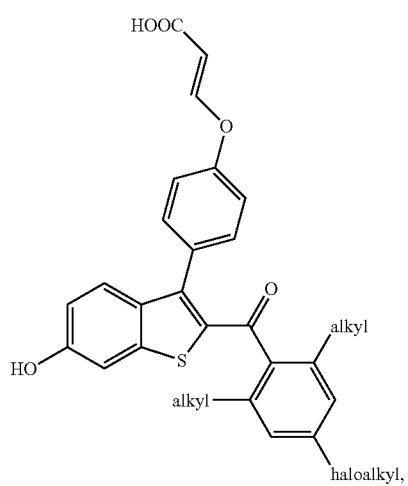
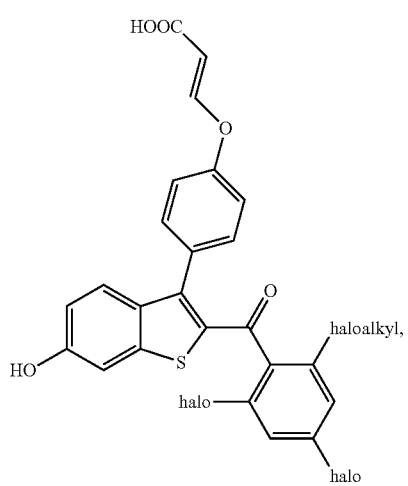

85
-continued
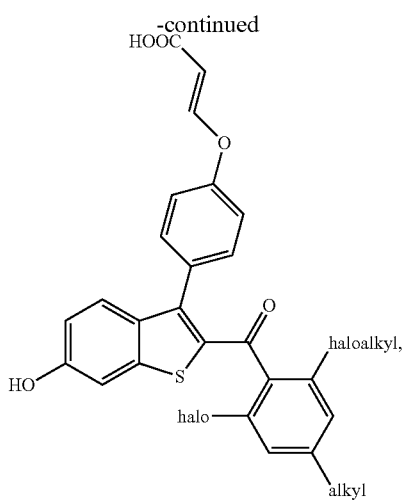
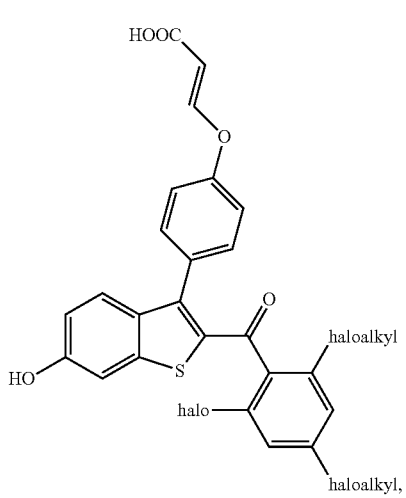
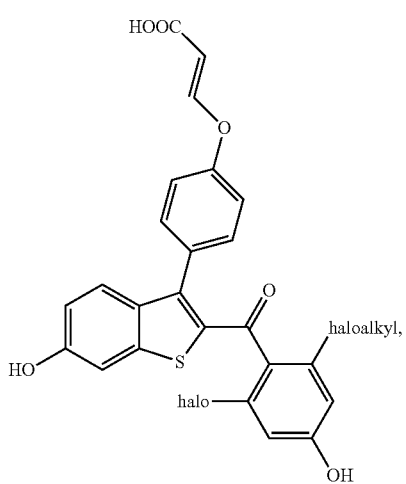
86
-continued
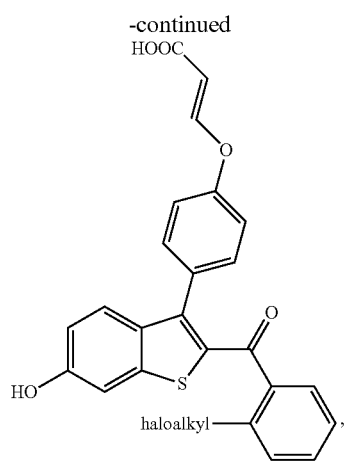
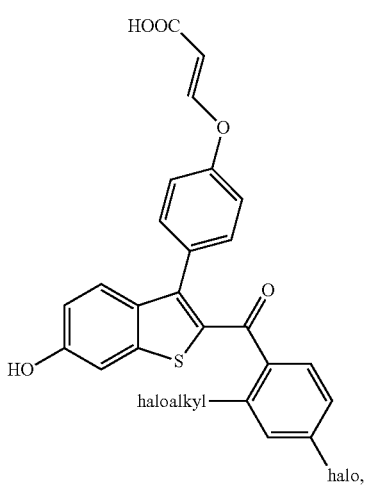
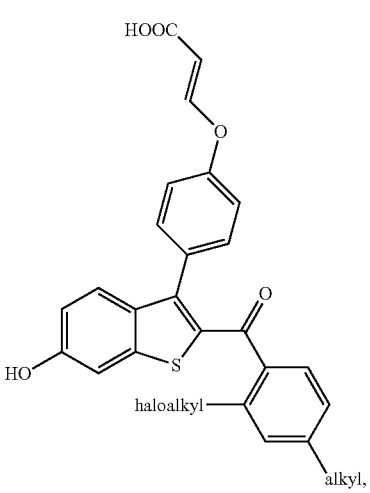

-continued
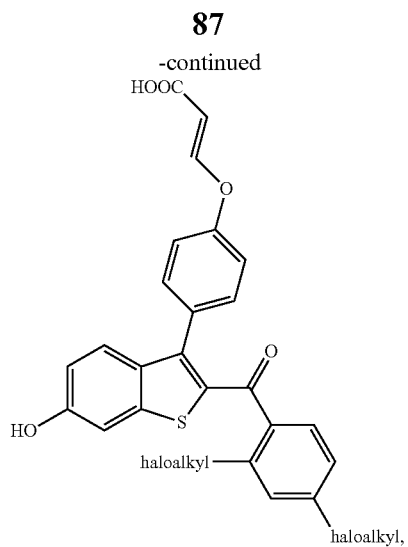
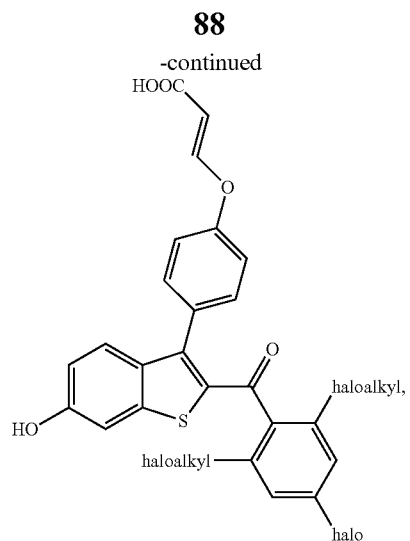
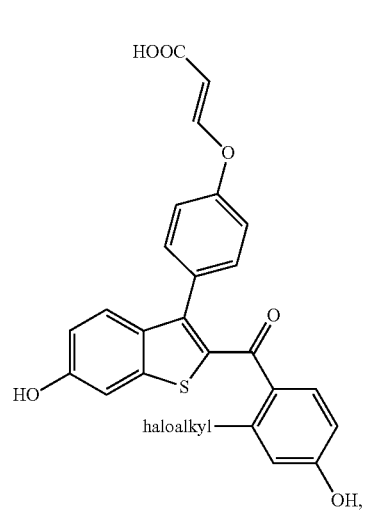
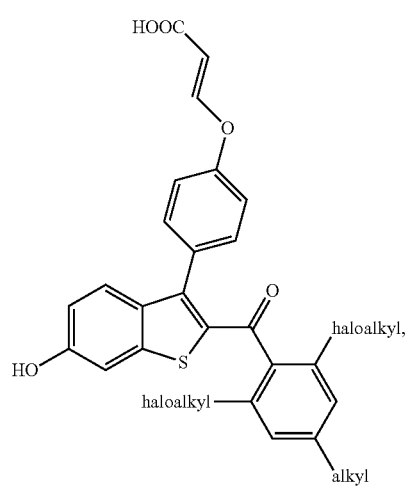
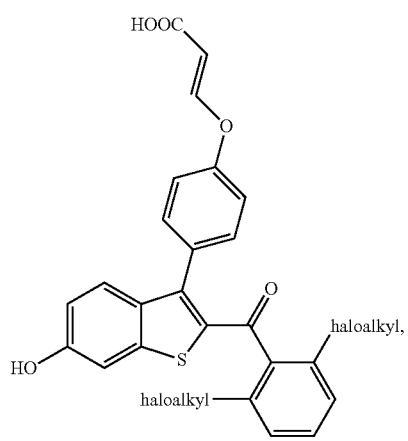
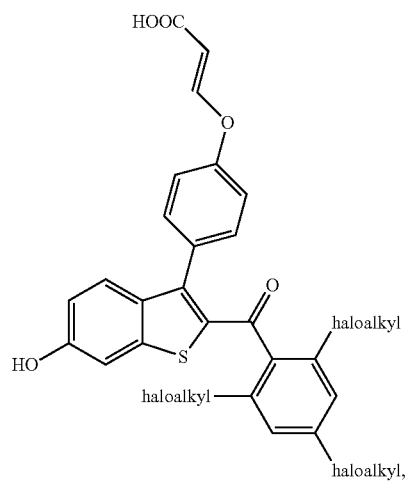

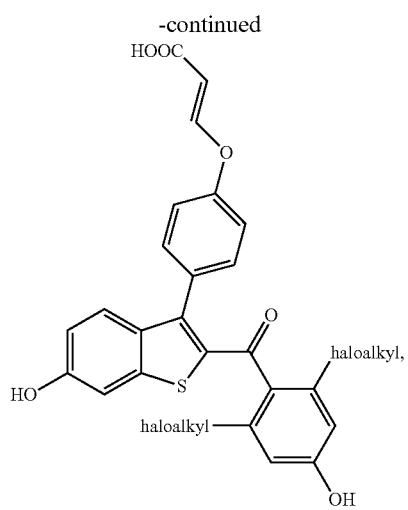
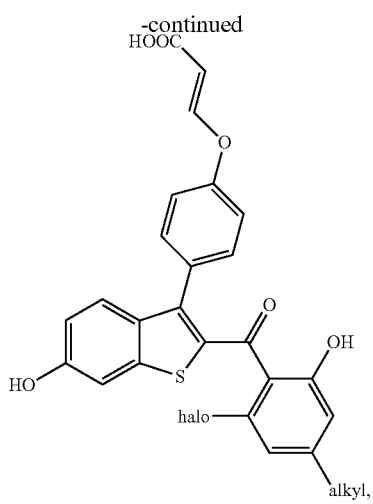
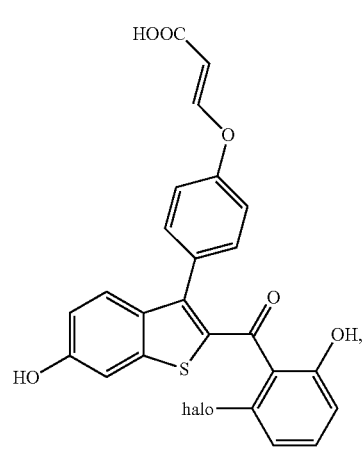
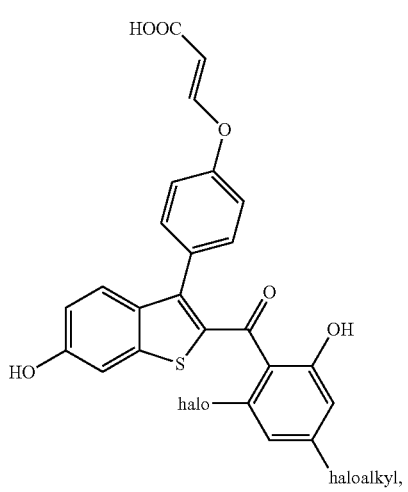
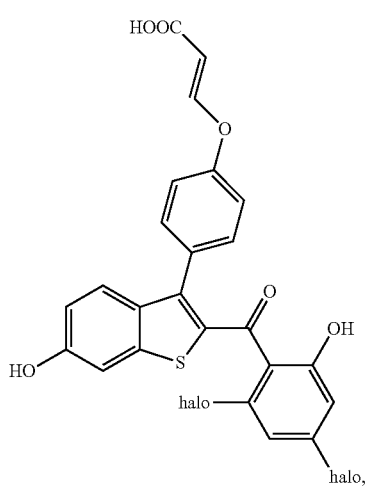
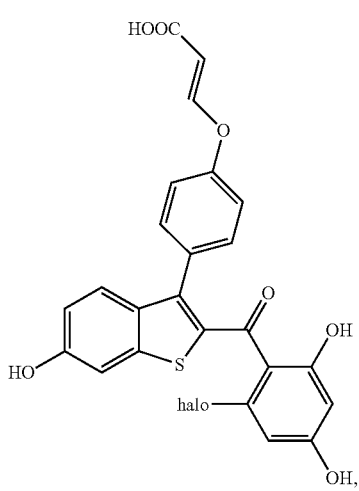

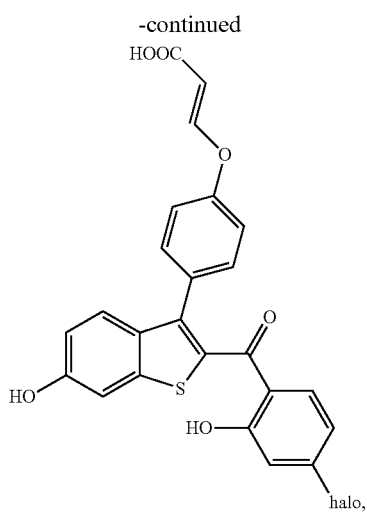
halo,
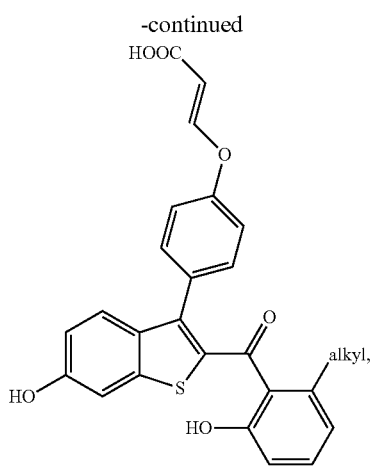
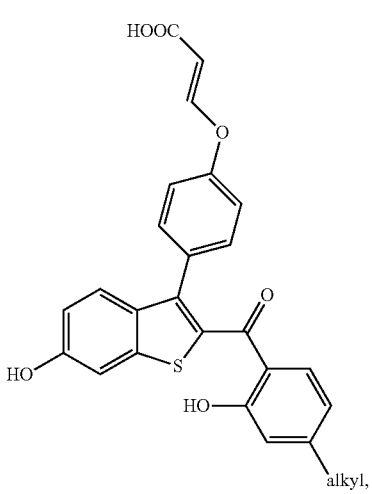
alkyl,
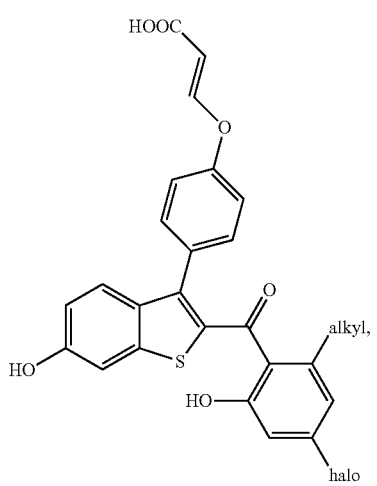
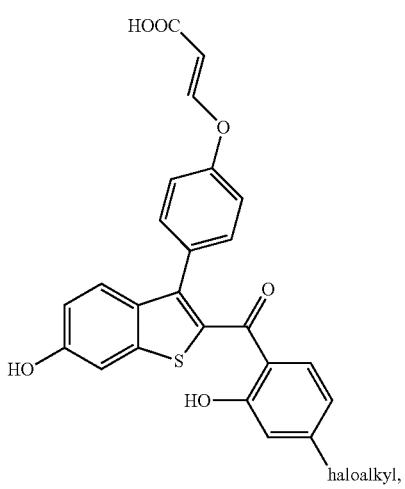
haloalkyl,
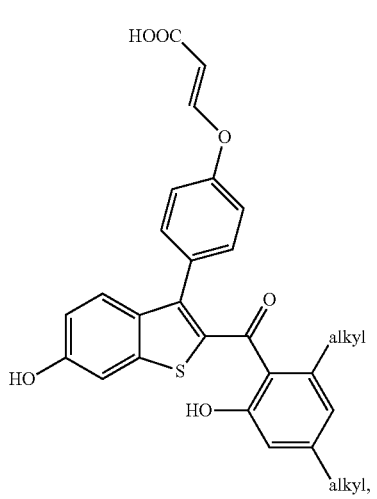

-continued
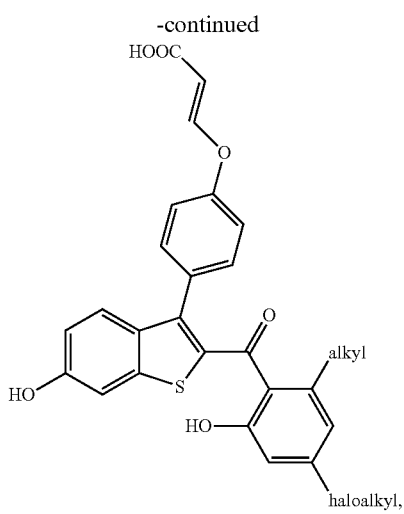
-continued
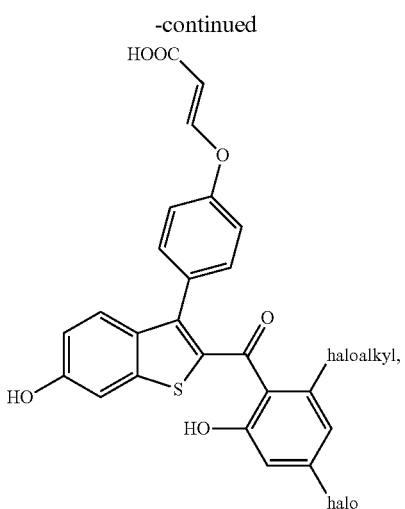
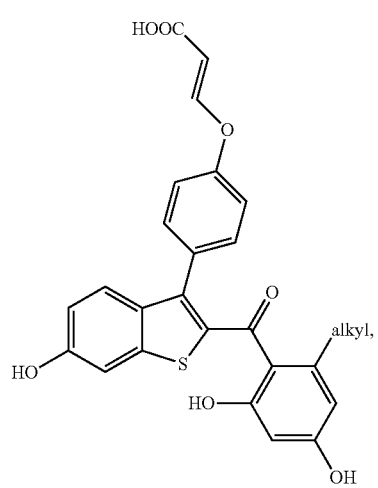
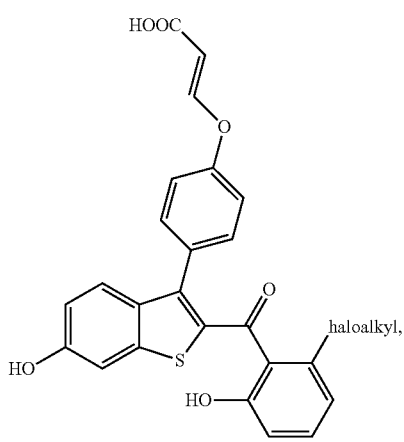
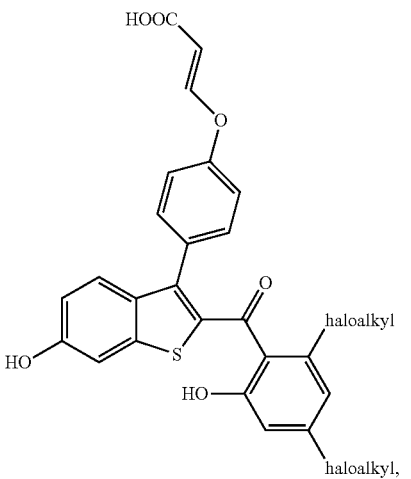

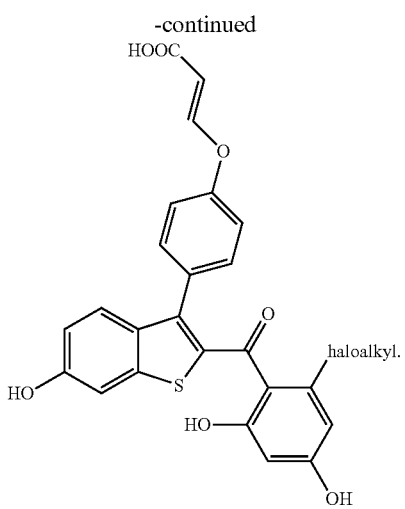

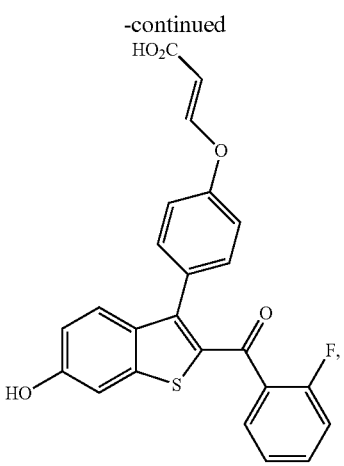

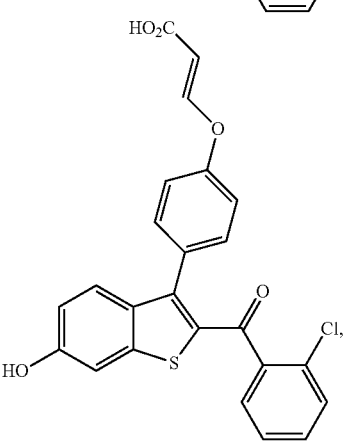

In certain embodiments of the above structures, alkyl is methyl. In other embodiments of the above structures embodiments, alkyl is independently methyl, ethyl, propyl, or cyclopropyl. In some embodiments of the above embodiments, halo is fluoro. In some of the above embodiments, halo is chloro. In some embodiments, haloalkyl is independently mono-, di- or trifluoromethyl. In certain embodiments where the benzene ring has two halos, the halos can be one fluoro and one chloro; two fluoros; or two chloros. In certain embodiments where the benzene ring has three halos, the halos can be one fluoro and two chloros; two fluoros and one chloro; three fluoros; or three chloros.

Additional representative compounds of the present invention include, but are not limited to, compounds of formula:

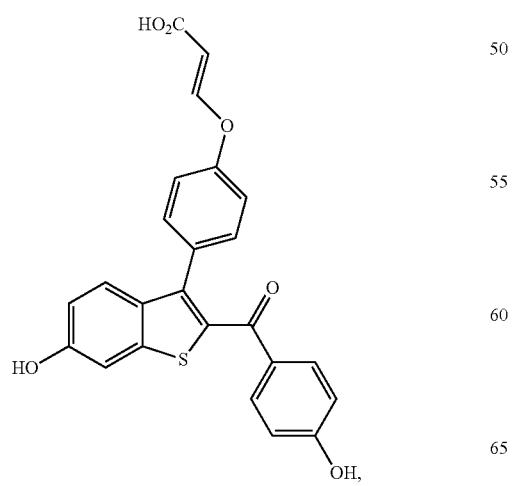

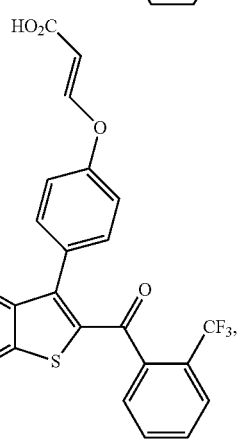

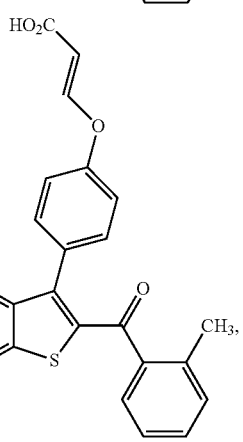

97
-continued
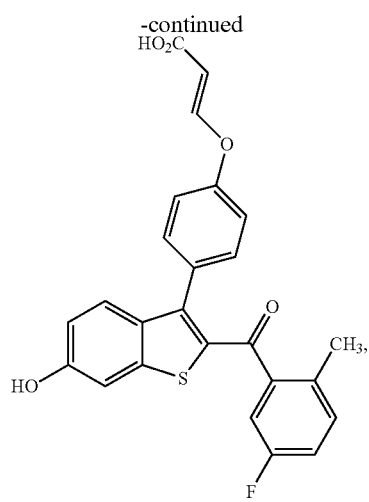
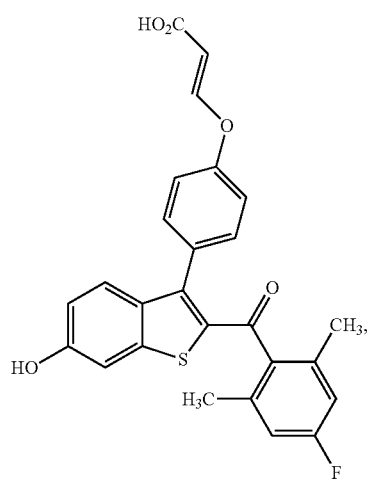
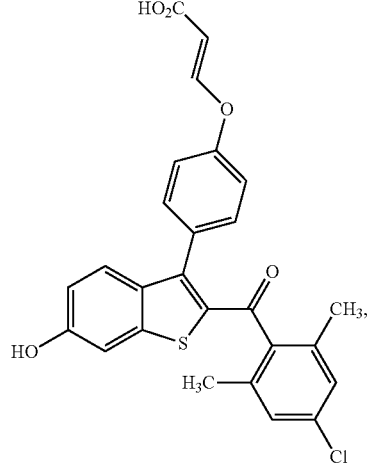
98
-continued
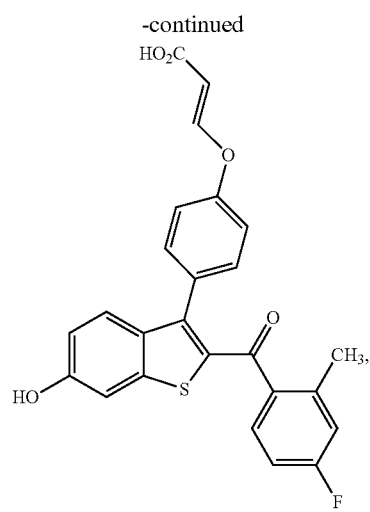
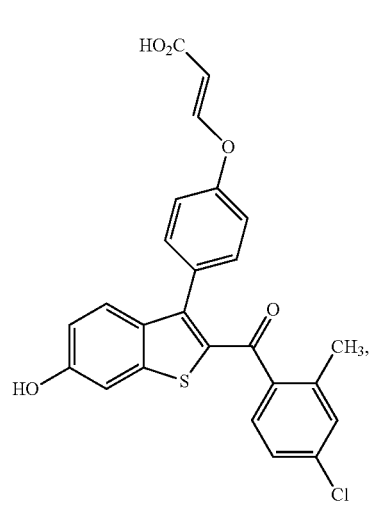
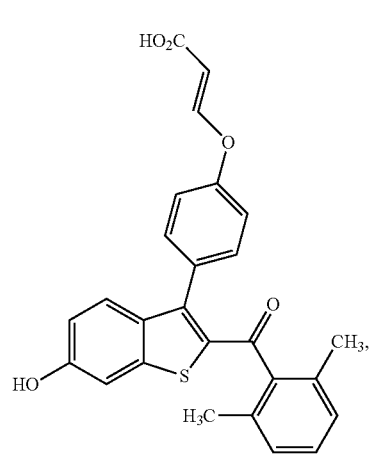

99
-continued
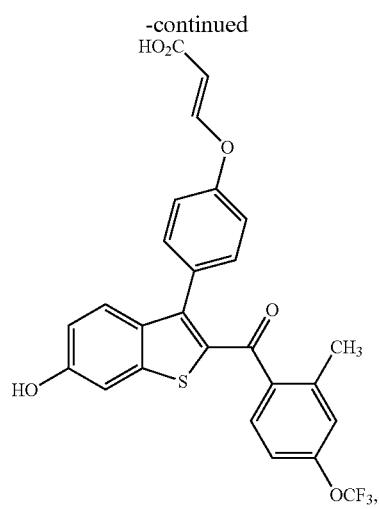
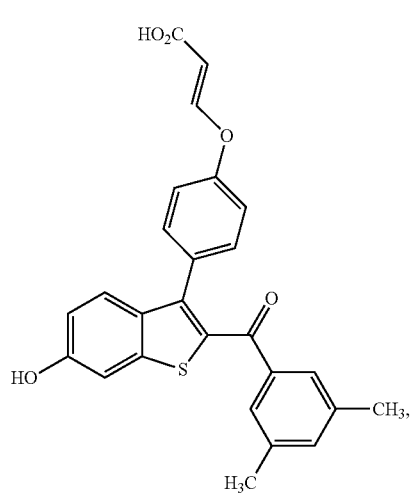
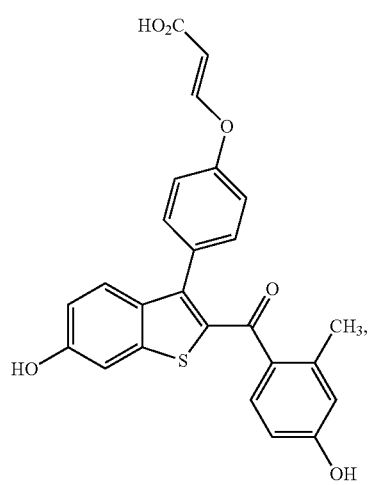
100
-continued
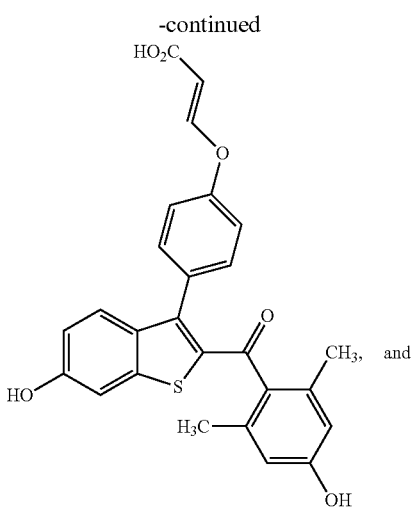
and
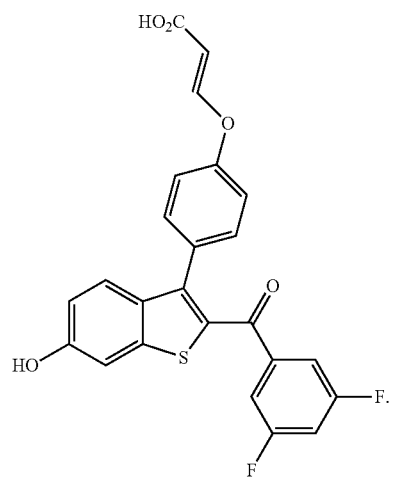
Additional non-limiting compounds of the present invention of include:
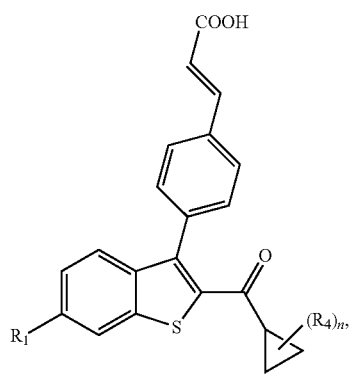

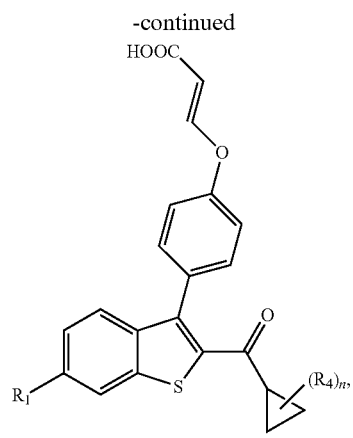
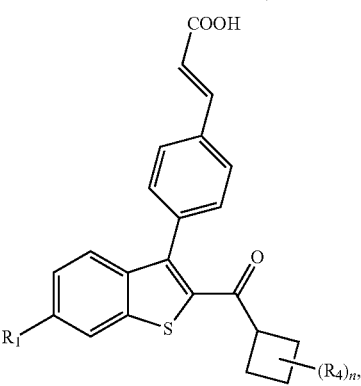
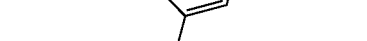
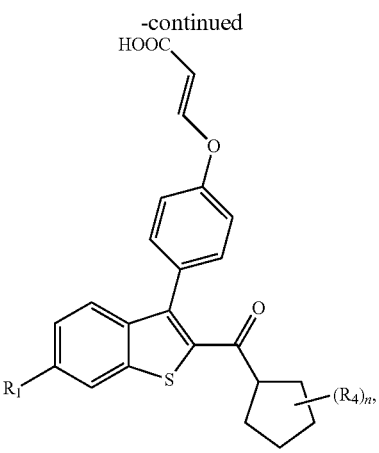
, and

Additional representative compounds of the present invention include compounds of the formula:
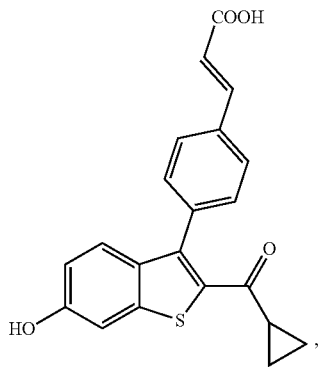
,
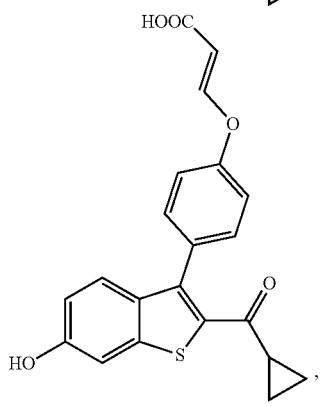
,
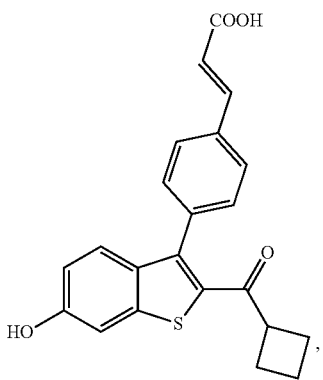
,
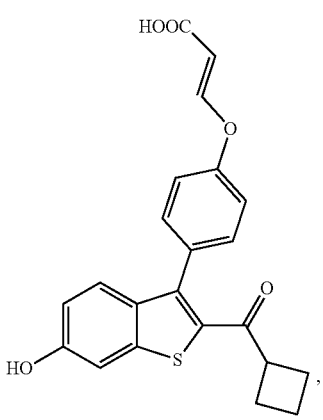
,
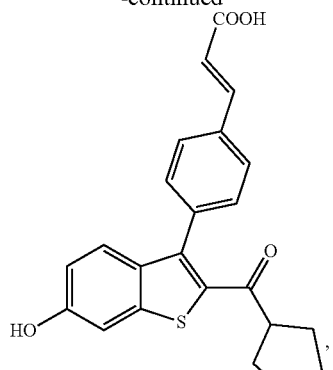
,
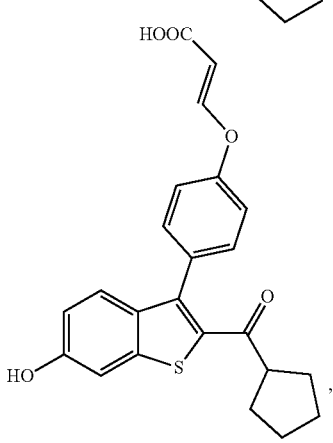
,
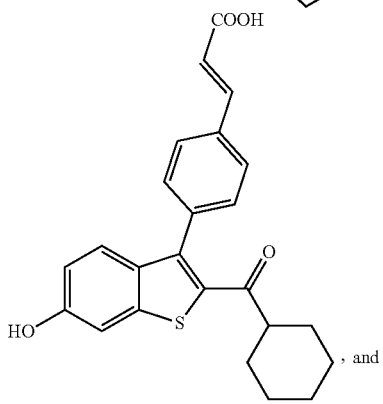
, and
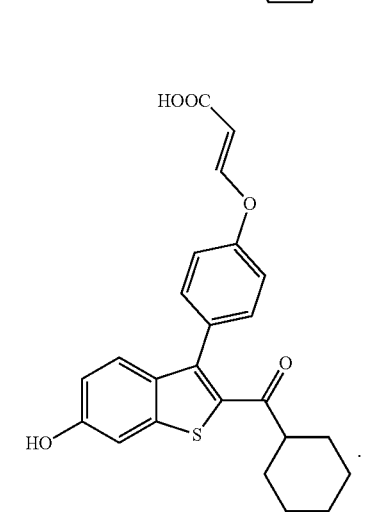
.

Additional non-limiting examples of compounds of the present invention of include:
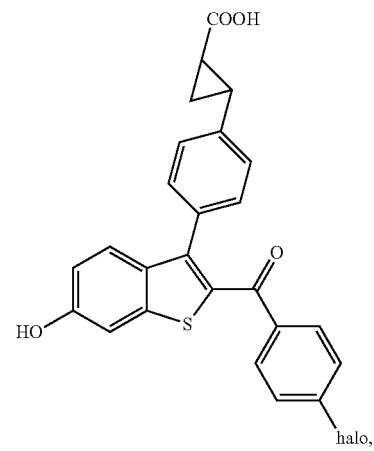
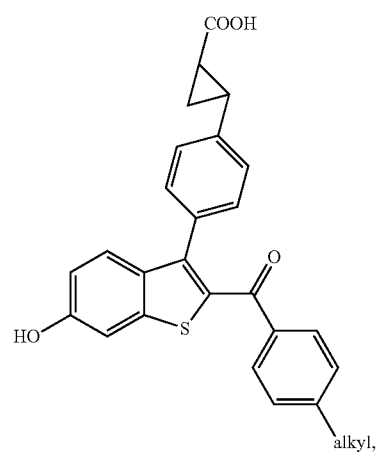
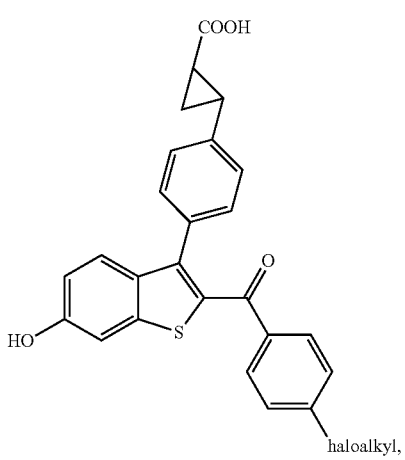
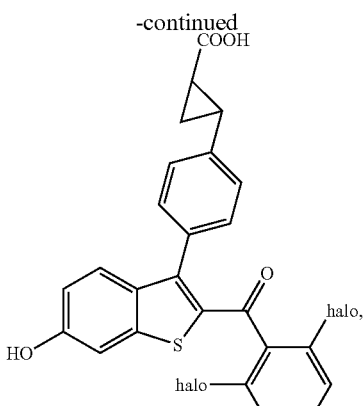
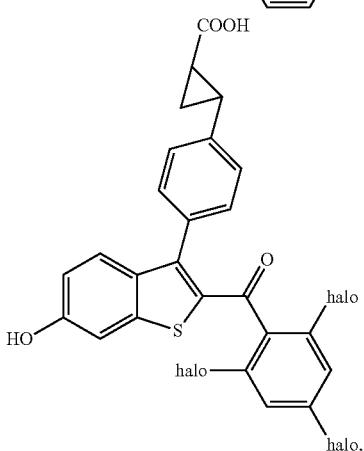
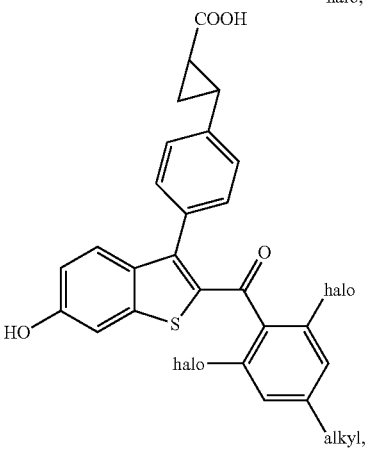
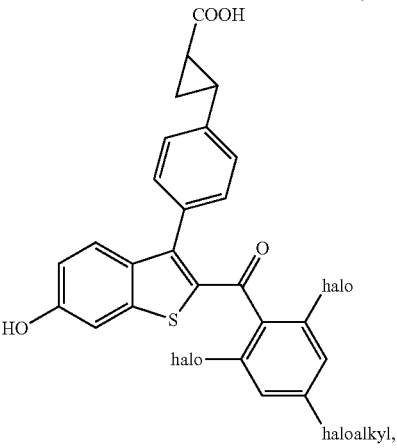

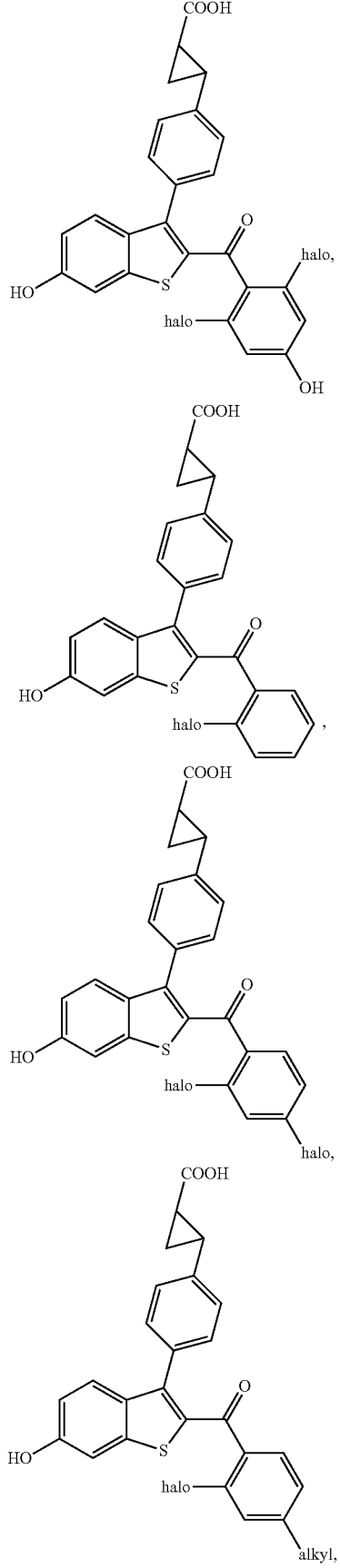
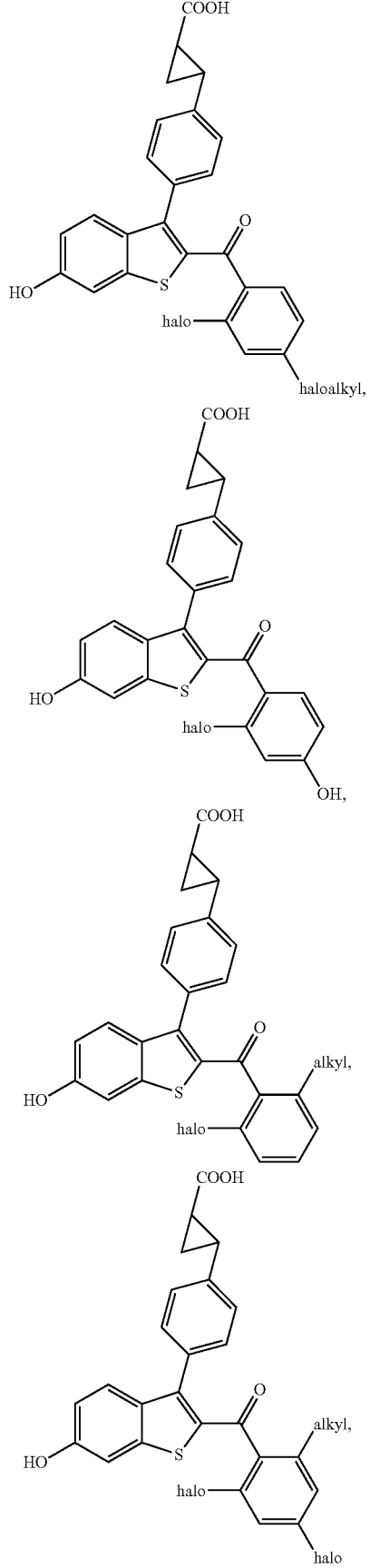

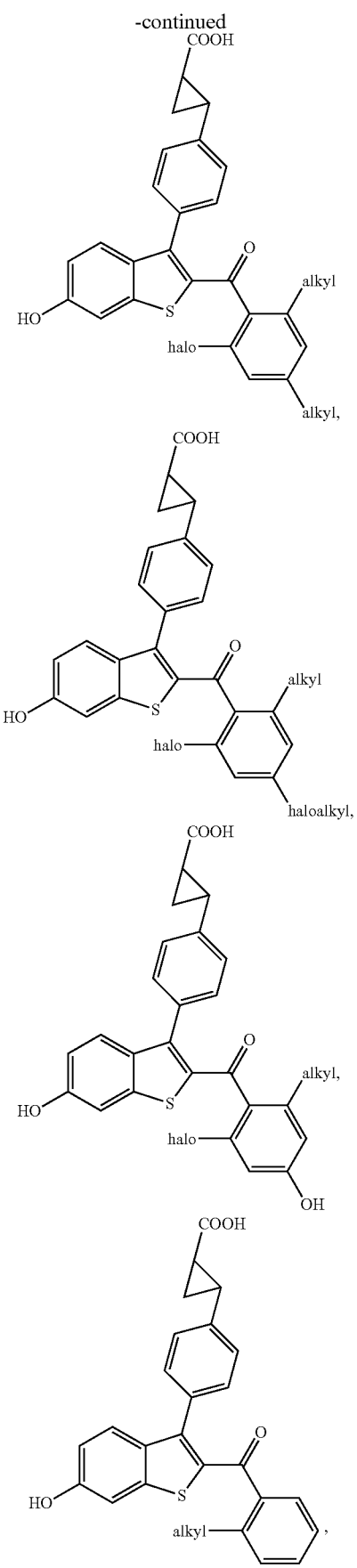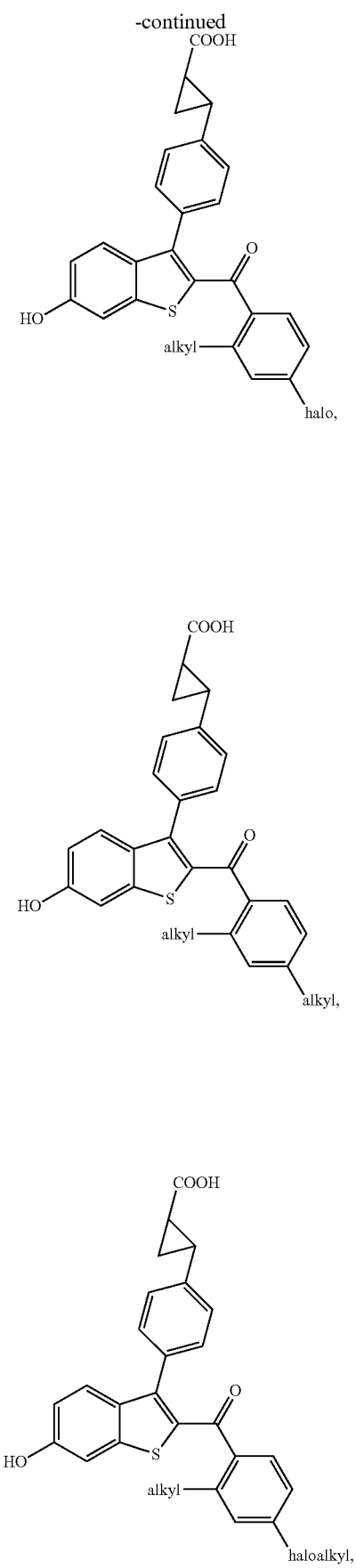

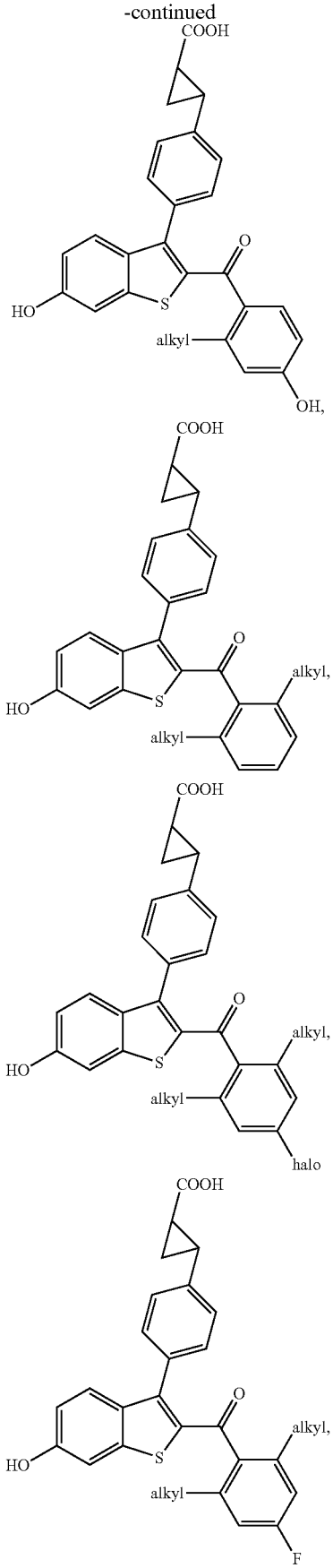
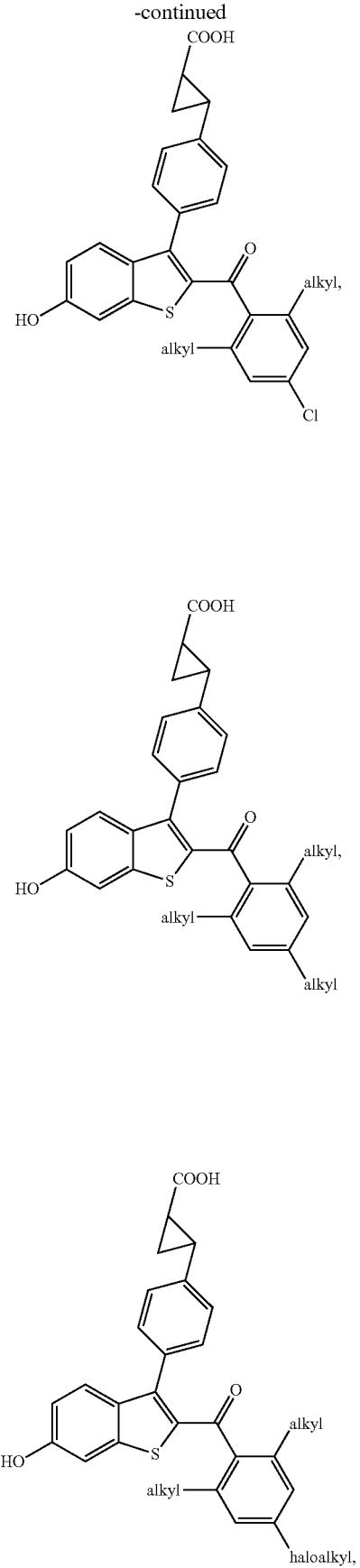

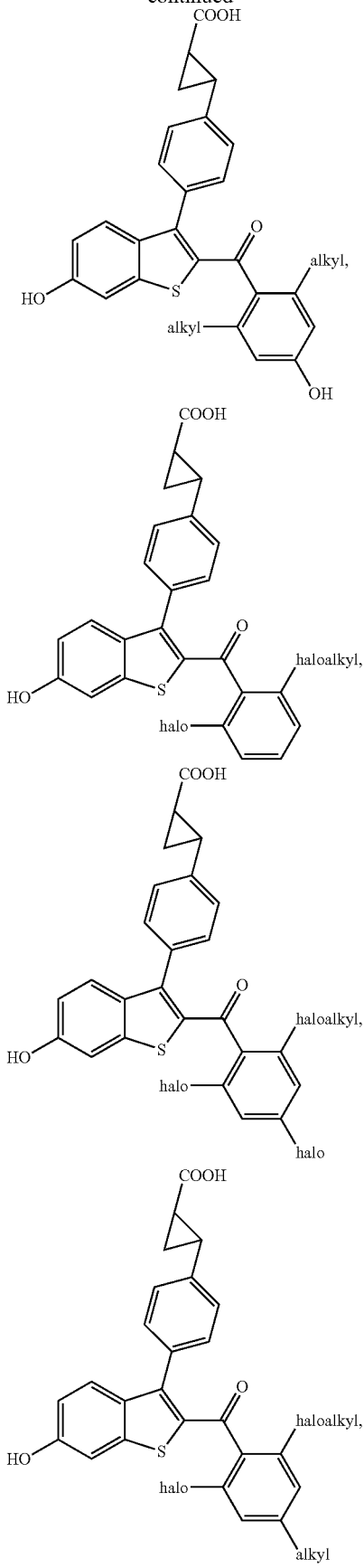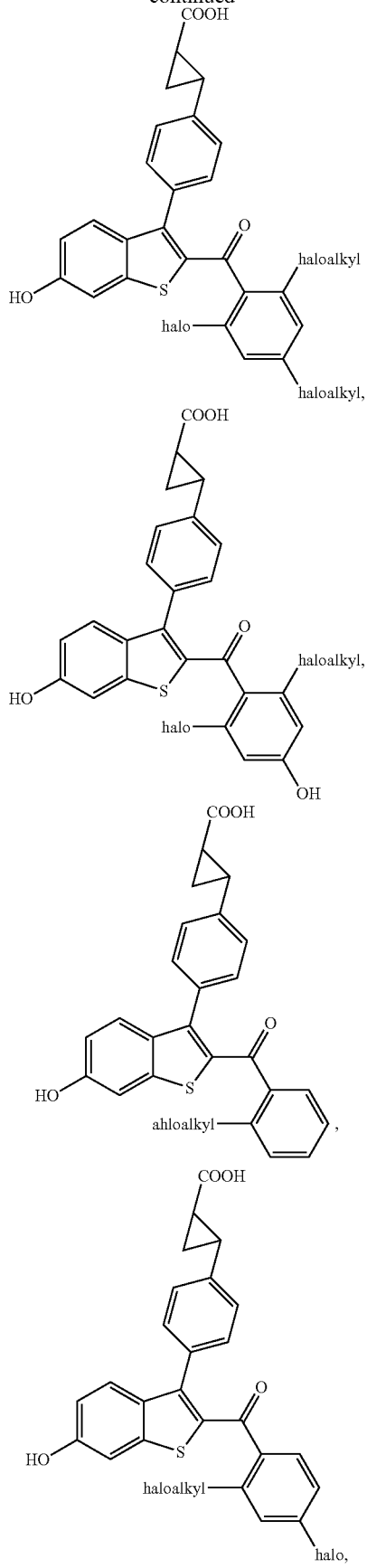

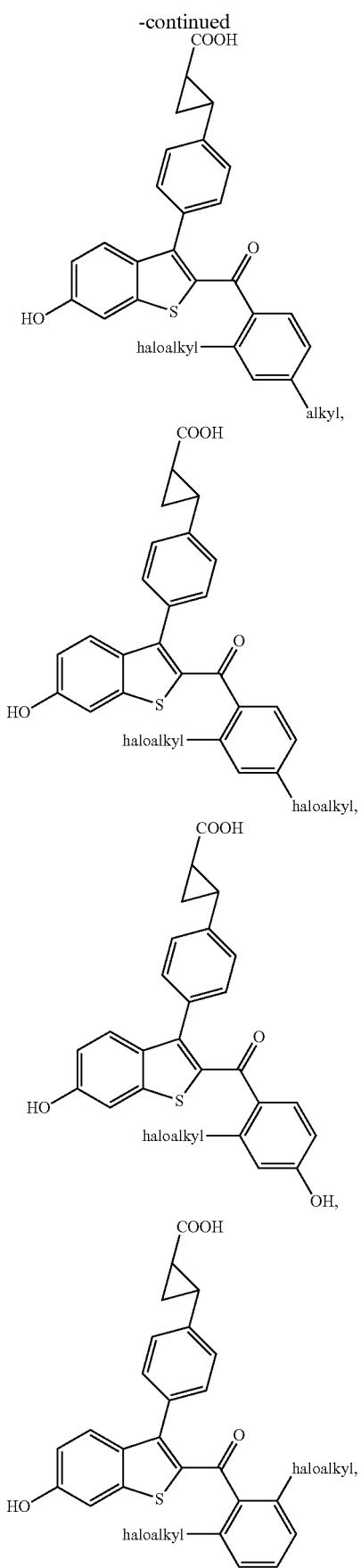
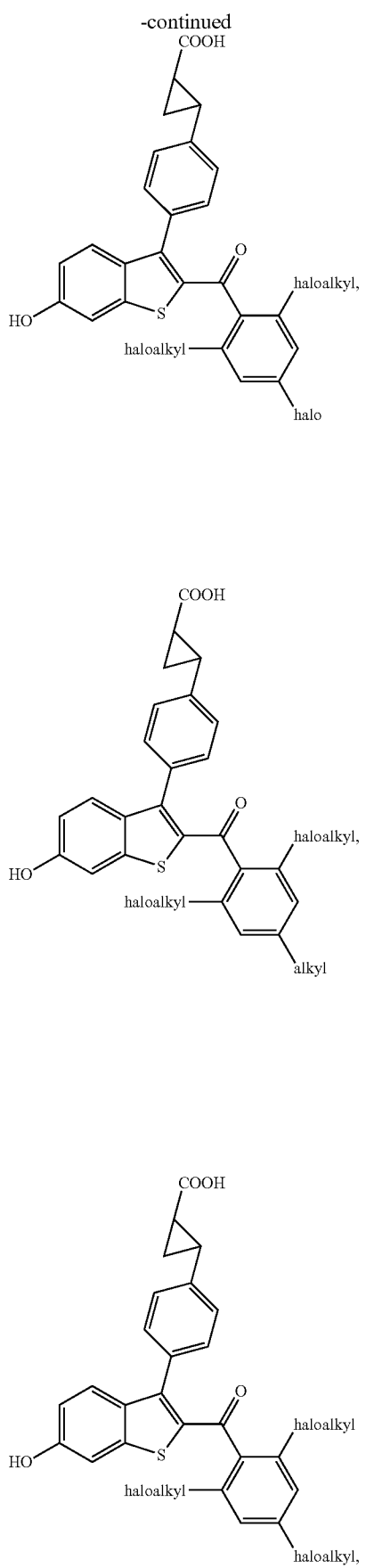

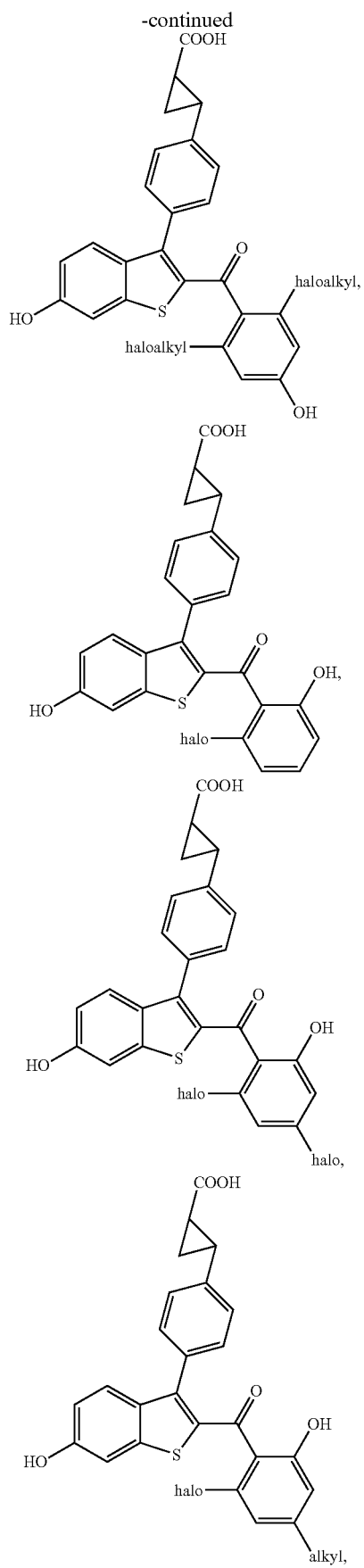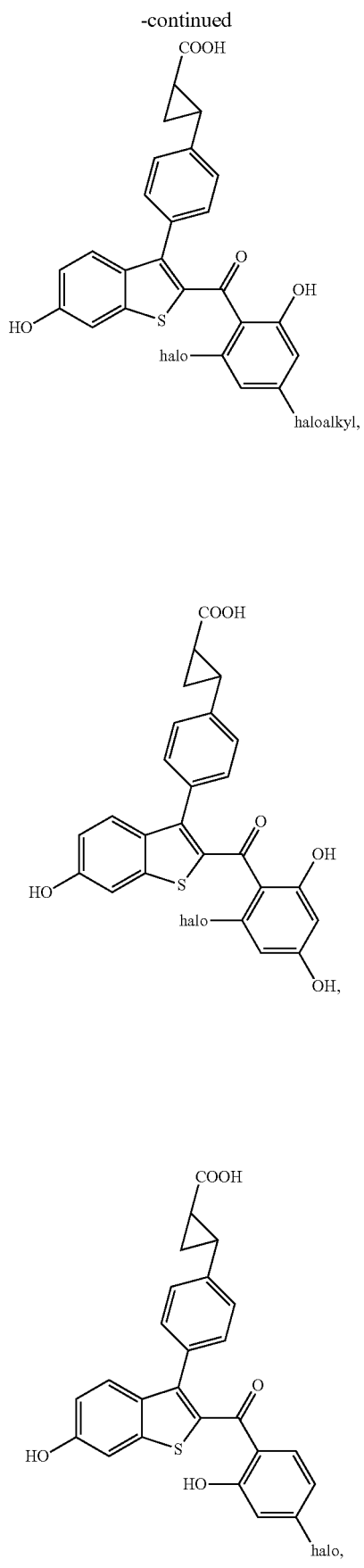

119
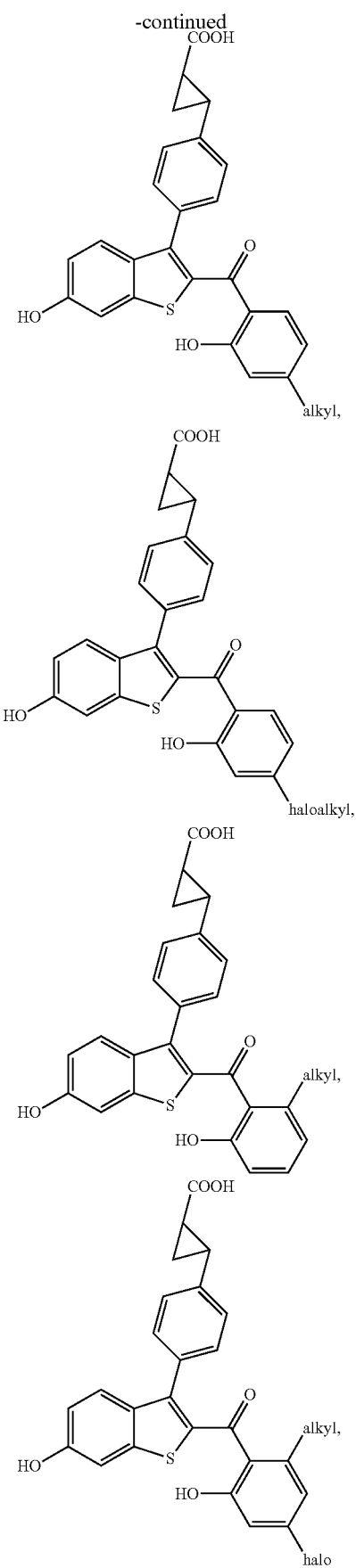
120
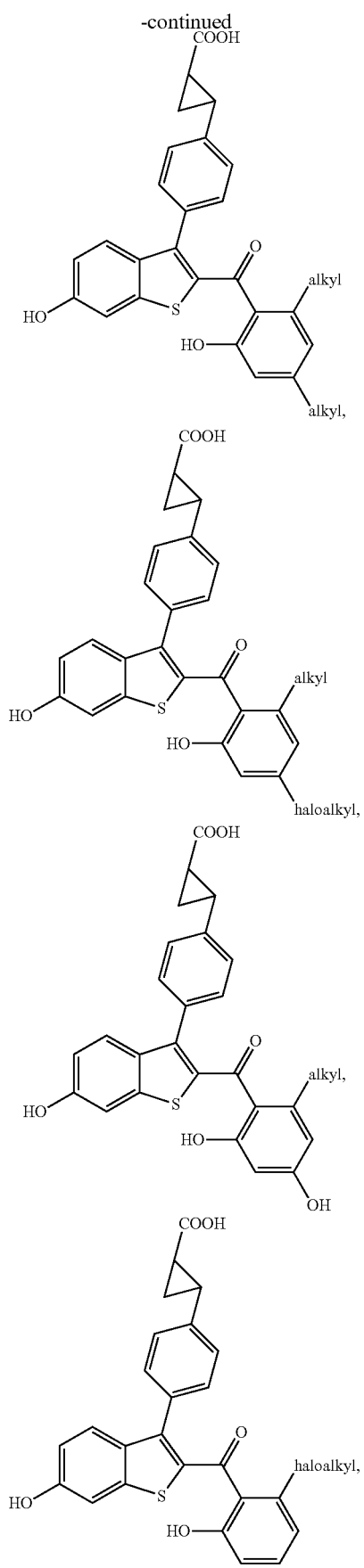

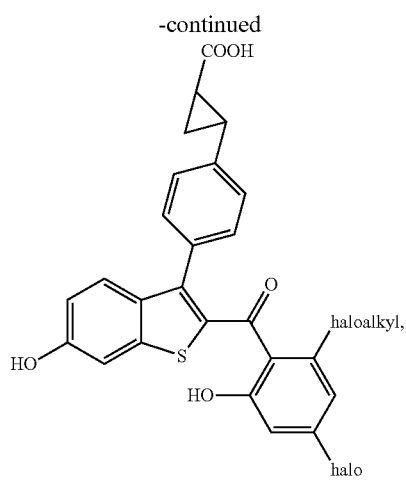
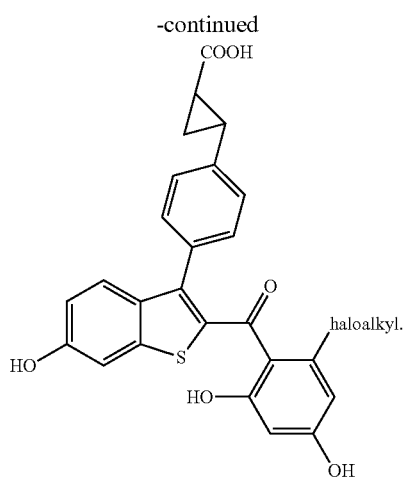
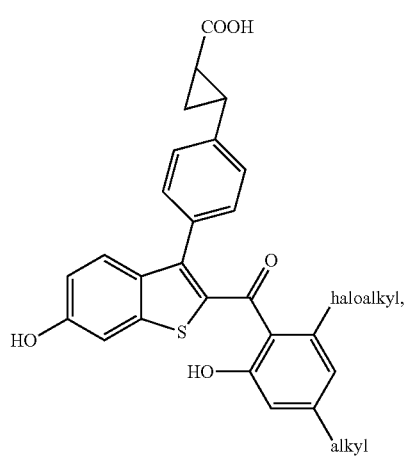
Additional representative compounds of the present invention include, but are not limited to, compounds of formula:
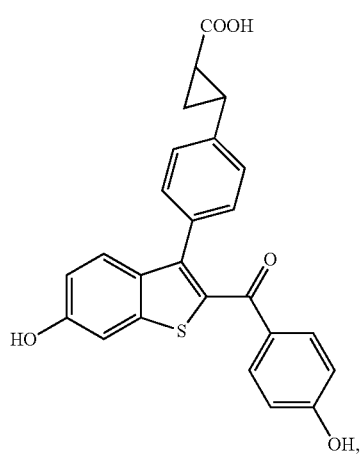
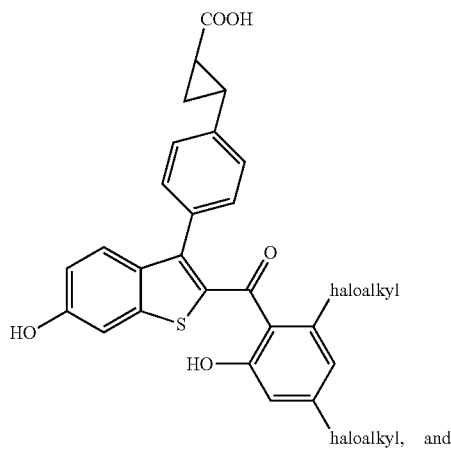
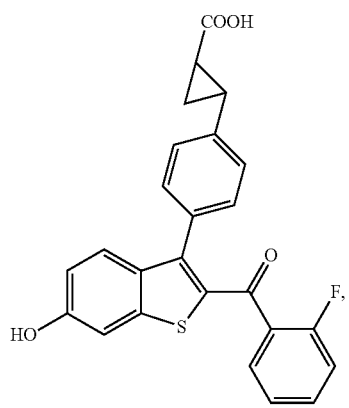

123
-continued
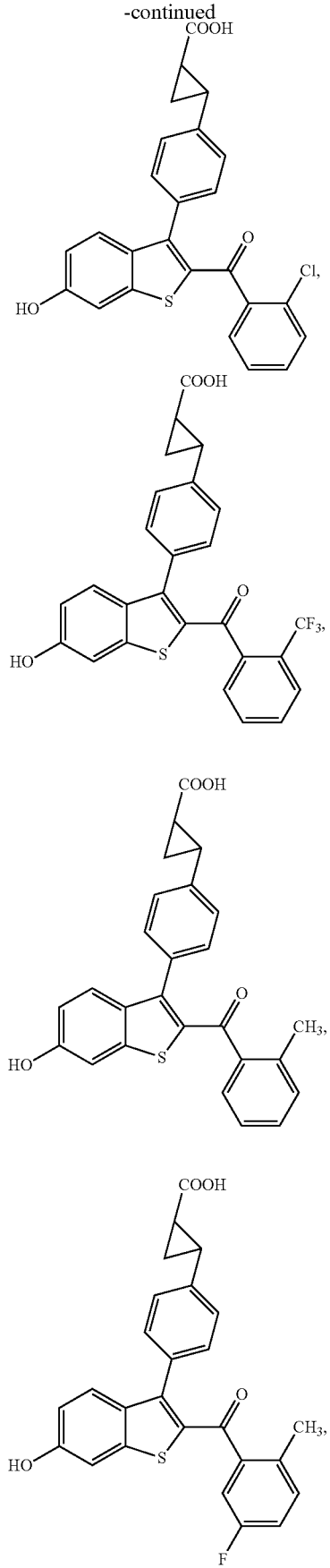
124
-continued
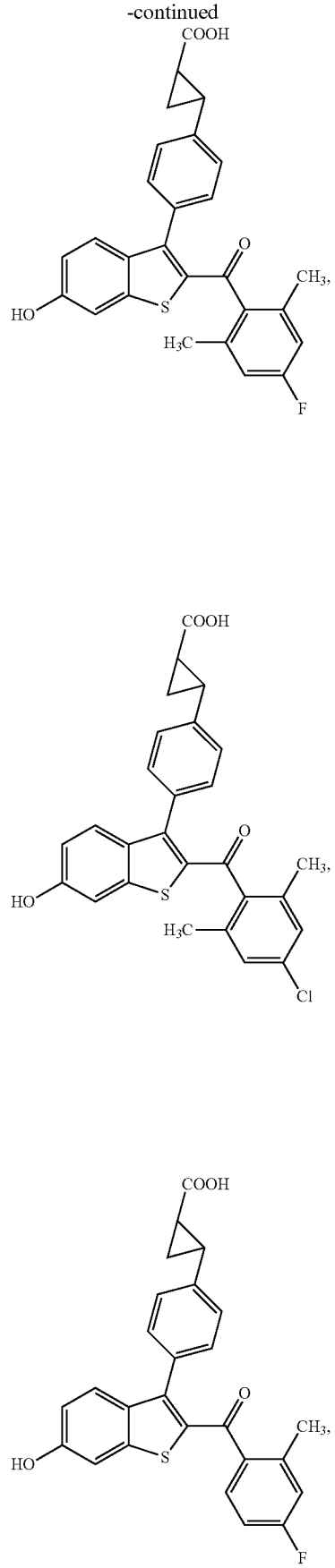

125
-continued
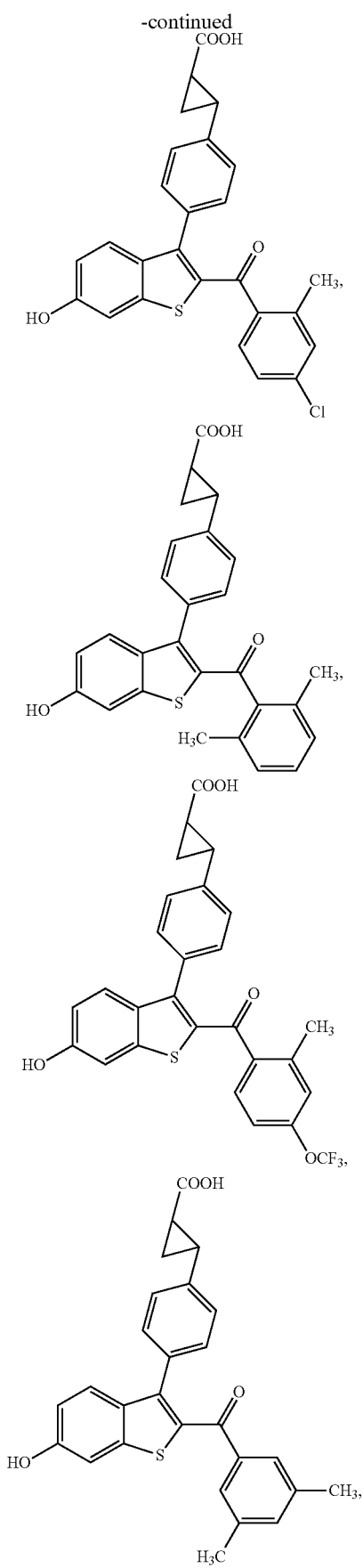
126
-continued
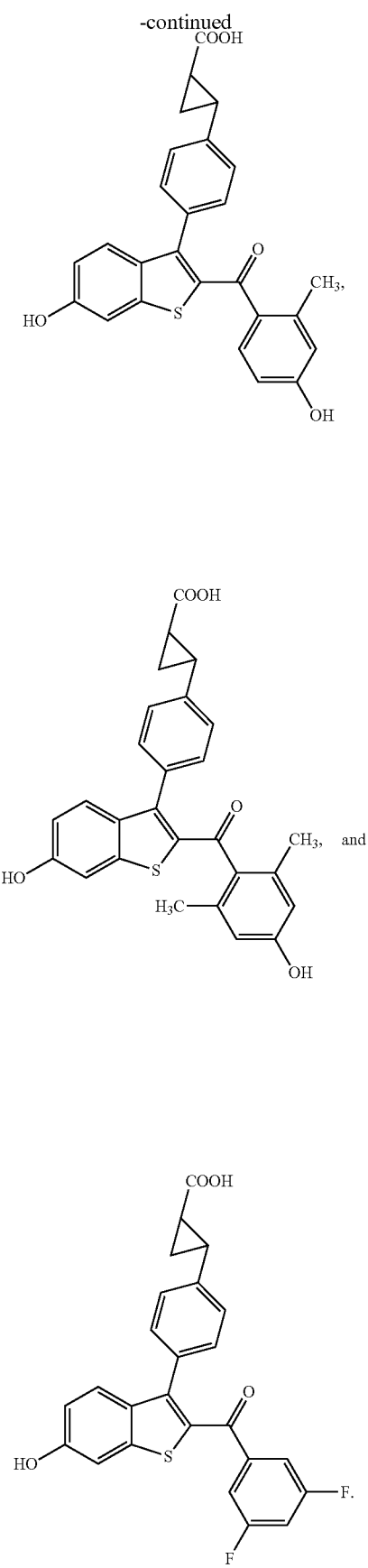

Additional non-limiting examples of the present invention of include:
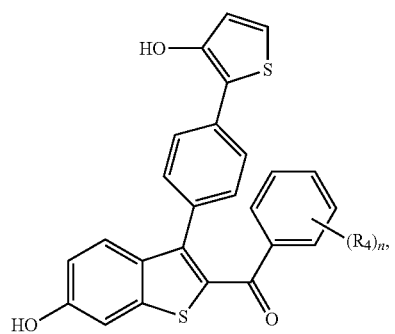
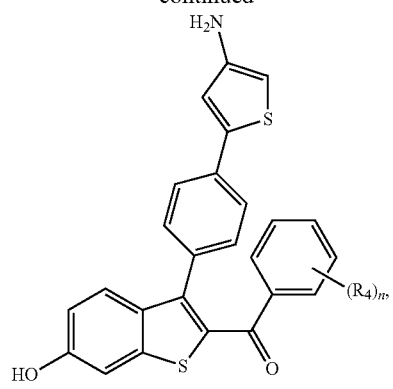
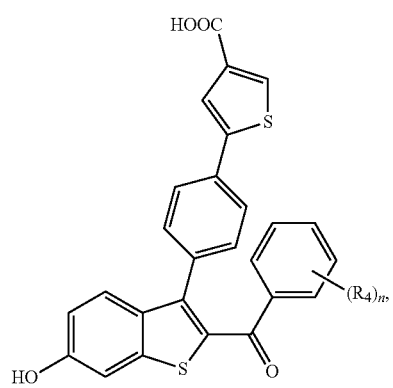
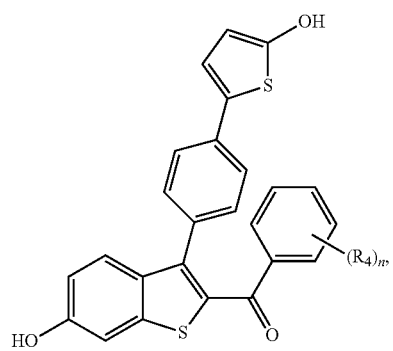
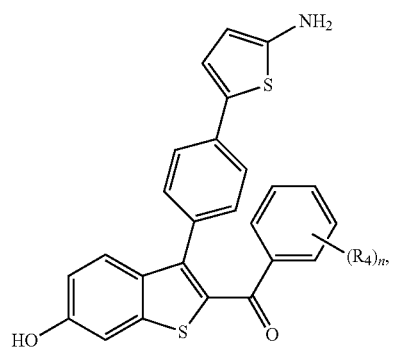

129
-continued
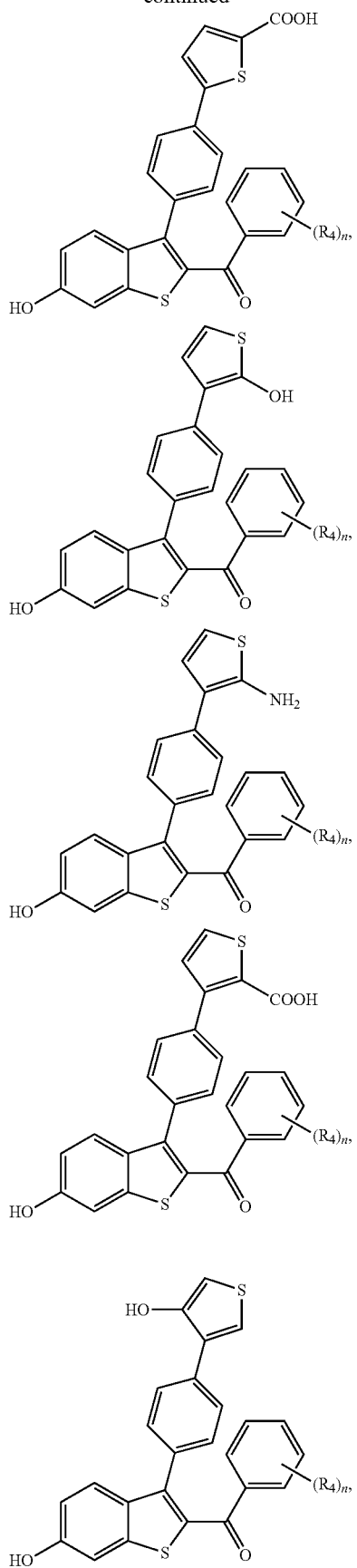
130
-continued
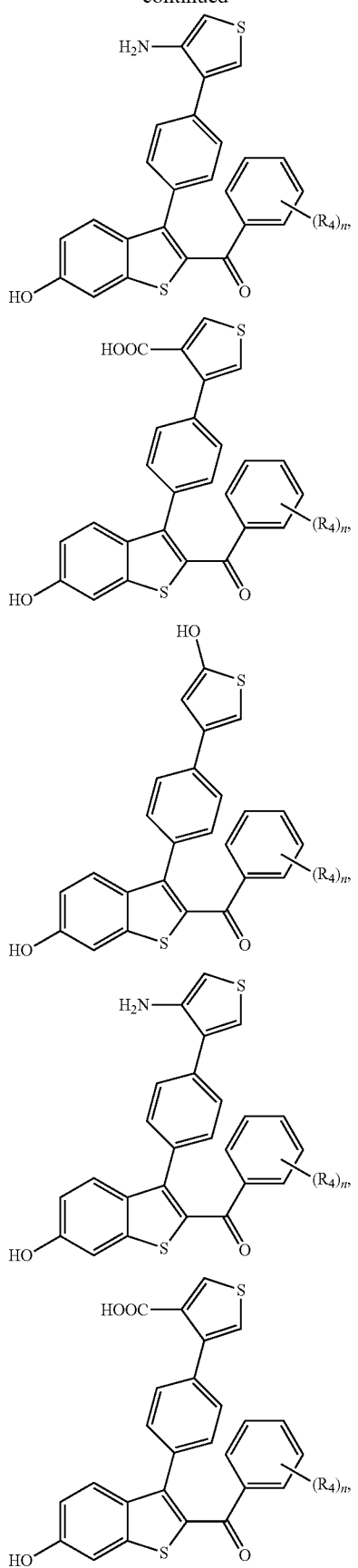

-continued
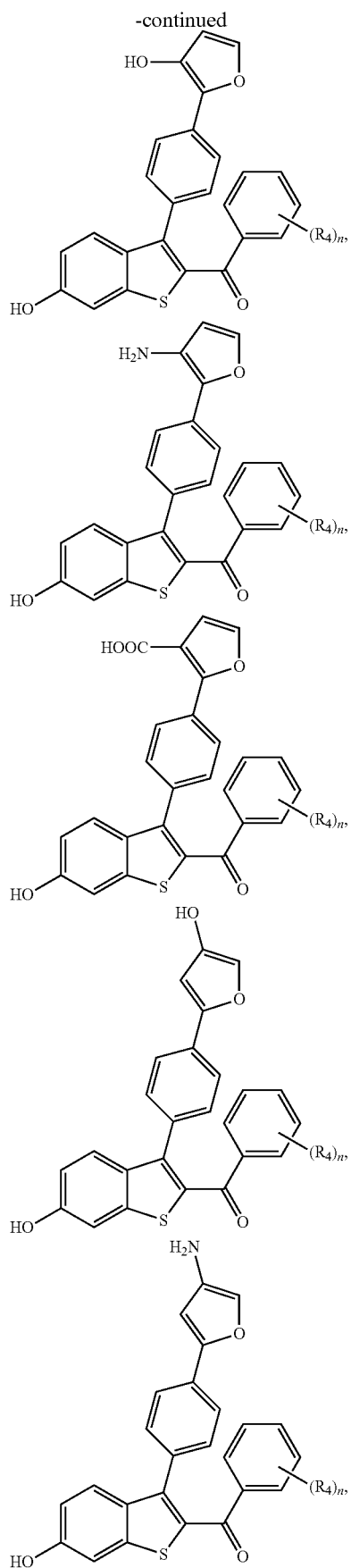
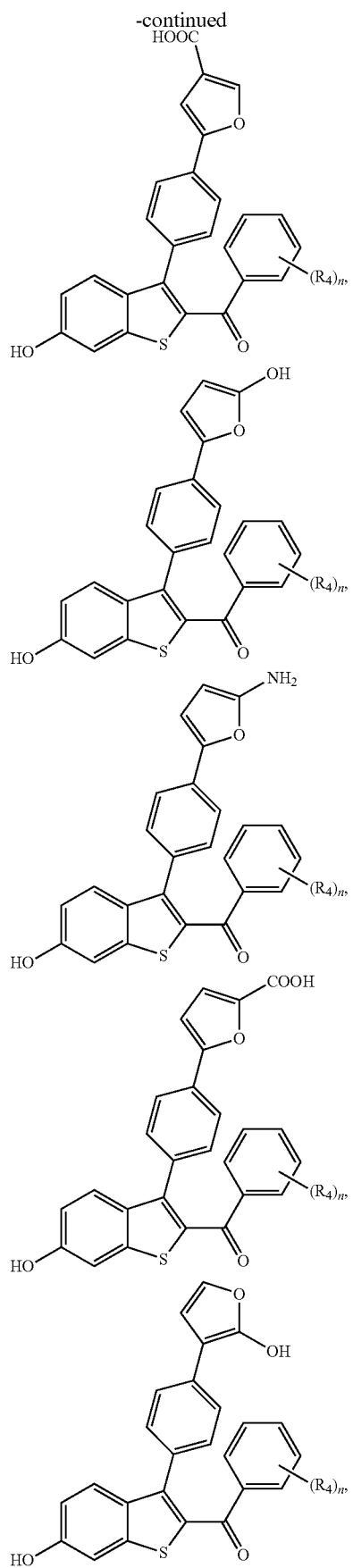

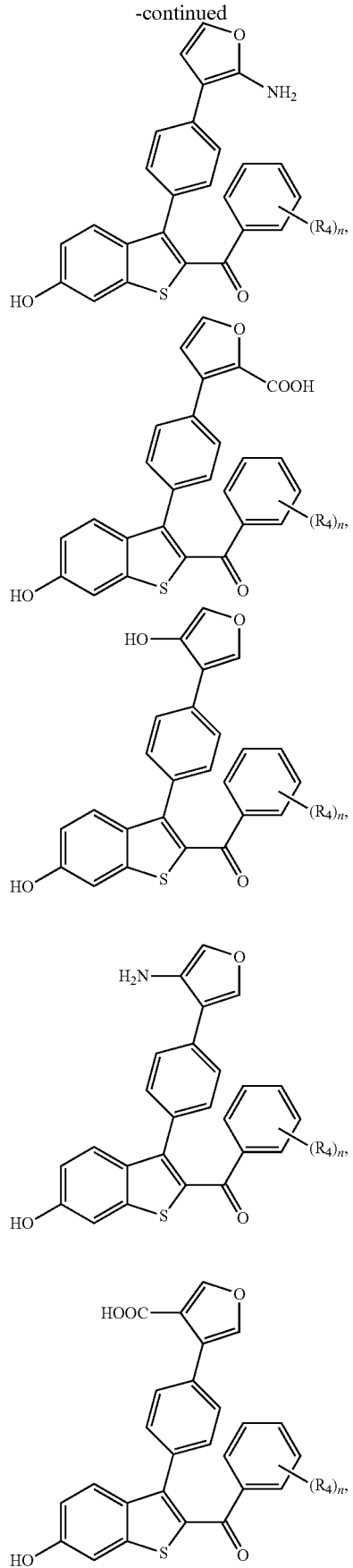
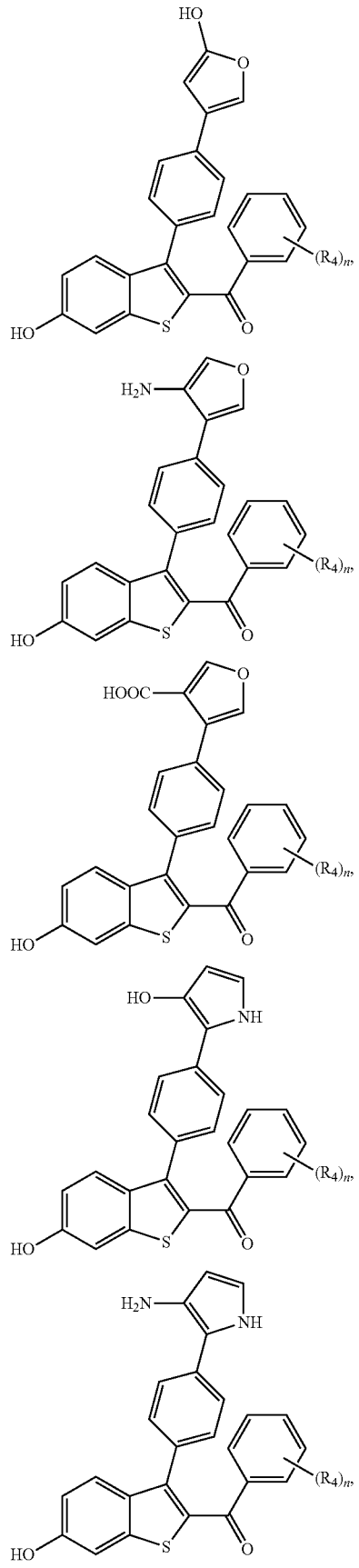

-continued
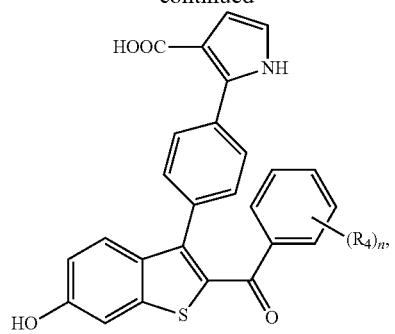
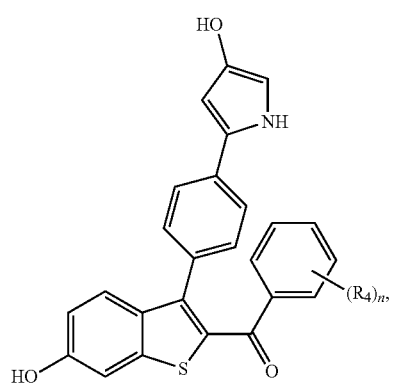
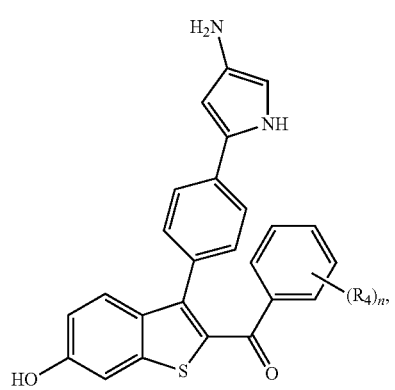
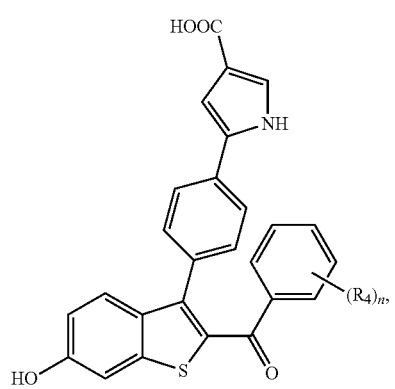
-continued
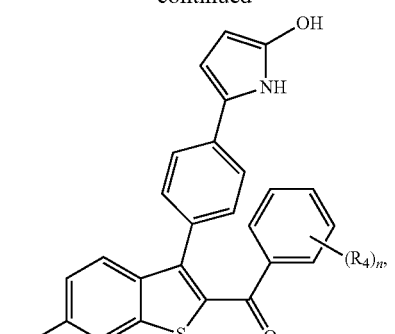
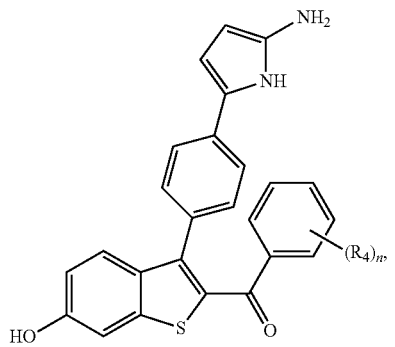
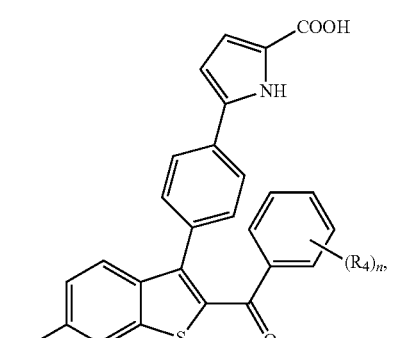
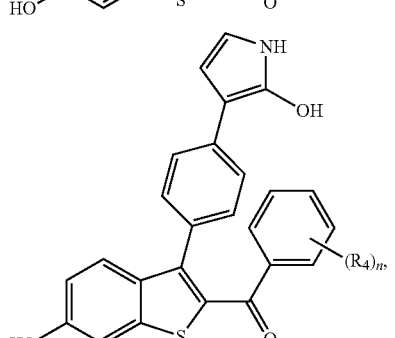
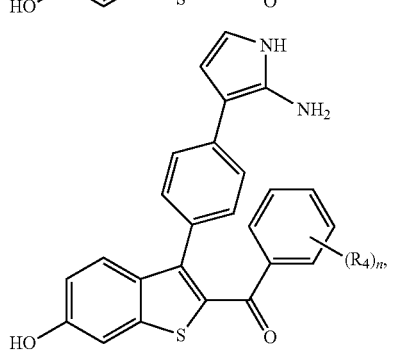

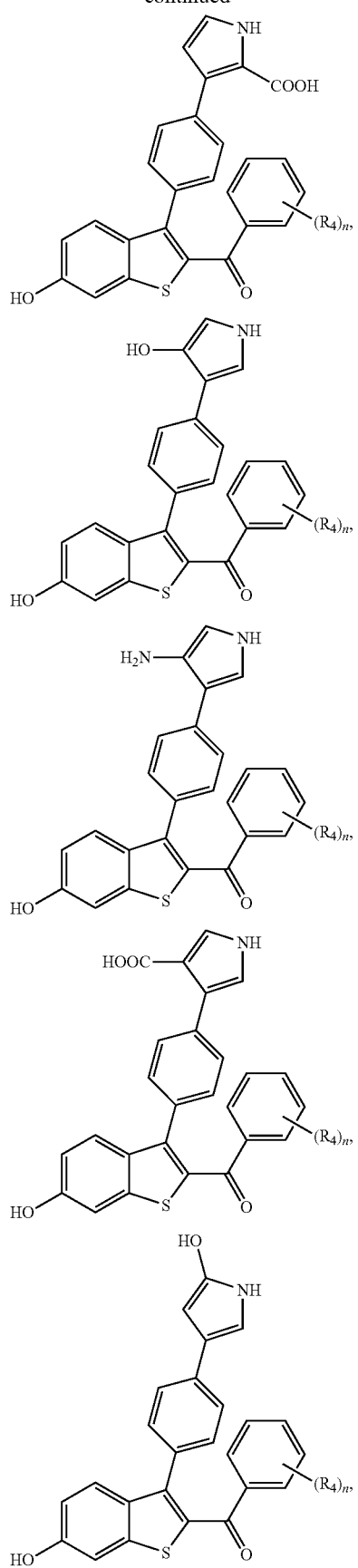
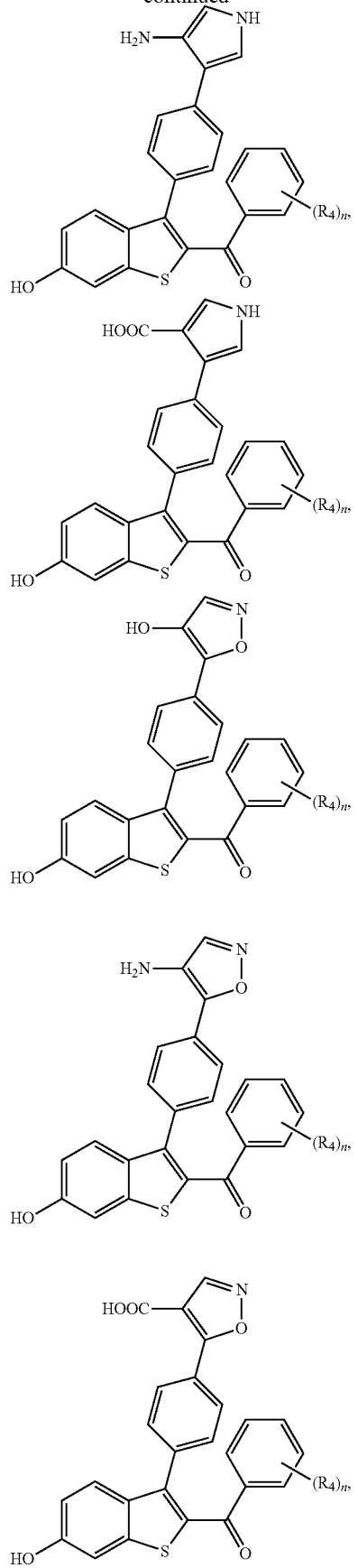

139
-continued
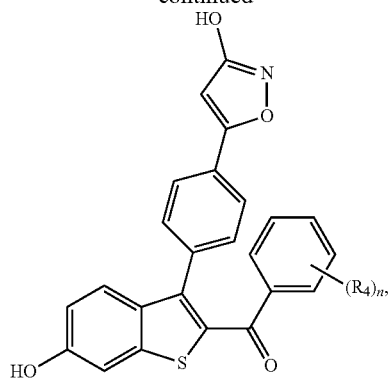
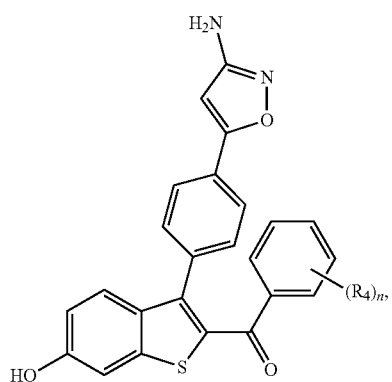
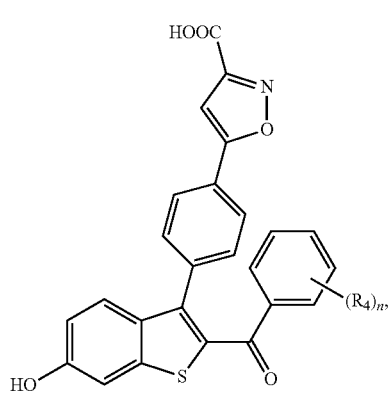
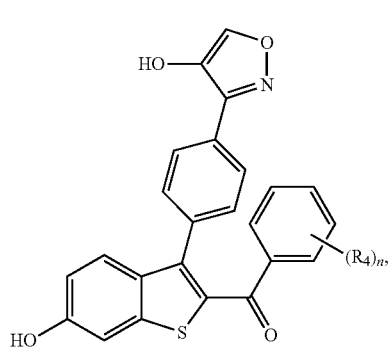
140
-continued
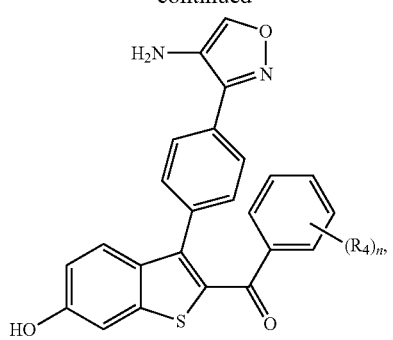
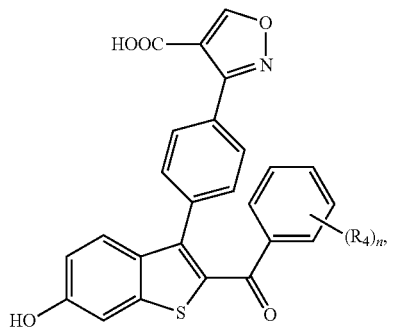
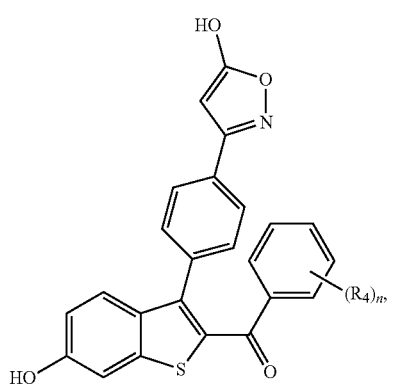
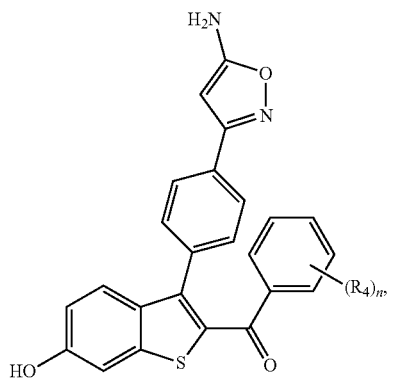

141
-continued
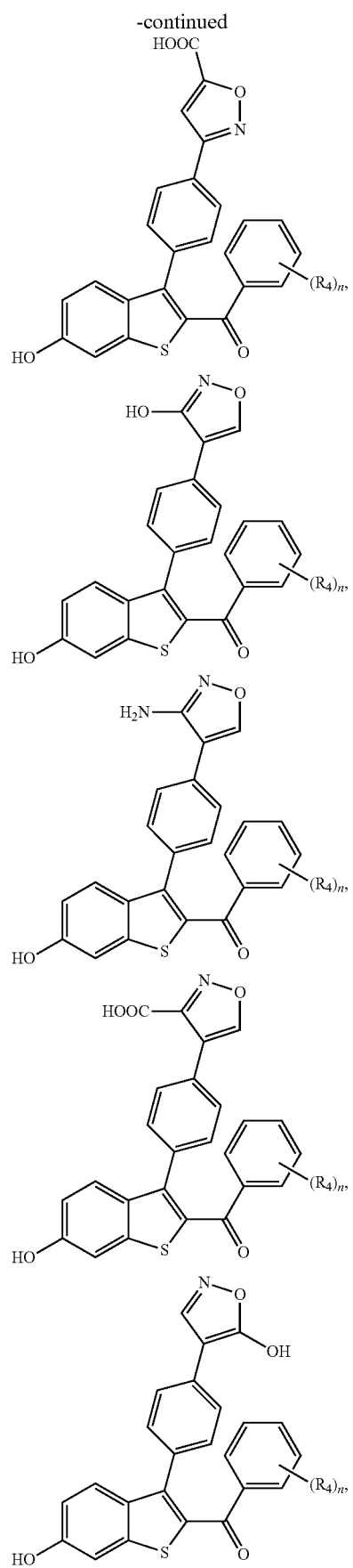
142
-continued
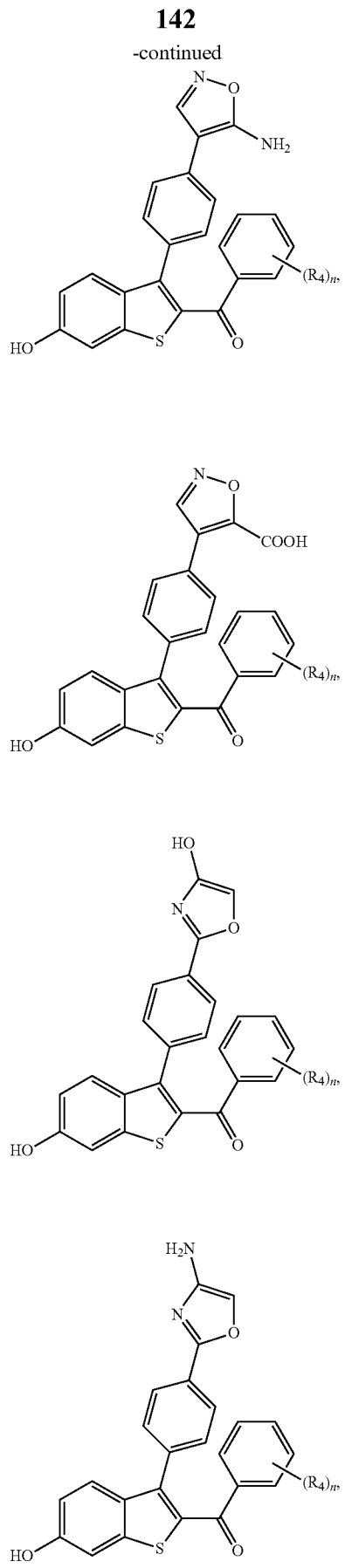

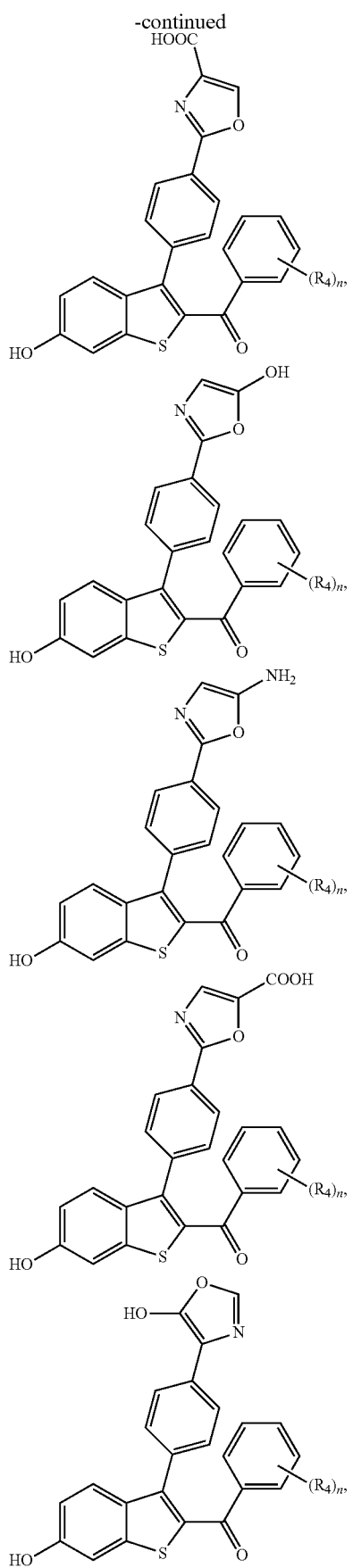
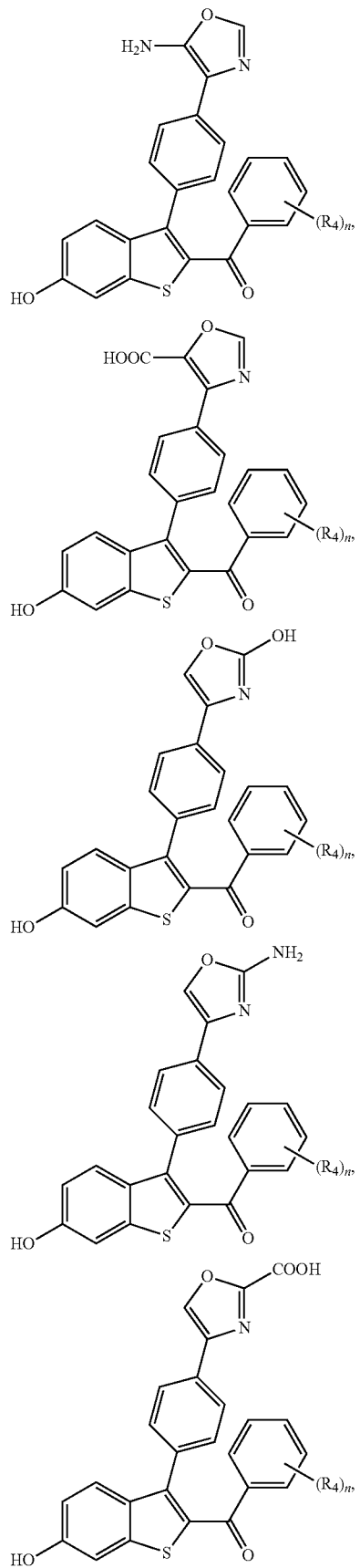

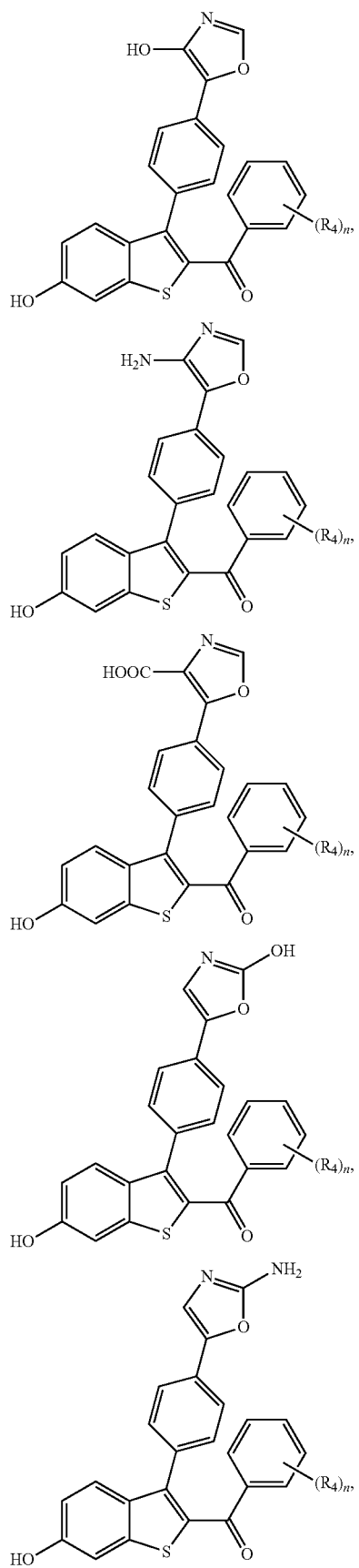
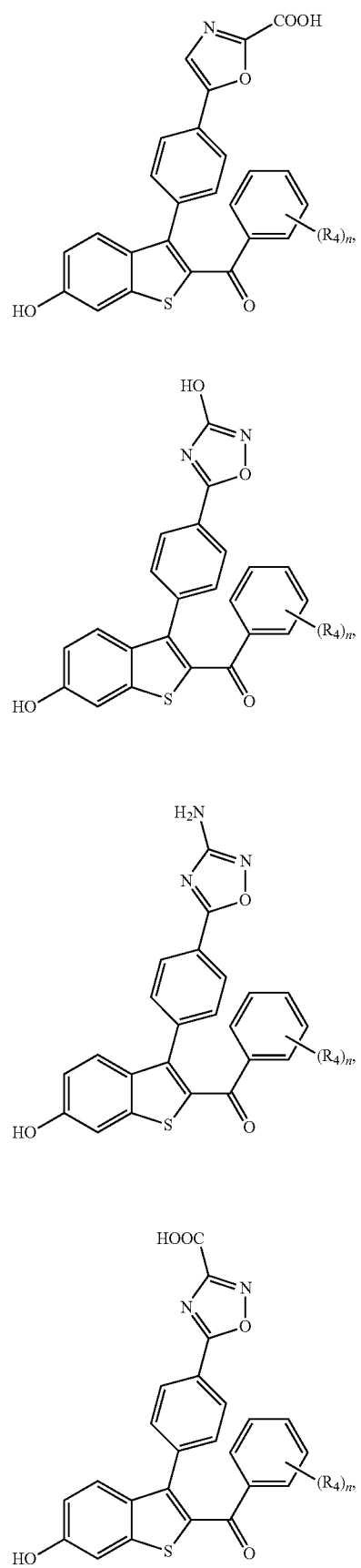

147
-continued
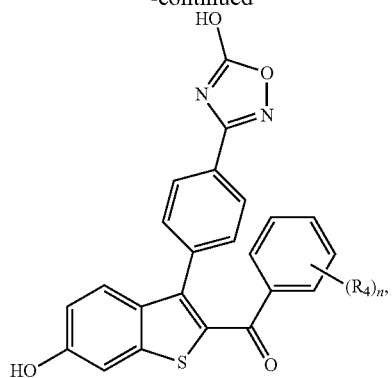
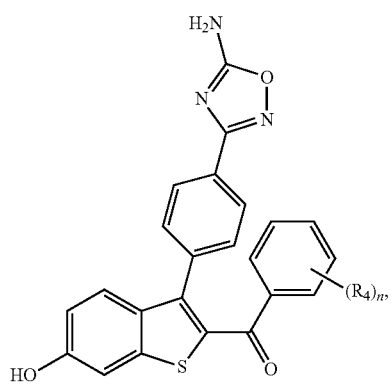
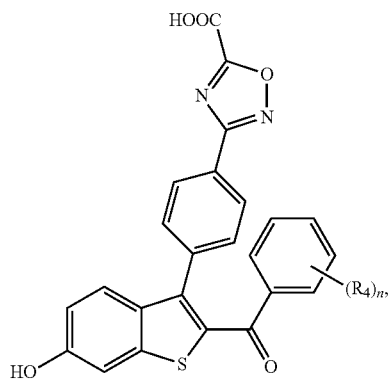
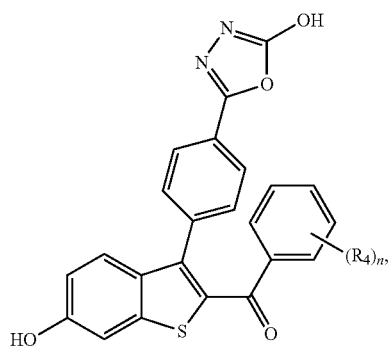
148
-continued
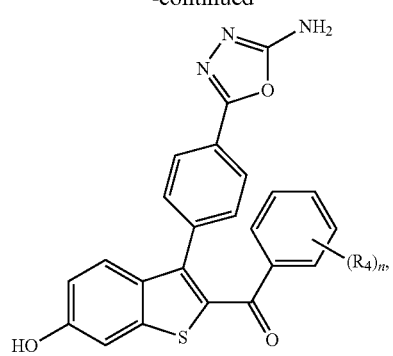
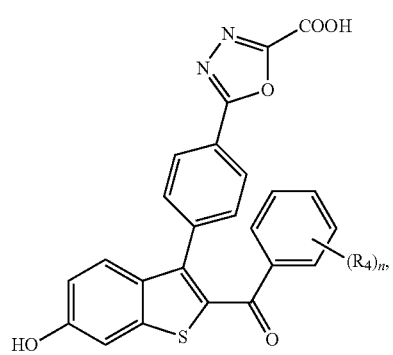
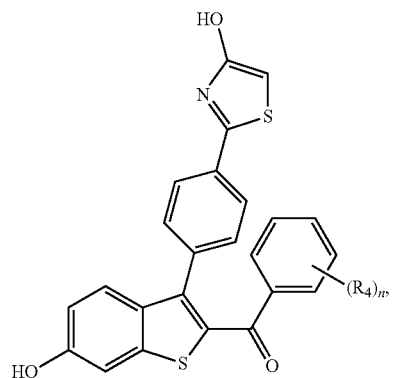
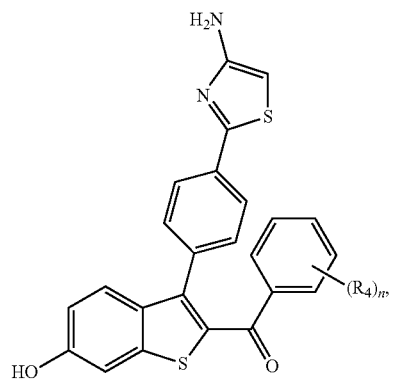

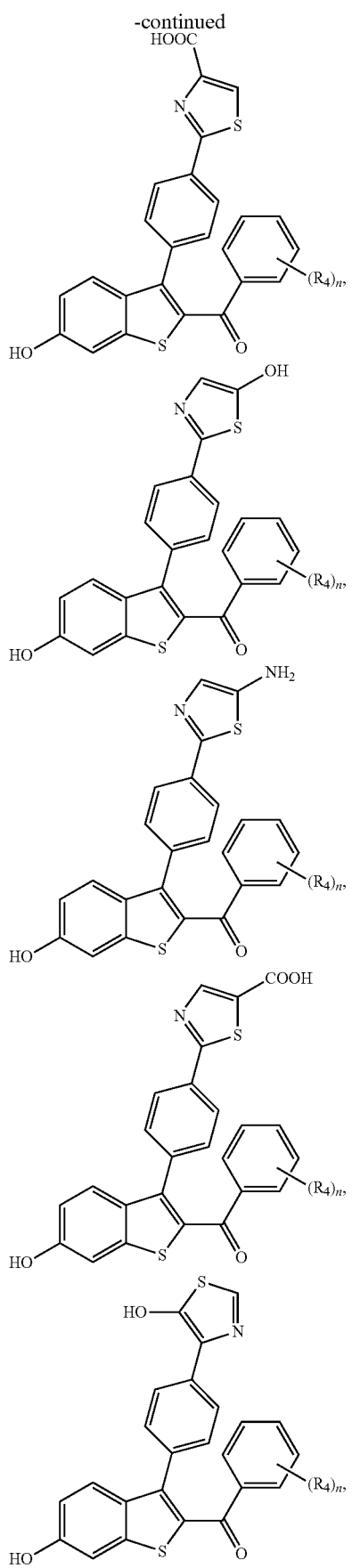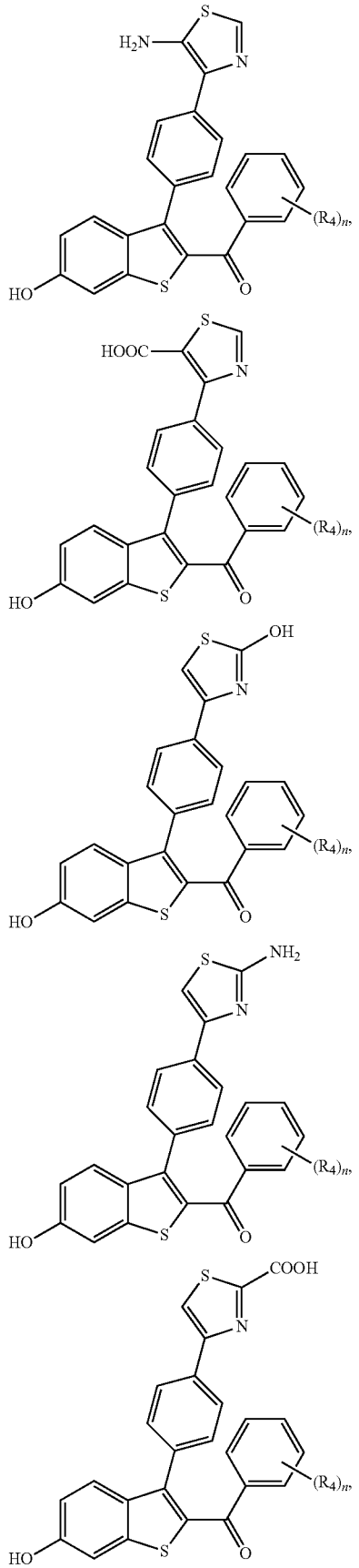

151
-continued
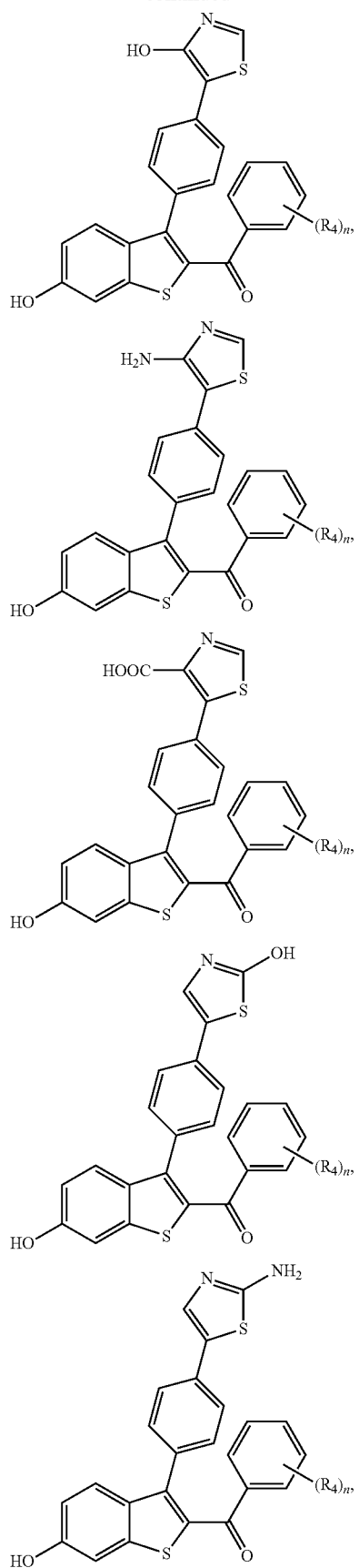
152
-continued
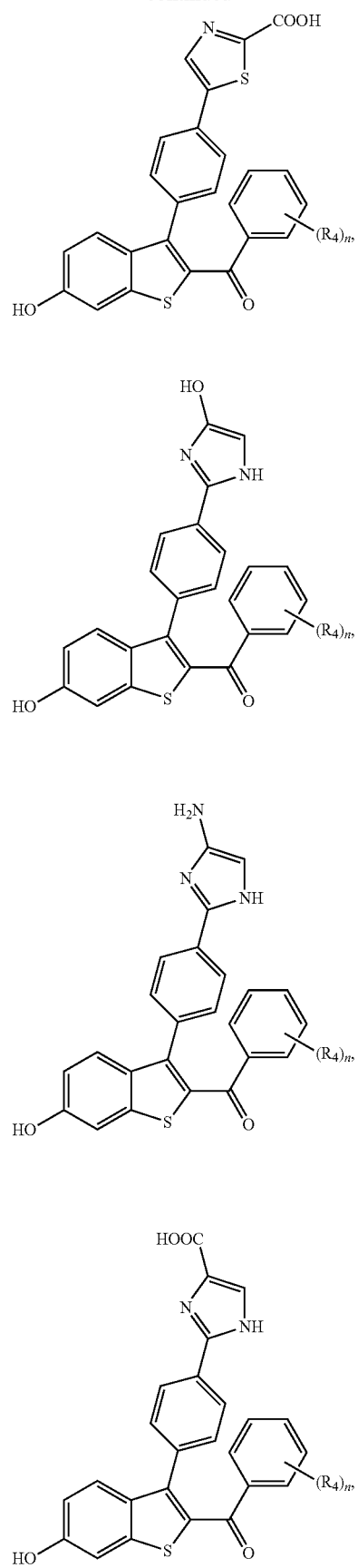

153
-continued
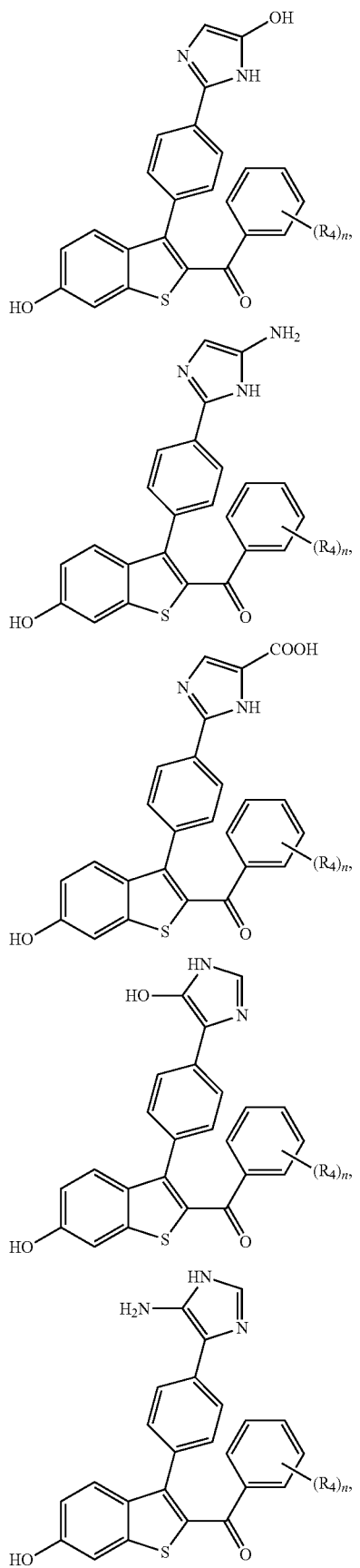
154
-continued
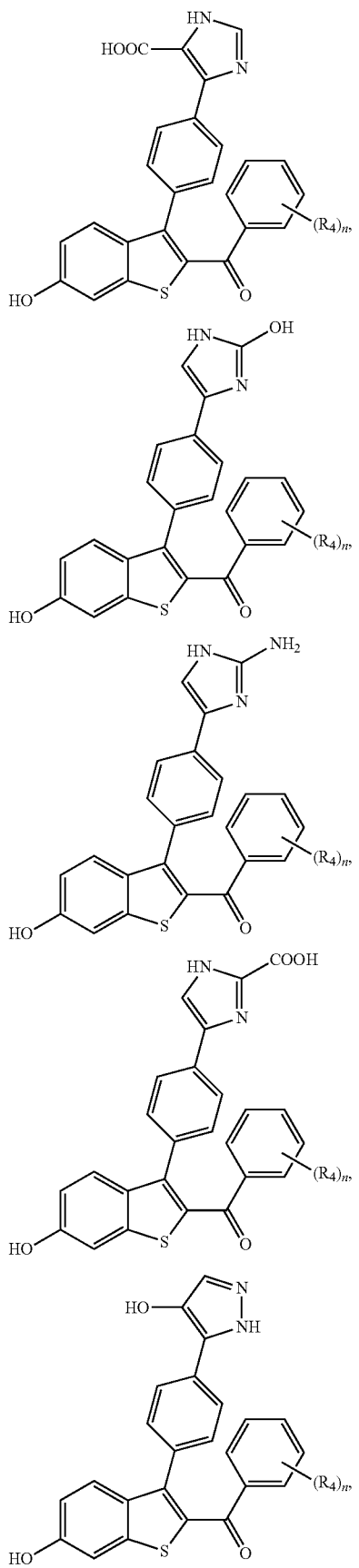

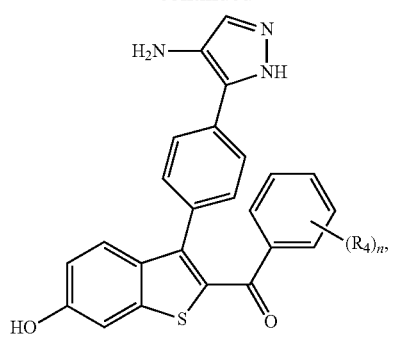
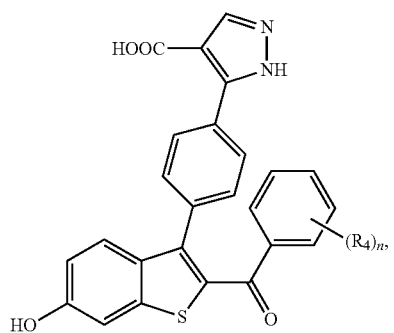
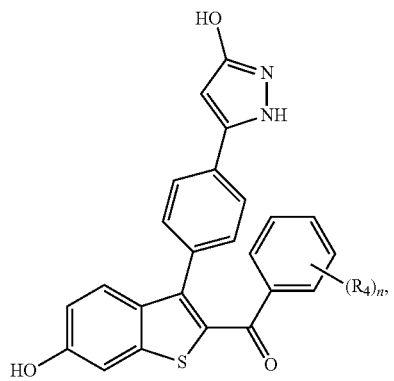
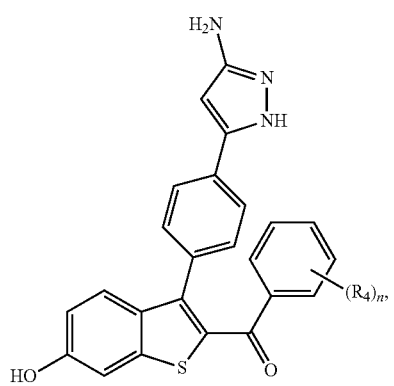
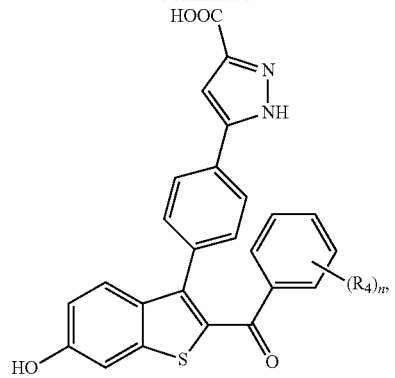
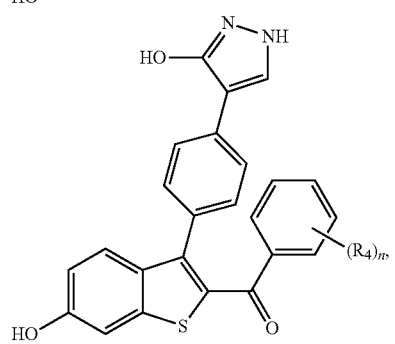
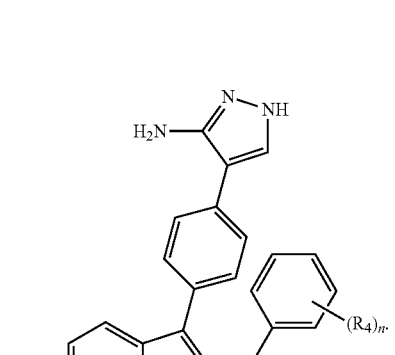
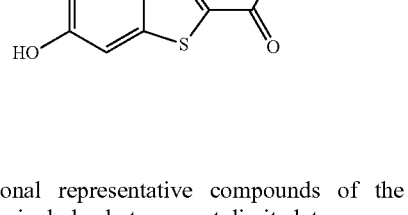
Additional representative compounds of the present invention include, but are not limited to, compounds of formula:

157
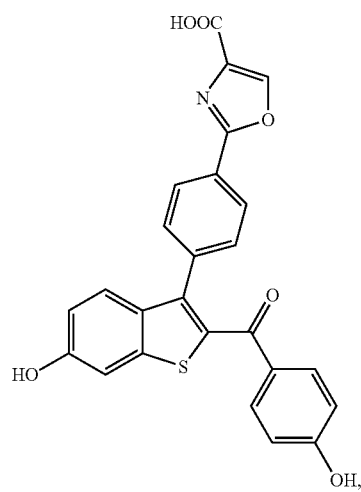
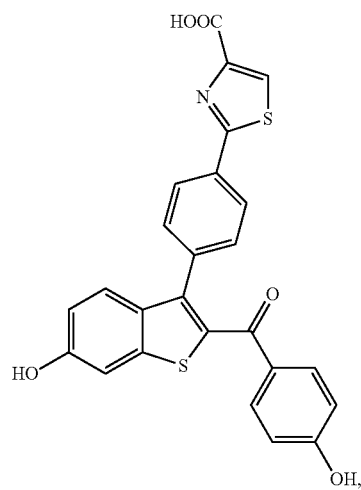
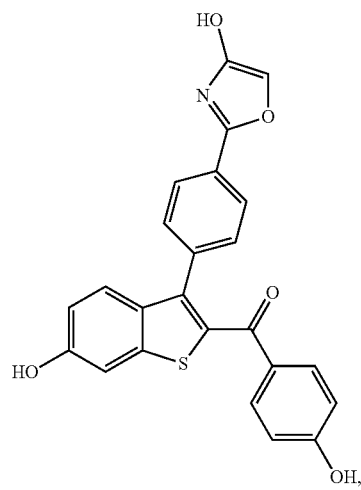
158
-continued
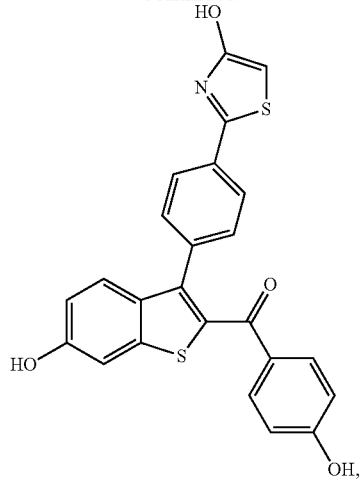
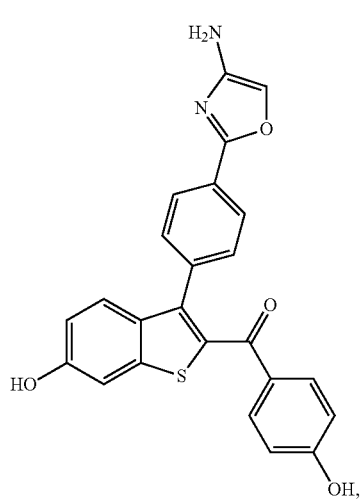
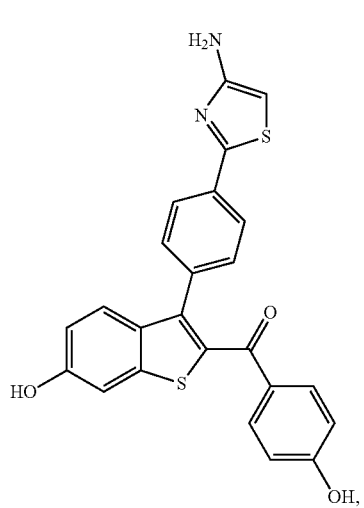

159
-continued
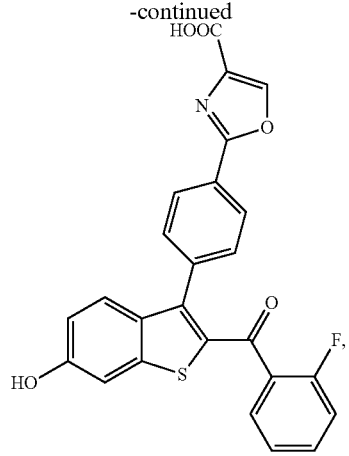
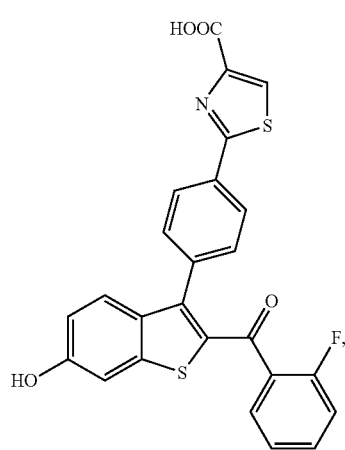
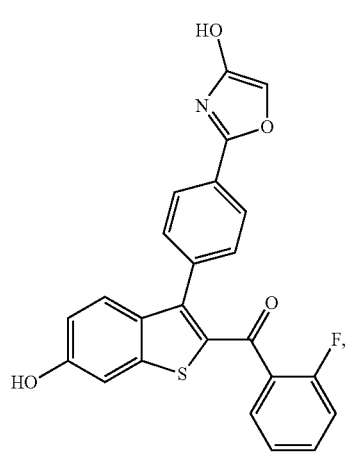
160
-continued
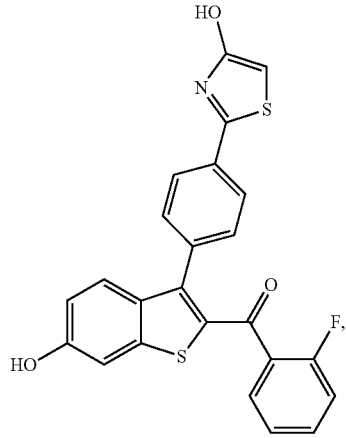
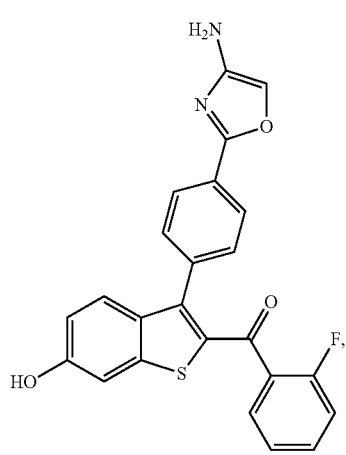
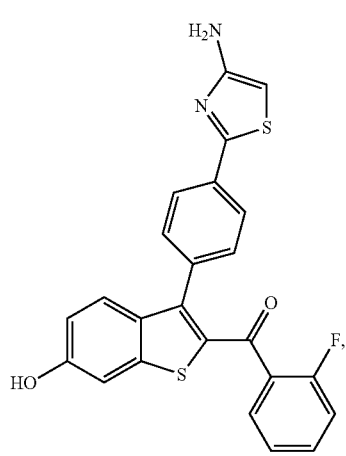

161
-continued
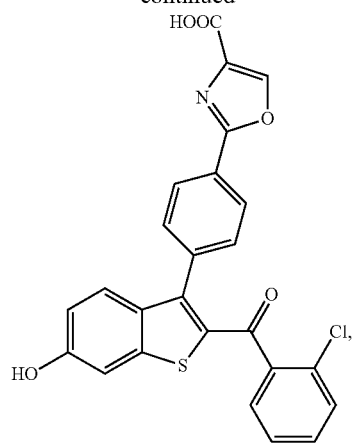
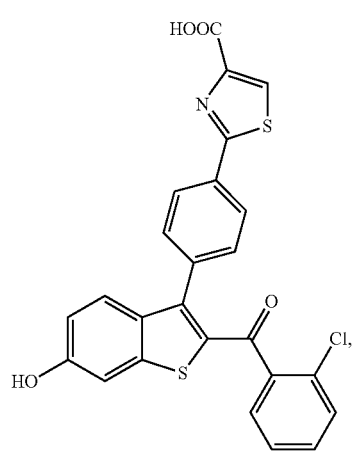
162
-continued
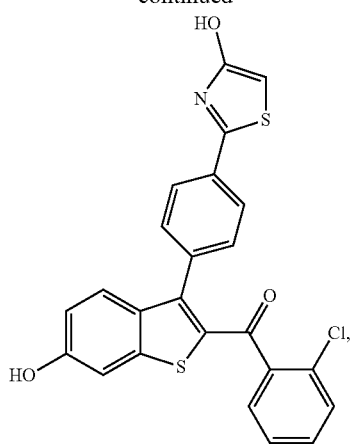
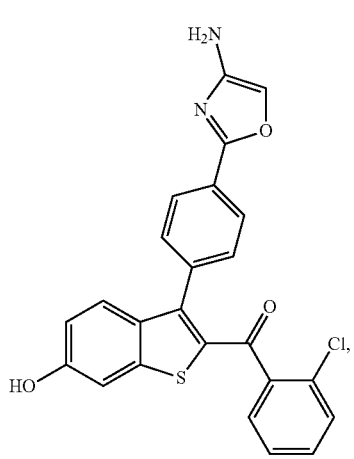
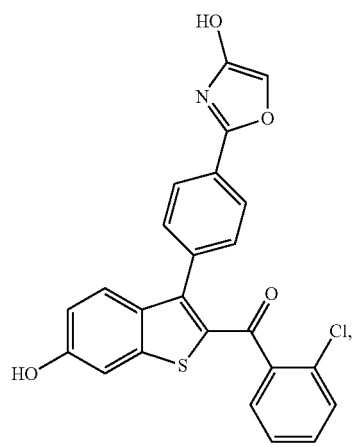
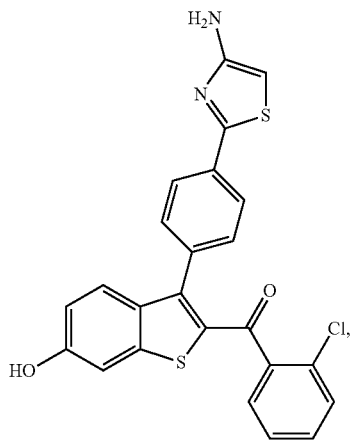

163
-continued
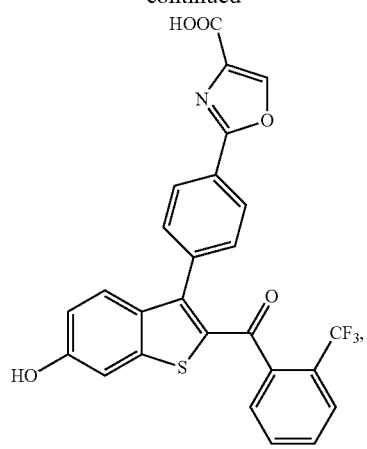
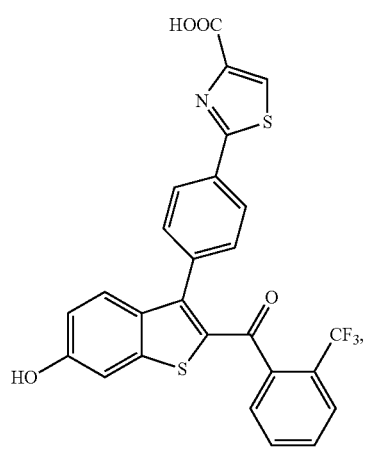
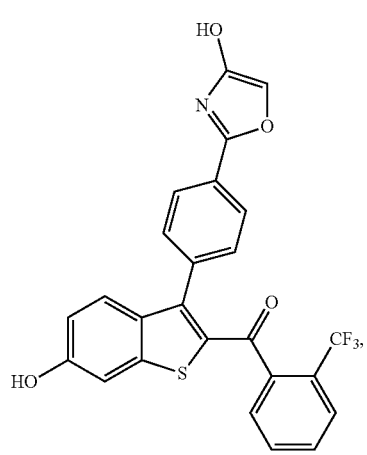
164
-continued
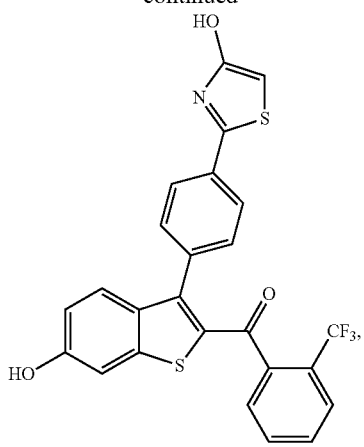
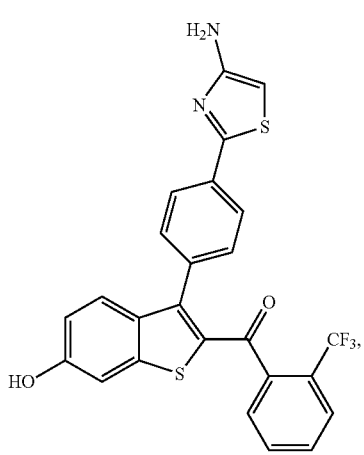

165
-continued
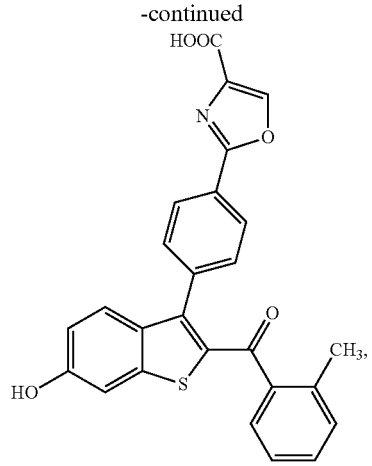
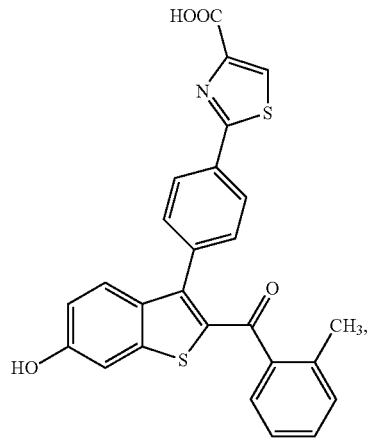
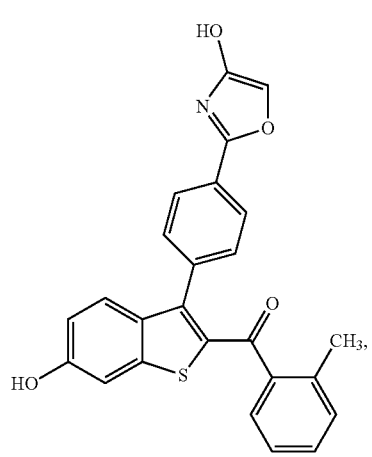
166
-continued
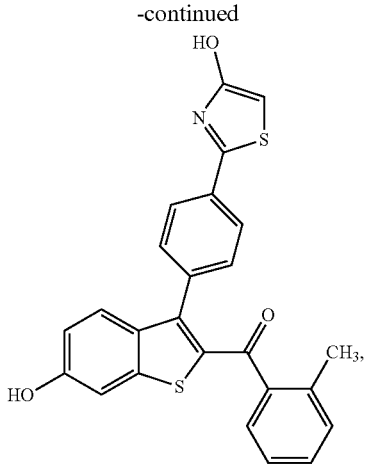
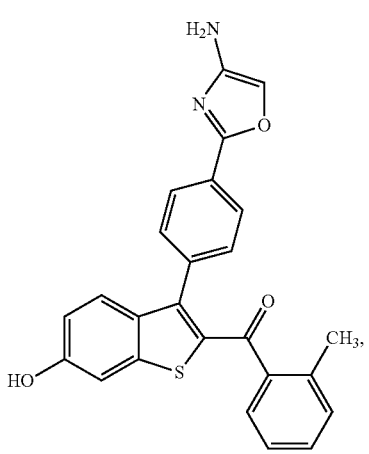
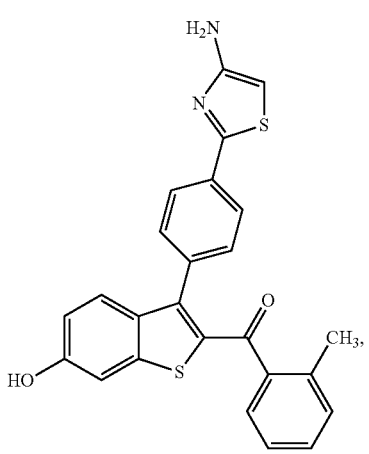

167
-continued
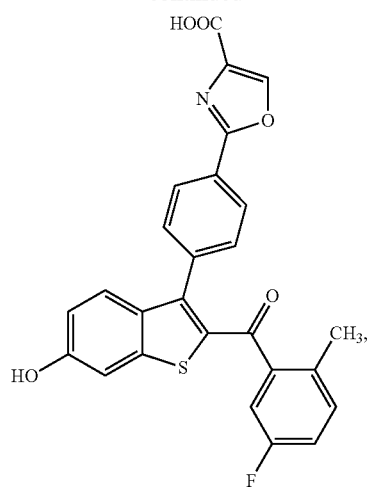
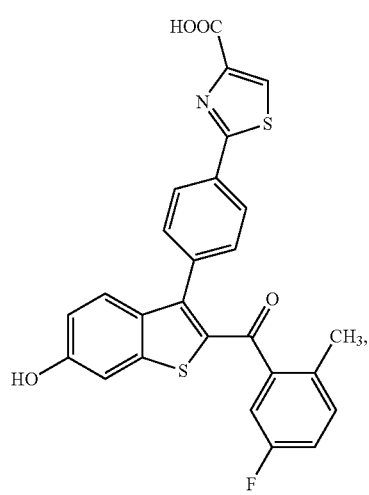
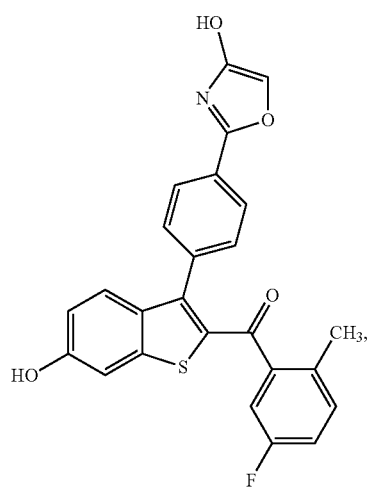
168
-continued
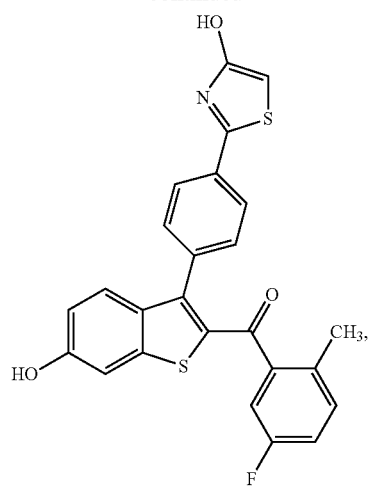
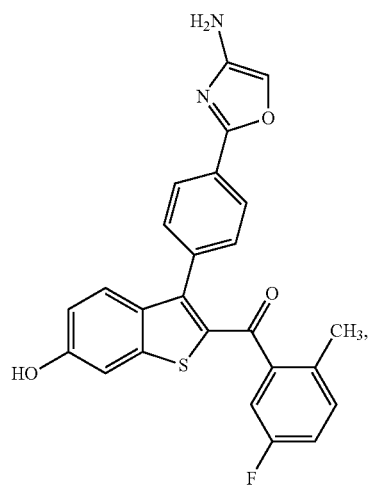
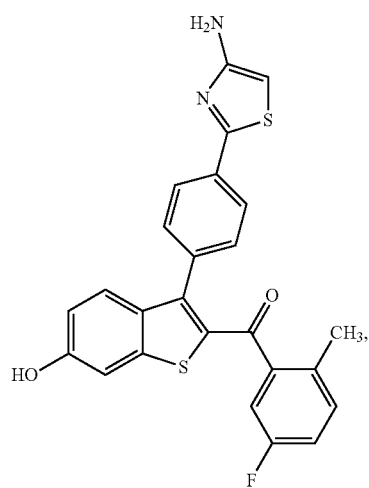

169
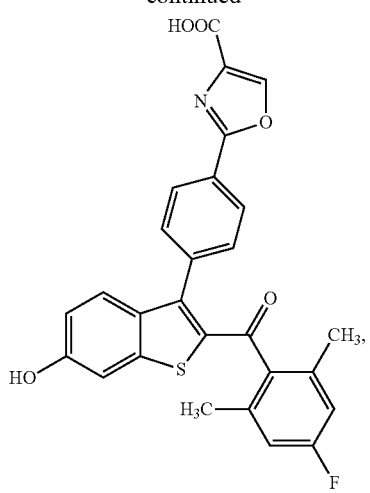
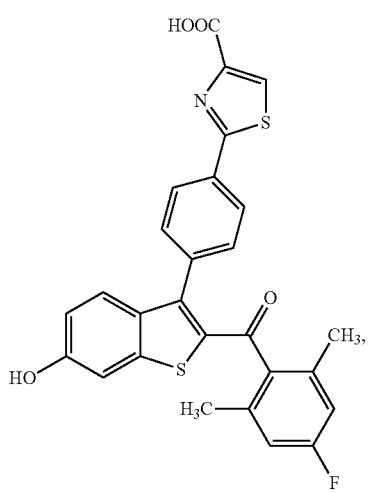
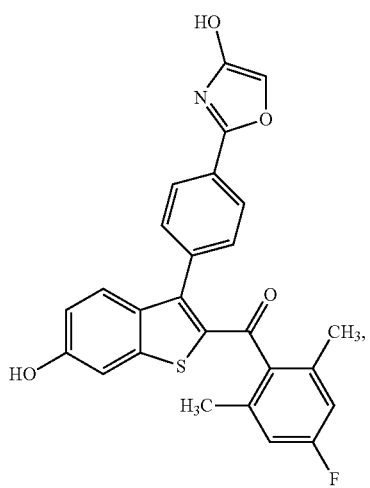
170
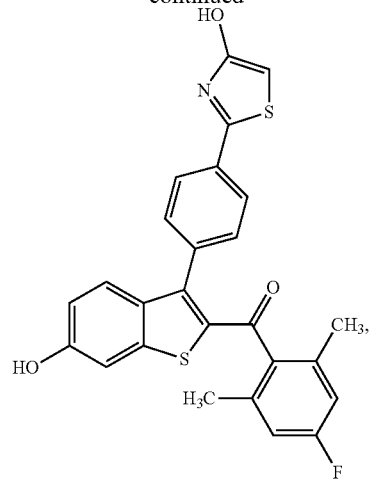
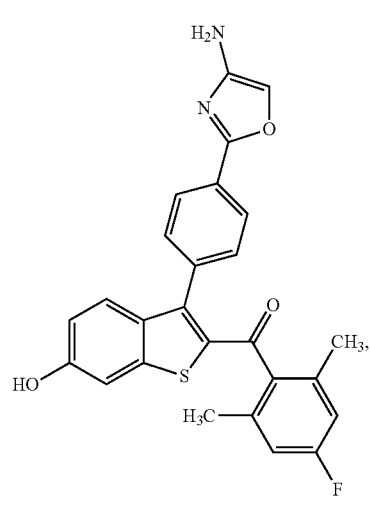
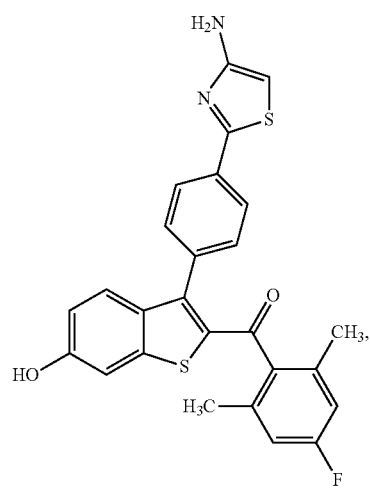

171
-continued
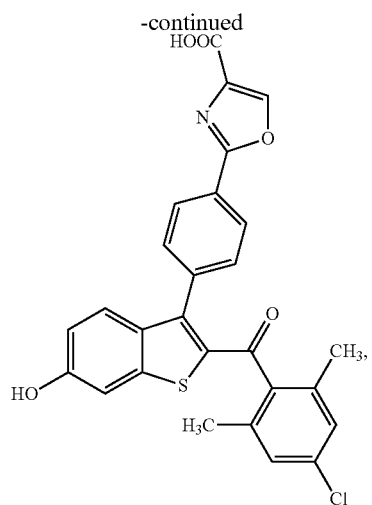
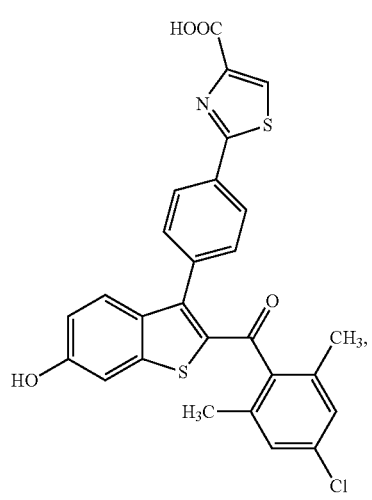
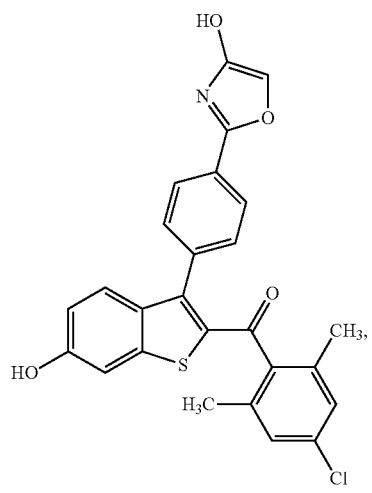
172
-continued
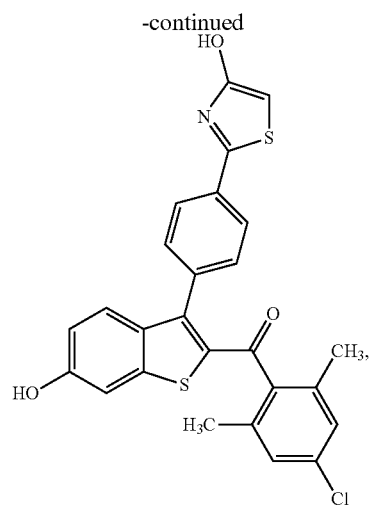
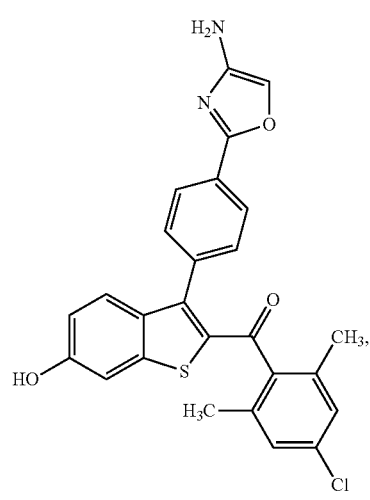
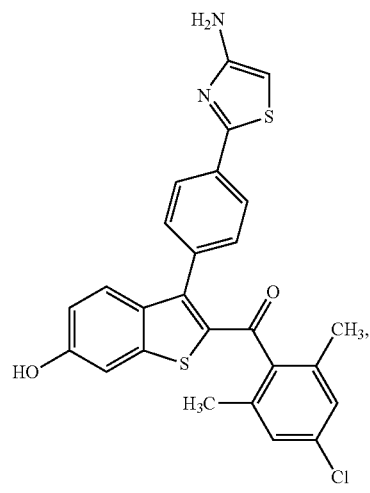

173
-continued
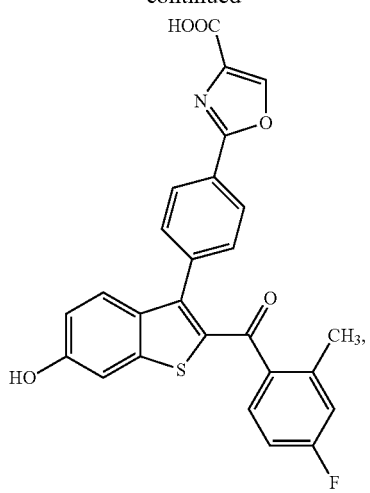
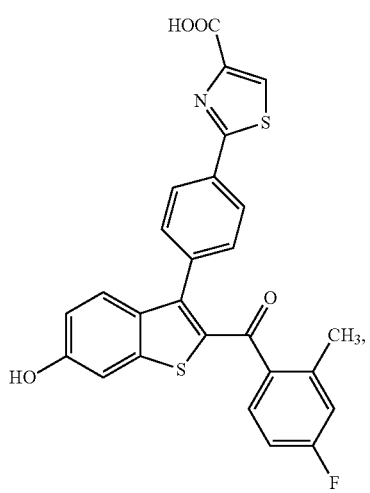
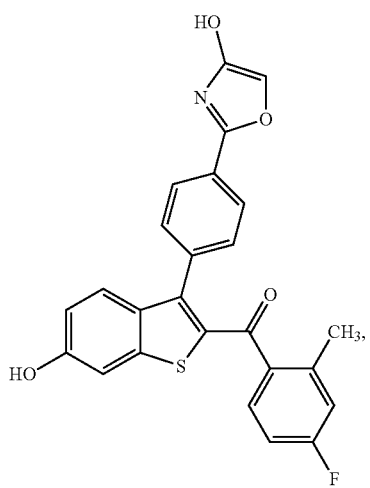
174
-continued
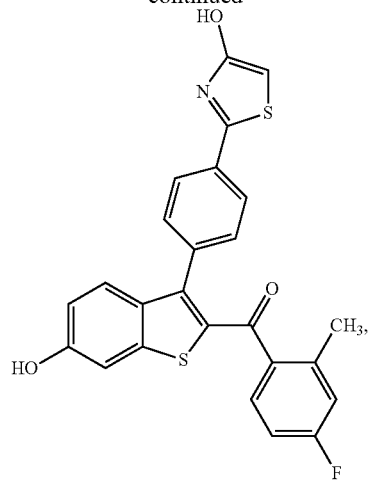
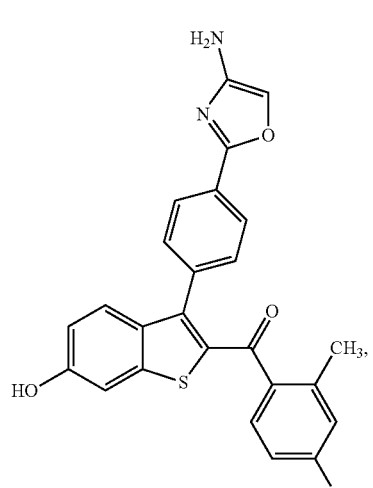
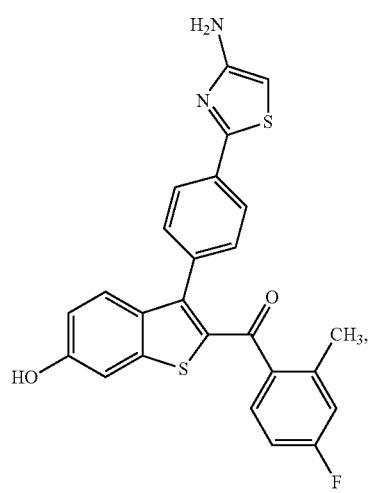

-continued
175
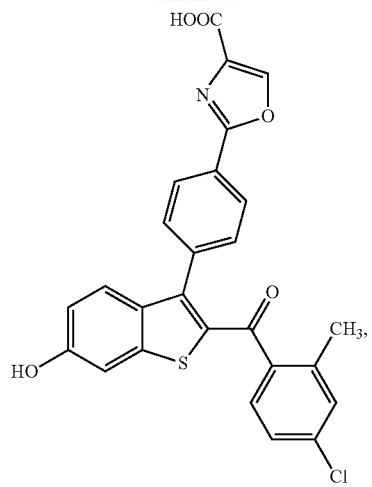
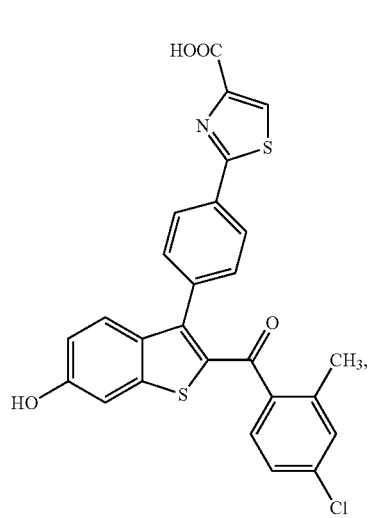
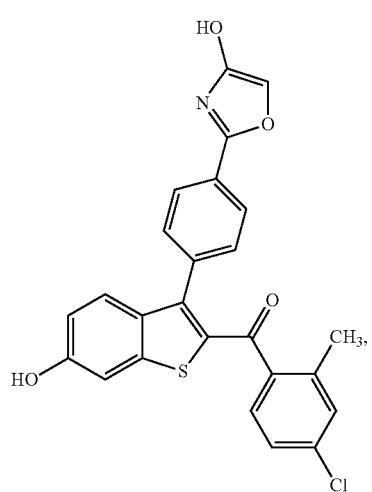
-continued
176
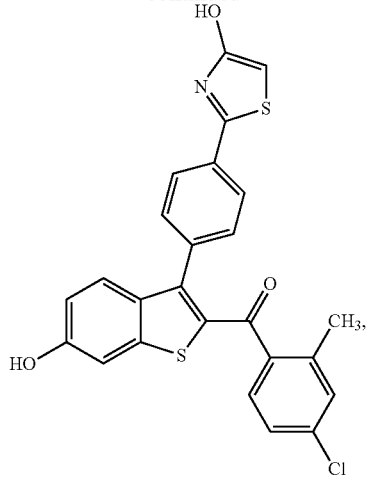
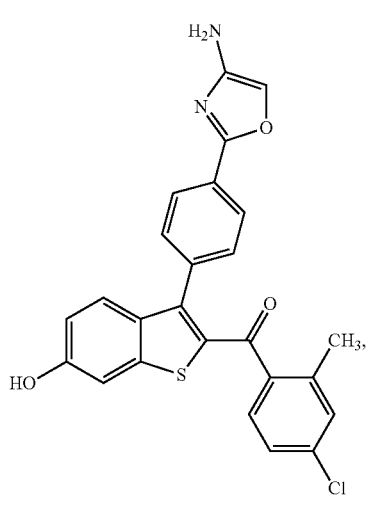
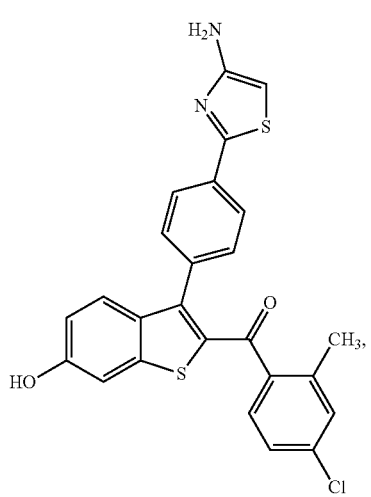

-continued
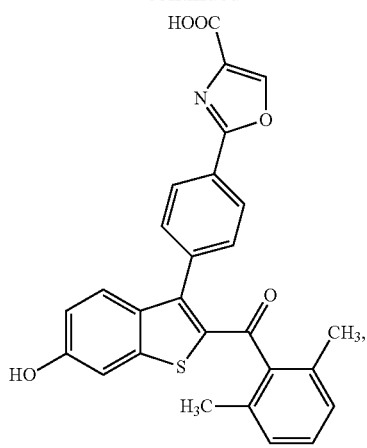
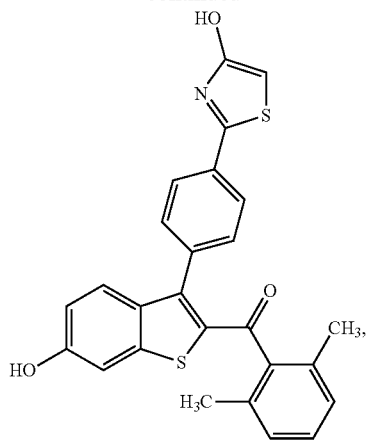
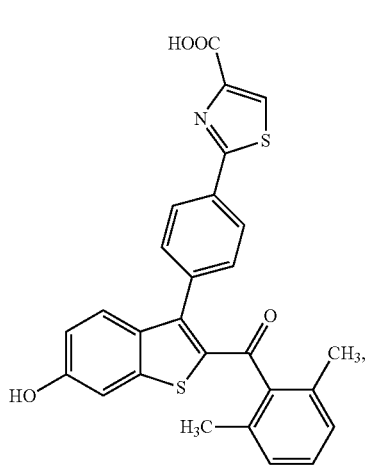
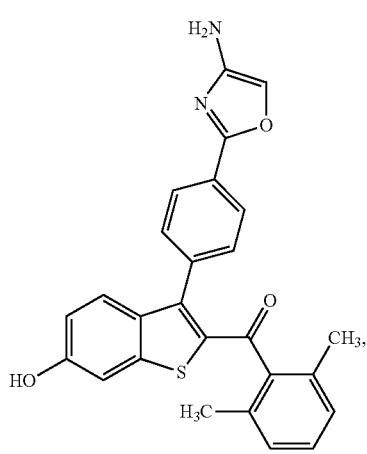
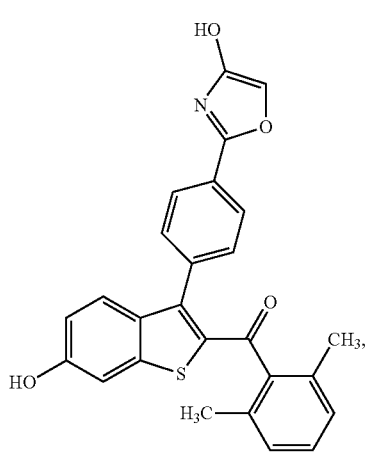
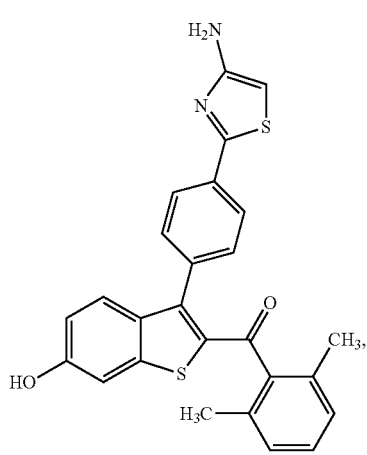

179
-continued
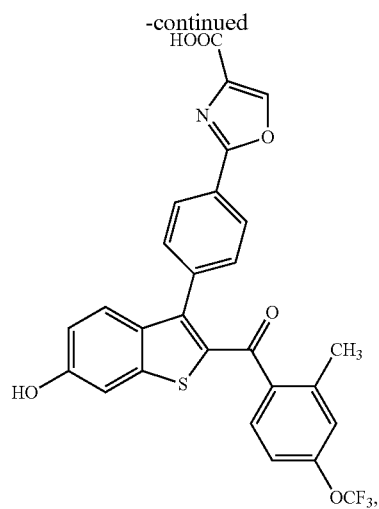
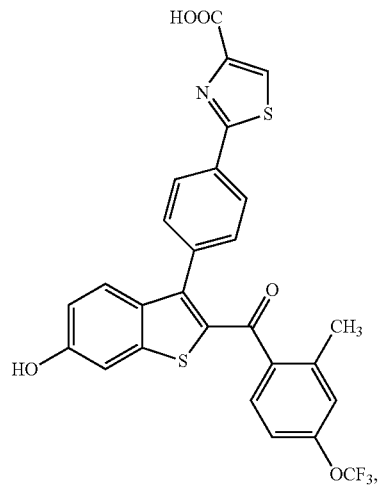
180
-continued
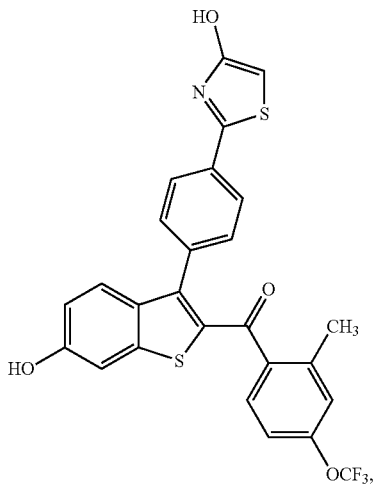
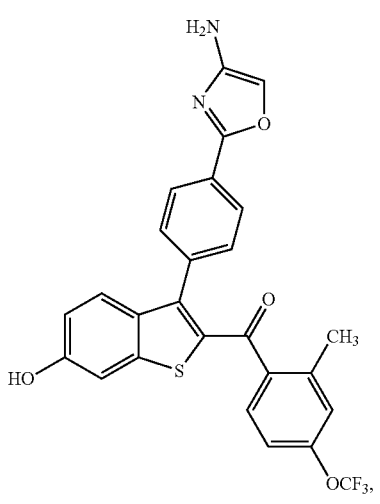
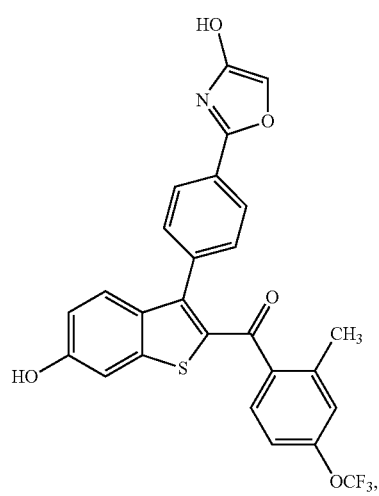
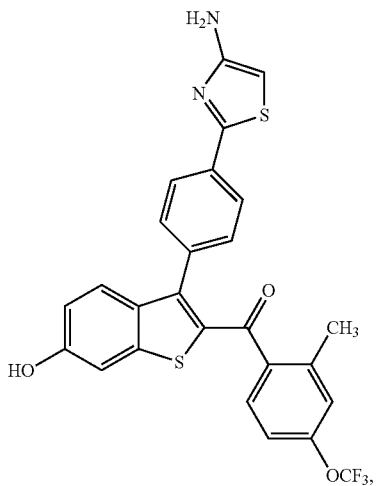

181
-continued
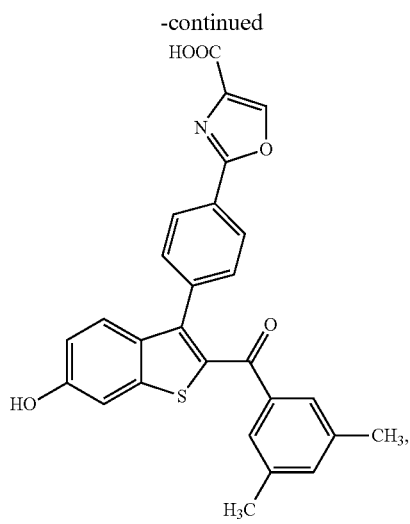
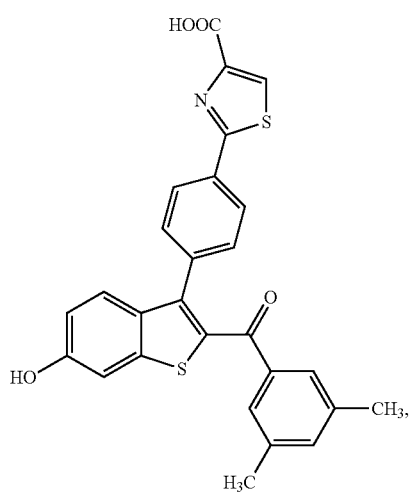
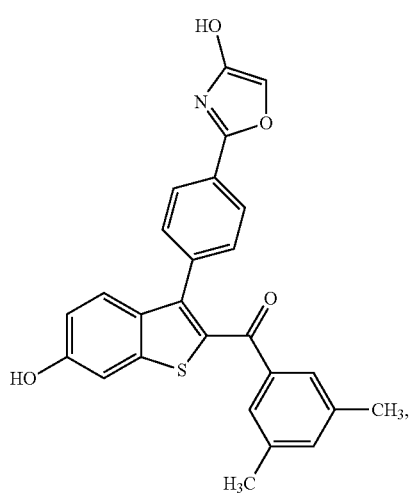
182
-continued
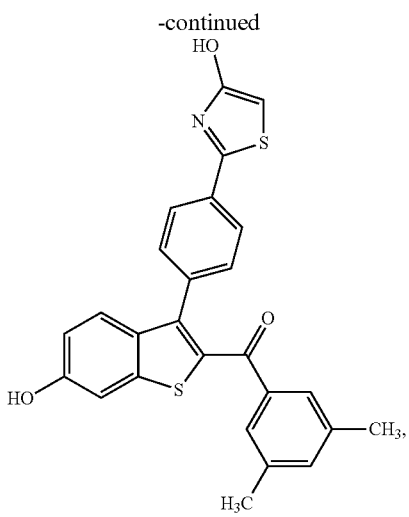
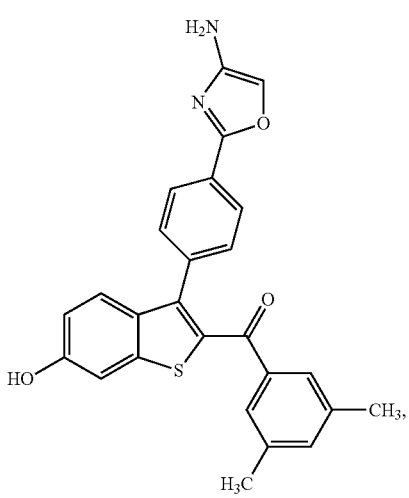
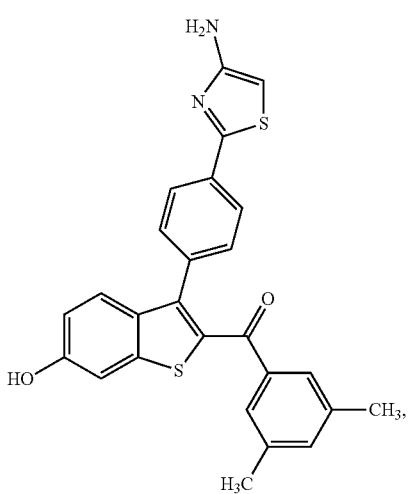

183
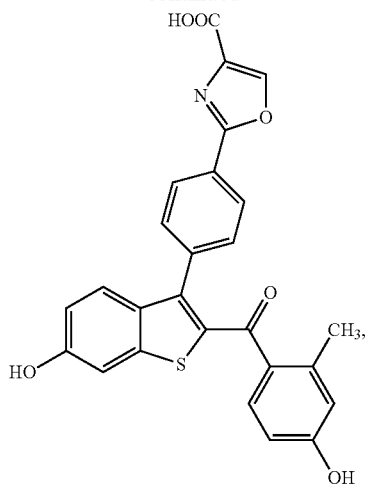
184
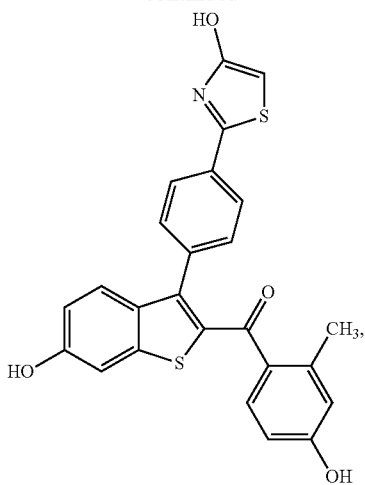

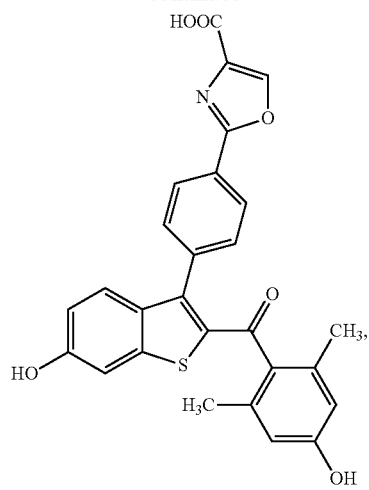
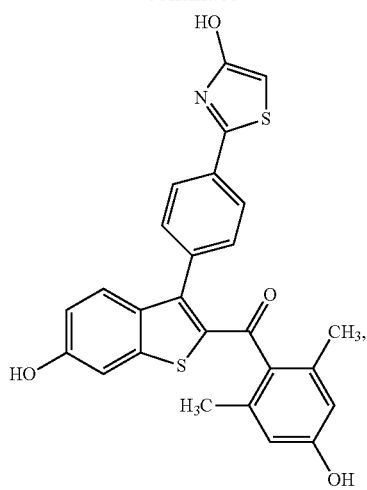

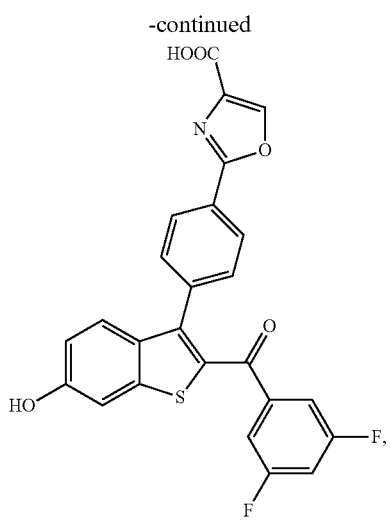

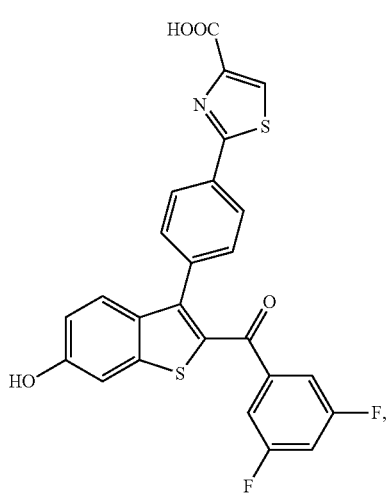

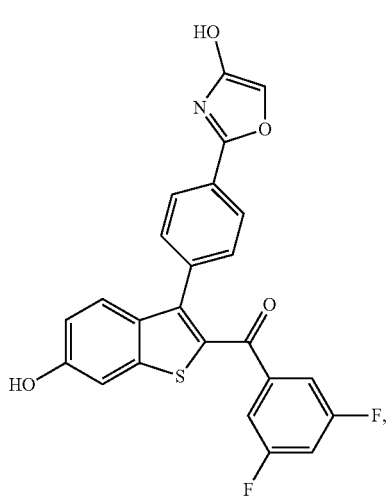 [SMILES: Nc1csc(-c2ccc(-c3c(C(=O)c4cc(F)cc(F)c4)sc4cc(O)ccc34)cc2)n1]

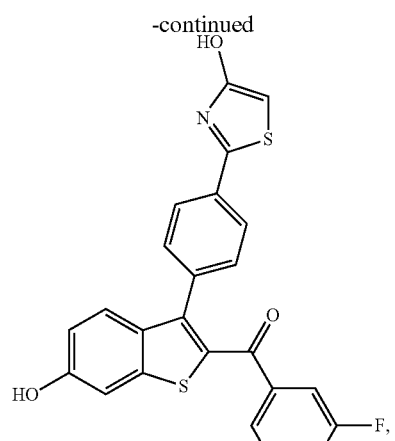

In one embodiment of any of the above structures that have a —CO₂H, the compound can be presented, for examples, as an ester, amide, or ether prodrug. The ester may be, for example, —CO₂R, wherein R is alkyl (including cycloalkyl), heteroalkyl, alkenyl, alkynyl, aryl, heteroaryl, heterocyclic, or any other moiety that is metabolized in vivo to provide the parent drug.

Pharmaceutical Compositions and Methods of Treatment

In an additional aspect, this invention provides a pharmaceutical composition that includes an effective amount of a compound of Formula (I), Formula (II), Formula (III), Formula (IV), Formula (V), Formula (VI), Formula (VII), or Formula (VIII) and a pharmaceutically acceptable carrier or excipient.

In another aspect, this invention is a method to treat or prevent a tumor or cancer (including breast, ovarian, uterine, kidney, or endometrial cancer) that includes administering to a subject, typically a human, in need of such treatment, a therapeutically effective amount of a compound of Formula (I), Formula (II), Formula (III), Formula (IV), Formula (V), Formula (VI), Formula (VII), or Formula (VIII), or a pharmaceutically acceptable salt thereof.

In alternative aspect, this invention provides a pharmaceutical composition that includes an effective amount of a compound of Formula (IX), Formula (X), Formula (XI), Formula (XII), Formula (XIII), or Formula (XIV) and a pharmaceutically acceptable carrier or excipient.

In another alternative aspect, this invention is a method to treat or prevent a tumor or cancer (including breast, ovarian, uterine, kidney, or endometrial cancer) that includes administering to a subject, typically a human, in need of such treatment, a therapeutically effective amount of a compound of Formula (IX), Formula (X), Formula (XI), Formula (XII), Formula (XIII), or Formula (XIV), or a pharmaceutically acceptable salt thereof.

This invention provides pharmaceutical compositions that include a therapeutically effective amount of a compound as described herein or its pharmaceutically acceptable salt or prodrug, and one or more of a pharmaceutically acceptable vehicle such as a diluent, preservative, solubilizer, emulsifier, adjuvant, excipient, or carrier. Excipients include, but are not limited to, liquids such as water, saline, glycerol, polyethylene glycol, hyaluronic acid, ethanol, and the like.

The term "pharmaceutically acceptable carrier" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation. "Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Compositions for administration of the active compound include but are not limited to those suitable for oral (including but not limited to a tablet, capsule, liquid, gel formulation), topical, rectal, nasal, pulmonary, parenteral (including intramuscular, intra-arterial, intrathecal, subcutaneous and intravenous), intramuscular, intravenous, sub-cutaneous, transdermal (which may include a penetration enhancement agent), vaginal and suppository administration. Enteric coated oral tablets may also be used to enhance bioavailability of the compounds for an oral route of administration. The most effective dosage form will depend upon the bioavailability/pharmacokinetics of the particular compound chosen as well as the severity of disease in the patient. Oral dosage forms are often typical, because of ease of administration and prospective favorable patient compliance.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

Yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a acceptable nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size, for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively, the active ingredients can be provided in the form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved inj ectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers"

(Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

A pharmaceutically or therapeutically effective amount of the composition should be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more preferably about 0.1 mg/kg to about 10 mg/kg, in at least one dose. In some non-limiting embodiments, the daily dosage may be from about 1 mg to 300 mg, one or more times per day, more preferably in the range of about 10 mg to 200 mg. The subject can be administered in as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In some embodiments, for example, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms are those with at least, or no greater than, 1, 2, 5, 10, 15, 20, 25, 50, 75, 100, 150, 200, 250, 300, 350, 400, 450, 500, 550, 600, 650, 700, or 750 mg of active compound, or its salt or prodrug. The pharmaceutical composition may also include a molar ratio of the active compound and an additional active agent, in a ratio that achieves the desired results.

The unit dosage form can be for example, a packaged preparation containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds and compositions of the invention may be used in methods for treatment or prevention of estrogen-related medical disorders, for example, cancer. The cancer may be for example a breast cancer, a uterine cancer, an ovarian cancer, endometrial, a prostate cancer, and a lung cancer. Particularly, the breast cancer may be a tamoxifen resistant breast cancer or a triple negative breast cancer.

The method of treatment may prevent or reduce the risk of cancer or a tumor. The method of treatment may cause partial or complete regression of cancer or a tumor in a subject.

The method of treatment may cause partial or complete regression of a tamoxifen resistant cancer or tumor. The method of treatment may cause partial or complete regression of a triple negative breast cancer.

In other embodiments, the compound or its pharmaceutically acceptable salt or prodrug or a pharmaceutical composition thereof can be used to prevent recurrence of a cancer or tumor after treatment, as adjunctive therapy. In one example, the compound or its pharmaceutically acceptable salt or prodrug or a pharmaceutical composition thereof can be used to prevent further breast cancer after breast cancer treatment or to treat node-positive breast cancer in women following mastectomy and/or radiation.

If desired, multiple doses of a compound described herein can be administered to the subject. Alternatively, the subject can be given a single dose of a compound described herein.

In one aspect of the invention, a compound disclosed herein can be beneficially administered in combination with any therapeutic regimen entailing radiotherapy, chemotherapy, or other therapeutic agents. In additional embodiments the compounds disclosed herein can be beneficially administered in combination with therapeutic agents targeting auto-immune disorders.

The compound or its pharmaceutically acceptable salt or prodrug or a pharmaceutical composition thereof may also be used to promote bone health or to prevent or treat osteopenia or osteoporosis.

The foregoing may be better understood by reference to the following Examples, which are presented for purposes of illustration and are not intended to limit the scope of the invention.

In one embodiment "cancer" refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In one embodiment, the cancer or tumor is estrogen-mediated. In an alternative embodiment, the cancer or tumor is not estrogen-mediated. In variable embodiments, the cancer or tumor is not hormone-mediated. Non-limiting examples of cancers include, acute lymphoblastic leukemia, acute myeloid leukemia, adrenocortical carcinoma, anal cancer, appendix cancer, astrocytomas, a typical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The method of treatment may prevent or reduce the risk of cancer. The method of treatment may cause partial or complete regression of cancer in a subject.

The method of treatment may cause partial or complete regression of a tamoxifen resistant cancer or tumor. The method of treatment may cause partial or complete regression of a triple negative breast cancer.

In some embodiments, compounds disclosed herein are used to treat or prevent cancer or a tumor in a mammal such as a human. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In one embodiment a compound of the present invention is used for hormone therapy.

The foregoing may be better understood by reference to the following Examples, which are presented for purposes of illustration and are not intended to limit the scope of the invention.

In one aspect, a compound of the present invention or its pharmaceutically acceptable salt or prodrug, can be used to treat a hormone-related cancer or tumor that has metastasized to the brain, bone or other organ. In one embodiment of this aspect, the hormone-related cancer is estrogen mediated. In another embodiment, the estrogen mediated cancer is selected from breast, uterine, ovarian and endometrial. In other embodiments, a compound of the present invention or its pharmaceutically acceptable salt or prodrug, can be used to prevent a hormone-related cancer or tumor from metastasizing to the brain, bone or other organ, including a hormone-related cancer that is estrogen mediated, for example, breast, uterine, ovarian or endometrial.

Combination Therapy

In one aspect, a method for the treatment of a disorder of abnormal cellular proliferation in a host such as a human is provided that includes administering an effective amount of a combination of one or more of the active compounds described herein in combination or alternation with another active compound.

In one aspect of this embodiment, the second active compound is an immune modulator, including but not limited to a checkpoint inhibitor. Checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combination thereof.

In one embodiment, the checkpoint inhibitor is a PD-1 inhibitor that blocks the interaction of PD-1 and PD-L1 by binding to the PD-1 receptor, and in turn inhibits immune suppression. In one embodiment, the checkpoint inhibitor is a PD-1 checkpoint inhibitor selected from nivolumab, pembrolizumab, pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.).

In one embodiment, the checkpoint inhibitor is a PD-L1 inhibitor that blocks the interaction of PD-1 and PD-L 1 by binding to the PD-L 1 receptor, and in turn inhibits immune suppression. PD-L1 inhibitors include, but are not limited to, avelumab, atezolizumab, durvalumab, KN035, and BMS-936559 (Bristol-Myers Squibb).

In one aspect of this embodiment, the checkpoint inhibitor is a CTLA-4 checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In another embodiment, the checkpoint inhibitor is a LAG-3 checkpoint inhibitor. Examples of LAG-3 checkpoint inhibitors include, but are not limited to, BMS-986016

(Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the checkpoint inhibitor is a TIM-3 checkpoint inhibitor. A specific TIM-3 inhibitor includes, but is not limited to, TSR-022 (Tesaro).

In yet another embodiment, one of the active compounds described herein is administered in an effective amount for the treatment of abnormal tissue of the female reproductive system such as breast, ovarian, kidney, endometrial, or uterine cancer, in combination or alternation with an effective amount of an estrogen inhibitor including but not limited to a SERM (selective estrogen receptor modulator), a SERD (selective estrogen receptor downregulator), a complete estrogen receptor downregulator, or another form of partial or complete estrogen antagonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to AstraZeneca. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

In another embodiment, one of the active compounds described herein is administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor downregulator and/or degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one aspect, a treatment regimen is provided comprising the administration of a compound of the present invention in combination with at least one additional chemotherapeutic agent. The combinations disclosed herein can be administered for beneficial, additive, or synergistic effect in the treatment of abnormal cellular proliferative disorders.

In specific embodiments, the treatment regimen includes the administration of a compound of the present invention in combination with at least one kinase inhibitor. In one embodiment, the at least one kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors that may be used in the present invention are well known. Examples of PI3 kinase inhibitors include but are not limited to Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methyl sulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N'-[4-(4, 6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4, 5h]isochromen-10-yl] acetate (also known as sonolisib)).

In one embodiment, the compound of the present invention is combined in a single dosage form with the PIk3 inhibitor.

BTK inhibitors for use in the present invention are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5- fluoro-2-((4-(2-methoxyethoxy)phenyl)amino)pyrimidin-4-yl)amino)phenyl)acryl amide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-(3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference. In one embodiment, the compound of the present invention is combined in a single dosage form with the BTK inhibitor.

Syk inhibitors for use in the present invention are well known, and include, for example, Cerdulatinib (4-(cyclopropylamino)-2-((4-(4-(ethyl sulfonyl)piperazin-1-yl)phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib di sodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R, 2S)-2-Amino-cyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'4(5-fluoropyrimidine-2,4-diyl)bis (azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein). In one embodiment, the compound of the present invention is combined in a single dosage form with the Syk inhibitor.

In one embodiment, the at least one additional chemotherapeutic agent is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl] sulfonyl]-2-[(1H-pyrrolo[2,3-b]pyridin-5-yl)oxy] benzamide), ABT-737 (4-[4-[[2-(4-chlorophenyl)phenyl] methyl]piperazin-1-yl]-N-[4-[[(2R)-4-(dimethylamino)-1-phenylsulfanylbutan-2-yl] amino]-3-nitrophenyl] sulfonylbenzamide), ABT-263 ((R)-4-(4-((4'-chloro-4,4-dimethyl-3,4,5,6-tetrahydro-[1,1'-biphenyl]-2-yl)methyl) piperazin-1-yl)-N-((4-((4-morpholino-1-(phenylthio)butan-2-yl)amino)-3((trifluoromethyl)sulfonyl)phenyl)sulfonyl) benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl] benzamide), Apogossypolone (ApoG2), or G3139 (Oblimersen). In one embodiment, the compound of the present invention is combined in a single dosage form with the at least one BCL-2 inhibitor.

The compound of the present invention or its pharmaceutically active salt can be combined with an immunotherapy. As discussed in more detail below, the compound of the present invention can be conjugated to an antibody, radioactive agent, or other targeting agent that directs the compound to the diseased or abnormally proliferating cell.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs, which bind to cell surface growth factor receptors, prevent the targeted receptors from sending their normal growth-promoting signals. They may also trigger apoptosis and activate the immune system to destroy tumor cells.

In some embodiments, the combination can be administered to the subject in further combination with other chemotherapeutic agents. If convenient, the combination described herein can be administered at the same time as another chemotherapeutic agent in order to simplify the treatment regimen. In some embodiments, the combination and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apoptotic compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus (Deforolimus), and sirolimus. Examples of MEK inhibitors include but are not limited to trametinib/GSK1120212 (N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-dihydroxypropoxy]-3,4-difluoro-2-[(2-fluoro-4-iodophenyl)amino]-benzamide), TAK733 ((R)-3-(2,3-dihydroxypropyl)-6-fluoro-5-(2-fluoro-4-iodophenylamino)-8-methylpyrido[2,3 d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD 8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, a compound of the present invention described herein can be combined with a chemotherapeutic selected from, but are not limited to, Imatinib mesylate (Gleevec®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Targretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™) Examples of additional suitable chemotherapeutic agents include but are not limited to 1-dehydrotestosterone, 5-fluorouracil, dacarbazine, 6-mercaptopurine, 6-thioguanine, actinomycin D, adriamycin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicine, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunorubicin HCl, daunorubicin citrate, denileukin diftitox, Dexrazoxane, Dibromomannitol, dihydroxy anthracin dione, Docetaxel, dolasetron mesylate, doxorubicin HCl, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon α-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptopurine, Mesna, methotrexate, methyltestosterone, mithramycin, mitomycin C, mitotane, mitoxantrone, nilutamide, octreotide acetate, ondansetron HCl, paclitaxel, pamidronate disodium, pentostatin, pilocarpine HCl, plicamycin, polifeprosan 20 with carmustine implant, porfimer sodium, procaine, procarbazine HCl, propranolol, sargramostim, streptozotocin, tamoxifen, taxol, teniposide, teniposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include 2-methoxyestradiol or 2ME2, finasunate, vatalanib, volociximab, etaracizumab (MEDI-522), cilengitide, dovitinib, figitumumab, atacicept, rituximab, alemtuzumab, aldesleukin, atlizumab, tocilizumab, lucatumumab, dacetuzumab, HLL1, huN901-DM1, atiprimod, natalizumab, bortezomib, marizomib, tanespimycin, saquinavir mesylate, ritonavir, nelfinavir mesylate, indinavir sulfate, belinostat, panobinostat, mapatumumab, lexatumumab, dulanermin, plitidepsin, talmapimod, P276-00, enzastaurin, tipifarnib, lenalidomide, thalidomide, pomalidomide, simvastatin, and celecoxib.

In one aspect of the present invention, a compound described herein can be combined with at least one immunosuppressive agent. The immunosuppressive agent in one embodiment is selected from the group consisting of a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3®), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, methotrexate, dexamethasone, ISAtx-247, SDZ ASM 981 (pimecrolimus, Elidel®), CTLA41g, Abatacept, belatacept, LFA31g, etanercept (sold as Enbrel® by ImmuneXcite), adalimumab (Humira®), infliximab (Remicade®), an anti-LFA-1 antibody, natalizumab (Antegren®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, aspirin, and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

Synthetic Methods

The compounds described herein can be prepared by methods known by those skilled in the art. In one non-limiting example the disclosed compounds can be prepared using the schemes.

As used herein alkenylene can encompass both cis and trans isomers of alkenes, unless indicated otherwise. In one embodiment the isomer is cis. In a preferred embodiment the isomer is trans. In one embodiment $R_2$ is —$C_2$-$C_6$alkenylene-$COOR_{17}$ and the alkene group is cis. In a preferred embodiment, $R_2$ is —$C_2$-$C_6$alkenylene-$COOR_{17}$ and the alkene group is trans.

Some of the compounds described herein can have a chiral center, and the compound can exist in isomeric or diastereomeric form. When multiple chiral variables are present on formulas of the present invention, the formula further encompasses every possible diastereomer unless indicated otherwise. For example (R,R), (S,R), (S,S), and (R,S) for a molecule with two chiral centers. One skilled in the art will recognize that pure enantiomers, diastereomers, and cis/trans isomers can be prepared by methods known in the art. Examples of methods to obtain optically active materials include at least the following.

i) Physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) Simultaneous crystallization—a technique whereby the individual enantiomers are separately crystallized from a solution of the racemate, possible only if the latter is a conglomerate in the solid state;

iii) Enzymatic resolutions—a technique whereby partial or complete separation of a racemate by virtue of differing rates of reaction for the enantiomers with an enzyme;

iv) Enzymatic asymmetric synthesis—a synthetic technique whereby at least one step of the synthesis uses an enzymatic reaction to obtain an enantiomerically pure or enriched synthetic precursor of the desired enantiomer;

v) Chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) Diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) First- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) Kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) Enantiospecific synthesis from non-racemic precursors—a synthetic technique whereby the desired enantiomer is obtained from non-chiral starting materials and where the stereochemical integrity is not or is only minimally compromised over the course of the synthesis;

x) Chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) Chiral gas chromatography—a technique whereby the racemate is volatilized and enantiomers are separated by virtue of their differing interactions in the gaseous mobile phase with a column containing a fixed non-racemic chiral adsorbent phase;

xii) Extraction with chiral solvents—a technique whereby the enantiomers are separated by virtue of preferential dissolution of one enantiomer into a particular chiral solvent;

xiii) Transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) Simulated moving bed chromatography, is used in one embodiment. A wide variety of chiral stationary phases are commercially available.

The compounds of the present invention can be synthesized by non-limiting methods provided in the following schemes:

Scheme 1

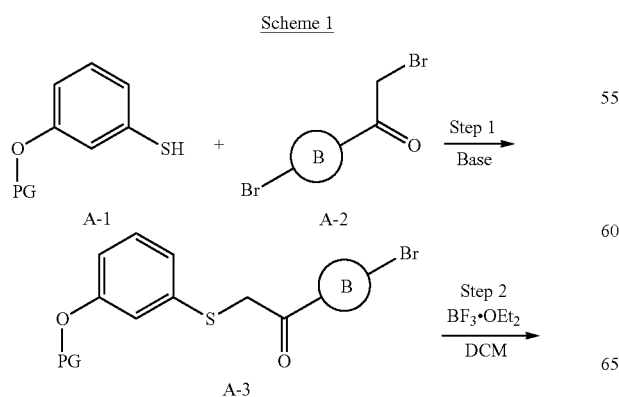

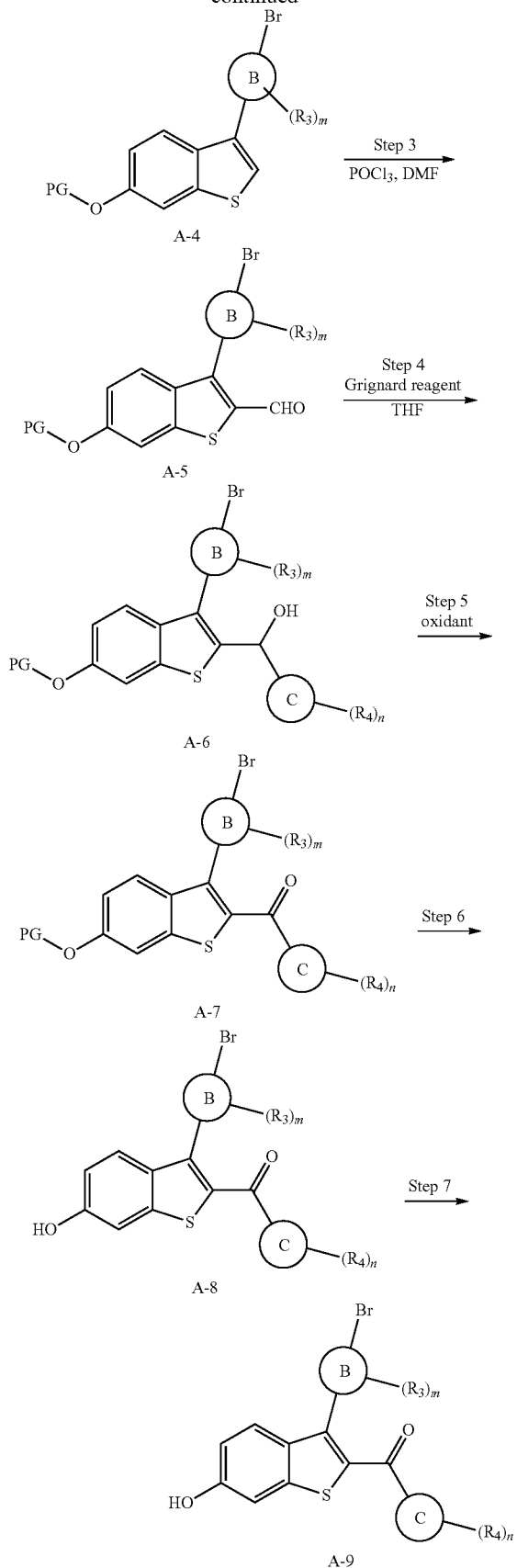

As demonstrated in the non-limiting illustrative example in Scheme 1, compounds falling within Formula (I) can be prepared from readily available starting materials. In Step 1, A-1 can be reacted with an appropriately substituted alkyl bromide A-2 in the presence of a base at elevated temperature to provide A-3. In Step 2, the reaction of A-3 with boron trifluoride diethyl etherate in organic solvent can provide A-4. In Step 3, the reaction of A-4 with phosphorous oxychloride and DMF can provide A-5. In Step 4, the addition of an appropriate Grignard reagent to A-5 can provide A-6. In one embodiment, the Grignard reagent is an aryl magnesium halide. In another embodiment, the Grignard reagent is a cycloalkyl magnesium halide. In Step 5, A-6 can be reacted with an oxidant to provide A-7. In one embodiment, the oxidant is pyridinium chlorochromate. In Step 6, PG can be removed by methods known to those skilled in the art to generate A-8. In Step 7, A-8 is coupled with $R_2$ using methods known to those having skill in the art to provide A-9.

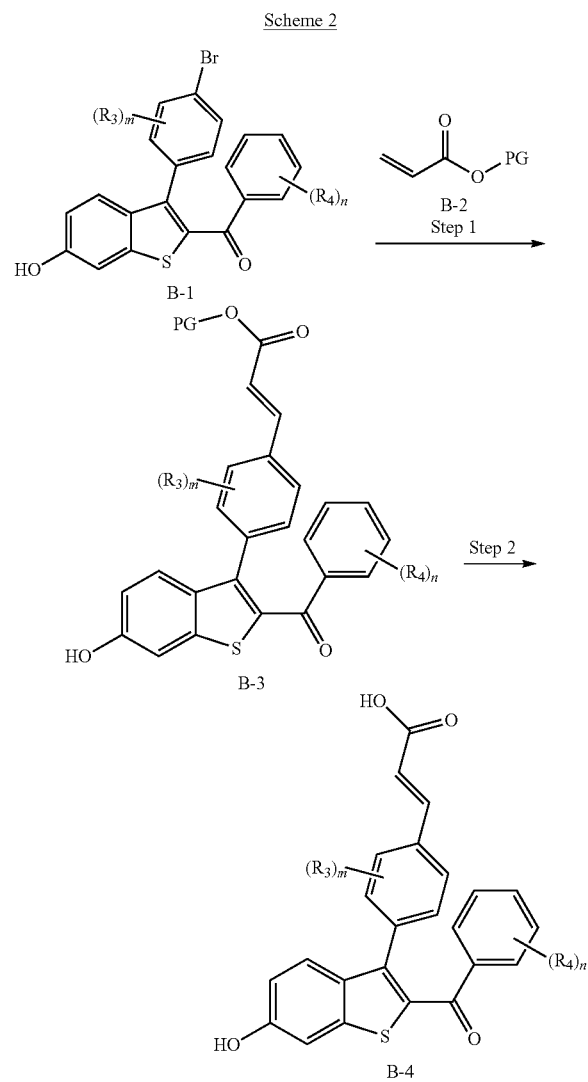

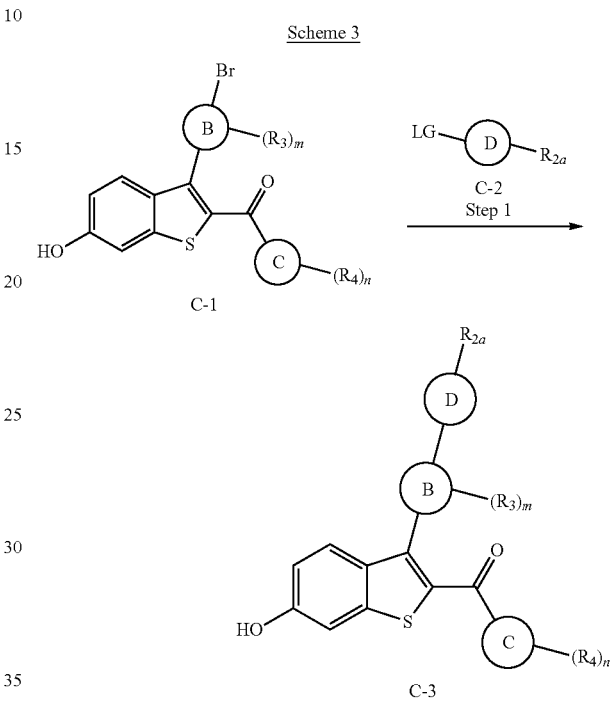

As demonstrated in the non-limiting illustrative example in Scheme 2, compounds falling within Formula (II) can be prepared by methods known to those skilled in the art. B-1 can be prepared in a similar manner to A-8. In Step 1, B-1 is coupled to B-2 using a catalyst in organic solvent to provide B-3. In one embodiment of B-2, ring D is a 5- to 6-membered heteroaryl. In some embodiments, the catalyst is a palladium catalyst. In one embodiment, the catalyst is $Pd(PPh_3)_2Cl_2$. In Step 2, PG is removed from B-3 to provide B-4. In one embodiment, B-3 is converted to B-4 with lithium hydroxide or sodium hydroxide.

As demonstrated in the non-limiting illustrative example in Scheme 3, compounds falling within Formula (IV) can be prepared by methods known to those skilled in the art. C-1 can be prepared in a similar manner to A-8. In Step 1, C-1 is coupled to C-2 using an organometallic catalyst to provide C-3. In some embodiments, Ring D is C-2 is 5- to 6-membered heteroaryl. In some embodiments, the organometallic catalyst is a palladium catalyst. In one embodiment, the palladium catalyst is $Pd(PPh_3)_2Cl_2$. In one embodiment, -LG is —$B(OH)_2$ or —$Sn(Bu)_3$.

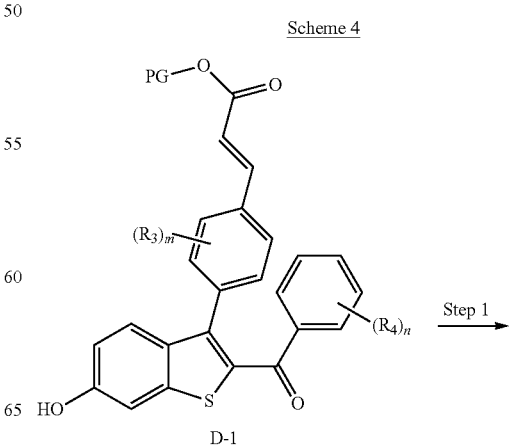

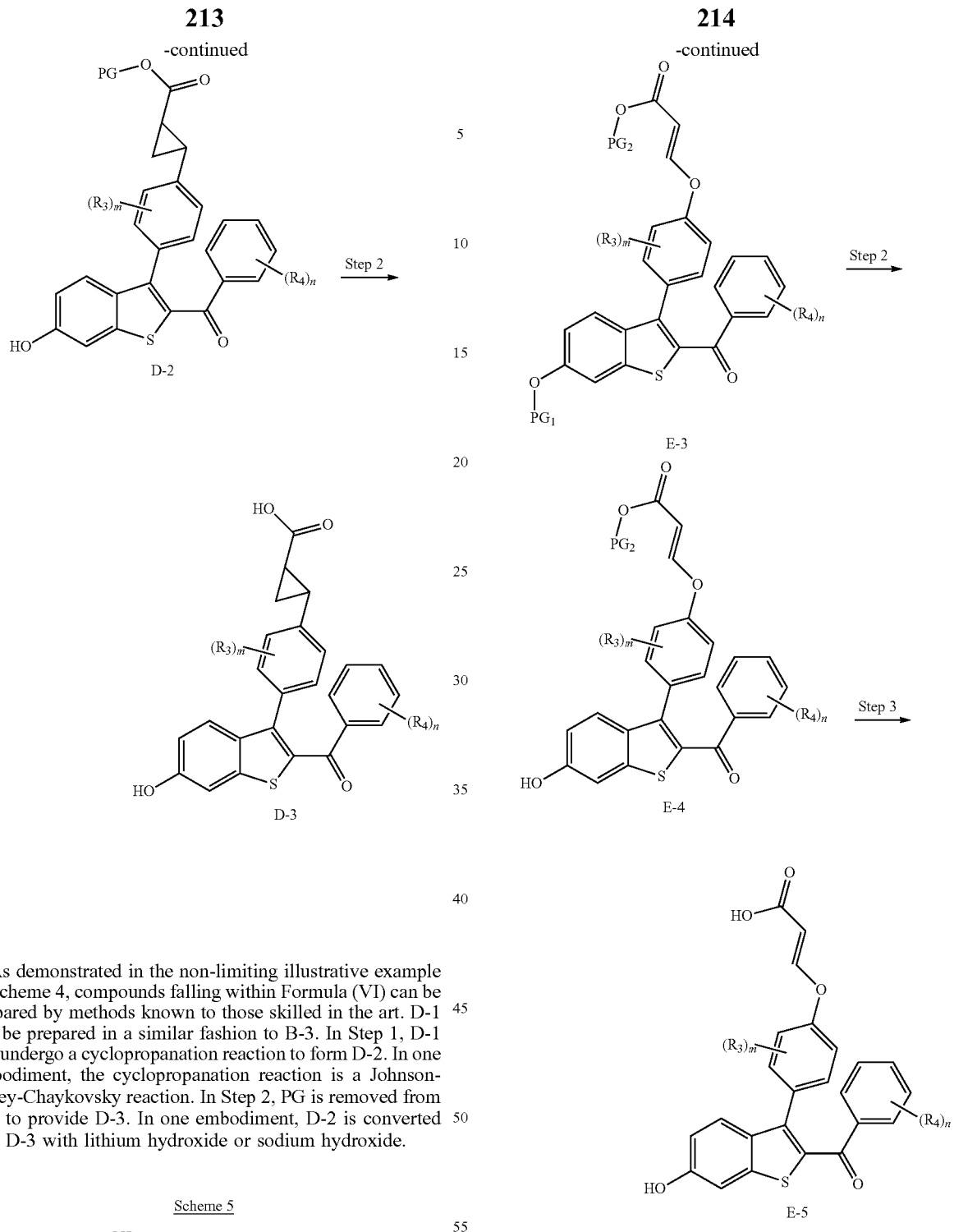

As demonstrated in the non-limiting illustrative example in Scheme 4, compounds falling within Formula (VI) can be prepared by methods known to those skilled in the art. D-1 can be prepared in a similar fashion to B-3. In Step 1, D-1 can undergo a cyclopropanation reaction to form D-2. In one embodiment, the cyclopropanation reaction is a Johnson-Corey-Chaykovsky reaction. In Step 2, PG is removed from D-2 to provide D-3. In one embodiment, D-2 is converted into D-3 with lithium hydroxide or sodium hydroxide.

Scheme 5

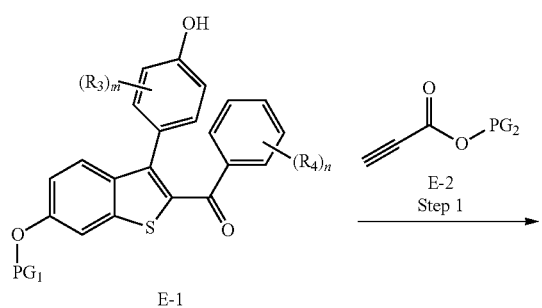

As demonstrated in the non-limiting illustrative example in Scheme 5, compounds falling within Formula (III) can be prepared by methods known to those skilled in the art. E-1 can be prepared in a similar fashion to A-7. In Step 1, E-1 can add to E-2 to form E-3. In Step 2, $PG_1$ is removed in E-3 to provide E-4. In one embodiment, $PG_1$ is removed with boron trifluoride dimethyl sulfide. In Step 3, $PG_2$ is removed in E-4 to provide E-5. In one embodiment, $PG_2$ is removed by reaction with lithium hydroxide or sodium hydroxide.

A Non-Limiting Example of a Synthetic Route
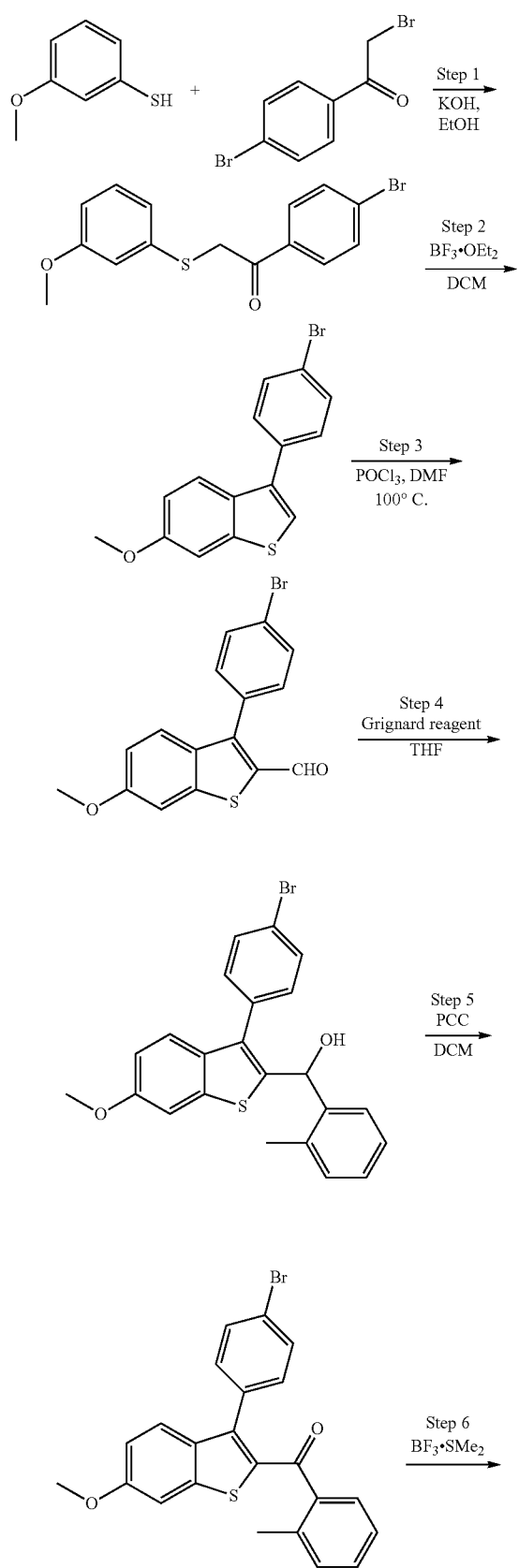
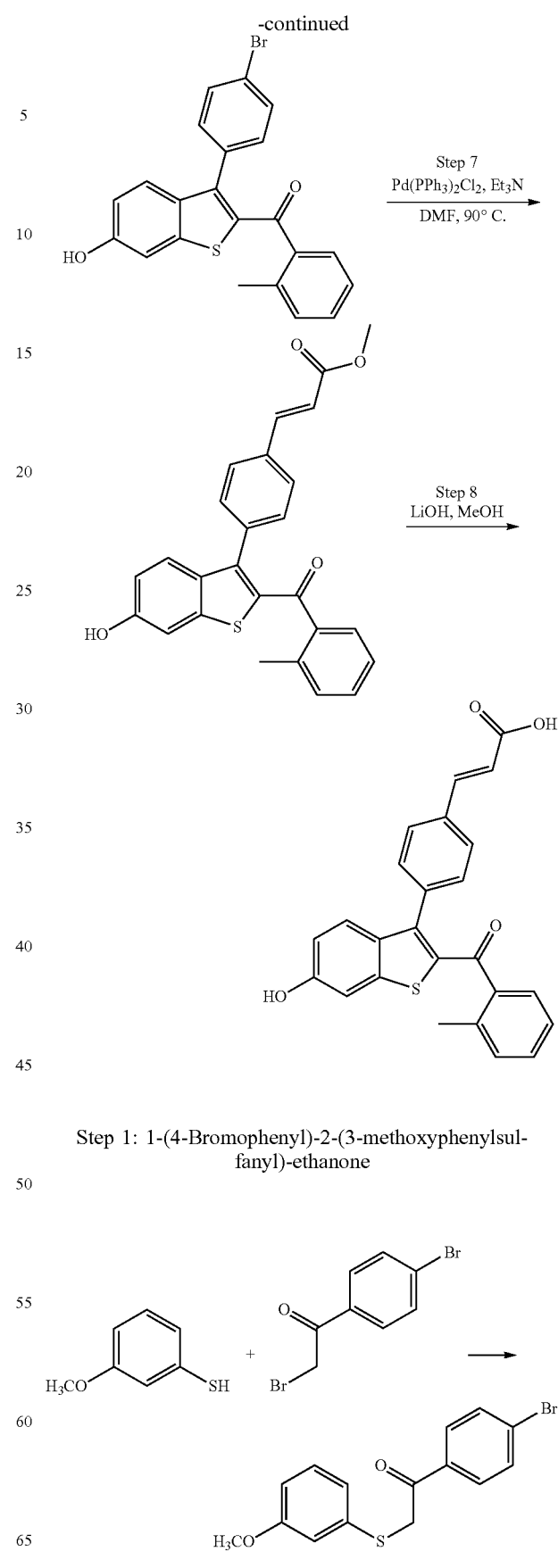
Step 1: 1-(4-Bromophenyl)-2-(3-methoxyphenylsulfanyl)-ethanone Methoxybenzenethiol (65 g, 7.1 mmol) was added to a round-bottom flask charged with a freshly prepared solution containing 300 mL of ethanol, 100 mL of water, and 30 g of KOH (538 mmol). The solution was cooled in an ice-water bath, and a solution of 2-bromo-1-(4-bromophenyl)ethanone (100 g, 461 mmol) in 100 mL of ethyl acetate was slowly added. The reaction mixture was monitored by TLC until completion. The solvents were evaporated under reduced pressure, and the residue mixture was partitioned between water and ethyl acetate. The combined organic phase was washed with brine and dried by $Na_2SO_4$ to give 120 g of product, which was used in the next step without further purification.

Step 2: 3-(4-Bromophenyl)-6-methoxybenzo[b]thiophene

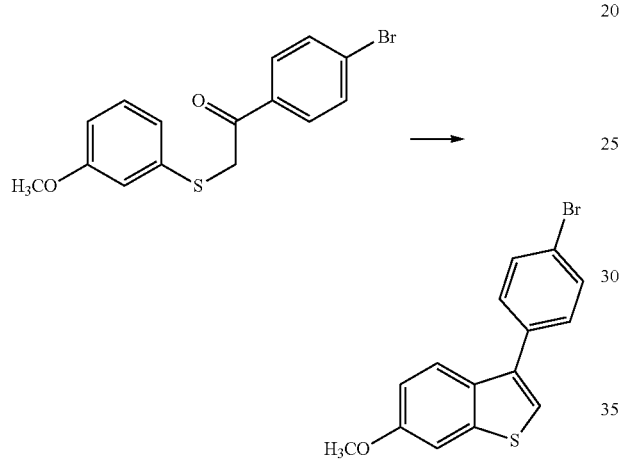

$BF_3.OEt_2$ was slowly added to a flask charged with 1-(4-bromophenyl)-2-(3-methoxy phenylsulfanyl)ethanone (120 g, 0.37 mol) under $N_2$ in an ice bath. The reaction mixture was stirred until starting material was consumed as monitored by TLC. The reaction mixture was poured into saturated $NaHCO_3$/ice-water, stirred 30 min, and extracted with dichloromethane. The crude product was purified by silica gel chromatography (5% dichloromethane in hexanes). The combined fractions from the column were concentrated and recrystallized to give 75 g of pale yellow solid.

Step 3: 3-(4-Bromophenyl)-6-methoxybenzo[b]thiophene-2-carbaldehyde

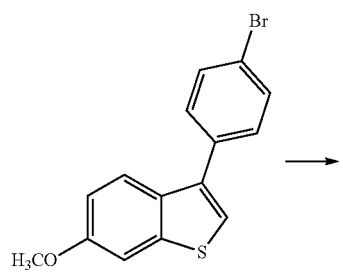

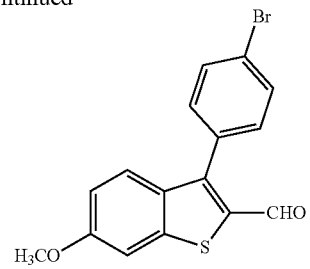

3-(4-Bromophenyl)-6-methoxybenzo[b]thiophene (2 g, 1.4 mmol) was dissolved in 10 mL DMF and stirred at 0° C. The reaction system was then degassed by N2 three times. $POCl_3$ (4.4 g, 6.9 mmol) was slowly added drop-wise to reaction mixture. The reaction was heated to 100° C. for 2 hrs. Upon completion, the reaction mixture was poured into cold water and extracted by EtOAc. The organic layer was combined and washed by water, brine and dried by $Na_2SO_4$. The crude product was purified by silica gel chromatography (10% EtOAc in hexanes) to give 1.5 g aldehyde. Yield 75%. $^1$H NMR (400 MHz, CDCl$^3$) δ 9.84 (s, 1H), 7.69 (d, J=8.3 Hz, 2H), 7.59 (d, J=9.0 Hz, 1H), 7.39 (d, J=8.3 Hz, 2H), 7.34 (d, J=2.1 Hz, 1H), 7.02 (dd, J=9.0, 2.2 Hz, 1H), 3.92 (s, 3H). $^{13}$C NMR (400 MHz, CDCl$_3$) δ 184.87, 160.73, 146.14, 144.28, 136.92, 132.90, 132.06, 131.89, 131.45, 126.03, 123.54, 116.48, 104.72, 77.38, 77.07, 76.75, 55.74.

Step 4: (3-(4-Bromophenyl)-6-methoxybenzo[b]thiophene-2-yl)(o-tolyl)methanol

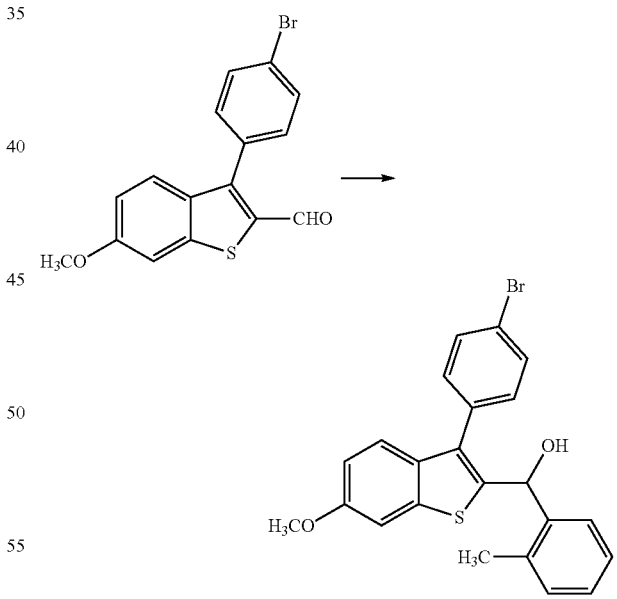

3-(4-Bromophenyl)-6-methoxybenzo[b]thiophene-2-carbaldehyde (0.6 g, 1.7 mmol) was added to a round bottom flask with 3 mL of fresh prepared anhydrous THF. The reaction system was degassed by N2 and stirred at 0° C. for 1 hr. o-Tolylmagnesium bromide (1.2 mL, 2.55 mmol) was slowly added drop-wise to the reaction mixture and stirred at room temperature upon addition. The reaction was monitored by TLC and quenched with ice water after completion. The reaction mixture was extracted by EtOAc, washed with water and brine, and dried by Na$_2$SO$_4$. The crude product was purified by silica gel chromatography (8% EtOAc in hexanes) to afford 0.6 g product. Yield 80%. $^1$H NMR (400 MHz, CDCl$_3$) δ 7.75 (d, J=7.4 Hz, 1H), 7.63 (d, J=8.4 Hz, 2H), 7.39 (d, J=8.9 Hz, 1H), 7.34 (d, J=7.8 Hz, 2H), 7.31-7.19 (m, 3H), 7.08 (d, J=7.2 Hz, 1H), 6.96 (dd, J=8.8, 2.2 Hz, 1H), 6.04 (s, 1H), 3.86 (s, 3H), 1.94 (s, 3H). $^{13}$C NMR (100 MHz, CDCl$_3$) δ 157.76, 141.21, 140.79, 140.58, 135.04, 133.81, 133.72, 133.50, 131.88, 131.46, 130.40, 127.93, 126.16, 125.15, 123.71, 122.05, 114.47, 105.01, 67.70, 55.65, 18.90.

Step 5: (3-(4-Bromophenyl)-6-methoxybenzo[b]thiophen-2-yl)(o-tolyl)methanone

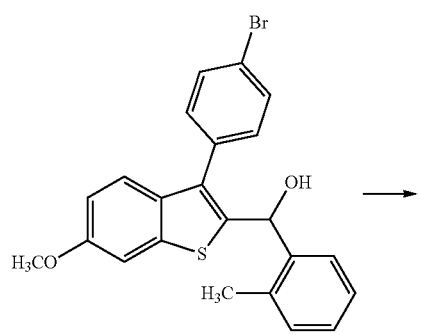

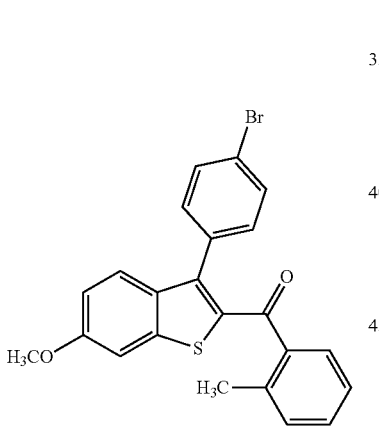

(3-(4-Bromophenyl)-6-methoxybenzo[b]thiophen-2-yl)(o-tolyl)methanol (0.5 g, 1.1 mmol) was dissolved in 5 mL DCM and stirred at room temperature. PCC (0.36 g, 1.7 mmol) was added to the reaction mixture by portion. The reaction was monitored by TLC and stirred for 2 hrs. Upon completion, the reaction mixture was filtered, extracted with DCM and washed with water and brine. The organic fractions were combined and dried by Na$_2$SO$_4$. The crude product was purified by silica gel chromatography (5% EtOAc in hexanes) to afford 0.3 g of product. Yield 60%. $^1$H NMR (400 MHz, CDCl$_3$) δ 7.44 (d, J=9.0 Hz, 1H), 7.35 (d, J=2.2 Hz, 1H), 7.30 (d, J=8.4 Hz, 2H), 7.22-7.09 (m, 2H), 7.04-6.97 (m, 4H), 6.92 (t, J=7.5 Hz, 1H), 3.93 (s, 3H), 2.32 (s, 3H). $^{13}$C NMR (100 MHz, CDCl$_3$) δ 192.46, 160.07, 143.40, 141.71, 138.86, 137.71, 136.00, 133.92, 133.05, 131.27, 130.95, 130.49, 130.10, 128.59, 126.25, 124.99, 122.11, 116.14, 104.20, 55.72, 19.75.

Step 6: (3-(4-Bromophenyl)-6-hydroxybenzo[b]thiophen-2-yl)(o-tolyl)methanone

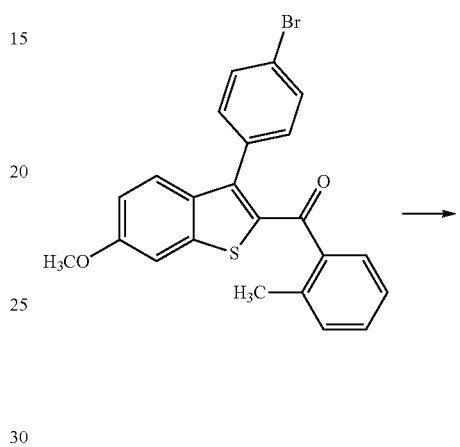

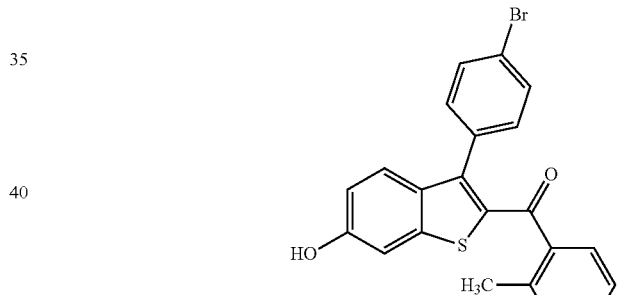

(3-(4-Bromophenyl)-6-methoxybenzo[b]thiophen-2-yl)(o-tolyl)methanone (0.3 g, 0.68 mmol) was dissolved in 3 mL DCM, degassed by N2 and stirred at 0° C. for 0.5 hr. BF$_3$.Me$_2$S (1.1 mL 10.2 mmol) was slowly added to reaction mixture and stirred at room temperature for 12 hrs after addition. Upon completion, the reaction mixture was cooled to 0° C. and quenched by ice water. The mixture was extracted by DCM, washed with water, and dried by Na$_2$SO$_4$. The crude product was purified by silica gel chromatography (25% EtOAc in hexanes) to obtain 0.15 g product. Yield 53%. $^1$H NMR (400 MHz, Acetone-d$_6$) δ 7.46 (d, J=2.1 Hz, 1H), 7.42 (d, J=8.9 Hz, 1H), 7.40-7.35 (m, 2H), 7.21-7.13 (m, 4H), 7.09-7.01 (m, 2H), 6.95 (t, J=7.4 Hz, 1H), 2.29 (s, 3H). $^{13}$C NMR (100 MHz, Acetone-d$_6$) δ 191.69, 158.17, 143.16, 141.65, 139.27, 137.03, 135.66, 133.41, 133.26, 131.65, 130.82, 130.27, 129.73, 128.44, 126.45, 124.98, 121.55, 116.11, 107.12, 18.81.

221

Step 7: Methyl (E)-3-(4-(6-hydroxy-2-(2-methyl-benzoyl)benzo[b]thiophen-3-yl)phenyl)acrylate

222

Step 8: (E)-3-(4-(6-Hydroxy-2-(2-methylbenzoyl)benzo[b]thiophen-3-yl)phenyl)acrylic acid

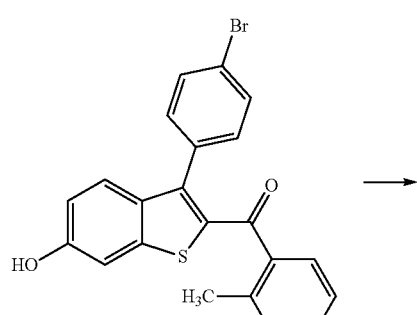

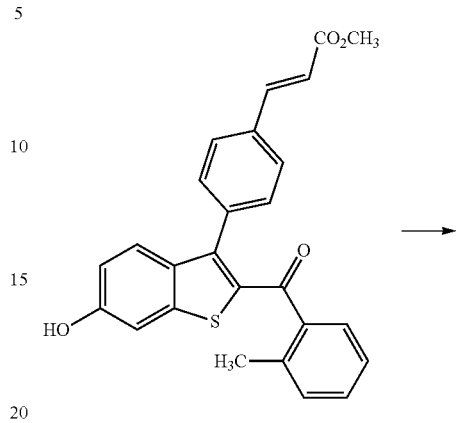

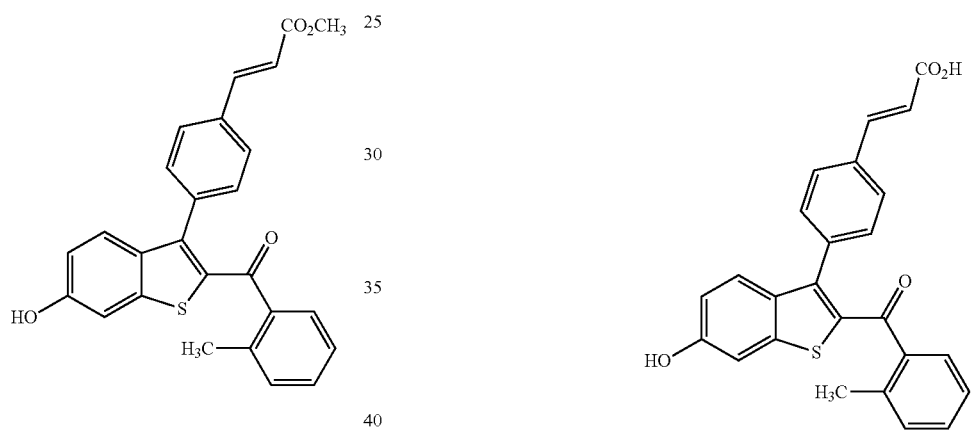

(3-(4-Bromophenyl)-6-hydroxybenzo[b]thiophen-2-yl)(o-tolyl)methanone (0.2 g, 0.47 mmol) was dissolved in 3 mL fresh prepared anhydrous DMF, followed by addition of $Et_3N$ (0.13 mL, 1.9 mmol), methyl acrylate (0.25 mL, 2.8 mmol) and Bis(triphenylphosphine) palladium(II) dichloride (32 mg, 0.047 mmol). The reaction mixture was heated to 100° C. for 5 hrs and monitored by TLC. Upon completion, the reaction mixture was cooled to room temperature and extracted with EtOAc, washed with water and brine, and dried by $Na_2SO_4$. The crude product was purified by silica gel chromatography (30% EtOAc in hexanes) to obtain 0.15 g product. Yield 75%. $^1$H NMR (400 MHz, Acetone-$d_6$) δ 9.06 (s, 1H), 7.56 (d, J=16.0 Hz, 1H), 7.45 (d, J=8.1 Hz, 2H), 7.40 (d, J=9.1 Hz, 2H), 7.21 (d, J=8.1 Hz, 2H), 7.13-7.08 (m, 1H), 7.04 (t, J=7.5 Hz, 1H), 7.01-6.92 (m, 2H), 6.84 (t, J=7.5 Hz, 1H), 6.46 (d, J=16.0 Hz, 1H), 3.70 (d, J=19.6 Hz, 3H), 2.24 (d, J=5.4 Hz, 3H). $^{13}$C NMR (100 MHz, Acetone-$d_6$) δ 191.37, 166.13, 157.76, 143.46, 142.79, 141.85, 138.87, 136.65, 135.94, 135.30, 133.43, 132.90, 130.00, 129.84, 129.34, 128.09, 127.12, 126.11, 124.52, 117.76, 115.70, 106.72, 50.48, 18.44.

Methyl (E)-3-(4-(6-hydroxy-2-(2-methylbenzoyl)benzo[b]thiophen-3-yl)phenyl)acrylate (0.1 g, 0.23 mmol) was dissolved in 2 mL methanol and stirred at room temperature. 10% (w %) of LiOH in water (0.6 mL, 2.3 mmol) was added to the reaction mixture and stirred at room temperature for 8 hrs. Upon completion, the reaction mixture was acidified by 1 M HCl to pH=2. The reaction was extracted with EtOAc, washed with water and brine, and dried by $Na_2SO_4$. The organic solvent was evaporated to afford 0.08 g of final product. Yield 83%. $^1$H NMR (400 MHz, Acetone-$d_6$) δ 9.18 (s, 1H), 7.61 (d, J=16.0 Hz, 1H), 7.53-7.42 (m, 3H), 7.25 (d, J=8.1 Hz, 3H), 7.15 (d, J=7.6 Hz, 1H), 7.09 (t, J=7.4 Hz, 1H), 7.06-6.98 (m, 3H), 6.89 (t, J=7.4 Hz, 1H), 6.49 (d, J=16.0 Hz, 1H), 2.30 (s, 3H). $^{13}$C NMR (101 MHz, Acetone-$d_6$) δ 191.40, 166.33, 157.69, 143.63, 142.79, 141.90, 138.85, 136.62, 135.84, 135.31, 133.53, 132.88, 130.00, 129.85, 129.36, 128.11, 127.11, 126.13, 124.53, 118.19, 115.63, 106.65, 18.46.

The following compounds were made by analogous or known procedures utilizing appropriate starting materials:

| Compound Structure | Compound Name | Physical Data |
|---|---|---|
| 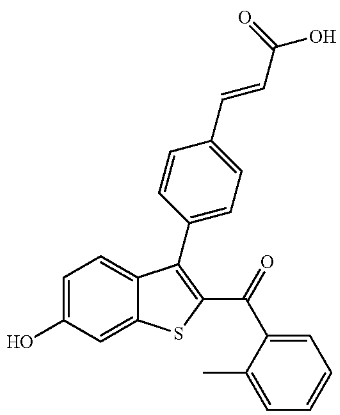 [SMILES: Cc1ccccc1C(=O)c1sc2cc(O)ccc2c1-c1ccc(/C=C/C(=O)O)cc1] | (E)-3-(4-(6-hydroxy-2-(2-methylbenzoyl)benzo[b]thiophen-3-yl)phenyl)acrylic acid | $^1$H NMR (400 MHz, Acetone-d$_6$) δ 9.18 (s, 1H), 7.61 (d, J = 16.0 Hz, 1H), 7.53-7.42 (m, 3H), 7.25 (d, J = 8.1 Hz, 3H), 7.15 (d, J = 7.6 Hz, 1H), 7.09 (t, J = 7.4 Hz, 1H), 7.06-6.98 (m, 3H), 6.89 (t, J = 7.4 Hz, 1H), 6.49 (d, J = 16.0 Hz, 1H), 2.30 (s, 3H). $^{13}$C NMR (101 MHz, Acetone-d$_6$) δ 191.40, 166.33, 157.69, 143.63, 142.79, 141.90, 138.85, 136.62, 135.84, 135.31, 133.53, 132.88, 130.00, 129.85, 129.36, 128.11, 127.11, 126.13, 124.53, 118.19, 115.63, 106.65, 18.46. [M + H]$^+$ = 415.3 |
| 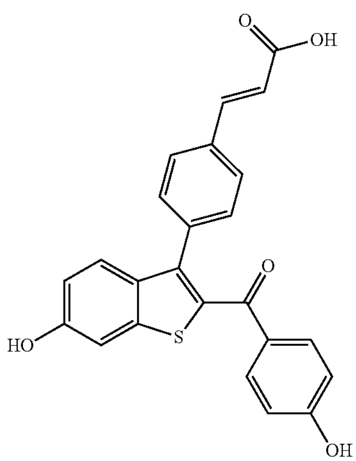 [SMILES: O=C(O)/C=C/c1ccc(-c2c(C(=O)c3ccc(O)cc3)sc3cc(O)ccc23)cc1] | (E)-3-(4-(6-hydroxy-2-(4-hydroxybenzoyl)benzo[b]thiophen-3-yl)phenyl)acrylic acid | [M + H]$^+$ = 417.5 |
| 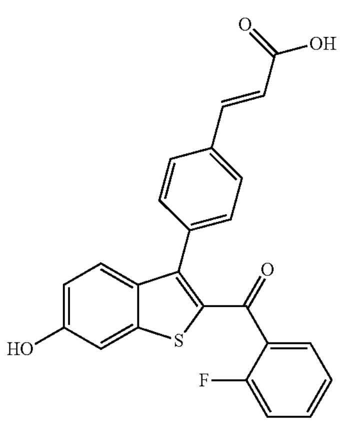 [SMILES: O=C(O)/C=C/c1ccc(-c2c(C(=O)c3ccccc3F)sc3cc(O)ccc23)cc1] | (E)-3-(4-(2-(2-fluorobenzoyl)-6-hydroxybenzo[b]thiophen-3-yl)phenyl)acrylic acid | [M + H]$^+$ = 419.1 |

-continued
| Compound Structure | Compound Name | Physical Data |
|---|---|---|
| 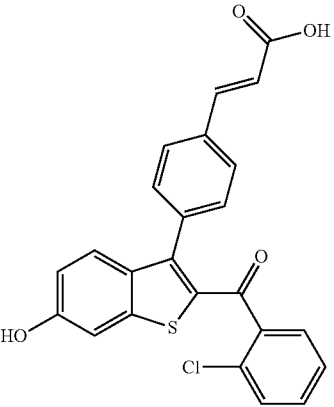 | (E)-3-(4-(2-(2-chlorobenzoyl)-6-hydroxybenzo[b]thiophen-3-yl)phenyl)acrylic acid | [M + H]$^+$ = 435.2 |
| 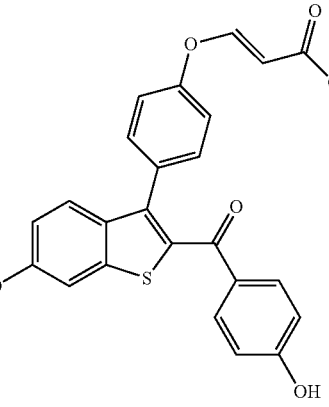 | (E)-3-(4-(6-hydroxy-2-(4-hydroxybenzoyl)benzo[b]thiophen-3-yl)phenoxy)acrylic acid | [M + H]$^+$ = 433.1 |
| 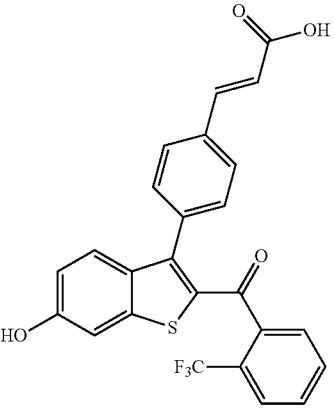 | (E)-3-(4-(6-hydroxy-2-(2-(trifluoromethyl)benzoyl)benzo[b]thiophen-3-yl)phenyl)acrylic acid | [M + H]$^+$ = 469.2 |

-continued
| Compound Structure | Compound Name | Physical Data |
|---|---|---|
| 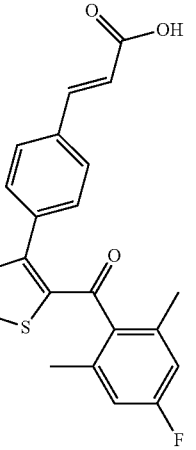 | (E)-3-(4-(2-(4-fluoro-2,6-dimethylbenzoyl)-6-hydroxybenzo[b]thiophen-3-yl)phenyl)acrylic acid | $[M + H]^+ = 447.4$ |
| 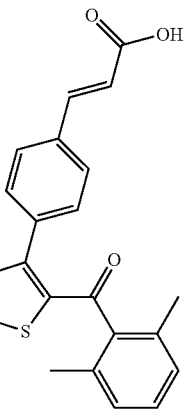 | (E)-3-(4-(2-(2,6-dimethylbenzoyl)-6-hydroxybenzo[b]thiophen-3-yl)phenyl)acrylic acid | $[M + H]^+ = 429.6$ |
| 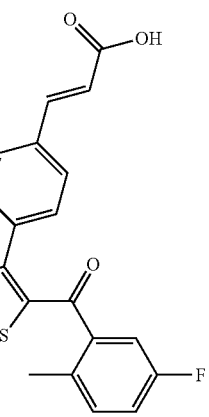 | (E)-3-(4-(2-(5-fluoro-2-methylbenzoyl)-6-hydroxybenzo[b]thiophen-3-yl)phenyl)acrylic acid | $[M + H]^+ = 433.3$ |

-continued
| Compound Structure | Compound Name | Physical Data |
|---|---|---|
| 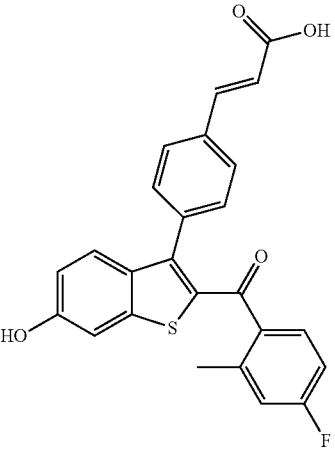 [SMILES: Cc1cc(F)ccc1C(=O)c1sc2cc(O)ccc2c1-c1ccc(/C=C/C(=O)O)cc1] | (E)-3-(4-(2-(4-fluoro-2-methylbenzoyl)-6-hydroxybenzo[b]thiophen-3-yl)phenyl)acrylic acid | $[M + H]^+ = 433.2$ |
| 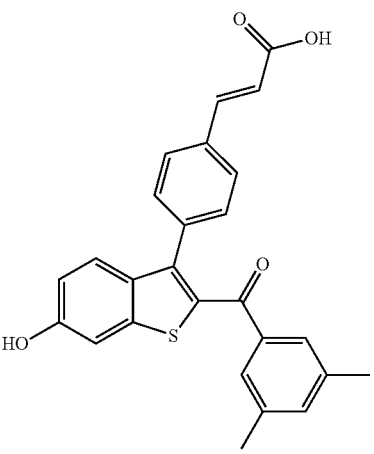 [SMILES: Cc1cc(C)cc(C(=O)c2sc3cc(O)ccc3c2-c2ccc(/C=C/C(=O)O)cc2)c1] | (E)-3-(4-(2-(3,5-dimethylbenzoyl)-6-hydroxybenzo[b]thiophen-3-yl)phenyl)acrylic acid | $[M + H]^+ = 429.3$ |
| 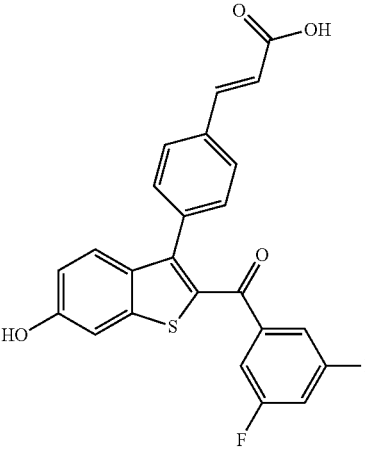 | (E)-3-(4-(2-(3,5-difluorobenzoyl)-6-hydroxybenzo[b]thiophen-3-yl)phenyl)acrylic acid | $[M + H]^+ = 437.1$ |

| Compound Structure | Compound Name | Physical Data |
|---|---|---|
| 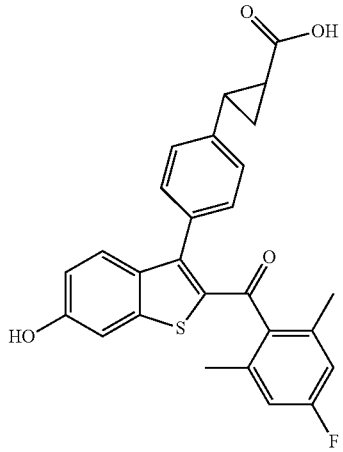 [SMILES: Cc1cc(F)cc(C)c1C(=O)c1sc2cc(O)ccc2c1-c1ccc(C2CC2C(=O)O)cc1] | 2-(4-(2-(4-fluoro-2,6-dimethylbenzoyl)-6-hydroxybenzo[b]thiophen-3-yl)phenyl)cyclopropane-1-carboxylic acid | [M + H]$^+$ = 461.2 |
| 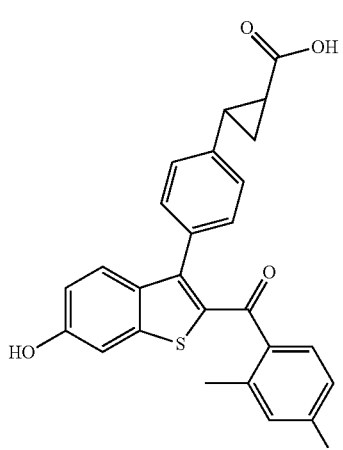 | 2-(4-(2-(4-fluoro-2-methylbenzoyl)-6-hydroxybenzo[b]thiophen-3-yl)phenyl)cyclopropane-1-carboxylic acid | [M + H]$^+$ = 447.2 |
| 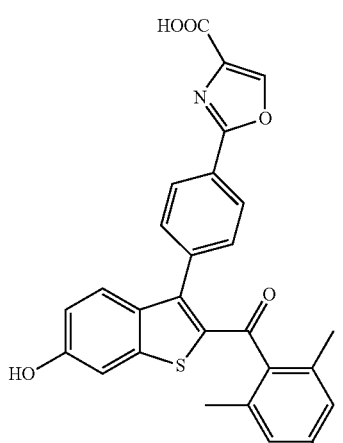 | 2-(4-(2-(4-fluoro-2,6-dimethylbenzoyl)-6-hydroxybenzo[b]thiophen-3-yl)phenyl)oxazole-4-carboxylic acid | [M + H]$^+$ = 488.2 |

| Compound Structure | Compound Name | Physical Data |
| --- | --- | --- |
| 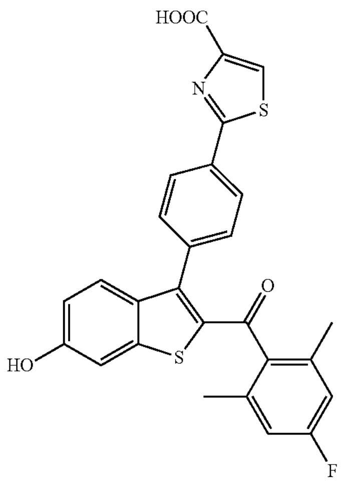 [SMILES: Cc1cc(F)cc(C)c1C(=O)c1sc2cc(O)ccc2c1-c1ccc(-c2nc(C(=O)O)cs2)cc1] | 2-(4-(2-(4-fluoro-2,6-dimethylbenzoyl)-6-hydroxybenzo[b]thiophen-3-yl)phenyl)thiazole-4-carboxylic acid | [M + H]$^+$ = 504.3 |
| 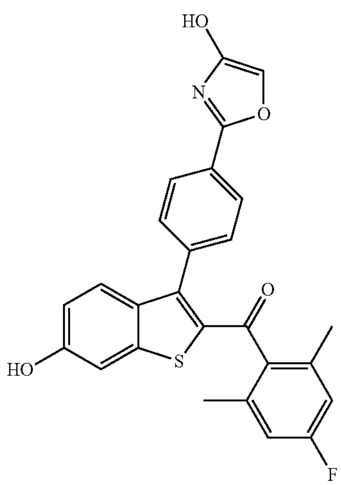 | (4-fluoro-2,6-dimethylphenyl)(6-hydroxy-3-(4-(4-hydroxyoxazol-2-yl)phenyl)benzo[b]thiophen-2-yl)methanone | [M + H]$^+$ = 460.1 |
| 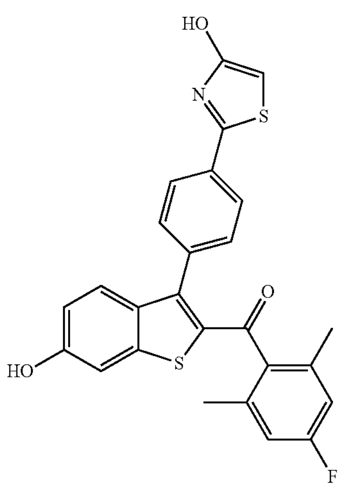 | (4-fluoro-2,6-dimethylphenyl)(6-hydroxy-3-(4-(4-hydroxythiazol-2-yl)phenyl)benzo[b]thiophen-2-yl)methanone | [M + H]$^+$ = 476.1 |

TABLE 1

Biological Data on Compounds 1-11

| Cmpd # | Structure | Name | MCF-5C growth inhibition IC$_{50}$$^a$ |
|---|---|---|---|
| 1 | 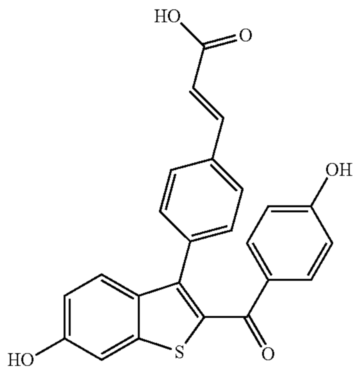 [SMILES: O=C(O)/C=C/c1ccc(-c2c(C(=O)c3ccc(O)cc3)sc3cc(O)ccc23)cc1] | (E)-3-(4-(6-hydroxy-2-(4-hydroxybenzoyl)benzo[b]thiophen-3-yl)phenyl)acrylic acid | +++ |
| 2 | 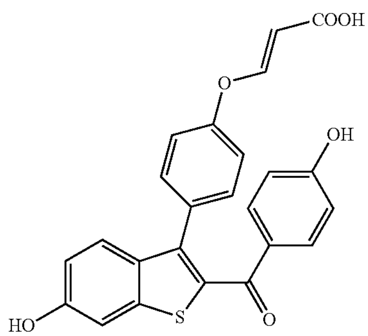 [SMILES: O=C(O)/C=C/Oc1ccc(-c2c(C(=O)c3ccc(O)cc3)sc3cc(O)ccc23)cc1] | (E)-3-(4-(6-hydroxy-2-(4-hydroxybenzoyl)benzo[b]thiophen-3-yl)phenoxy)acrylic acid | ++++ |
| 3 | 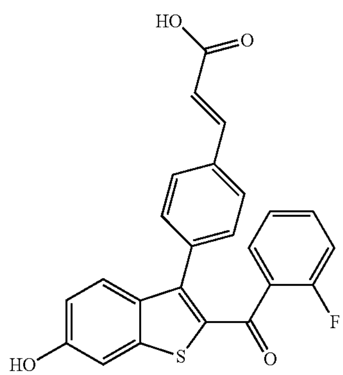 [SMILES: O=C(O)/C=C/c1ccc(-c2c(C(=O)c3ccccc3F)sc3cc(O)ccc23)cc1] | (E)-3-(4-(2-(2-fluorobenzoyl)-6-hydroxybenzo[b]thiophen-3-yl)phenyl)acrylic acid | + |
| 4 | 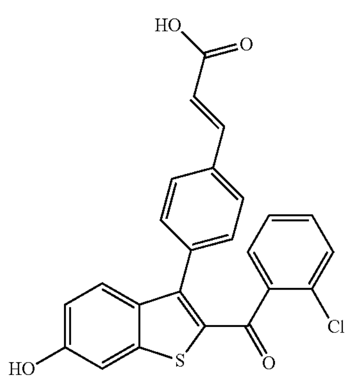 [SMILES: O=C(O)/C=C/c1ccc(-c2c(C(=O)c3ccccc3Cl)sc3cc(O)ccc23)cc1] | (E)-3-(4-(2-(2-chlorobenzoyl)-6-hydroxybenzo[b]thiophen-3-yl)phenyl)acrylic acid | + |

TABLE 1-continued

Biological Data on Compounds 1-11

| Cmpd # | Structure | Name | MCF-5C growth inhibition IC$_{50}$$^a$ |
|---|---|---|---|
| 5 | 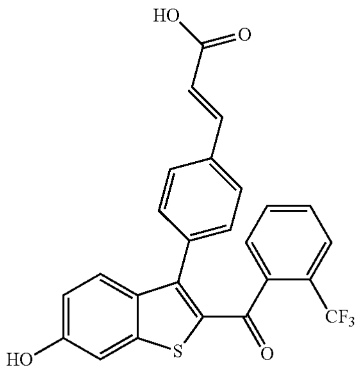 [SMILES: O=C(O)/C=C/c1ccc(-c2c(C(=O)c3ccccc3C(F)(F)F)sc3cc(O)ccc23)cc1] | (E)-3-(4-(6-hydroxy-2-(2-(trifluoromethyl)benzoyl)benzo[b]thiophen-3-yl)phenyl)acrylic acid | + |
| 6 | 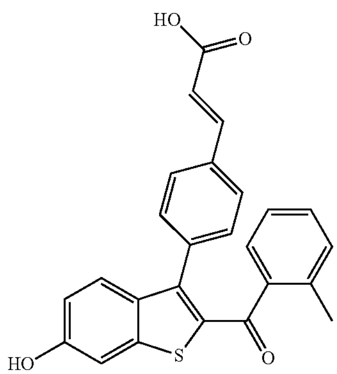 [SMILES: Cc1ccccc1C(=O)c1sc2cc(O)ccc2c1-c1ccc(/C=C/C(=O)O)cc1] | (E)-3-(4-(6-hydroxy-2-(2-methylbenzoyl)benzo[b]thiophen-3-yl)phenyl)acrylic acid | + |
| 7 | 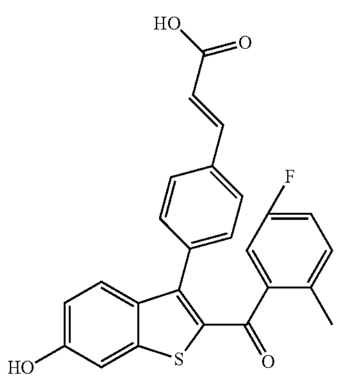 [SMILES: Cc1ccc(F)cc1C(=O)c1sc2cc(O)ccc2c1-c1ccc(/C=C/C(=O)O)cc1] | (E)-3-(4-(2-(5-fluoro-2-methylbenzoyl)-6-hydroxybenzo[b]thiophen-3-yl)phenyl)acrylic acid | + |
| 8 | 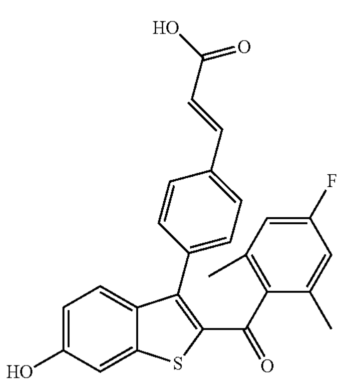 [SMILES: Cc1cc(F)cc(C)c1C(=O)c1sc2cc(O)ccc2c1-c1ccc(/C=C/C(=O)O)cc1] | (E)-3-(4-(2-(4-fluoro-2,6-dimethylbenzoyl)-6-hydroxybenzo[b]thiophen-3-yl)phenyl)acrylic acid | + |

TABLE 1-continued

Biological Data on Compounds 1-11

| Cmpd # | Structure | Name | MCF-5C growth inhibition IC$_{50}$$^a$ |
|---|---|---|---|
| 9 | 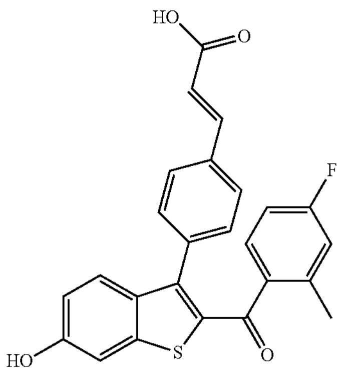 [SMILES: Cc1cc(F)ccc1C(=O)c1sc2cc(O)ccc2c1-c1ccc(/C=C/C(=O)O)cc1] | (E)-3-(4-(2-(4-fluoro-2-methylbenzoyl)-6-hydroxybenzo[b]thiophen-3-yl)phenyl)acrylic acid | + |
| 10 | 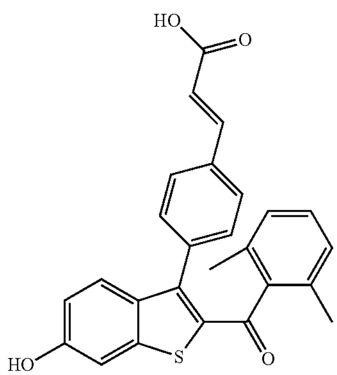 [SMILES: Cc1cccc(C)c1C(=O)c1sc2cc(O)ccc2c1-c1ccc(/C=C/C(=O)O)cc1] | (E)-3-(4-(2-(2,6-dimethylbenzoyl)-6-hydroxybenzo[b]thiophen-3-yl)phenyl)acrylic acid | + |
| 11 | 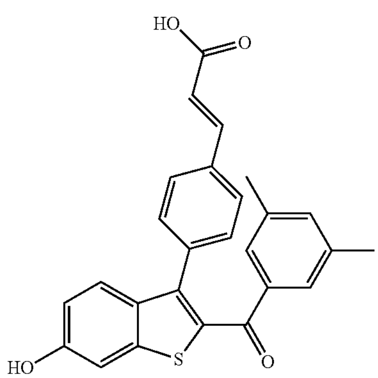 [SMILES: Cc1cc(C)cc(C(=O)c2sc3cc(O)ccc3c2-c2ccc(/C=C/C(=O)O)cc2)c1] | (E)-3-(4-(2-(3,5-dimethylbenzoyl)-6-hydroxybenzo[b]thiophen-3-yl)phenyl)acrylic acid | + |

$^a$Data are normalized to 1 uM fulvestrant.
"++++" means IC$_{50}$ < 10 nM;
"+++" < 100 nM";
"++" < 200 nM;
"+" > 200 nM.

TABLE 2

Biological Data of Compounds 12 to 15

| Cmpd # | Structure | Name | MCF-5C growth inhibition IC$_{50}$$^a$ |
|---|---|---|---|
| 12 | 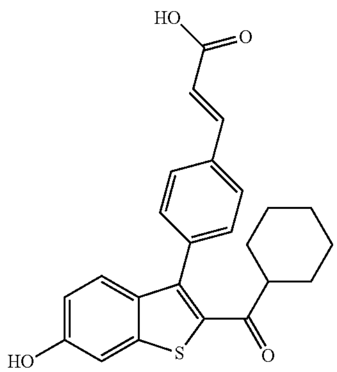 [SMILES: O=C(O)/C=C/c1ccc(-c2c(C(=O)C3CCCCC3)sc3cc(O)ccc23)cc1] | (E)-3-(4-(2-(cyclohexanecarbonyl)-6-hydroxybenzo[b]thiophen-3-yl)phenyl)acrylic acid | ++ |
| 13 | 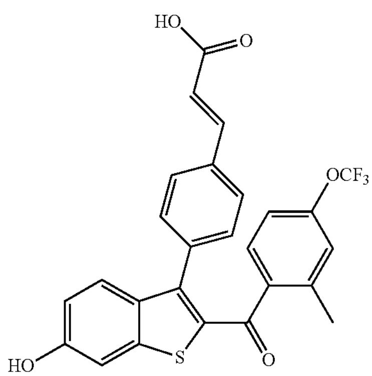 [SMILES: Cc1cc(OC(F)(F)F)ccc1C(=O)c1sc2cc(O)ccc2c1-c1ccc(/C=C/C(=O)O)cc1] | (E)-3-(4-(6-hydroxy-2-(2-methyl-4-(trifluoromethoxy)benzoyl)benzo[b]thiophen-3-yl)phenyl)acrylic acid | + |
| 14 | 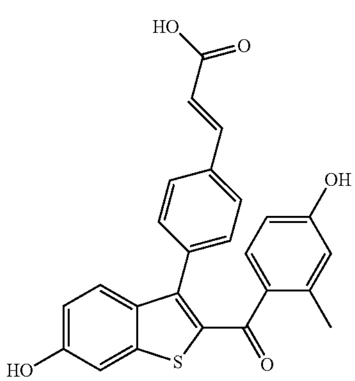 [SMILES: Cc1cc(O)ccc1C(=O)c1sc2cc(O)ccc2c1-c1ccc(/C=C/C(=O)O)cc1] | (E)-3-(4-(6-hydroxy-2-(4-hydroxy-2-methylbenzoyl)benzo[b]thiophen-3-yl)phenyl)acrylic acid | + |

TABLE 2-continued

Biological Data of Compounds 12 to 15

| Cmpd # | Structure | Name | MCF-5C growth inhibition IC$_{50}$$^a$ |
|---|---|---|---|
| 15 | 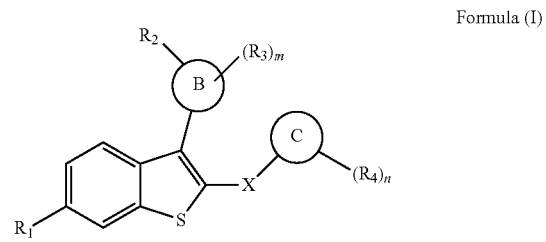 | (E)-3-(4-(6-hydroxy-2-(4-hydroxy-2,6-dimethylbenzoyl)benzo[b]thiophen-3-yl)phenyl)acrylic acid | + |

$^a$Data are normalized to 1 uM fulvestrant.
"++++" means IC$_{50}$ < 10 nM;
"+++" < 100 nM";
"++" < 200 nM;
"+" > 200 nM.

Assays
Cell Viability of MCF7:5C (Tamoxifen Resistant)

The DNA content of the cells was determined as previously described using a Fluorescent DNA Quantitation kit (cat. No. 170-2480; Bio-Rad Laboratories, Hercules, Calif.). Briefly, five thousand cells were plated per well in 96-well plates, and treatment with indicated concentrations of compounds was started at the same time in each well. On day 6, the cells in the plates were lysed and frozen at −80° C. To measure the total DNA in each well, the plates were allowed to warm to room temperature, incubated with Hoechst dye, and mixed well. The fluorescence was measured using a Synergy H4 Hybrid Multi-Mode Microplate Reader. For each analysis, six replicate wells were used and at least three independent experiments were performed.

FIG. 1 is a graph of the efficacy of Compound 1 against tamoxifen-resistant MCF-7:5 cells normalized to 1 uM fulvestrant. The y-axis is cell survival as a percent of the control and the x-axis is the concentration of the compound measured in nanomolar units.

Western Blot

Whole-cell extracts of cultured cells were prepared in lysis buffer (200 mmol/L Tris, 1% Triton X-100, 5 mmol/L EDTA) with protease and phosphatase inhibitor cocktails (1:50, both from Sigma-Aldrich) after scraping from the culture plates. Protein concentration was measured using the Bradford method (Bio-Rad). Proteins were separated under denaturing conditions and blotted onto nitrocellulose membrane (Bio-Rad) using a wet transfer system (Bio-Rad). Images of blots were acquired on a Bio-Rad ChemiDoc System following incubation with SuperSignal West Dura luminol solution (Thermo Fisher Scientific).

Figure 2:
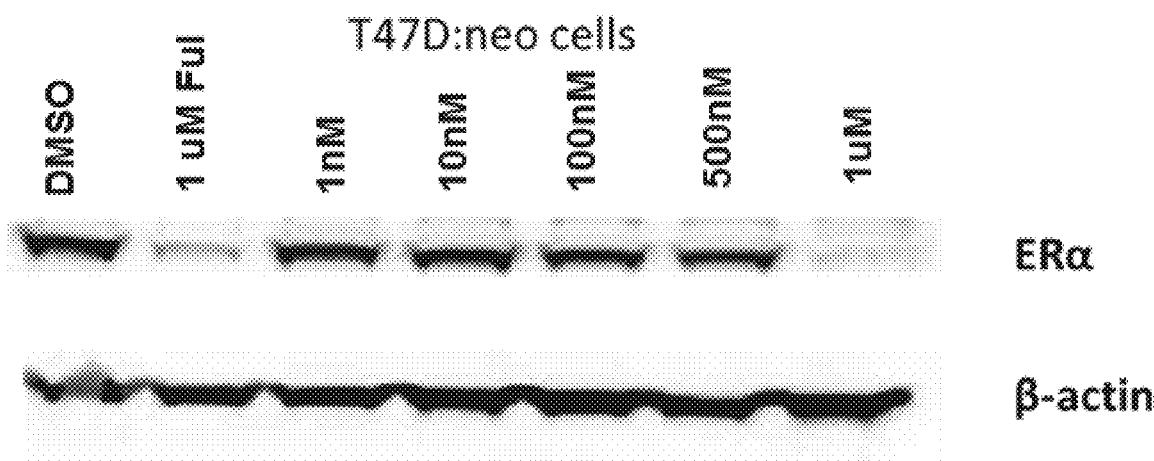
FIG. 2 is a western blot analysis that shows estrogen receptor downregulation when T47D:neo cells were treated with compound 1 for 24 hours at concentrations of 1 nM to 1 uM. Fulvestrant at 1 uM concentration was assayed as a positive control.

FIG. 2 is a western blot analysis that shows estrogen receptor downregulation when T47D:neo cells were treated with compound 1 for 24 hours at concentrations of 1 nM to 1 uM. Fulvestrant at 1 uM concentration was assayed as a positive control.

Figure 3:
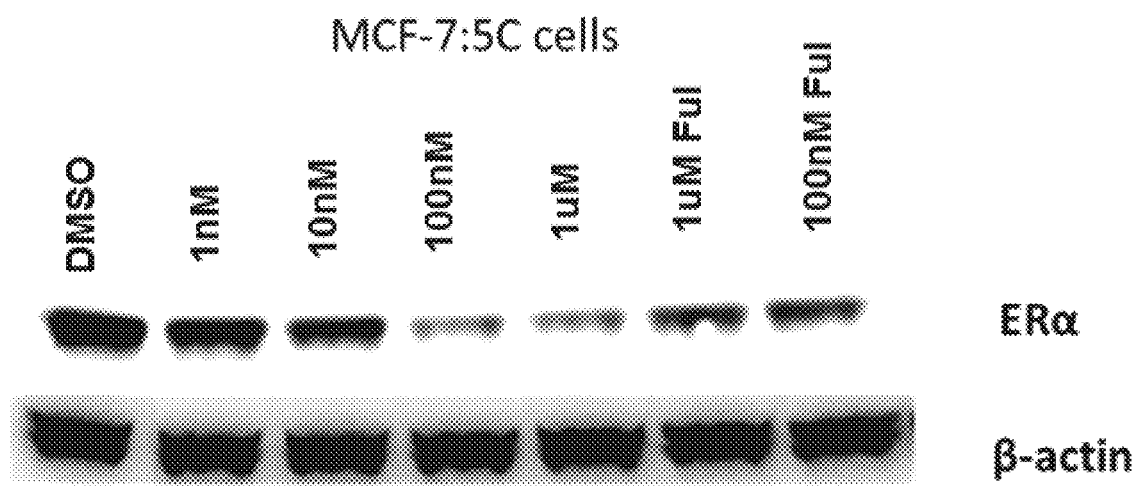
FIG. 3 is a western blot analysis that shows estrogen receptor downregulation when MCF-7:5C cells were treated with compound 1 for 24 hours at concentrations of 1 nM to 1 uM. Fulvestrant at 1 uM concentration was assayed as a positive control.
Figure 4:
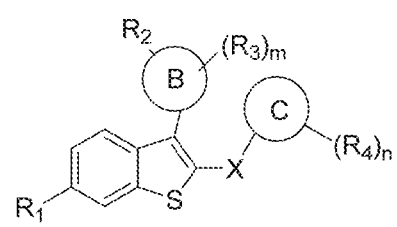
FIG. 4 is a compound of Formula (I), a selective mixed estrogen receptor degrader (SMERD).

FIG. 3 is a western blot analysis that shows estrogen receptor downregulation when MCF-7:5C cells were treated with compound 1 for 24 hours at concentrations of 1 nM to 1 uM. Fulvestrant at 1 uM concentration was assayed as a positive control.

This specification has been described with reference to embodiments of the invention. However, one of ordinary skill in the art will appreciate that various modifications and changes can be made without departing from the scope of the invention as set forth in the claims below. While only certain representative materials, methods, and aspects of these materials and methods are specifically described, other materials and methods and combinations of various features of the materials and methods are intended to fall within the scope of the appended claims, as if specifically recited. Accordingly, the specification is to be regarded in an illustrated rather than a restrictive sense, and all such modifications are intended to be included within the scope of the invention.

We claim:
1. A compound of Formula (I), or a pharmaceutically acceptable salt thereof:

Formula (I)

wherein:
m is 0, 1, 2, 3, or 4;
n is 0, 1, 2, 3, or 4;
X is —C(O)—;
Ring B is phenyl, or naphthyl;
Ring C is phenyl, or C$_3$-C$_6$cycloalkyl;

$R_1$ is selected from hydroxyl, hydrogen, halogen, —O($C_1$-$C_6$alkyl), —OC(O)($C_1$-$C_6$alkyl), —OC(O)$C_6H_5$, —OC(O)O($C_1$-$C_6$alkyl), —OC(O)O$C_6H_5$, and —OSO$_2$($C_2$-$C_6$alkyl);

$R_2$ is selected from —OCH=CHCOOH, —NHC(O)COOH, —COOH, —$C_2$-$C_6$alkylene-COOH, and —$C_2$-$C_6$alkynylene-COOH; and $R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

2. The compound of claim 1, wherein Ring B is phenyl.

3. The compound of claim 1, wherein R2 is selected from —OCH=CHCOOH and —$C_2$-$C_6$alkylene-COOH.

4. The compound of claim 1, wherein $R_4$ is selected from halogen, hydroxyl, $C_1$-$C_6$alkyl, $C_1$-$C_6$fluoroalkyl, and —O($C_1$-$C_6$fluoroalkyl).

5. The compound of claim 1, wherein R4 is hydroxyl.

6. The compound of claim 1, wherein m is 0.

7. The compound of claim 1, or a pharmaceutically acceptable salt thereof, of Formula (II):

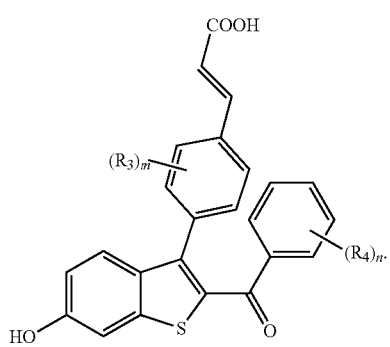

Formula (II)

8. The compound of claim 1, or a pharmaceutically acceptable salt thereof, of Formula (III):

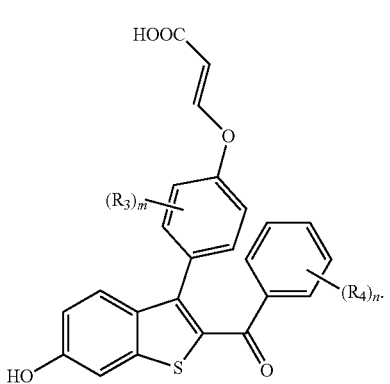

Formula (III)

9. The compound of claim 1, or a pharmaceutically acceptable salt thereof, of Formula (IV):

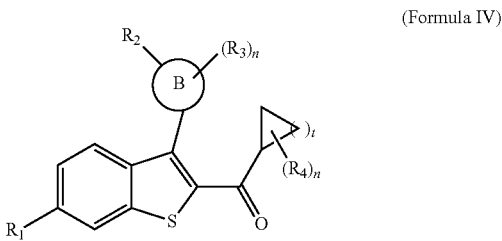

(Formula IV)

wherein t is 1, 2, 3, or 4.

10. A compound of Formula (V), or a pharmaceutically acceptable salt thereof:

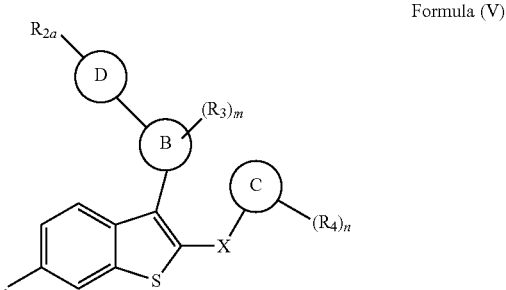

Formula (V)

wherein:
m is 0, 1, 2, 3, or 4;
n is 0, 1, 2, 3, or 4;
X is —C(O)—;
Ring B is phenyl, or naphthyl;
Ring C is phenyl, or $C_3$-$C_6$cycloalkyl;
Ring D is $C_3$-$C_6$cycloalkyl;
$R_1$ is selected from hydroxyl, hydrogen, halogen, —O($C_1$-$C_6$alkyl), —OC(O)($C_1$-$C_6$alkyl), —OC(O)$C_6H_5$, —OC(O)O($C_1$-$C_6$alkyl), —OC(O)O$C_6H_5$, and —OSO$_2$($C_2$-$C_6$alkyl);

$R_{2a}$ is selected from —OH, —NH(CO)NHOH, —CH=CHCOOH, —NH(CO)COOH, —COOH, —NH$_2$, —$C_2$-$C_6$alkylene-COOH, and —$C_2$-$C_6$alkynylene-COOH; and $R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

11. The compound of claim 10, wherein Ring B is phenyl.

12. The compound of claim 10, wherein $R_{2a}$ is selected from —OH, —COOH, and —NH$_2$.

13. The compound of claim 10, wherein m is 0.

14. A compound of Formula (VII), or a pharmaceutically acceptable salt thereof:

Formula (VII)

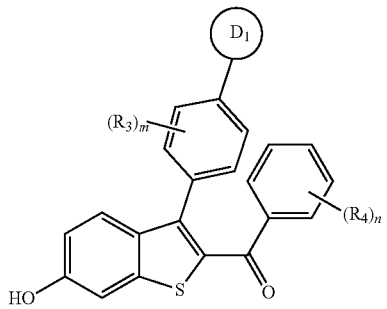

wherein:
m is 0, 1, 2, 3, or 4;
n is 0, 1, 2, 3, or 4;
Ring $D_1$ is selected from

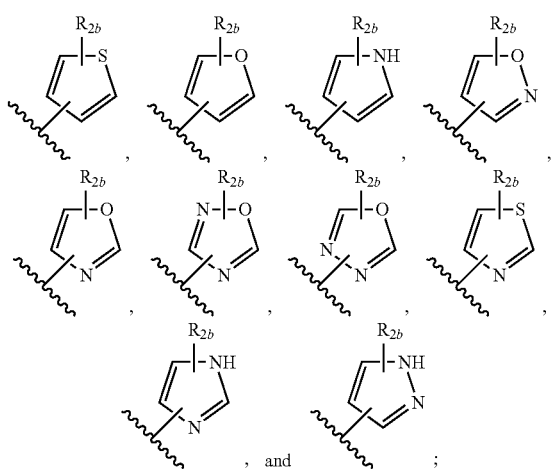

, and

;

$R_{2b}$ is selected from —OH, —NH$_2$, and —COOH; and
$R_3$ and $R_4$ are independently selected at each occurrence from hydrogen, halogen, hydroxyl, —NO$_2$, $C_1$-$C_6$alkyl, $C_1$-$C_6$fluoroalkyl, —CN, —O($C_1$-$C_6$alkyl), and —O($C_1$-$C_6$fluoroalkyl).

15. The compound of claim 14, wherein R4 is selected from halogen, hydroxyl, $C_1$-$C_6$alkyl, $C_1$-$C_6$fluoroalkyl, and —O($C_1$-$C_6$fluoroalkyl).

16. The compound of claim 14, wherein m is 0.

17. The compound of claim 14, wherein R4 is independently selected from halogen, $C_1$-$C_6$alkyl, and $C_1$-$C_6$fluoroalkyl.

18. A pharmaceutically composition comprising a compound of claim 1 and a pharmaceutically acceptable carrier or excipient.

19. A pharmaceutically composition comprising a compound of claim 10 and a pharmaceutically acceptable carrier or excipient.

20. A pharmaceutically composition comprising a compound of claim 14 and a pharmaceutically acceptable carrier or excipient.

21. A method of treating a hormone-related cancer that is an estrogen-mediated disorder in a subject in need thereof comprising administering a therapeutically effective amount of a compound according to claim 1 or a pharmaceutically acceptable salt thereof.

22. A method of treating a hormone-related cancer that is an estrogen-mediated disorder in a subject in need thereof comprising administering a therapeutically effective amount of a compound according to claim 10 or a pharmaceutically acceptable salt thereof.

23. A method of treating a hormone-related cancer that is an estrogen-mediated disorder in a subject in need thereof comprising administering a therapeutically effective amount of a compound according to claim 14 or a pharmaceutically acceptable salt thereof.

24. The method of claim 21, wherein the hormone-related cancer is breast cancer, uterine cancer, ovarian cancer, lung cancer, prostate cancer or endometrial cancer.

25. The method of claim 22, wherein the hormone-related cancer is breast cancer, uterine cancer, ovarian cancer, lung cancer, prostate cancer or endometrial cancer.

26. The method of claim 23, wherein the hormone-related cancer is breast cancer, uterine cancer, ovarian cancer, lung cancer, prostate cancer or endometrial cancer.

27. The compound of claim 1, wherein Ring B is naphthyl.

28. The compound of claim 1, wherein the compound is selected from:

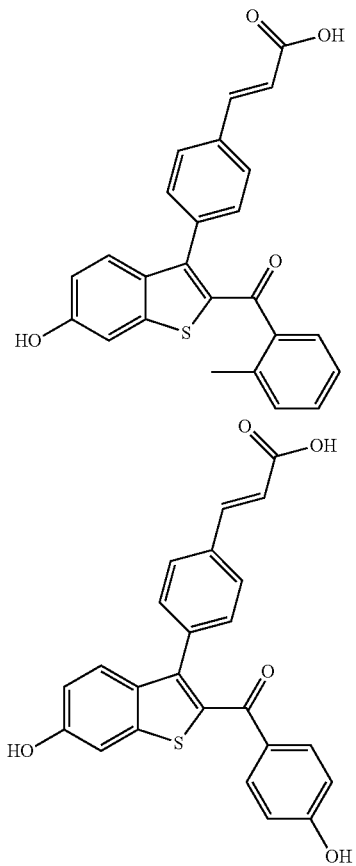

249
-continued
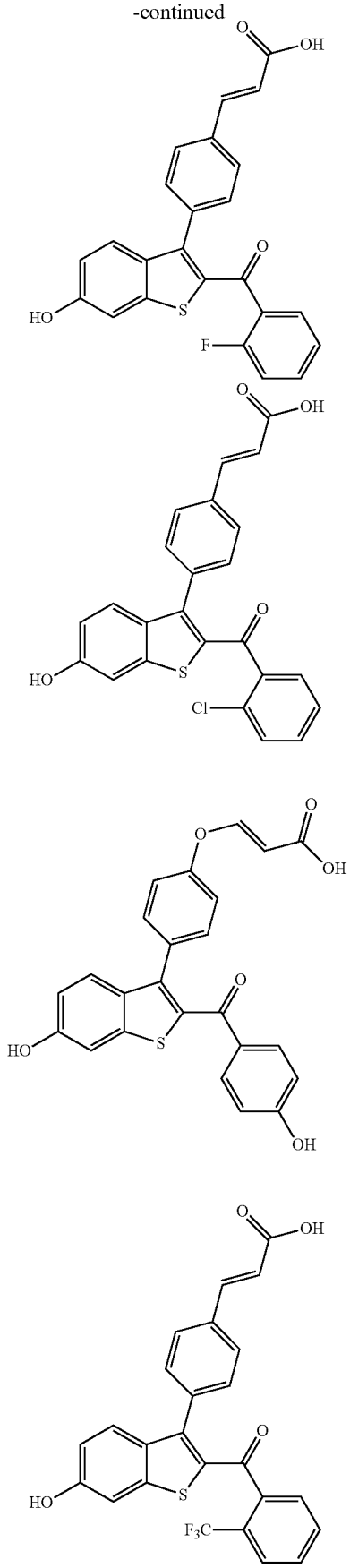
250
-continued
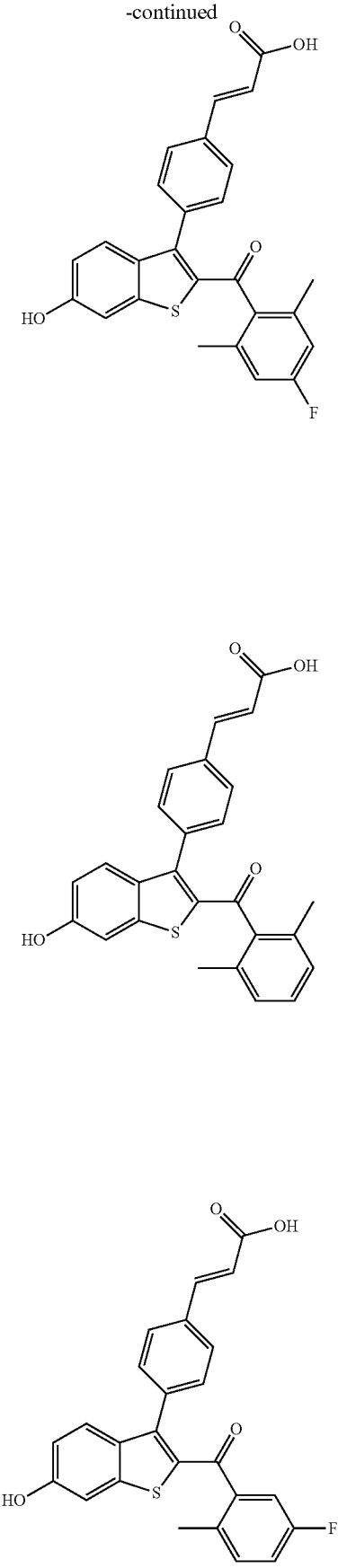

-continued
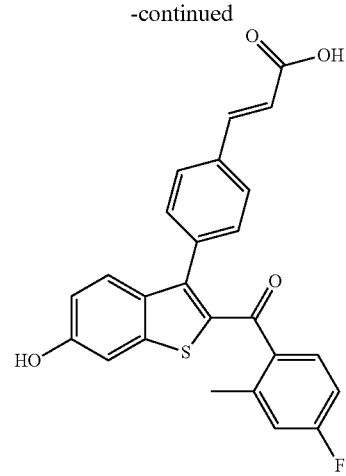
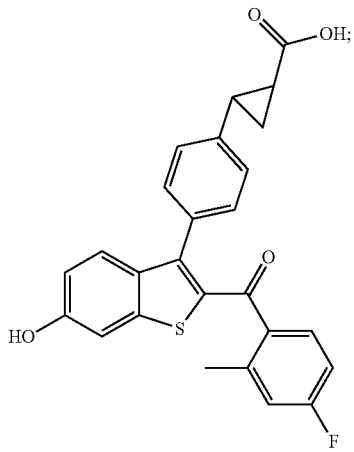
or a pharmaceutically acceptable salt thereof.
29. The compound of claim 1, wherein the compound is selected from:
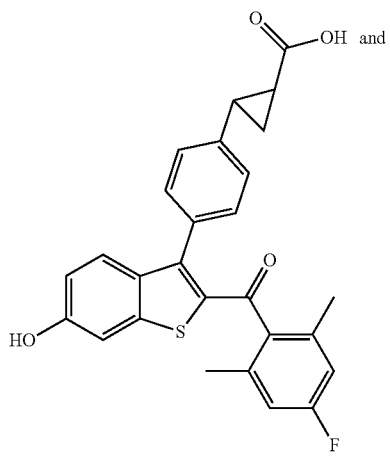
or a pharmaceutically acceptable salt thereof.

30. The compound of claim 14, wherein the compound is selected from:
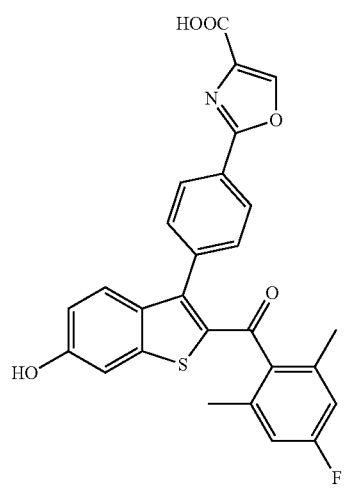
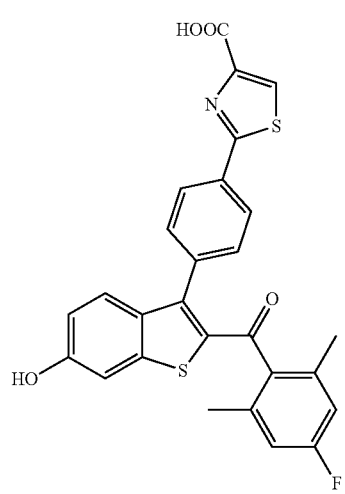
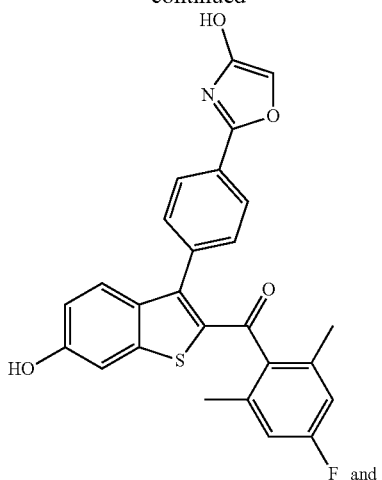
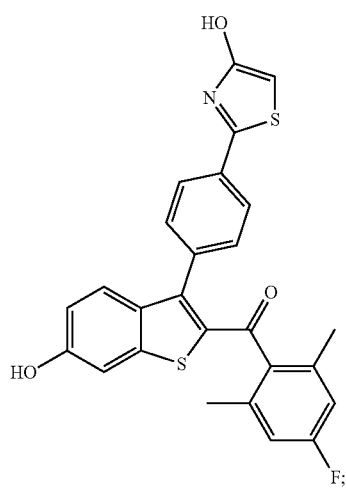 [SMILES: Cc1cc(F)cc(C)c1C(=O)c1sc2cc(O)ccc2c1-c1ccc(-c2nc(O)cs2)cc1]
or a pharmaceutically acceptable salt thereof.
* * * * *